United States Patent
Hummel et al.

(10) Patent No.: US 12,098,374 B2
(45) Date of Patent: Sep. 24, 2024

(54) OPTIMIZED PLANT CRISPR/CPF1 SYSTEMS

(71) Applicant: KWS SAAT SE & CO. KGaA, Einbeck (DE)

(72) Inventors: Aaron Hummel, Hillsborough, NC (US); Zarir Vaghchhipawala, Ballwin, MO (US)

(73) Assignee: KWS SAAT SE & CO. KGaA, Einbeck (DE)

( * ) Notice: Subject to any disclaimer, the term of this patent is extended or adjusted under 35 U.S.C. 154(b) by 335 days.

(21) Appl. No.: 16/961,303

(22) PCT Filed: Jan. 11, 2019

(86) PCT No.: PCT/EP2019/050655
§ 371 (c)(1),
(2) Date: Jul. 10, 2020

(87) PCT Pub. No.: WO2019/138052
PCT Pub. Date: Jul. 18, 2019

(65) Prior Publication Data
US 2021/0163968 A1    Jun. 3, 2021

Related U.S. Application Data

(60) Provisional application No. 62/616,136, filed on Jan. 11, 2018.

(51) Int. Cl.
*C12N 15/82* (2006.01)
*C12N 9/22* (2006.01)

(52) U.S. Cl.
CPC ............... *C12N 15/82* (2013.01); *C12N 9/22* (2013.01); *C12N 2310/20* (2017.05)

(58) Field of Classification Search
None
See application file for complete search history.

(56) References Cited

U.S. PATENT DOCUMENTS

2017/0335300 A1   11/2017   Frisch et al.

FOREIGN PATENT DOCUMENTS

| CN | 107012164 A | * | 8/2017 | ......... C12N 15/8213 |
| EP | 3199632 A1 | * | 8/2017 | ........... C12N 15/102 |
| WO | 2016/021973 A1 | | 2/2016 | |
| WO | 2017/066175 A1 | | 4/2017 | |
| WO | 2017/184768 A1 | | 10/2017 | |
| WO | 2017218185 A1 | | 12/2017 | |
| WO | 2017222370 A1 | | 12/2017 | |

OTHER PUBLICATIONS

He, Self-cleaving ribozymes enable the production of guide RNAs from unlimited choices of promoters for CRISPR/Cas9 mediated genome editing, Journal of Genetics and Genomics, 44(9), Sep. 20, 2017, pp. 469-472 (Year: 2017).*

Zetsche, Cpf1 is a Single RNA-Guided Endonuclease of a Class 2 CRISPR-Cas System, Cell, Oct. 2015 (Year: 2015).*

Zalatan, Engineering Complex Synthetic Transcriptional Programs with CRISPR RNA Scaffolds, Cell, Jan. 2015 (Year: 2015).*

Birikh, The Structure, Function and Application of the Hammerhead Ribozyme, European Journal of Biochemistry, Apr. 1998 (Year: 1998).*

Zhao, CRISPR-Cas9-mediated functional dissection of 3'-UTRs, Nucleic Acids Research, Aug. 2017 (Year: 2017).*

Alexander, Patrick A., et al. "The design and characterization of two proteins with 88% sequence identity but different structure and function." Proceedings of the National Academy of Sciences 104.29 (2007): 11963-11968. (Year: 2007).*

Amack, Stephanie C., and Mauricio S. Antunes. "CaMV35S promoter—A plant biology and biotechnology workhorse in the era of synthetic biology." Current Plant Biology 24 (2020): 100179. (Year: 2020).*

Bandyopadhyay, Anindya, et al. "CRISPR: From prokaryotic immune systems to plant genome editing tools." Precision Medicine, CRISPR, and Genome Engineering: Moving from Association to Biology and Therapeutics (2017): 101-120. (Year: 2017).*

Chadhoury, Ankur. "Molecular Biology: Every Sequence has three possible reading frames", Molecular Study Blog, (2012) (Year: 2012).*

F de Felippes, Felipe, et al. "The key role of terminators on the expression and post-transcriptional gene silencing of transgenes." The Plant Journal 104.1 (2020): 96-112. (Year: 2020).*

Gao, Linyi, et al. "Engineered Cpf1 variants with altered PAM specificities." Nature biotechnology 35.8 (2017): 789-792. (Year: 2017).*

Lam, Eric, et al. "Site-specific mutations alter in vitro factor binding and change promoter expression pattern in transgenic plants." Proceedings of the National Academy of Sciences 86.20 (1989): 7890-7894. (Year: 1989).*

(Continued)

*Primary Examiner* — Matthew R Keogh
(74) *Attorney, Agent, or Firm* — Troutman Pepper Hamilton Sanders LLP

(57) ABSTRACT

The present invention relates to optimized systems for the genome editing of eukaryotic cells, preferably plant cells. Also provided is a plant delivery system comprising at least one Cpf1 enzyme, or a plant optimized construct encoding the same, to be synergistically combined with a Cpf1 guide RNA system. Further provided is a Cpf1 guide RNA system being flanked by a Hammerhead ribozyme sequence at the 5' end and by a plant-derived Hepatitis Delta Vims (HDV)-like ribozyme sequence at the 3' end, or being embedded within a coding or non-coding region, of a sequence encoding a frame sequence. Novel plant-derived HDV-like ribozyme sequences are also provided. Further provided are methods for improved genome editing, and the use of the various systems provided herein to obtain transformed plants, plant cells, tissues, organs, or a progeny thereof, or a plant material, modified in a targeted way even at difficult to access target sites.

44 Claims, 23 Drawing Sheets

Specification includes a Sequence Listing.

(56) References Cited

OTHER PUBLICATIONS

Murovec, Jana, Žan Pirc, and Bing Yang. "New variants of CRISPR RNA-guided genome editing enzymes." Plant biotechnology journal 15.8 (2017): 917-926. (Year: 2017).*
Shaner, Nathan C., et al. "Improved monomeric red, orange and yellow fluorescent proteins derived from *Discosoma* sp. red fluorescent protein." Nature biotechnology 22.12 (2004): 1567-1572. (Year: 2004).*
Wang, Mugui, et al. "Multiplex gene editing in rice using the CRISPR-Cpf1 system." Molecular plant 10.7 (2017): 1011-1013. (Year: 2017).*
Zhong, Guocai, et al. "Cpf1 proteins excise CRISPR RNAs from mRNA transcripts in mammalian cells." Nature chemical biology 13.8 (2017): 839-841. (Year: 2017).*
Belhaj, Khaoula, et al. "Editing plant genomes with CRISPR/Cas9." Current opinion in biotechnology 32 (2015): 76-84. (Year: 2015).*
Webb, Chiu-Ho T., and Andrej Lupták. "HDV-like self-cleaving ribozymes." RNA biology 8.5 (2011): 719-727. (Year: 2011).*
Strauss-Soukup, Juliane K., and Scott A. Strobel. "Ribozyme enzymology." RNA (2001): 187-206. (Year: 2001).*
Hirt, H., et al. "Evolutionary conservation of transcriptional machinery between yeast and plants as shown by the efficient expression from the CaMV 35S promoter and 35S terminator." Current genetics 17 (1990): 473-479. (Year: 1990).*
De Felippes, Felipe F., and Peter M. Waterhouse. "Plant terminators: the unsung heroes of gene expression." Journal of Experimental Botany (2022). (Year: 2022).*
Burstein et al., "New CRISPR-Cas systems from uncultivated microbes", Nature, 2017, vol. 542, Article 7640, pp. 237-241.
Endo et al., "Efficient targeted mutagenesis of rice and tobacco genomes using Cpf1 from Francisella novicida", Scientific Reports, 2016, 6: 38169, 9 pages.
He et al., "Self-cleaving ribozymes enable the production of guide RNAs from unlimited choices of promoters for CRISPR/Cas9 mediated genome editing." J Genet Genomics, 2017, vol. 44, No. 9, pp. 469-472.
Jinek et al, "A programmable dual-RNA-guided DNA endonuclease in adaptive bacterial immunity", Science, 2012, vol. 337, pp. 816-821.
Li et al., Expanding the scope of CRISPR/Cpf1-mediated genome editing in rice, Molecular Plant, 2018, vol. 11, pp. 995-998.
Makarova et al., "An updated evolutionary classification of CRISPR-Cas systems", Nature Rev. Microbiol., 2015, vol. 13, No. 11, pp. 722-736.
Sander et al., "CRISPR-Cas systems for genome editing, regulation and targeting", Nat. Biotechnol., 2014, vol. 32, No. 4, pp. 347-355.
Sharmeen et al., Antigenomic RNA of Human Hepatitis Delta Virus Can Undergo Self-Cleavage, Journal of Virology, 1988, vol. 62, No. 8, pp. 2674-2679.
Zetsche et al., "Cpf1 is a single RNA-guided endonuclease of a Class 2 CRISPR-Cas system", Cell, 2015, vol. 163, No. 3, pp. 759-771.
Zetsche et al., "Multiplex gene editing by CRISPR-Cpf1 through autonomous processing of a single crRNA array", Nat Biotechnol., 2017, vol. 35, No. 1, pp. 31-34.
Zhong et al., "Plant genome editing using FnCpf1 and LbCpf1 nucleases at redefined and altered PAM sites", 2018, Molecular Plant, vol. 11, No. 7, pp. 999-1002.
Fonfara et al., "The CRISPR-associated DNA-cleaving enzyme Cpf1 also processes precursor CRISPR RNA", Nature, 2016, vol. 532, Article 7600, pp. 517-521.
Kishchenko et al., "Production of transgenetic sugarbeet (*Beta vulgaris* L.) plants resistant to phosphinothricin", Cell Biology International, 2005, vol. 29, No. 1, pp. 15-19.
International Search Report and Written Opinion issued in International Application No. PCT/EP2019/050655 dated May 16, 2019.
Xu Tang et al, "A CRISPR-Cpf1 system for efficient genome editing and transcriptional repression in plants", Nature Plants, vol. 3, No. 3, Feb. 17, 2017 (Feb. 17, 2017), p. 1-5.
Chiu-Ho T. Webb et al, "HDV-like self-cleaving ribozymes", RNA Biology, vol. 8, No. 5, Sep. 1, 2011 (Sep. 1, 2011), p. 719-727.
Rongfang Xu et al, "Generation of targeted mutant rice using a CRISPR-Cpf1 system", Plant Biotechnology Journal, vol. 15, No. 6, Jun. 1, 2017 (Jun. 1, 2017), p. 713-717.
Linyi Gao et al, "Engineered Cpf1 variants with altered PAM specificities", Nature Biotechnology, vol. 35, No. 8, Jun. 5, 2017 (Jun. 5, 2017), p. 789-792.
Guocai Zhong et al, "Cpf1 proteins excise CRISPR RNAs from mRNA transcripts in mammalian cells", Nature Chemical Biology, vol. 13, No. 8, Jun. 19, 2017 (Jun. 19, 2017), p. 839-841.
Chance M. Nowak et al, "Guide RNA engineering for versatile Cas9 functionality", Nucleic Acids Research, vol. 44, No. 20, Oct. 12, 2016 (Oct. 12, 2016), p. 9555-9564.
Kabin Xie et al, "Boosting CRISPR/Cas9 multiplex editing capability with the endogenous tRNA-processing system", Proceedings of the National Academy of Sciences, vol. 112. No. 11, Mar. 2, 2015 (Mar. 2, 2015), p. 3570-3575.
Mugui Wang et al, "Multiplex Gene Editing in Rice Using the CRISPR-Cpf1 System", Molecular Plant, vol. 10, No. 7, Jul. 1, 2017 (Jul. 1, 2017), p. 1011-1013.

* cited by examiner

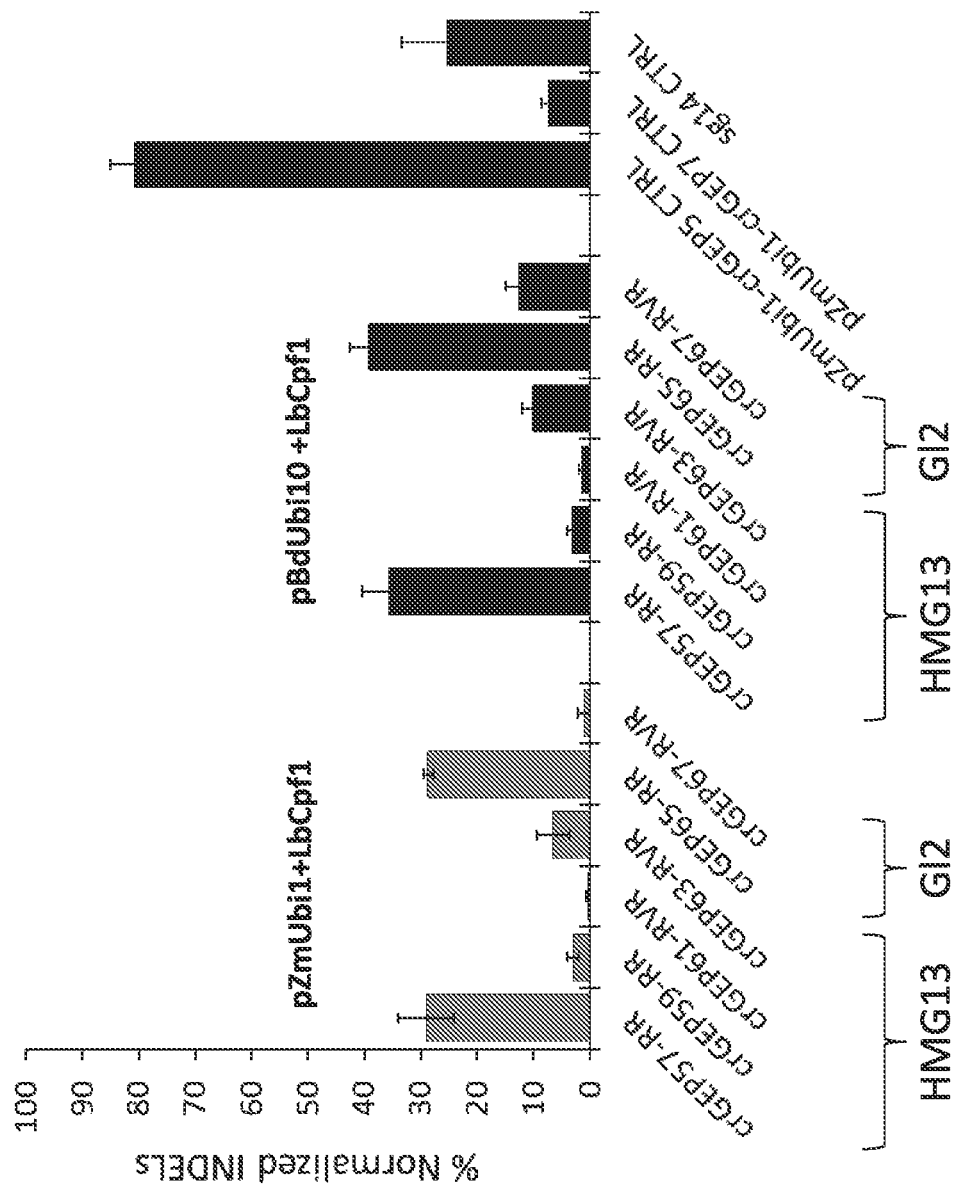

Figure 11A

InDels at crGEP5 target locus (wt LbCpf1)

```
TTTAATTTACTGTCACGATTCCCCTC|TCCTGG|TCGAACTTTTCAGGTGGGGAAAGCTGC    (SEQ ID NO: 104)
TTTGATTTACTGTCACGATTCCC----|----TGG|TCGAACTTTTCAGGTGGGGAAAGCTGC  (SEQ ID NO: 105)
TTTGATTTACTGTCACGATTCCCCTC|TCCTG-|TCGAACTTTTCAGGTGGGGAAAGCTGC    (SEQ ID NO: 106)
TTTGATTTACTGTCT-----------|------|----AACTTTTCAGGTGGGGAAAGCTGC   (SEQ ID NO: 109)
TTTGATTTACTGTCATGATTCCCCTC|-CCTGG|TCGAACTTTTCAGGTGGGGAAAGCTGC    (SEQ ID NO: 110)
```

Figure 11B

InDels at crGEP75 target locus (LbCpf1_RR variant)

```
CTGTGGCACTACCAAGCTCCTGCTCAC|CATTCC|AAGAATCCTTGAGCTTGCTGAAGAGCT   (SEQ ID NO: 111)
CTGTGGCACTACCAAGCTCCTGCTCAC|C-----|-AGAATCCTTGAGCTTGCTGAAGAGCT   (SEQ ID NO: 112)
CTGTGGCACTACCAAGCTCCTGCTCAC|CTT---|-GGAATCCTTGAGCTTGCTGAAGAGCT   (SEQ ID NO: 113)
CTGTGGCACTACCAAGCTCCTGCTC--|------|-AGAATCCTTGAGCTTGCTGAAGAGCT   (SEQ ID NO: 114)
CTGTGGCACTACCAAGCTCCT------|------|---------GCTTGCTGAAGAGCT     (SEQ ID NO: 115)
CTGTGGCACTACCAAGCTCCTGCTCA-|------|ATGAATCCTTGAGCTTGCTGAAGAGCT   (SEQ ID NO: 116)
```

Figure 11C

InDels at crGEP77 target locus (LbCpf1_RR variant)

```
GCAGGAGCTGCCTGGAGGCGGGCTCCT|CGTGTA|CCAGAGCTTCTGTGCTGAAGACGC      (SEQ ID NO: 117)
GCAGGAGCTGCCTGGAGGCGGGCTCCT|C-----|----GAGCTTCTGTGCTGAAGACGC    (SEQ ID NO: 118)
GCAGGAGCTGCCTGGAGGCGGGC----|------|----------TCTGTGCTGAAGACGC   (SEQ ID NO: 119)
GCAGGAGCTGCCTGGAGGCGGGCTCCT|CGT---|----GAGCTTCTGTGCTGAAGACGC    (SEQ ID NO: 120)
GCAGGAGCTGCCTGGAGGCGGGCTCCT|------|---GAGCTTCTGTGCTGAAGACGC     (SEQ ID NO: 121)
GCAGGAGCTGCCTGGAGGCGGGCTCCT|------|---GGAGCTTCTGTGCTGAAGACGC    (SEQ ID NO: 122)
GCAGGAGCTGCCTGGAGGCGGGCTCCT|CG----|---GGAGCTTCTGTGCTGAAGACGC    (SEQ ID NO: 123)
GCAGGAGCTGCCTGGAGGCGGGCTCCT|C-----|----AGCTTCTGTGCTGAAGACGC     (SEQ ID NO: 124)
```

Figure 12A

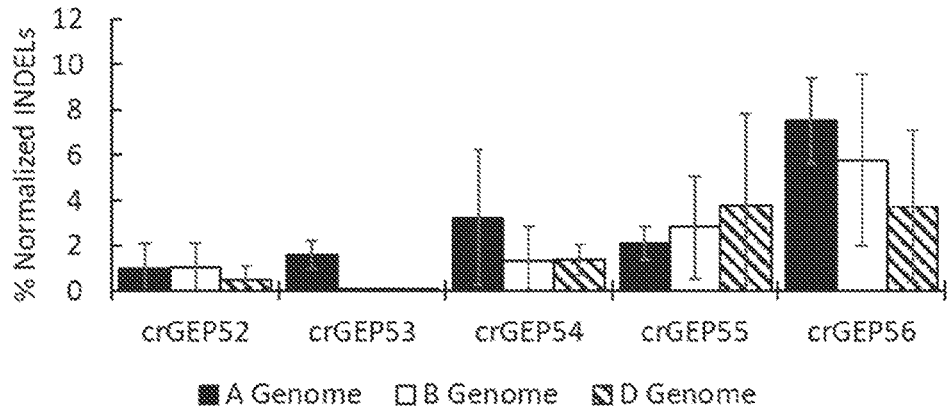

Figure 12B

A genome

| | | | |
|---|---|---|---|
| GCTCTTCCCGCACCGCTTCAGCCCTGC | AGCACG | CACCCATCCATGACGCAACACACATCA | (SEQ ID NO: 125) |
| GCTCTTCCCGCACCGCTTCAGCCCTGC | A---CG | CACCCATCCATGACGCAACACACATCA | (SEQ ID NO: 126) |
| GCTCTTCCCGCACCGCTTCAGCCC--- | ----CG | CACCCATCCATGACGCAACACACATCA | (SEQ ID NO: 127) |
| GCTCTTCCCGCACCGCTTCAGCCCT-- | ----ACG | CACCCATCCATGACGCAACACACATCA | (SEQ ID NO: 128) |
| GCTCTTCCCGCACCGCTTCAGCCT--- | -GCACG | CACCCATCCATGACGCAACACACATCA | (SEQ ID NO: 129) |
| GCTCTTCCCGCACCGCTTCAGCCCTG- | -----G | CACCCATCCATGACGCAACACACATCA | (SEQ ID NO: 130) |
| GCTCTTCCCGCACCGCTTCAGCCC--- | ------ | -----ATCCATGACGCAACACACATCA | (SEQ ID NO: 131) |
| GCTCTTCCCGCACCGCTTCAGCCC--- | ------ | ----CCATCCATGACGCAACACACATCA | (SEQ ID NO: 132) |
| GCTCTTCCCGCACCGCTTCAGC----- | ------ | -ACCCATCCATGACGCAACACACATCA | (SEQ ID NO: 133) |

Figure 12C

B genome

| | | | |
|---|---|---|---|
| GCTCTTCCCGCACCGCTTCAGCCCTGC | AGCACG | CACCCATCCATGACGCAACACACATCA | (SEQ ID NO: 134) |
| GCTCTTCCCGCACCGCTTCAGCCC--- | ------ | -ACCCATCCATGACGCAACACACATCA | (SEQ ID NO: 135) |
| GCTCTTCCCGCACCGCTTCAGCCC--- | ---ACG | CACCCATCCATGACGCAACACACATCA | (SEQ ID NO: 136) |
| GCTCTTCCCGCACCGCTTCAGCC---- | ---ACG | CACCCATCCATGACGCAACACACATCA | (SEQ ID NO: 137) |
| GCTCTTCCCGCACCGCTTCAGCC---- | -----G | CACCCATCCATGACGCAACACACATCA | (SEQ ID NO: 138) |
| GCTCTTCCCGCACCGCTTCAGC----- | -----G | CACCCATCCATGACGCAACACACATCA | (SEQ ID NO: 139) |
| CATCCATGACGCACCACACATCAGCCC | AGCACG | CACCCATCCATGACGCAACACACATCA | (SEQ ID NO: 140) |

Figure 12D

D genome

| | | | |
|---|---|---|---|
| GCTCTTCCCGCACCGCTTCAGCCCTGC | AGCACG | CACCCATCCATGACGCAACACACATCA | (SEQ ID NO: 141) |
| GCTCTTCCCGCACCGCTTCAGCCC--- | ----CG | CACCCATCCATGACGCAACACACATCA | (SEQ ID NO: 142) |
| GCTCTTCCCGCACCGCTTCAGCC---- | ------ | ---CCATCCATGACGCAACACACATCA | (SEQ ID NO: 143) |
| GCTCTTCCCGCACCGCTTCAGCCCT-- | ------ | -ACCCATCCATGACGCAACACACATCA | (SEQ ID NO: 144) |

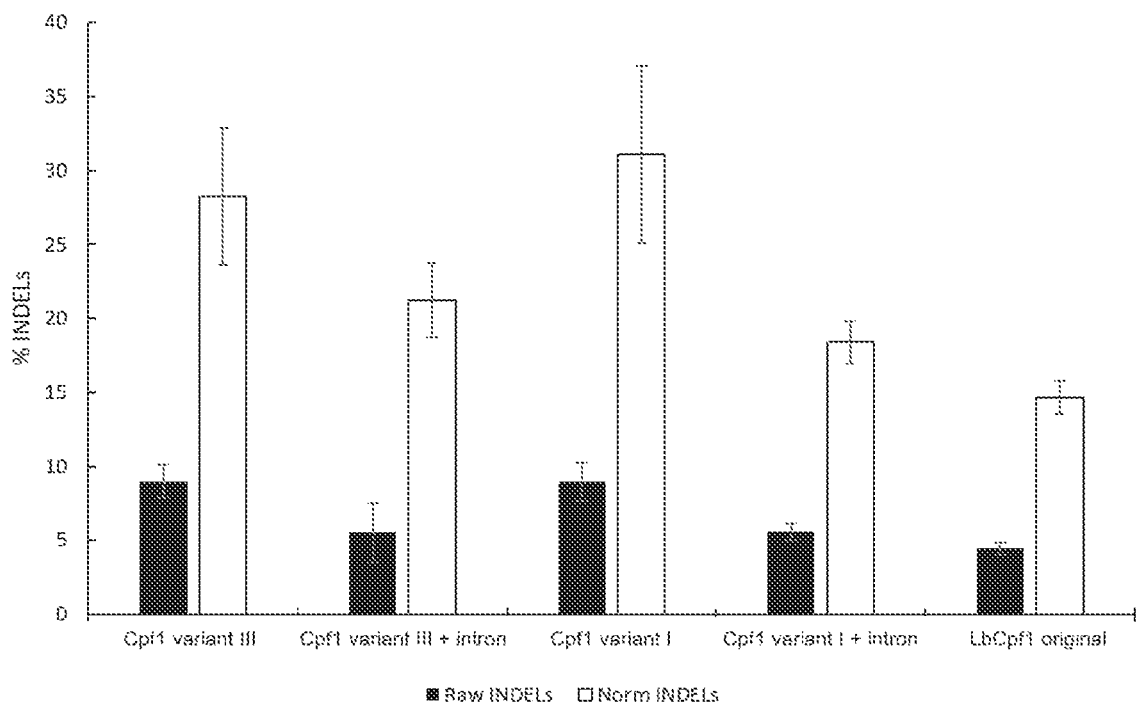

OPTIMIZED PLANT CRISPR/CPF1 SYSTEMS

CROSS-REFERENCE TO RELATED APPLICATIONS

This application is a U.S. National Phase of International Patent Application No. PCT/EP2019/050655, filed on Jan. 11, 2019, which claims priority to U.S. Provisional Application No. 62/616,136, filed Jan. 11, 2018. The entire contents of these applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Jan. 27, 2021, is named 245761_000114_SL.txt and is 332,518 bytes in size.

TECHNICAL FIELD

The present invention relates to optimized systems for the genome editing of eukaryotic cells, preferably plant cells. Also provided is a plant delivery system comprising at least one Cpf1 enzyme, or a plant optimized construct encoding the same, to be synergistically combined with a Cpf1 guide RNA system. Further provided is a Cpf1 guide RNA system being flanked by a Hammerhead ribozyme sequence at the 5' end and by a plant-derived Hepatitis Delta Virus (HDV)-like ribozyme sequence at the 3' end, or being embedded within a coding or non-coding region, of a sequence encoding a frame sequence. Novel plant-derived HDV-like ribozyme sequences are also provided. Further provided are methods for improved genome editing, and the use of the various systems provided herein to obtain transformed plants, plant cells, tissues, organs, or a progeny thereof, or a plant material, modified in a targeted way even at difficult to access target sites.

BACKGROUND OF THE INVENTION

Site-directed modification of a given genome of interest has been the leading edge in plant biological researches for the recent years. Since 1996, researchers have reported the directed DNA cleaving activities of zinc finger nucleases (ZFNs) (Kim et al., 1996), transcription activator-like effector nucleases (TALENs) (Christian et al., 2010), or the clustered regularly interspaced short palindromic repeat (CRISPR), mainly the CRISPR/Cas9 technology (Jinek et al., 2012), which have been widely applied in animal and plant genome site-directed modifications, and significantly promoted the basic and applied researches on the genetic engineering of eukaryotes. The CRISPR/Cas9 system discovered recently is a genomic immune system in the (ancient) bacteria against the invasion of exogenous nucleic acid molecules which is different from the "restriction-modification" system: it is clear through researches that, the homologous sequences in the DNA double helix can be recognized, after pairing the homologous regions of a sequence specific crRNA (CRISPR RNA) and another tracrRNA molecule (trans-activating crRNA), so as to guide Cas9 protein to recognize and cleave the target DNA double helix, and create site-directed DSB (Jinek et al., 2012). In artificial CRISPR systems, a synthetic non-coding RNA and a CRISPR nuclease and/or optionally a modified CRISPR nuclease, modified to act as nickase or lacking any nuclease function, can be used in combination with at least one synthetic or artificial guide RNA or (s)gRNA combining the function of a crRNA and/or a tracrRNA (Makarova et al., Nature Rev. Microbiol., 2015).

Since the cell endogenous DNA site-directed modification activity of the CRISPR/Cas9 system has been proven in 2013, researchers have adopted CRISPR/Cas9 system to realize the RNA-guided site-directed modification of the genomes in animal and plant systems, such as the macaque *Macaca fascicularis*, zebrafish, mice and human cell line, *Arabidopsis thaliana* and rice. Although CRISPR is much simpler than the previous gene editing methods, and also considered as a revolutionary technology in the genetic research field, researchers still urgently seek for improvements and developments of the CRISPR technology, in hope to realize an even simpler and more precise genome site-directed modification, in particular in complex eukaryotic genomes, like plant genome, where poor accessibility of certain target sequences and the problem of off-target effects and transformation/transfection problems are still a dominating issue hampering the broad applicability of site-directed gene or genome editing (GE) in eukaryotic cells, including plant and animal cells.

In 2015 (Zetsche et al. (2015) Cell, 163 (3):759-771.), the researchers discovered a novel CRISPR system (CRISPR/Cpf1), which can cleave DNA substrates in human cells. When comparing with CRISPR/Cas9 system, CRISPR/Cpf1 has the following four advantages: 1) Cpf1 protein is smaller than the standard Cas9 protein, and only one crRNA molecule is required for CRISPR/Cpf1 to cleave DNA, while CRISPR/Cas9 requires two molecules tracrRNA and crRNA with a longer sequence to jointly recognize and cleave the DNA substrate; 2) CRISPR/Cpf1 is a sticky-end cleaving, while CRISPR/Cas9 is blunt-end cleaving, whereas it has been shown that DNA insertion is more controllable with sticky-end cleaving which is also more beneficial for the editing and repair after the DNA cleaving; 3) CRISPR/Cpf1 and CRISPR/Cas9 recognize different PAM (protospacer adjacent motif) sites on the DNA substrate (CRISPR/Cpf1 recognizes inter alia the PAM site of 5'-TTTN-3, while CRISPR/Cas9 recognizes inter alia the PAM site of 5'-NGG-3'), which has broadened the options for the design of CRISPR editing loci; 4) the CRISPR/Cpf1 cleaving locus is located at the 3'-end of the PAM site, while the CRISPR/Cas9 cleaving locus is located at the 5'-end of the PAM site, which can introduce more flexibility to design GE experiments.

Existing evidence shows that CRISPR/Cpf1 can be applied in human cells and mice to carry out genetic editing, which indicates it has an application prospect. Recent research also showed that CRISPR/Cpf1 can be applied in plants to efficiently carry out genome editing. Two research groups have published initial reports on CRISPR/Cpf1 (Endo A et al. (2006) Scientific Reports, 6: 38169 and Xu et al. (2016) Plant Biotechnol. Journal, doi:10.1111/pbi.12669.), however, the results indicated that CRISPR/Cpf1 has a low cleaving and editing efficiency and poor genetic stability in plant cells and might thus be a far less promising tool for plant biotechnological applications. This has cast the doubt as to whether CRISPR/Cpf1 can be similarly used as CRISPR/Cas9 as an effective site-directed GE tool in plants, which presently strongly limits the research and application of CRISPR/Cpf1 in the site-directed genome modification of plants.

In view of the outstanding challenges associated with the implementation of an effective CRISPR/Cpf1 platform in plants, there remains an ongoing need to provide improved CRISPR/Cpf1 systems that allow for efficient GE in plant cells, in particular for relevant crop plants like wheat and corn (*Zea mays*).

Another problem frequently associated with any CRISPR-based GE approach is the fact that the CRISPR systems are RNA-guided systems. Therefore, availability of the gRNA and its stability play a crucial role for any CRISPR-based GE assay. Production of gRNAs directly in a cell, in particular in plant cells, is still strongly limited due to the lack of suitable promoters and expression constructs. For example, commonly used promoters, like the small nuclear RNA U6 and U3 promoter, do not provide sufficient specificity and in vitro transcription rates to guarantee sufficient gRNA availability. For example, the RNA polymerase III-dependent U6 promoter or the T7 promoter require a G or GG, respectively, at the 5' end of the RNA to be transcribed. As a result, standard full-length or truncated gRNAs expressed from these promoters are limited to targeting sites that match the forms GN16-19NGG or GGN15-18NGG (SEQ ID NO: 159), sites that each occur every 1 in 32 bps or 1 in 128 bps, respectively, in random DNA strongly limiting the targeting range when applied in a CRISPR-based GE approach (Sander and Young, 2014, Nat. Biotechnol., 32(4):347-355).

The design of suitable gRNAs depends on a variety of factors, i.e., inter alia the kind of edit planned, the target genome and its complexity, including potential off-target sites, the availability of PAM sequences, the optimum interaction of a design gRNA and the cognate CRISPR effector (the complex formation between gRNA/CRISPR effector) and the stability of the gRNA provided pre-synthesized, or on a suitable expression construct. PAM specificity and in turn target range restrictions are a common problem in any CRISPR-based GE approach, as the CRISPR effector and the cognate gRNA must be able to interact with each other for proper PAM recognition. Therefore, many adjusting screws have to be individually adapted to provide a CRISPR-based system including all components needed for functionality in a target cell of interest—to ultimately edit a genomic target site of interest successfully. Despite recent progress in this area, the predictability of a successful GE experiment planned in silico is thus still rather low, in particular for plant genomes, as many of the CRISPR work is performed in animal cells, whereas the complexity and specific features of plant genomes and plant metabolism still require fundamental research effort to establish suitable CRISPR systems effective in a variety of different plants, including economically relevant crop plants.

The objective underlying the present invention therefore was to provide improved CRISPR systems, mainly CRISPR/Cpf1 systems recently described to be less efficient in plant cells, which systems can be used for efficient plant GE approaches. It was another aim of the present invention to overcome poor guide RNA availability by identifying new plant-compatible systems for providing gRNAs in a stable manner and thus to dramatically increase successful GE rates suitable for in vitro and in vivo applications.

Furthermore, it was an aim to identify ribozyme-based gRNA delivery systems, in particular systems not relying on common systems like the hepatitis-delta virus (HDV) ribozyme derived from a human pathogenic virus, to provide safe and plant-optimized gRNA delivery tools having superior performance, in particular in the plant system, and not necessitating complex deregulation processes in product development.

To this end, it was an aim to provide GE tools relying on optimized CRISPR effector nucleases as well as optimized guide RNA delivery techniques, including embedding and ribozyme activation of guide RNAs, to provide active GE tools having superior qualities in a synergistic manner, in particular for targeted GE in plants and plant cells.

It was a final aim of the present invention to combine the optimized tools to achieve reliable and predictable GE in a variety of different plant cells, wherein the methods and uses should be practicable for multiplexing to generate targeted GE events for different loci of interest with significantly reduced costs and time expenses.

SUMMARY OF THE INVENTION

The present invention thus relates to several aspects to establish and improve the efficiency of CRISPR/Cpf1 systems in plants cells; in particular in corn (e.g. *Zea mays*), by providing individual components fine-tuned to each other to obtain optimum genome editing efficiencies.

The above objectives have been achieved by providing, in a first aspect, a plant delivery system, the delivery system comprising (a) at least one Cpf1 enzyme or an active fragment thereof, or a nucleic acid sequence encoding the same; and (b) at least one Cpf1 guide RNA system, or a nucleic acid sequence encoding the same, the at least one Cpf1 guide RNA system comprising at least one Cpf1 guide RNA specific for a genomic target sequence of interest in a plant or part of a plant; wherein the at least one Cpf1 guide RNA, or the nucleic acid sequence encoding the same, is (i) flanked by a Hammerhead ribozyme sequence at the 5'-end and by a plant-derived Hepatitis Delta Virus (HDV)-like ribozyme sequence at the 3'-end; and/or is (ii) embedded within a non-coding region, preferably a 3' untranslated region (UTR), of a sequence encoding a frame sequence.

In one embodiment there is provided a plant delivery system, wherein the plant delivery system comprises a first nucleotide molecule comprising a nucleic acid sequence encoding the at least one Cpf1 enzyme or an active fragment thereof, and a second nucleotide molecule comprising a nucleic acid sequence encoding the at least one Cpf1 guide RNA system, preferably wherein the first and the second molecule are provided on separate constructs, or wherein the first and the second molecule are provided on a single transcript construct.

In another embodiment there is provided a plant delivery system, wherein the first construct comprising the first nucleotide molecule and the second construct comprising the second nucleotide molecule each comprise at least one promoter functional in a plant or part of a plant, preferably wherein the at least one promoter driving expression of the first and the second nucleotide molecule is different in the first and the second construct, respectively.

In yet another embodiment there is provided a plant delivery system, wherein the at least one promoter is independently selected from a (p)BdUbi10 promoter (SEQ ID NO: 1, a (p)ZmUbi1 promoter (SEQ ID NO: 2), a (p)OsActin promoter (SEQ ID NO: 3), and a single or double 35S promoter (SEQ ID NO: 4), optionally including an ZmUbi1 intron, an BdUbi10 intron and/or an Adh1 intron, (SEQ ID NOs: 5 to 10 or 67), or any combination thereof, or a sequence having at least 90%, 91%, 92%, 93%, 94%, 95%, 96%, 97%, 98%, or 99% identity when compared over the whole length of the respective sequence of any one of SEQ ID NOs: 1 to 10, or 67. Bd means originating from *Brachypodium distachyon*, Zm means originating from *Zea mays*, Adh1 means originating from alcohol dehydrogenase-1, and Os means originating from *Oryza sativa*.

In yet a further embodiment there is provided a plant delivery system, wherein the first construct comprising the first nucleotide molecule and the second construct comprising the second nucleotide molecule comprise at least one terminator functional in a plant or part of a plant.

In one embodiment there is provided a plant delivery system, wherein the at least one terminator is a NosT terminator (SEQ ID NO: 11) or a 35S terminator (SEQ ID NO: 12), or any combination thereof, or a sequence having at least 90%, 91%, 92%, 93%, 94%, 95%, 96%, 97%, 98%, or 99% identity when compared over the whole length of the respective sequence of any one of SEQ ID NOs: 11 or 12.

In a further embodiment there is provided a plant delivery system, wherein the nucleic acid sequence encoding the Cpf1 enzyme or an active fragment thereof is codon-optimized for expression in a plant or part of a plant. In a further embodiment there is provided a plant delivery system, wherein the nucleic acid sequence encoding the Cpf1 enzyme or an active fragment thereof contains at least one intron. In another further embodiment there is provided a plant delivery system, wherein the nucleic acid sequence encoding the Cpf1 enzyme or an active fragment thereof is codon-optimized for expression in a plant or part of a plant and contains at least one intron.

In yet a further embodiment there is provided a plant delivery system, wherein the nucleic acid sequence encoding the Cpf1 enzyme or an active fragment thereof is selected from SEQ ID NOs: 13, 14, 38, 39, 72, 73, 74, 75, 76, 157, or 158, or a sequence having at least 85%, 86%, 87%, 88%, 89%, 90%, 91%, 92%, 93%, 94%, 95%, 96%, 97%, 98%, or 99% identity over the whole length of the respective sequence of SEQ ID NOs: 13, 14, 38, 39, 72, 73, 74, 75, 76, 157, or 158. Preferably the nucleic acid sequence encoding the Cpf1 enzyme or an active fragment thereof is SEQ ID NO: 72 or 75, or a sequence having at least 85%, 86%, 87%, 88%, 89%, 90%, 91%, 92%, 93%, 94%, 95%, 96%, 97%, 98%, or 99% identity over the whole length of the respective sequence of SEQ ID NO: 72 or 75.

In one embodiment there is provided a plant delivery system, wherein the Hammerhead ribozyme sequence, or a sequence encoding the same, is selected from SEQ ID NO: 17 or 18 (HH Ribozyme sequence), and/or wherein the plant-derived Hepatitis Delta Virus (HDV)-like ribozyme sequence, or a sequence encoding the same, is selected from any one of SEQ ID NOs: 19 to 26, or a sequence having at least 95%, 96%, 97%, 98%, or 99% identity over the whole length of any one of SEQ ID NOs: 17 to 26.

In another embodiment there is provided a plant delivery system, wherein the at least one Cpf1 guide RNA, or the nucleotide sequence encoding the same, which is (i) flanked by the Hammerhead ribozyme sequence at the 5' and the plant-derived Hepatitis Delta Virus (HDV)-like ribozyme sequence at the 3'-end, further comprises a scaffold RNA sequence, or a sequence encoding the same, at the 5'-end; and/or which is (ii) embedded within the non-coding region, preferably the 3' untranslated region (UTR), of the sequence encoding a frame sequence, further comprises a scaffold RNA sequence, or a sequence encoding the same, at the 5' and 3'-end.

In yet another embodiment there is provided a plant delivery system, wherein the scaffold RNA sequence, or a sequence encoding the same, is selected from SEQ ID NO: 29 or 30, or a sequence having at least 95%, 96%, 97%, 98%, or 99% identity over the whole length of SEQ ID NO: 29 or 30.

In one embodiment there is provided a plant delivery system, wherein the at least one Cpf1 enzyme or an active fragment thereof, or a nucleic acid sequence encoding the same, is selected from any one of SEQ ID NOs: 13 to 16 or 38 to 41 or 72 to 76 or 152 to 156 or 157 to 158, or a sequence having at least 60%, 65%, 70%, 75%, 80%, 85%, 90%, 91%, 92%, 93%, 94%, 95%, 96%, 97%, 98%, 99% or more sequence identity over the whole length of the respective nucleic acid sequence of SEQ ID NOs: 13, 14, 38, 39, 72, 73, 74, 75, 76, 157, or 158 or a sequence having at least 90%, 91%, 92%, 93%, 94%, 95%, 96%, 97%, 98%, or 99% identity over the whole length of the respective amino acid sequence of SEQ ID NOs: 15, 16, 40, 41, 152, 153, 154, 155, or 156, respectively.

In another embodiment there is provided a plant delivery system, wherein the at least one Cpf1 enzyme, or an active fragment thereof, or a nucleic acid sequence encoding the same, comprises at least one mutation in comparison to a wild-type sequence resulting in an altered PAM recognition, preferably wherein the at least mutation is selected from G532R/K595R, or G532R/K538V/Y542R in comparison to the sequence of SEQ ID NO: 16.

In still another embodiment there is provided a plant delivery system, wherein the at least one Cpf1 enzyme, or an active fragment thereof, or a nucleic acid sequence encoding the same, comprises at least one mutation in comparison to a wild-type sequence (SEQ ID NO: 16) resulting in an altered PAM recognition, wherein the altered PAM recognition is a recognition of a TYCV, or of a TATV PAM sequence.

In one embodiment there is provided a plant delivery system, wherein the at least one Cpf1 enzyme or an active fragment thereof, or a nucleic acid sequence encoding the same, and/or the at least one Cpf1 guide RNA system, or a nucleic acid sequence encoding the same, are provided as at least one vector construct, or are provided as at least one linear construct.

In a further embodiment there is provided a plant delivery system, wherein the at least one Cpf1 guide RNA system comprises at least two guide RNAs, wherein the at least two guide RNAs are separated by a nucleotide sequence comprising direct repeats.

In yet a further embodiment there is provided a plant delivery system, wherein the sequence encoding a frame sequence is selected from a translatable or non-translatable sequence being selected from a marker gene, including an antibiotic marker or a fluorescent marker, a gene encoding a structural protein, a gene encoding an RNA species, an internal ribosomal entry site (IRES) encoding sequence.

In another embodiment there is provided a plant delivery system, wherein the sequence encoding a frame sequence is selected from any one of SEQ ID NOs: 31, 32, 13, 14, 38, 39, 72, 73, 74, 75, 76, 157, or 158, or a sequence having at least 85%, 86%, 87%, 88%, 89%, 90%, 91%, 92%, 93%, 94%, 95%, 96%, 97%, 98%, or 99% identity over the whole length of the respective sequence of SEQ ID NOs: 31, 32, 13, 14, 38, 39, 72, 73, 74, 75, 76, 157, or 158.

In still another embodiment there is provided a plant delivery system, wherein the part of a plant is selected from the group consisting of a plant cell, a plant tissue and a plant organ. leaves, stems, roots, emerged radicles, flowers, flower parts, petals, fruits, pollen, pollen tubes, anther filaments, ovules, embryo sacs, egg cells, ovaries, zygotes, embryos, zygotic embryos, somatic embryos, apical meristems, vascular bundles, pericycles, seeds, roots, gametophytes, spores and cuttings.

In one embodiment there is provided a plant delivery system, wherein the plant or part of a plant originates from a genus selected from the group consisting of Hordeum,

*Sorghum, Saccharum, Zea, Setaria, Oryza, Triticum, Secale, Triticale, Malus, Brachypodium, Aegilops, Daucus, Beta, Eucalyptus, Nicotiana, Solanum, Coffea, Vitis, Erythrante, Genlisea, Cucumis, Marus, Arabidopsis, Crucihimalaya, Cardamine, Lepidium, Capsella, Olmarabidopsis, Arabis, Brassica, Eruca, Raphanus, Citrus, Jatropha, Populus, Medicago, Cicer, Cajanus, Phaseolus, Glycine, Gossypium, Astragalus, Lotus, Torenia, Allium,* or *Helianthus.* More preferably, the plant or part of a plant originates from a species selected from the group consisting of *Hordeum vulgare, Hordeum bulbusom, Sorghum bicolor, Saccharum officinarium, Zea* spp., including *Zea mays, Setaria italica, Oryza minuta, Oryza sativa, Oryza australiensis, Oryza alta, Triticum aestivum, Triticum durum, Secale cereale, Triticale, Malus domestica, Brachypodium distachyon, Hordeum marinum, Aegilops tauschii, Daucus glochidiatus, Beta* spp., including *Beta vulgaris, Daucus pusillus, Daucus muricatus, Daucus carota, Eucalyptus grandis, Nicotiana sylvestris, Nicotiana tomentosiformis, Nicotiana tabacum, Nicotiana benthamiana, Solanum lycopersicum, Solanum tuberosum, Coffea canephora, Vitis vinifera, Erythrante guttata, Genlisea aurea, Cucumis sativus, Marus notabilis, Arabidopsis arenosa, Arabidopsis lyrata, Arabidopsis thaliana, Crucihimalaya himalaica, Crucihimalaya wallichii, Cardamine nexuosa, Lepidium virginicum, Capsella bursa pastoris, Olmarabidopsis pumila, Arabis hirsute, Brassica napus, Brassica oleracea, Brassica rapa, Raphanus sativus, Brassica juncacea, Brassica nigra, Eruca vesicaria* subsp. *sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanifolius, Cajanus scarabaeoides, Phaseolus vulgaris, Glycine max, Gossypium* sp., *Astragalus sinicus, Lotus japonicas, Torenia foumieri, Allium cepa, Allium fistulosum, Allium sativum, Helianthus annuus, Helianthus tuberosus* and/or *Allium tuberosum.* Particularly preferred are *Beta vulgaris, Zea mays, Triticum aestivum, Hordeum vulgare, Secale cereale, Helianthus annuus, Solanum tuberosum, Sorghum bicolor, Brassica rapa, Brassica napus, Brassica juncacea, Brassica oleracea, Raphanus sativus, Oryza sativa, Glycine max,* and/or *Gossypium* sp.

In another aspect there is provided a host cell comprising a plant delivery system of the various aspects and embodiments disclosed herein.

In a further aspect there is provided a plant, or a plant cell, tissue, organ or material, or a derivative or progeny thereof, comprising a plant delivery system of the various aspects and embodiments disclosed herein.

In one embodiment, there is provided a plant delivery system, wherein the genomic target sequence of interest is a difficult to access target site.

In yet a further aspect there is provided a method for modifying a genomic target sequence of interest in a plant or part of a plant, wherein the method comprises the steps of: (a) providing at least one Cpf1 enzyme or an active fragment thereof, or a nucleic acid sequence encoding the same; preferably, wherein the at least one nucleic acid sequence encoding the Cpf1 enzyme or an active fragment thereof is codon-optimized for the expression in the plant or part of the plant; and (b) providing at least one Cpf1 guide RNA system, or a nucleic acid sequence encoding the same, the at least one Cpf1 guide RNA system comprising at least one Cpf1 guide RNA specific for a genomic target sequence of interest in the plant or part of the plant; wherein the at least one Cpf1 guide RNA, or the nucleic acid sequence encoding the same, is (i) flanked by a Hammerhead ribozyme sequence at the 5' and a plant-derived Hepatitis Delta Virus (HDV)-like ribozyme sequence at the 3'-end; and/or is (ii) embedded within a non-coding region, preferably a 3' untranslated region (UTR), of a sequence encoding a frame sequence (c) optionally: providing at least one repair template nucleic acid sequence, wherein the at least one repair template nucleic acid sequence is preferably flanked by one or more homology sequence(s) complementary to one or both adjacent region(s) of the genomic sequence of interest in the plant or part of the plant; (d) introducing the at least one Cpf1 enzyme or an active fragment thereof, or a nucleic acid sequence encoding the same from step (a); and introducing the at least one Cpf1 guide RNA system, or a nucleic acid sequence encoding the same from step (b) and optionally: introducing the at least one repair template nucleic acid sequence from step (c) into the plant or part of the plant; and (e) obtaining a plant or part of a plant, or a progeny thereof, comprising a modification in the genomic target sequence of interest.

In one embodiment there is provided a method, wherein the at least one Cpf1 enzyme or an active fragment thereof, or a nucleic acid sequence encoding the same, and the at least one Cpf1 guide RNA system, or a nucleic acid sequence encoding the same, and optionally wherein the at least one repair template nucleic acid sequence, are provided on separate constructs, wherein the at least two separate constructs are introduced simultaneously, or subsequently.

In another embodiment there is provided a method, wherein the at least one Cpf1 enzyme or an active fragment thereof, or a nucleic acid sequence encoding the same, and the at least one Cpf1 guide RNA system, or a nucleic acid sequence encoding the same, are provided on a single transcript construct.

In still another embodiment there is provided a method, wherein the at least one Cpf1 enzyme or an active fragment thereof, or a nucleic acid sequence encoding the same, and the at least one Cpf1 guide RNA system, or a nucleic acid sequence encoding the same, are provided on a multiplexing construct.

In a further embodiment there is provided a method, wherein the molecules of step (a), (b) and optionally of step (c) are provided as plant delivery system as defined according to the first aspect of the present invention, wherein the plant delivery system comprises a first nucleotide molecule comprising a nucleic acid sequence encoding the at least one Cpf1 enzyme or an active fragment thereof, and a second nucleotide molecule comprising a nucleic acid sequence encoding the at least one Cpf1 guide RNA system, wherein the first and the second molecule are provided on separate constructs, or wherein the first and the second molecule are provided on a single transcript construct.

In one embodiment there is provided a method, wherein (i) the at least one nucleic acid sequence encoding the Cpf1 enzyme or an active fragment thereof, and the nucleic acid sequence encoding at least one Cpf1 guide RNA system; or (ii) wherein the first construct comprising the first nucleotide molecule and the second construct comprising the second nucleotide molecule, each comprise at least one promoter functional in a plant or part of a plant.

In another embodiment there is provided a method, wherein the at least one promoter is independently selected from a (p)BdUbi10 promoter (SEQ ID NO: 1), a (p)ZmUbi1 promoter (SEQ ID NO: 2), a (p)OsActin promoter (SEQ ID NO: 3), and a single or double 35S promoter (SEQ ID NO: 4), optionally including an ZmUbi1 intron, an BdUbi10 intron and/or an Adh1 intron, (SEQ ID NOs: 5 to 10, or 67), or any combination thereof, or a sequence having at least 90%, 91%, 92%, 93%, 94%, 95%, 96%, 97%, 98%, or 99% identity when compared over the whole length of the respective sequence of any one of SEQ ID NOs: 1 to 10, or 67.

In yet another embodiment there is provided a method, wherein (i) the at least one nucleic acid sequence encoding the Cpf1 enzyme or an active fragment thereof, and the nucleic acid sequence encoding at least one Cpf1 guide RNA system; or (ii) wherein the first construct comprising the first nucleotide molecule and the second construct comprising the second nucleotide molecule; comprise at least one terminator functional in a plant or part of a plant.

In still another embodiment there is provided a method, wherein the at least one terminator is independently selected from a NosT terminator (SEQ ID NO: 11), or a 35S terminator (SEQ ID NO: 12), or any combination thereof or a sequence having at least 90%, 91%, 92%, 93%, 94%, 95%, 96%, 97%, 98%, or 99% identity when compared over the whole length of the respective sequence of any one of SEQ ID NOs: 11 or 12.

In one embodiment there is provided a method, wherein the nucleic acid sequence encoding the Cpf1 enzyme or an active fragment thereof is codon-optimized for expression in a plant or part of a plant.

In another embodiment there is provided a method, wherein the nucleic acid sequence encoding the Cpf1 enzyme or an active fragment thereof is selected from SEQ ID NOs: 13, 14, 38, 39, 72, 73, 74, 75, 76, 157, or 158, or a sequence having at least 85%, 86%, 87%, 88%, 89%, 90%, 91%, 92%, 93%, 94%, 95%, 96%, 97%, 98%, or 99% identity over the whole length of the respective sequence of SEQ ID NOs: 13, 14, 38, 39, 72, 73, 74, 75, 76, 157, or 158.

In still another embodiment there is provided a method, wherein the Hammerhead ribozyme sequence, or a sequence encoding the same, is selected from SEQ ID NO: 17 or 18, and/or wherein the plant-derived Hepatitis Delta Virus (HDV)-like ribozyme sequence, or a sequence encoding the same, is selected from any one of SEQ ID NOs: 19 to 26, or a sequence having at least 95%, 96%, 97%, 98%, or 99% identity over the whole length of any one of SEQ ID NOs: 17 to 26.

In one embodiment there is provided a method, wherein the at least one Cpf1 guide RNA, or the nucleotide sequence encoding the same, which is (i) flanked by the Hammerhead ribozyme sequence at the 5' and the plant-derived Hepatitis Delta Virus (HDV)-like ribozyme sequence at the 3' end, further comprises a scaffold RNA sequence at the 5'-end; and/or which is (ii) embedded within the non-coding region, preferably the 3' untranslated region (UTR), of the sequence encoding a frame sequence, further comprises a scaffold RNA sequence at the 5' and 3'-end.

In another embodiment there is provided a method, wherein the scaffold RNA sequence, or a sequence encoding the same, is selected from SEQ ID NO: 29 or 30, or a sequence having at least 95%, 96%, 97%, 98%, or 99% identity over the whole length of SEQ ID NO: 29 or 30.

In yet another embodiment there is provided a method, wherein the at least one Cpf1 enzyme or an active fragment thereof, or a nucleic acid sequence encoding the same, is selected from any one of SEQ ID NOs: 13 to 16 or 38 to 41 or 72 to 76 or 152 to 156 or 157 to 158, or a sequence having at least 60%, 65%, 70%, 75%, 80%, 85%, 90%, 91%, 92%, 93%, 94%, 95%, 96%, 97%, 98%, 99% or more sequence identity over the whole length of the respective nucleic acid sequence of SEQ ID NOs: 13, 14, 38, 39, 72, 73, 74, 75, 76, 157, or 158, or a sequence having at least 90%, 91%, 92%, 93%, 94%, 95%, 96%, 97%, 98%, or 99% identity over the whole length of the respective amino acid sequence of SEQ ID NOs: 15, 16, 40, 41, 152, 153, 154, 155, or 156, respectively.

In another embodiment there is provided a method, wherein the at least one Cpf1 enzyme, or an active fragment thereof, or a nucleic acid sequence encoding the same, comprises at least one mutation in comparison to a wild-type sequence (SEQ ID NO: 16) resulting in an altered PAM recognition, preferably wherein the at least one mutation is selected from G532R/K595R, or G532R/K538V/Y542R in comparison to the sequence of SEQ ID NO: 16.

In one embodiment there is provided a method, wherein the at least one Cpf1 enzyme, or an active fragment thereof, or a nucleic acid sequence encoding the same, comprises at least one mutation in comparison to a wild-type sequence (SEQ ID NO: 16) resulting in an altered PAM recognition, wherein the altered PAM recognition is a recognition of a TYCV, or of a TATV PAM sequence.

In another embodiment there is provided a method, wherein the at least one Cpf1 enzyme or an active fragment thereof, or a nucleic acid sequence encoding the same, and/or the at least one Cpf1 guide RNA system, or a nucleic acid sequence encoding the same, are provided as at least one vector construct, or are provided as at least one linear construct.

In yet another embodiment there is provided a method, wherein the at least one Cpf1 guide RNA system comprises at least two guide RNAs, wherein the at least two guide RNAs are separated by a nucleotide sequence comprising direct repeats and wherein the at least two guide RNAs, or nucleotide sequences encoding the same, may each further comprise a scaffold RNA sequence at their 5'-ends.

In one embodiment there is provided a method, wherein the sequence encoding a frame sequence is selected from a translatable or non-translatable sequence being selected from a marker gene, including an antibiotic marker or a fluorescent marker, a gene encoding a structural protein, a gene encoding an RNA species, an IRES encoding sequence.

In a further embodiment there is provided a method, wherein the sequence encoding a frame sequence is selected from any one of SEQ ID NOs: 31, 32, 13, 14, 38, 39, 72, 73, 74, 75, 76, 157, or 158 or a sequence having at least 85%, 86%, 87%, 88%, 89%, 90%, 91%, 92%, 93%, 94%, 95%, 96%, 97%, 98%, or 99% identity over the whole length of the respective sequence of SEQ ID NOs: 31, 32, 13, 14, 38, 39, 152, 153, 154, 155, or 156.

In yet a further embodiment there is provided a method, wherein the part of a plant is selected from the group consisting of a plant cell, a plant tissue and a plant organ.

In one embodiment there is provided a method, wherein the plant or a part of a plant originates from a genus selected from the group consisting of *Hordeum, Sorghum, Saccharum, Zea, Setaria, Oryza, Triticum, Secale, Triticale, Malus, Brachypodium, Aegilops, Daucus, Beta, Eucalyptus, Nicotiana, Solanum, Coffea, Vitis, Erythrante, Genlisea, Cucumis, Marus, Arabidopsis, Crucihimalaya, Cardamine, Lepidium, Capsella, Olmarabidopsis, Arabis, Brassica, Eruca, Raphanus, Citrus, Jatropha, Populus, Medicago, Cicer, Cajanus, Phaseolus, Glycine, Gossypium, Astragalus, Lotus, Torenia, Allium,* or *Helianthus*. More preferably, the plant or part of a plant originates from a species selected from the group consisting of *Hordeum vulgare, Hordeum bulbusom, Sorghum bicolor, Saccharum officinarium, Zea* spp., including *Zea mays, Setaria italica, Oryza minuta, Oryza sativa, Oryza australiensis, Oryza alta, Triticum aestivum, Triticum durum, Secale cereale, Triticale, Malus domestica, Brachypodium distachyon, Hordeum marinum,*

*Aegilops tauschii, Daucus glochidiatus, Beta* spp., including *Beta vulgaris, Daucus pusillus, Daucus muricatus, Daucus carota, Eucalyptus grandis, Nicotiana sylvestris, Nicotiana tomentosiformis, Nicotiana tabacum, Nicotiana benthamiana, Solanum lycopersicum, Solanum tuberosum, Coffea canephora, Vitis vinifera, Erythrante guttata, Genlisea aurea, Cucumis sativus, Marus notabilis, Arabidopsis arenosa, Arabidopsis lyrata, Arabidopsis thaliana, Crucihimalaya himalaica, Crucihimalaya wallichii, Cardamine nexuosa, Lepidium virginicum, Capsella bursa pastoris, Olmarabidopsis pumila, Arabis hirsute, Brassica napus, Brassica oleracea, Brassica rapa, Raphanus sativus, Brassica juncacea, Brassica nigra, Eruca vesicaria* subsp. *sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanifolius, Cajanus scarabaeoides, Phaseolus vulgaris, Glycine max, Gossypium* sp., *Astragalus sinicus, Lotus japonicas, Torenia foumieri, Allium cepa, Allium fistulosum, Allium sativum, Helianthus annuus, Helianthus tuberosus* and/or *Allium tuberosum*. Particularly preferred are *Beta vulgaris, Zea mays, Triticum aestivum, Hordeum vulgare, Secale cereale, Helianthus annuus, Solanum tuberosum, Sorghum bicolor, Brassica rapa, Brassica napus, Brassica juncacea, Brassica oleracea, Raphanus sativus, Oryza sativa, Glycine max*, and/or *Gossypium* sp.

In a further embodiment there is provided a method, wherein the plant or part of the plant is a monocotyledonous plant, preferably *Zea mays*.

In another aspect, there is provided a plant or a part of a plant, or a progeny thereof, obtainable by a method as detailed above.

Further provided is a use of a plant delivery system as defined according to the first aspect of the present invention; or use of a Cpf1 enzyme or an active fragment thereof, or of a nucleic acid sequence encoding the same as defined according to the first aspect of the present invention; and/or a use of at least one guide RNA system, or the nucleic acid sequence encoding the same as defined according to the first aspect of the present invention; in a method of modifying a genomic target sequence of interest in a plant or part of a plant.

In one embodiment of the above use, there is provided a use, wherein the genomic target sequence of interest is a difficult to access target site.

Due to the fact that the present invention provides a variety of constructs to be combined with each other in a modular manner, the various embodiments as disclosed herein can be independently combined in the various aspects provided herein based on the disclosure provided herein.

Further aspects and embodiments of the present invention can be derived from the subsequent detailed description, the drawings, the sequence listing as well as the attached set of claims.

BRIEF DESCRIPTION OF THE DRAWINGS

FIG. 3 (FIGS. 3A and B) shows (FIG. 3A) exemplary LbCpf1 construct. On top, a schematic LbCpf1 construct and a ribozyme-flanked crRNA expression cassette, both under the control of an individual pZmUbi1 promoter and a NosT terminator is depicted. This construct can be provided as two separate expression constructs, as further disclosed below. In the middle, A LbCpf1 RR mutant variant is shown, i.e., the CRISPR nuclease expression construct (SEQ ID NO: 35). On the bottom.

FIG. 5 (FIGS. 5A and B) shows.

FIG. 6 (FIG. 6) shows an experiment for the testing of promoter strength to drive expression of RR or RVR version of LbCpf1. pZmUbi1 versus pBdUbi10 were tested in a targeted manner for driving nuclease expression and testing activity at same targets (cf. Table 1) for both constructs. For details, see Example 9 below.

FIG. 11 (FIGS. 11A, B and C): Sequencing of target loci through NGS shows LbCpf1 activity inducing InDels in the expected sequence context downstream from the PAM sequence (in bold). Sequences in (A) are targets of WT LbCpf1 which recognizes a TTTV PAM, while sequences in (B) and (C) are targets of the RR variant of LbCpf1 which recognizes a TYCV PAM sequence. FIG. 12 (FIGS. 12A, B, C and D): LbCpf1 activity demonstration in wheat protoplasts at the TaTDF target in the wheat genome. (A) Normalized INDELs percentage resulting from LbCpf1 activity across the three wheat genomes and 5 guides (crGEP52-56). (B-C-D) Sequence alignment resulting from NGS showing LbCpf1 activity at a single target site across the A genome (FIG. 12B), B genome (FIG. 12C) and D genome (FIG. 12D). Sequences shown in bold box are insertions at the target site.

FIG. 13 discloses SEQ ID NOS 160-162, respectively, in order of appearance.

FIG. 14 discloses SEQ ID NO: 163.

FIG. 20 (FIG. 20) shows INDELs activity of Cpf1 variants containing introns in the CDS vs. without introns in protoplast assay system at target crGEP5. The black bars represent raw indels from ddPCR based quantification and the white bars represent normalized scores to the transformation efficiency.

DEFINITIONS

Figures 1A, 1B:
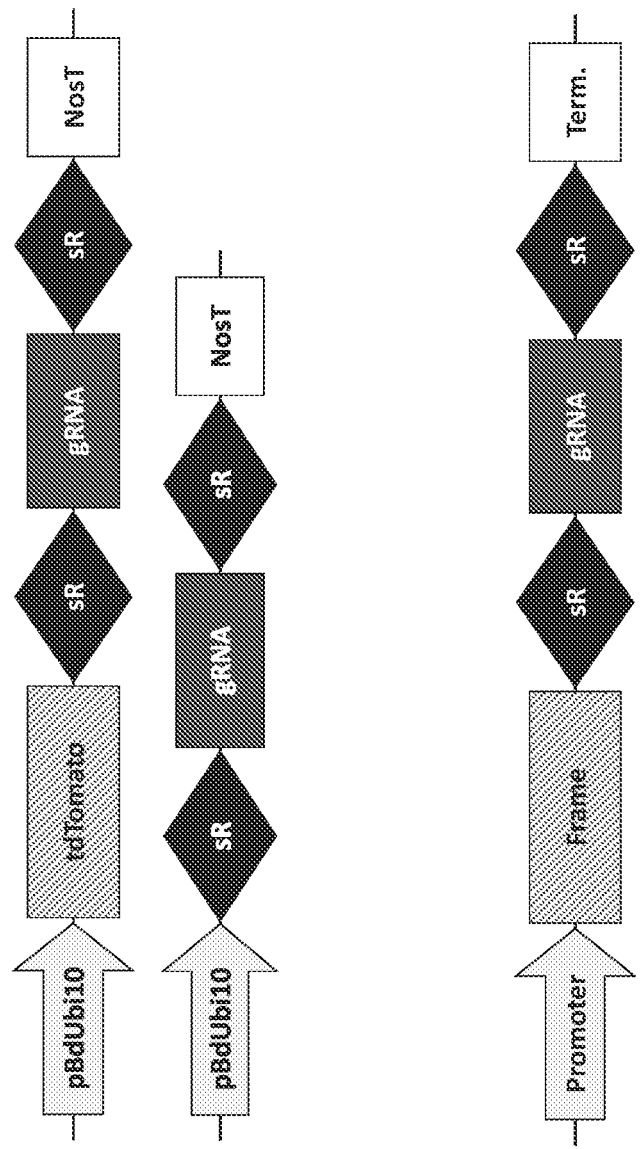
FIG. 1B shows a generic embedded RNA construct, wherein the frame sequence (frame) may be selected from any naturally occurring or artificial sequence that is transcribable when introduced into a target cell or cellular system of interest, which is long enough to guarantee that it can be properly transcribed by RNA polymerase II and/or recognized by a Cpf1 enzyme of interest. The construct further comprise a promoter and terminator (Term.) which are suitable for optimized expression in a target cell or cellular system of interest. The gRNA/crRNA is located between the scaffold RNA sequences (sR) which are required for proper recognition and processing of the gRNA/crRNA by a Cpf1 enzyme.

The terms "amino acid (sequence)", "polypeptide" and "protein" are used interchangeably herein for specifying an amino acid based structure linked by peptidic bonds. Usually, polypeptides comprising at least 100 amino acids are referred to as proteins, whereas smaller condensation products of amino acids, comprising two to around 100 amino acid building blocks, are denoted as "peptides".

The terms "associated with" or "in association with" according to the present disclosure are to be construed broadly and, therefore, according to present invention imply that a molecule (DNA, RNA, amino acid, comprising naturally occurring and/or synthetic building blocks) is provided in physical association with another molecule, the association being either of covalent or non-covalent nature. For example, a repair template can be associated with a gRNA of a CRISPR nuclease, wherein the association can be of non covalent nature (complementary base pairing), or the molecules can be physically attached to each other by a covalent bond.

The term "(catalytically) active fragment" as used herein referring to amino acid sequences denotes the core sequence derived from a given template amino acid sequence, or a nucleic acid sequence encoding the same, comprising all or part of the active site of the template sequence with the proviso that the resulting catalytically active fragment still possesses the activity characterizing the template sequence, for which the active site of the native enzyme or a variant thereof is responsible. Said modifications are suitable to generate less bulky amino acid sequences still having the same activity as a template sequence making the catalytically active fragment a more versatile or more stable tool being sterically less demanding.

A "covalent attachment" or "covalent bond" is an attachment that involves the sharing of electron pairs between atoms of the molecules or sequences covalently attached to each other. A "non-covalent" interaction differs from a covalent bond in that it does not involve the sharing of electrons, but rather involves more dispersed variations of electromagnetic interactions between molecules/sequences or within a molecule/sequence. Non-covalent interactions or attachments thus comprise electrostatic interactions, van der Waals forces, π-effects and hydrophobic effects. Of special importance in the context of nucleic acid molecules are hydrogen bonds as electrostatic interaction. A hydrogen bond (H-bond) is a specific type of dipole-dipole interaction that involves the interaction between a partially positive hydrogen atom and a highly electronegative, partially negative oxygen, nitrogen, sulfur, or fluorine atom not covalently bound to said hydrogen atom. Any "association" or "physical association" as used herein thus implies a covalent or non-covalent interaction or attachment. In the case of molecular complexes, e.g. a complex formed by a CRISPR nuclease, a gRNA and a RT, more covalent and non-covalent interactions can be present for linking and thus associating the different components of a molecular complex of interest.

The terms "CRISPR polypeptide", "CRISPR endonuclease", "CRISPR nuclease", "CRISPR protein", "CRISPR effector" or "CRISPR enzyme" are used interchangeably herein and refer to any naturally occurring or artificial amino acid sequence, or the nucleic acid sequence encoding the same, acting as site-specific DNA nuclease or nickase, wherein the "CRISPR polypeptide" is derived from a CRISPR system of any organism, which can be cloned and used for targeted genome engineering. The terms "CRISPR nuclease" or "CRISPR polypeptide" also comprise mutants or catalytically active fragments or fusions of a naturally occurring CRISPR effector sequences, or the respective sequences encoding the same. A "CRISPR nuclease" or "CRISPR polypeptide" may thus, for example, also refer to a CRISPR nickase or even a nuclease-deficient variant of a CRISPR polypeptide having endonucleolytic function in its natural environment. Preferably, the disclosure of the present invention relies on nuclease-deficient CRISPR nucleases, still possessing their inherent DNA recognition and binding properties assisted by a cognate CRISPR RNA.

Nucleic acid sequences disclosed herein can be "codon-optimized". "Codon optimization" implies that a DNA or RNA synthetically produced or isolated from a donor organism is adapted to the codon usage of different acceptor organism to improve transcription rates, mRNA processing and/or stability, and/or translation rates, and/or subsequent protein folding of said recombinant nucleic acid in the cell or organism of interest. The skilled person is well aware of the fact that a target nucleic acid can be modified at one position due to the codon degeneracy, whereas this modification will still lead to the same amino acid sequence at that position after translation, which is achieved by codon optimization to take into consideration the species-specific codon usage of a target cell or organism. In turn, nucleic acid sequences as defined herein may have a certain degree of identity to a different sequence, encoding the same protein, but having been codon optimized.

"Complementary" or "complementarity" as used herein describes the relationship between two (c) DNA, two RNA, or between an RNA and a (c) DNA nucleic acid region. Defined by the nucleobases of the DNA or RNA, two nucleic acid regions can hybridize to each other in accordance with the lock-and-key model. To this end the principles of Watson-Crick base pairing have the basis adenine and thymine/uracil as well as guanine and cytosine, respectively, as complementary bases apply. Furthermore, also non-Watson-Crick pairing, like reverse-Watson-Crick, Hoogsteen, reverse-Hoogsteen and Wobble pairing are comprised by the term "complementary" as used herein as long as the respective base pairs can build hydrogen bonding to each other, i.e. two different nucleic acid strands can hybridize to each other based on said complementarity.

The term "derivative" or "descendant" or "progeny" as used herein in the context of a eukaryotic cell, preferably a plant or plant cell or plant material according to the present disclosure relates to the descendants of such a cell or material which result from natural reproductive propagation including sexual and asexual propagation. It is well known to the person having skill in the art that said propagation can lead to the introduction of mutations into the genome of an organism resulting from natural phenomena which results in a descendant or progeny, which is genomically different to the parental organism or cell, however, still belongs to the same genus/species and possesses mostly the same characteristics as the parental recombinant host cell. Such derivatives or descendants or progeny resulting from natural phenomena during reproduction or regeneration are thus comprised by the term of the present disclosure and can be readily identified by the skilled person when comparing the "derivative" or "descendant" or "progeny" to the respective parent or ancestor.

Furthermore, the term "derivative", in the context of a chemical substance or nucleic acid or amino acid molecule and not referring to a replicating cell or organism, can imply a substance or molecule derived from or originating from the original substance or molecule by chemical and/or biotechnological means, or natural phenomena, like naturally occurring mutations. The resulting derivative will have characteristics allowing the skilled person to clearly define the original or parent molecule the derivative stems from. Furthermore, the derivative might have additional or varying biological functionalities, still a derivative or an "active fragment" of an original molecule will still share at least one biological function of the parent molecule, even though the derivative or active fragment might be shorter/longer than the parent sequence and might comprise certain mutations, deletions or insertions in comparison to the respective parent sequence. A "derivative" in the chemical sense will thus imply a compound that is derived from a similar compound by a chemical reaction. For biomolecules, the term implies that the derivative is not an arbitrary combination of any nucleic acid or amino acid sequence, but the derivative shows a significant degree of identity to the parent sequence when comparing a contiguous stretch of the derivative to a contiguous stretch of the parent sequence.

A "eukaryotic cell" as used herein refers to a cell having a true nucleus, a nuclear membrane and organelles belonging to any one of the kingdoms of Protista, Plantae, Fungi, or Animalia. Eukaryotic organisms can comprise monocellular and multicellular organisms. Preferred eukaryotic cells and organisms according to the present invention are plant cells (see below).

As used herein, "fusion" can refer to a protein and/or nucleic acid sequence, or a domain and/or part thereof, comprising one or more non-native sequences (e.g., moieties) covalently or non-covalently associated with each other to artificially create a fusion molecule. A fusion molecule can comprise different building blocks including nucleic acid sequences (DNA and/or RNA), amino acid sequences and/or non-naturally occurring sequences.

"Functional" in the context of a construct or sequence as disclosed herein implies that a construct comprises at least one coding sequence encoding a RNA or protein sequence as well as further sequences, including, for example regulatory sequences, including promoters and terminators, optimized for a cell or cellular system of interest, or including sequences encoding localization sequences for proper targeting of at least one coding sequence to a subcellular compartment of interest, wherein the thus assembled construct covalently and operably liked together results in the transcription and/or translation of the at least one coding sequence in a cell or cellular system of interest.

Any nucleic acid sequence or amino acid sequence according to the present invention can thus be provided in the form of a fusion molecule by, for example, artificially combining moieties, per se occurring or not occurring in nature, to form a new molecule of at least two molecular building blocks. A fusion can be attached to the N-terminal or C-terminal end of the modified nucleic acid sequence or protein, respectively, or both, or within the molecule as separate domain. For nucleic acid molecules, the fusion molecule can be attached at the 5' or 3'-end, or at any suitable position in between. A fusion can be a transcriptional and/or translational fusion. A fusion can comprise one or more of the same non-native sequences. A fusion can comprise one 10 or more of different non-native sequences. A fusion can be a chimera. A fusion can comprise a nucleic acid affinity tag. A fusion can comprise a barcode. A fusion can comprise a peptide affinity tag. A fusion can provide for subcellular localization of the at least one synthetic transcription factor as disclosed herein (e.g., a nuclear localization signal (NLS) for targeting (e.g., a site-specific nuclease) to the nucleus, a mitochondrial localization signal for targeting to the mitochondria, a chloroplast localization signal for targeting to a chloroplast, an endoplasmic reticulum (ER) retention signal, and the like).

Further, a "fusion" can result in a "promoter swap" and/or a "terminator swap", i.e., the exchange of at least one promoter/terminator against another promoter/terminator to identify the best regulatory sequence of a fusion construct of interest for being functional in a cell or organism of interest.

A fusion can provide a non-native sequence (e.g., affinity tag) that can be used to track or purify. A fusion can be a small molecule such as biotin or a dye such as alexa fluor dyes, Cyanine3 dye, Cyanine5 dye. The fusion can provide for increased or decreased stability. In some embodiments, a fusion can comprise a detectable label, including a moiety that can provide a detectable signal. Suitable detectable labels and/or moieties that can provide a detectable signal can include, but are not limited to, an enzyme, a radioisotope, a member of a specific binding pair; a fluorophore; a fluorescent reporter or fluorescent protein; a quantum dot;

and the like. A fusion can comprise a member of a FRET pair, or a fluorophore/quantum dot donor/acceptor pair. A fusion can comprise an enzyme. Suitable enzymes can include, but are not limited to, horse radish peroxidase, luciferase, beta-25 galactosidase, and the like. A fusion can comprise a fluorescent protein. Suitable fluorescent proteins can include, but are not limited to, a green fluorescent protein (GFP), (e.g., a GFP from *Aequoria victoria*, fluorescent proteins from *Anguilla japonica*, or a mutant or derivative thereof), a red fluorescent protein, a yellow fluorescent protein, a yellow-green fluorescent protein (e.g., mNeonGreen derived from a tetrameric fluorescent protein from the cephalochordate *Branchiostoma lanceolatum*) any of a variety of fluorescent and colored proteins. A fusion can comprise a nanoparticle. Suitable nanoparticles can include fluorescent or luminescent nanoparticles, and magnetic nanoparticles, or nanodiamonds, optionally linked to a nanoparticle. Any optical or magnetic property or characteristic of the nanoparticle(s) can be detected. A fusion can comprise a helicase, a nuclease (e.g., FokI), an endonuclease, an exonuclease (e.g., a 5' exonuclease and/or 3' exonuclease), a ligase, a nickase, a nuclease-helicase (e.g., Cas3), a DNA methyltransferase (e.g., Dam), or DNA demethylase, a histone methyltransferase, a histone demethylase, an acetylase (including for example and not limitation, a histone acetylase), a deacetylase (including for example and not limitation, a histone deacetylase), a phosphatase, a kinase, a transcription (co-) activator, a transcription (co-) factor, an RNA polymerase subunit, a transcription repressor, a DNA binding protein, a DNA structuring protein, a long noncoding RNA, a DNA repair protein (e.g., a protein involved in repair of either single- and/or double-stranded breaks, e.g., proteins involved in base excision repair, nucleotide excision repair, mismatch repair, NHEJ, HR, microhomology-mediated end joining (MMEJ), and/or alternative non-homologous end-joining (ANHEJ), such as for example and not limitation, HR regulators and HR complex assembly signals), a marker protein, a reporter protein, a fluorescent protein, a ligand binding protein (e.g., mCherry or a heavy metal binding protein), a signal peptide (e.g., Tat-signal sequence), a targeting protein or peptide, a subcellular localization sequence (e.g., nuclear localization sequence, a chloroplast localization sequence), and/or an antibody epitope, or any combination thereof.

A "gene" as used herein refers to a DNA region encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

The term "gene expression" or "expression" as used herein refers to the conversion of the information, contained in a gene, into a "gene product". A "gene product" can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

The term "gene activation" or "augmentation/augmenting/activating/upregulating (of) gene expression" refer to any process which results in an increase in production of a gene product. A gene product can be either RNA (including, but not limited to, mRNA, rRNA, tRNA, and structural RNA) or a protein. Accordingly, gene activation includes those processes which increase transcription of a gene and/or translation of an mRNA. Examples of gene activation processes which increase transcription include, but are not limited to, those which facilitate formation of a transcription initiation complex, those which increase transcription initiation rate, those which increase transcription elongation rate, those which increase processivity of transcription and those which relieve transcriptional repression (by, for example, blocking the binding of a transcriptional repressor). Gene activation can constitute, for example, inhibition of repression as well as stimulation of expression above an existing level. Examples of gene activation processes which increase translation include those which increase translational initiation, those which increase translational elongation and those which increase mRNA stability. In general, gene activation comprises any detectable increase in the production of a gene product, preferably an increase in production of a gene product by about 2-fold, more preferably from about 2- to about 5-fold or any integral value therebetween, more preferably between about 5- and about 10-fold or any integral value therebetween, more preferably between about 10- and about 20-fold or any integral value therebetween, still more preferably between about 20- and about 50-fold or any integral value therebetween, more preferably between about 50- and about 100-fold or any integral value therebetween, more preferably 100-fold or more.

In contrast, the terms "gene repression" or "inhibition/inhibiting/repressing/downregulating (of) gene expression" refer to any process which results in a decrease in production of a gene product. A gene product can be either RNA (including, but not limited to, mRNA, rRNA, tRNA, and structural RNA) or protein. Accordingly, gene repression includes those processes which decrease transcription of a gene and/or translation of a mRNA. Examples of gene repression processes which decrease transcription include, but are not limited to, those which inhibit formation of a transcription initiation complex, those which decrease transcription initiation rate, those which decrease transcription elongation rate, those which decrease processivity of transcription and those which antagonize transcriptional activation (by, for example, blocking the binding of a transcriptional activator). Gene repression can constitute, for example, prevention of activation as well as inhibition of expression below an existing level. Examples of gene repression processes which decrease translation include those which decrease translational initiation, those which decrease translational elongation and those which decrease mRNA stability. Transcriptional repression includes both reversible and irreversible inactivation of gene transcription. In general, gene repression comprises any detectable decrease in the production of a gene product, preferably a decrease in production of a gene product by about 2-fold, more preferably from about 2- to about 5-fold or any integral value therebetween, more preferably between about 5- and about 10-fold or any integral value therebetween, more preferably between about 10- and about 20-fold or any integral value therebetween, still more preferably between about 20- and about 50-fold or any integral value therebetween, more preferably between about 50- and about 100 fold or any integral value therebetween, more preferably 100-fold or more. Most preferably, gene repression results in complete inhibition of gene expression, such that no gene product is detectable.

The terms "genetic construct" or "recombinant construct", "vector", or "plasmid (vector)" (e.g., in the context of at least one nucleic acid sequence to be introduced into a cellular system) are used herein to refer to a construct comprising, inter alia, plasmids or (plasmid) vectors, cosmids, artificial yeast- or bacterial artificial chromosomes (YACs and BACs), phagemides, bacterial phage based vectors, an expression cassette, isolated single-stranded or double-stranded nucleic acid sequences, comprising DNA and RNA sequences in linear or circular form, or amino acid sequences, viral vectors, including modified viruses, and a combination or a mixture thereof, for introduction or transformation, transfection or transduction into any prokaryotic or eukaryotic target cell, including a plant, plant cell, tissue, organ or material according to the present disclosure. The construct or vector can thus have a circular, or a linear architecture.

"Recombinant" in the context of a biological material, e.g., a cell or vector, thus implies an artificially produced material comprising at least one human intervention in vitro. A recombinant construct according to the present disclosure can comprise an effector domain, either in the form of a nucleic acid or an amino acid sequence, wherein an effector domain represents a molecule, which can exert an effect in a target cell and includes a transgene, an single-stranded or double-stranded RNA molecule, including a guide RNA ((s)gRNA), a miRNA or an siRNA, or an amino acid sequences, including, inter alia, an enzyme or a catalytically active fragment thereof, a binding protein, an antibody, a transcription factor, a nuclease, preferably a site specific nuclease, and the like. Furthermore, the recombinant construct can comprise regulatory sequences and/or localization sequences. The recombinant construct can be integrated into a vector, including a plasmid vector, and/or it can be present isolated from a vector structure, for example, in the form of a polypeptide sequence or as a non-vector connected single-stranded or double-stranded nucleic acid. After its introduction, e.g. by transformation or transfection by biological or physical means, the genetic construct can either persist extrachromosomally, i.e. non integrated into the genome of the target cell, for example in the form of a double-stranded or single-stranded DNA, a double-stranded or single-stranded RNA or as an amino acid sequence. Alternatively, the genetic construct, or parts thereof, according to the present disclosure can be stably integrated into the genome of a target cell, including the nuclear genome or further genetic elements of a target cell, including the genome of plastids like mitochondria or chloroplasts. The term plasmid vector as used in this connection refers to a genetic construct originally obtained from a plasmid. A plasmid usually refers to a circular autonomously replicating extrachromosomal element in the form of a double-stranded nucleic acid sequence. In the field of genetic engineering these plasmids are routinely subjected to targeted modifications by inserting, for example, genes encoding a resistance against an antibiotic or an herbicide, a gene encoding a target nucleic acid sequence, a localization sequence, a regulatory sequence, a tag sequence, a marker gene, including an antibiotic marker or a fluorescent marker, a sequence, optionally encoding, a readily identifiable and the like. The structural components of the original plasmid, like the origin of replication, are maintained. According to certain embodiments of the present invention, the localization sequence can comprise a nuclear localization sequence (NLS), a plastid localization sequence, preferably a mitochondrion localization sequence or a chloroplast localization sequence. Said localization sequences are available to the skilled person in the field of plant biotechnology. A variety of plasmid vectors for use in different target cells of interest is commercially available and the modification thereof is known to the skilled person in the respective field.

A "genome" as used herein includes both the genes (the coding regions), the non-coding DNA and, if present, the genetic material of the mitochondria and/or chloroplasts, or the genomic material encoding a virus, or part of a virus. The "genome" or "genetic material" of an organism usually consists of DNA, wherein the genome of a virus may consist of RNA (single-stranded or double-stranded).

The terms "genome editing", "gene editing", "GE" and "genome engineering" are used interchangeably herein and refer to strategies and techniques for the targeted, specific modification of any genetic information or genome of a living organism at at least one position. As such, the terms comprise gene editing, but also the editing of regions other than gene encoding regions of a genome. It further comprises the editing or engineering of the nuclear (if present) as well as other genetic information of a cell. Furthermore, the terms "genome editing" and "genome engineering" also comprise an epigenetic editing or engineering, i.e. the targeted modification of, e.g. methylation, histone modification or of non-coding RNAs possibly causing heritable changes in gene expression.

The terms "guide RNA", "gRNA", "CRISPR nucleic acid sequence", "single guide RNA", or "sgRNA" are used interchangeably herein and either refer to a synthetic fusion of a CRISPR RNA (crRNA) and a trans-activating crRNA (tracrRNA), or the term refers to a single RNA molecule consisting only of a crRNA and/or a tracrRNA, or the term refers to a gRNA individually comprising a crRNA or a tracrRNA moiety. A tracr and a crRNA moiety, if present as required by the respective CRISPR polypeptide, thus do not necessarily have to be present on one covalently attached RNA molecule, yet they can also be comprised by two individual RNA molecules, which can associate or can be associated by non-covalent or covalent interaction to provide a gRNA according to the present disclosure. In the case of single RNA-guided endonucleases like Cpf1 (see Zetsche et al., 2015), for example, a crRNA as single guide nucleic acid sequence might be sufficient for mediating DNA targeting.

The term "hybridization" as used herein refers to the pairing of complementary nucleic acids, i.e., DNA and/or RNA, using any process by which a strand of nucleic acid joins with a complementary strand through base pairing to form a hybridized complex. Hybridization and the strength of hybridization (i.e., the strength of the association between the nucleic acids) is impacted by such factors as the degree and length of complementarity between the nucleic acids, stringency of the conditions involved, the Tm of the formed hybrid, and the G:C ratio within the nucleic acids. The term hybridized complex refers to a complex formed between two nucleic acid sequences by virtue of the formation of hydrogen bounds between complementary G and C bases and between complementary A and T/U bases. A hybridized complex or a corresponding hybrid construct can be formed between two DNA nucleic acid molecules, between two RNA nucleic acid molecules or between a DNA and an RNA nucleic acid molecule. For all constellations, the nucleic acid molecules can be naturally occurring nucleic acid molecules generated in vitro or in vivo and/or artificial or synthetic nucleic acid molecules. Hybridization as detailed above, e.g., Watson-Crick base pairs, which can form between DNA, RNA and DNA/RNA sequences, are dictated by a specific hydrogen bonding pattern, which thus represents a non-covalent attachment form according to the present invention. In the context of hybridization, the term "stringent hybridization conditions" should be understood to mean those conditions under which a hybridization takes place primarily only between homologous nucleic acid molecules. The term "hybridization conditions" in this respect refers not only to the actual conditions prevailing during actual agglomeration of the nucleic acids, but also to the conditions prevailing during the subsequent washing steps. Examples of stringent hybridization conditions are conditions under which primarily only those nucleic acid molecules that have at least 70%, preferably at least 75%, at least 80%, at least 85%, at least 90%, at least 91%, at least 92%, at least 93%, at least 94%, at least 95%, at least 96%, at least 97%, at least 98%, at least 99%, or at least 99.50% sequence identity undergo hybridization. Stringent hybridization conditions are, for example: 4×SSC at 65° C. and subsequent multiple washes in 0.1×SSC at 65° C. for approximately 1 hour. The term "stringent hybridization conditions" as used herein may also mean: hybridization at 68° C. in 0.25 M sodium phosphate, pH 7.2, 7% SDS, 1 mM EDTA and 1% BSA for 16 hours and subsequently washing twice with 2×SSC and 0.1% SDS at 68° C. Preferably, hybridization takes place under stringent conditions.

The term "indel" or "INDEL" as used herein means and insertion and/or deletion in the genome of an organism, or in the genomic material of a cell or cellular system of interest.

The terms "nucleotide" and "nucleic acid" with reference to a sequence or a molecule are used interchangeably herein and refer to a single- or double-stranded DNA or RNA of natural or synthetic origin. The term nucleotide sequence is thus used for any DNA or RNA sequence independent of its length, so that the term comprises any nucleotide sequence comprising at least one nucleotide, but also any kind of larger oligonucleotide or polynucleotide. The term(s) thus refer to natural and/or synthetic deoxyribonucleic acids (DNA) and/or ribonucleic acid (RNA) sequences, which can optionally comprise synthetic nucleic acid analoga. A nucleic acid according to the present disclosure can optionally be codon optimized. Codon optimization implies that the codon usage of a DNA or RNA is adapted to that of a cell or organism of interest to improve the transcription rate of said recombinant nucleic acid in the cell or organism of interest. The skilled person is well aware of the fact that a target nucleic acid can be modified at one position due to the codon degeneracy, whereas this modification will still lead to the same amino acid sequence at that position after translation, which is achieved by codon optimization to take into consideration the species-specific codon usage of a target cell or organism. Nucleic acid sequences according to the present application can carry specific codon optimization for the following non limiting list of organisms: *Hordeum vulgare, Hordeum bulbusom, Sorghum bicolor, Saccharum officinarium, Zea* spp., including *Zea mays, Setaria italica, Oryza minuta, Oryza sativa, Oryza australiensis, Oryza alta, Triticum aestivum, Triticum durum, Secale cereale, Triticale, Malus domestica, Brachypodium distachyon, Hordeum marinum, Aegilops tauschii, Daucus glochidiatus, Beta* spp., including *Beta vulgaris, Daucus pusillus, Daucus muricatus, Daucus carota, Eucalyptus grandis, Nicotiana sylvestris, Nicotiana tomentosiformis, Nicotiana tabacum, Nicotiana benthamiana, Solanum lycopersicum, Solanum tuberosum, Coffea canephora, Vitis vinifera, Erythrante guttata, Genlisea aurea, Cucumis sativus, Marus notabilis, Arabidopsis arenosa, Arabidopsis lyrata, Arabidopsis thaliana, Crucihimalaya himalaica, Crucihimalaya wallichii, Cardamine nexuosa, Lepidium virginicum, Capsella bursa pastoris, Olmarabidopsis pumila, Arabis hirsute, Brassica napus, Brassica oleracea, Brassica rapa, Raphanus sativus, Brassica juncacea, Brassica nigra, Eruca vesicaria* subsp. *sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanifolius, Cajanus scarabaeoides, Phaseolus vulgaris, Glycine max, Gossypium* sp., *Astragalus sinicus, Lotus japonicas, Torenia foumieri, Allium cepa, Allium fistulosum, Allium sativum, Helianthus annuus, Helianthus tuberosus* and/or *Allium tuberosum*. Particularly preferred are *Beta vulgaris, Zea mays, Triticum aestivum, Hordeum vulgare, Secale cereale, Helianthus annuus, Solanum tuberosum, Sorghum bicolor, Brassica rapa, Brassica napus, Brassica juncacea, Brassica oleracea, Raphanus sativus, Oryza sativa, Glycine max*, and/or *Gossypium* sp.

As used herein, "non-native", or "non-naturally occurring", or "artificial", or "synthetic" can refer to a nucleic acid or polypeptide sequence, or any other biomolecule like biotin or fluorescein that is not found in a native nucleic acid or protein. Non-native can refer to affinity tags. Non-native can refer to fusions. Non-native can refer to a naturally occurring nucleic acid or polypeptide sequence that comprises mutations, insertions and/or deletions. A non-native sequence may exhibit and/or encode for an activity (e.g., enzymatic activity, methyltransferase activity, acetyltransferase activity, kinase activity, ubiquitinating activity, etc.) that can also be exhibited by the nucleic acid and/or polypeptide sequence to which the non-native sequence is fused. A non-native nucleic acid or polypeptide sequence may be linked to a naturally-occurring nucleic acid or polypeptide sequence (or a variant thereof) by genetic engineering to generate a chimeric nucleic acid and/or polypeptide sequence encoding a chimeric nucleic acid and/or polypeptide. A non-native sequence can refer to a 3' hybridizing extension sequence, or a nucleas localization signal attached to a molecule. A "synthetic transcription factor" as used herein thus refers to a molecule comprising at least two domains, a recognition domain and an activation domain not naturally occurring in nature.

An "organism" as used herein refers to an individual eukaryotic life form, including a plant, part of a plant, plant organ, plant tissue or plant cell.

The term "particle bombardment" as used herein, also named "biolistic transfection" or "biolistic bombardment" or "microparticle-mediated gene transfer", refers to a physical delivery method for transferring a coated microparticle or nanoparticle comprising a nucleic acid or a genetic construct of interest into a target cell or tissue. The micro- or nanoparticle functions as projectile and is fired on the target structure of interest under high pressure using a suitable device, often called "gene-gun". The transformation via particle bombardment uses a microprojectile of metal covered with the gene of interest, which is then shot onto the target cells using an equipment known as "gene-gun" (Sandford et al. 1987) at high velocity fast enough to penetrate the cell wall of a target tissue, but not harsh enough to cause cell death. For protoplasts, which have their cell wall entirely removed, the conditions are different logically. The precipitated nucleic acid or the genetic construct on the at least one microprojectile is released into the cell after bombardment, and integrated into the genome or expressed transiently according to the definition given above. The acceleration of microprojectiles is accomplished by a high voltage electrical discharge or compressed gas (helium). Concerning the metal particles used it is mandatory that they are non-toxic, non-reactive, and that they have a smaller diameter than the target cell. The most commonly used are gold or tungsten. There is plenty of information publicly available from the manufacturers and providers of gene-guns and associated system concerning their general use.

The terms "plant" or "plant cell" as used herein refer to a plant organism, a plant organ, differentiated and undifferentiated plant tissues, plant cells, seeds, and derivatives and progeny thereof. Plant cells include without limitation, for example, cells from seeds, from mature and immature cells or organs, including embryos, meristematic tissues, seedlings, callus tissues in different differentiation states, leaves, flowers, roots, shoots, male or female gametophytes, sporophytes, pollen, pollen tubes and microspores, protoplasts, macroalgae and microalgae. The different eukaryotic cells, for example plant cells, can have any degree of ploidy, i.e. they may either be haploid, diploid, tetraploid, hexaploid or polyploid.

A "promoter" refers to a DNA sequence capable of controlling expression of a coding sequence, i.e., a gene or part thereof, or of a functional RNA, i.e. a RNA which is active without being translated, for example, a miRNA, a siRNA, an inverted repeat RNA or a hairpin forming RNA. A promoter is usually located at the 5' part of a gene. Promoter structures occur in all kingdoms of life, i.e., in bacteria, archaea, and eucaryots, where they have different architectures. The promoter sequence usually consists of proximal and distal elements in relation to the regulated sequence, the latter being often referred to as enhancers. Promoters can have a broad spectrum of activity, but they can also have tissue or developmental stage specific activity. For example, they can be active in cells of roots, seeds and meristematic cells, etc. A promoter can be active in a constitutive way, or it can be inducible. The induction can be stimulated by a variety of environmental conditions and stimuli. There exist strong promoters which can enable a high transcription of the regulated sequence, and weak promoters. Often promoters are highly regulated. A promoter of the present disclosure may include an endogenous promoter natively present in a cell, or an artificial or transgenic promoter, either from another species, or an artificial or chimeric promoter, i.e. a promoter that does not naturally occur in nature in this composition and is composed of different promoter elements. The process of transcription begins with the RNA polymerase (RNAP) binding to DNA in the promoter region, which is in the immediate vicinity of the transcription start site (TSS). A typical promoter sequence is thought to comprise some sequence motifs positioned at specific sites relative to the TSS. For example, a prokaryotic promoter is observed to have two hexameric motifs centered at or near −10 (Pribnow box) and −35 positions relative to the TSS. Furthermore, there can be an AT rich UP ("upstream") element upstream of the −35 region. Procaryotic promoters are recognized by sigma factors as transcription factors. The structure of eukaryotic promoters is generally more complex and they have several different sequence motifs, such as TATA box, INR box, BRE, CCAAT-box and GC-box (Bucher P., J. Mol. Biol. 1990 Apr. 20; 212(4):563-78.). Eukaryotic cells posses three RNAPs, RNA polymerase I, II, and III, respectively. RNAP I generates ribosomal RNA (rRNA), RNAP II generates messenger RNA (mRNA) and small nuclear RNA (snRNA), and RNAP III generates transfer RNA (tRNA), snRNA and 5S-RNA.

The term "regulatory sequence" as used herein refers to a nucleic acid or amino acid sequence, which can direct the transcription and/or translation and/or modification of a nucleic acid sequence of interest. Regulatory sequences can comprise sequences acting in cis or acting in trans. Exemplary regulatory sequences comprise promoters, enhancers, terminators, operators, transcription factors, transcription factor binding sites, introns and the like.

The term "terminator", as used herein, refers to DNA sequences located downstream, i.e. in 3' direction, of a coding sequence and can include a polyadenylation signal and other sequences, i.e. further sequences encoding regulatory signals that are capable of affecting mRNA processing and/or gene expression. The polyadenylation signal is usually characterized in that it adds poly-A-nucleotides at the 3'-end of an mRNA precursor.

The terms "transient" or "transient introduction" as used herein refer to the transient introduction of at least one nucleic acid and/or amino acid sequence according to the present disclosure, preferably incorporated into a delivery vector and/or into a recombinant construct, with or without the help of a delivery vector, into a target structure, for example, a plant cell or cellular system, wherein the at least one nucleic acid or nucleotide sequence is introduced under suitable reaction conditions so that no integration of the at least one nucleic acid sequence into the endogenous nucleic acid material of a target structure, the genome as a whole, occurs, so that the at least one nucleic acid sequence will not be integrated into the endogenous DNA of the target cell. As a consequence, in the case of transient introduction, the introduced genetic construct will not be inherited to a progeny of the target structure, for example a prokaryotic, an animal or a plant cell. The at least one nucleic acid and/or amino acid sequence or the products resulting from transcription, translation, processing, post-translational modifications or complex building thereof are only present temporarily, i.e., in a transient way, in constitutive or inducible form, and thus can only be active in the target cell for exerting their effect for a limited time. Therefore, the at least one sequence introduced via transient introduction will not be heritable to the progeny of a cell. The effect mediated by at least one sequence or effector introduced in a transient way can, however, potentially be inherited to the progeny of the target cell. A "stable" introduction therefore implies the integration of a nucleic acid or nucleotide sequence into the genome of a target cell or cellular system of interest, wherein the genome comprises the nuclease genome as well as the genome comprised by further organelles.

The term "variant(s)" as used herein in the context of amino acid or nucleic acid sequences is intended to mean substantially similar sequences. For nucleic acid sequences, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For nucleic acid sequences, conservative variants include those sequences that, because of the degeneracy of the genetic code, encode the same amino acid sequence as a reference sequence of the present disclosure. A variant of a given nucleic acid sequence will thus also include synthetically derived nucleic acid sequences, such as those generated, for example, by using site-directed mutagenesis but which still encode the same protein as the reference sequence. Generally, variants of a particular polynucleotide of the disclosure will have at least about 60%, 65%, 70%, 75%, 80%, 85%, 90%, 91%, 92%, 93%, 94%, 95%, 96%, 97%, 98%, 99% or more sequence identity to that particular nucleic acid sequence has determined by sequence alignment programs and parameters described further below under this section. Notably, two sequences being a parent and a variant will be compared over their whole length of contiguous sequences.

Whenever the present disclosure relates to the percentage of identity of nucleic acid or amino acid sequences to each other these values define those values as obtained by using the EMBOSS Water Pairwise Sequence Alignments (nucleotide) programme (www.ebi.ac.uk/Tools/psa/emboss_water/nucleotide.html) nucleic acids or the EMBOSS Water Pairwise Sequence Alignments (protein) programme (www.ebi.ac.uk/Tools/psa/emboss_water/) for amino acid sequences. Alignments or sequence comparisons as used herein refer to an alignment over the whole length of two sequences compared to each other. Those tools provided by the European Molecular Biology Laboratory (EMBL) European Bioinformatics Institute (EBI) for local sequence alignments use a modified Smith-Waterman algorithm (see www.ebi.ac.uk/Tools/psa/ and Smith, T. F. & Waterman, M. S. "Identification of common molecular subsequences" *Journal of Molecular Biology*, 1981 147 (1):195-197). When conducting an alignment, the default parameters defined by the EMBL-EBI are used. Those parameters are (i) for amino acid sequences: Matrix=BLOSUM62, gap open penalty=10 and gap extend penalty=0.5 or (ii) for nucleic acid sequences: Matrix=DNAfull, gap open penalty=10 and gap extend penalty=0.5. The skilled person is well aware of the fact that, for example, a sequence encoding a protein can be "codon-optimized" if the respective sequence is to be used in another organism in comparison to the original organism a molecule originates from.

Whenever the present invention discloses vector plasmid sequences as disclosed in the attached sequence listing, the skilled person can easily visualize and analyze the relevant sequences by using software for visualizing sequences like DNA plasmid sequences, e.g., SnapGene Viewer (www.snapgene.com/products/snapgene_viewer/) and further to identify restriction enzyme sites, primers and individual sub-elements of a plasmid sequence, including promoter sequences, nuclear localization sequences, terminator sequences, selection marker encoding sequences and coding sequences, etc.

DETAILED DESCRIPTION

The skilled person will understand that the herein described aspects and embodiments of the present invention are not limited to the specific context in which they are disclosed but may rather be combined with other aspects and embodiments disclosed throughout the present specification independently from their context.

The present invention provides several individual aspects to be modulated to establish and improve the efficiency of CRISPR/Cpf1 system in plants or plant cells; in particular in monocots, e.g., corn (e.g. *Zea mays*).

In a first aspect, there is provided a plant delivery system, wherein the delivery system may comprise (a) at least one Cpf1 enzyme or an active fragment thereof, or a nucleic acid sequence encoding the same; and (b) at least one Cpf1 guide RNA system, or a nucleic acid sequence encoding the same, the at least one Cpf1 guide RNA system comprising at least one Cpf1 guide RNA specific for a genomic target sequence of interest in a plant or part of a plant; wherein the at least one Cpf1 guide RNA, or the nucleic acid sequence encoding the same, is (i) flanked by a Hammerhead ribozyme sequence at the 5' end and by a plant-derived Hepatitis Delta Virus (HDV)-like ribozyme sequence at the 3'-end; and/or is (ii) embedded within a non-coding region, preferably a 3' untranslated region (UTR), of a sequence encoding a frame sequence.

In one embodiment according to the various aspects of the present disclosure, the plant delivery system may comprise a first nucleotide molecule comprising a nucleic acid sequence encoding the at least one Cpf1 enzyme or an active fragment thereof, and a second nucleotide molecule comprising a nucleic acid sequence encoding the at least one Cpf1 guide RNA system, preferably wherein the first and the second molecule are provided on separate constructs, or wherein the first and the second molecule are provided on a single transcript construct. Therefore, as further detailed below, the constructs of the present invention will have a modular character. Separate constructs may have certain advantages by individually regulating the expression of the at least one Cpf1 enzyme or an active fragment thereof, and an individually provided properly regulated at least one Cpf1 guide RNA system. Single transcript units simultaneously providing the Cpf1 nuclease and the Cpf1 guide RNA system—both components under the control of individual regulatory sequences—may be preferred depending on the plant target cell or cellular system of interest. In one embodiment, the invention thus provides a single transcript CRISPR/Cpf1 system for efficient gene editing. Specifically, the invention provides the generation of a single mRNA transcript comprising a Cpf1 open reading frame at the 5' end followed by gRNA and a terminator sequence.

In one embodiment according to the various aspects of the present disclosure, the first construct comprising the first nucleotide molecule and the second construct comprising the second nucleotide molecule may each comprise at least one promoter functional in a plant or part of a plant, preferably wherein the at least one promoter driving expression of the first and the second nucleotide molecule is different in the first and the second construct, respectively. In another embodiment, the promoters may be the same. Choosing different promoters, as shown herein, might provide for an optimum performance of these regulatory sequences to provide the CRISPR components such expressed in a functional manner in an amount sufficient to allow successful genome editing (GE) outcomes.

A CRISPR system in its natural environment describes a molecular complex comprising at least one small and individual non-coding RNA in combination with a Cas nuclease or another CRISPR nuclease like a Cpf1 nuclease (Zetsche et al., 2015, supra) which can produce a specific DNA double-stranded break. Presently, CRISPR systems are categorized into 2 classes comprising five types of CRISPR systems, the type II system, for instance, using Cas9 as effector and the type V system using Cpf1 as effector molecule (Makarova et al., Nature Rev. Microbiol., 2015). In artificial CRISPR systems, a synthetic non-coding RNA and a CRISPR nuclease and/or optionally a modified CRISPR nuclease, modified to act as nickase or lacking any nuclease function, can be used in combination with at least one synthetic or artificial guide RNA or gRNA combining the function of a crRNA and/or a tracrRNA (Makarova et al., 2015, supra). The immune response mediated by CRISPR/Cas in natural systems requires CRISPR-RNA (crRNA), wherein the maturation of this guiding RNA, which controls the specific activation of the CRISPR nuclease, varies significantly between the various CRISPR systems which have been characterized so far. Firstly, the invading DNA, also known as a spacer, is integrated between two adjacent repeat regions at the proximal end of the CRISPR locus. Type II CRISPR systems, for example, can code for a Cas9 nuclease as key enzyme for the interference step, which system contains both a crRNA and also a trans-activating RNA (tracrRNA) as the guide motif. These hybridize and form double-stranded (ds) RNA regions which are recognized by RNAseIII and can be cleaved in order to form mature crRNAs. These then in turn associate with the Cas molecule in order to direct the nuclease specifically to the target nucleic acid region. Recombinant gRNA molecules can comprise both the variable DNA recognition region and also the Cas interaction region and thus can be specifically designed, independently of the specific target nucleic acid and the desired Cas nuclease. As a further safety mechanism, PAMs (protospacer adjacent motifs) must be present in the target nucleic acid region; these are DNA sequences which follow on directly from the Cas9/RNA complex-recognized DNA. The PAM sequence for the Cas9 from *Streptococcus pyogenes* has been described to be "NGG" or "NAG" (Standard IUPAC nucleotide code) (Jinek et al, "A programmable dual-RNA-guided DNA endonuclease in adaptive bacterial immunity", Science 2012, 337: 816-821). The PAM sequence for Cas9 from *Staphylococcus aureus* is "NNGRRT" or "NNGRR(N)". Further variant CRISPR/Cas9 systems are known. Thus, a *Neisseria meningitidis* Cas9 cleaves at the PAM sequence NNNNGATT. A *Streptococcus thermophilus* Cas9 cleaves at the PAM sequence NNAGAAW. Recently, a further PAM motif NNNNRYAC has been described for a CRISPR system of *Campylobacter* (WO 2016/021973 A1). For Cpf1 nucleases it has been described that the Cpf1-crRNA complex, without a tracrRNA, efficiently recognize and cleave target DNA proceeded by a short T-rich PAM in contrast to the commonly G-rich PAMs recognized by Cas9 systems (Zetsche et al., supra). Furthermore, by using modified CRISPR polypeptides, specific single-stranded breaks can be obtained. The combined use of Cas nickases with various recombinant gRNAs can also induce highly specific DNA double-stranded breaks by means of double DNA nicking. By using two gRNAs, moreover, the specificity of the DNA binding and thus the DNA cleavage can be optimized. Further CRISPR effectors like CasX and CasY effectors originally described for bacteria, are meanwhile available and represent further effectors, which can be used for genome engineering purposes (Burstein et al., "New CRISPR-Cas systems from uncultivated microbes", Nature, 2017, 542, 237-241).

Synthetic CRISPR systems consisting of two components, a guide RNA (gRNA) also called single guide RNA (sgRNA) and a non-specific CRISPR-associated endonuclease can be used to generate knock-out plant cells by co-expressing a gRNA specific to the gene to be targeted and capable of association with the cognate CRISPR endonuclease.

Despite the huge research efforts in the field of CRISPR for providing suitable genome editing (GE) tools, no plant-optimized system for highly efficient and reliable GE even for difficult to access target sites is available relying on a Cpf1 effector nuclease.

A "plant delivery system" as used herein thus means a vector construct, or at least two or a plurality of vector constructs suitable to introduce all effector components of a Cpf1-based CRISPR system optimized for GE in a plant cell or cellular system. A plant delivery system as provided herein thus provides a plant-optimized Cpf1 effector, preferably a LbCpf1 effector originating from *Lachnospiraceae bacterium*, preferably *Lachnospiraceae bacterium* ND2006, comprising an optimum sequence and individually tested regulatory sequences, including promoters and terminators, as well as a Cpf1 guide RNA system, or a nucleic acid sequence encoding the same, the at least one Cpf1 guide RNA system comprising at least one Cpf1 guide RNA, i.e., a guide RNA specific for the cognate Cpf1 effector, which Cpf1 guide RNA system can also comprise more than one gRNA to be suitable for multiplex targeting. Furthermore, the Cpf1 guide RNA system has an specific architecture either relying on a plant-derived Hepatitis Delta Virus (HDV)-like ribozyme and/or using an embedding technique, i.e., a construct design, wherein the at least one Cpf1 crRNA is placed within a non-coding region, preferably a 3' untranslated region (UTR), of a sequence encoding a frame sequence to guarantee optimum stability, transcription and thus efficient GE rates.

In one aspect, it was found that Cpf1 has certain features in comparison to Cas9 that make it advantageous for certain use cases, e.g., the editing in AT-rich genomes/regions, or single nucleotide polymorphism (SNP)-specific editing. All characterized genome editing nucleases before Cpf1 required at least one G in their PAMs. Cpf1's PAM is TTTN, so it broadens the range of genome editing experiments. This is particularly useful in AT-rich genomes, or regions, e.g. scaffold/matrix attachment regions. It may also be useful if a particular SNP is present that results in an AT-rich site, or for applications (e.g. chemically modified guides) where shorter RNA species are useful. Cpf1 only requires a crRNA to process crRNA arrays without needing tracrRNA. Cpf1-crRNA can cut target DNA without needing any other RNA types. Furthermore, the staggered cut introduced by Cpf1 may be advantageous for certain HDR-free knock-in strategies. Furthermore, an increased efficiency of HDR-based knock-ins may be achieved using Cpf1. Finally, Cpf1 cleaves its target DNA relatively far away from the PAM at the end of the protospacer, unlike Cas9. The indels caused by Cpf1 will therefore be located far from the target site. Cpf1 can continue cutting at the target site as a result, which may increase the chance that new DNA can be inserted at that site.

Still, many of this aspects have only been confirmed in an animal/mammalian system for selected Cpf1 species, wherein data for successful optimizations of a Cpf1 of interest together with specific crRNA tools used in combination with said optimized Cpf1 to achieve efficient GE by synergistically optimizing a Cpf1 and the cognate crRNA guide RNA system are not available for relevant crop plants, including *Zea mays*.

In one aspect of the present invention, there is thus provided an LbCpf1 enzyme or a catalytically active fragment thereof, or the nucleic acid sequence encoding the same, which sequence originates from *Lachnospiraceae bacterium* (Lb) and which has been optimized for the expression in corn. In one embodiment, the plant-optimized LbCpf1 sequence (comprising a 5' sequence encoding an enhancer and a SV40 NLS and a 3' sequence encoding a nucleoplasmin NLS) is SEQ ID NO: 13 or 15, or the core sequence is selected from SEQ ID NO: 14 or 16, or a sequence having at least 85%, 86%, 87%, 88%, 89%, 90%, 91%, 92%, 93%, 94%, 95%, 96%, 97%, 98%, or 99% identity over the whole length of the respective sequence of SEQ ID NOs: 13 to 16. A suitable expression construct for SEQ ID NO: 13 is provided with SEQ ID NO: 37.

Notably, the skilled person is well aware of the fact that certain regulatory elements and markers within SEQ ID NO: 37 may be replaced, or that the sequence encoding SEQ ID NO: 16 may be further truncated or modified within the scope of the present invention.

Notably, the nucleic acid sequence encoding LbCpf1 of SEQ ID NO: 13 has been specifically corn codon-optimized and further carries a 5'/N-terminal portion derived from eGFP (enhanced green fluorescent protein), a mass enhancer and a SV40 NLS as well as a 3' located nucleoplasmin NLS.

Figure 4A:
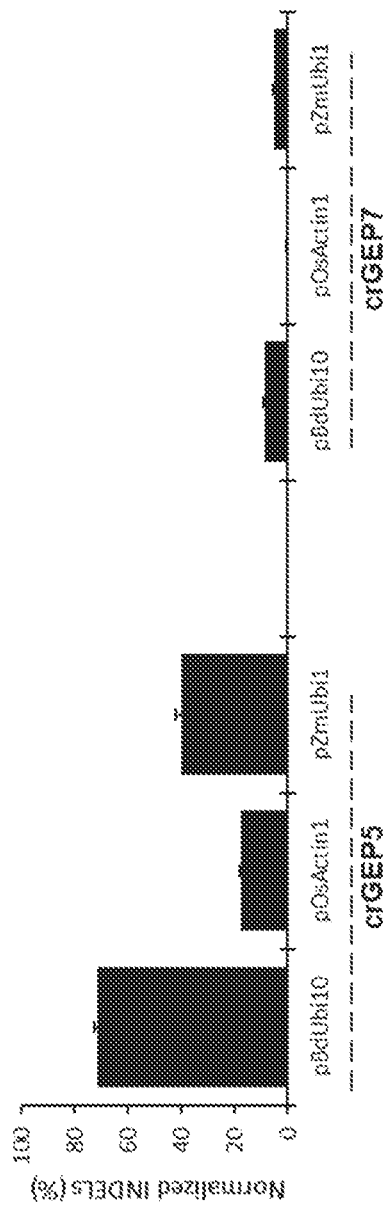
FIG. 4 (FIGS. 4A and B) shows promoter swaps on Cpf1 and crRNA modules to identify optimum expression strategies. Each bar represents the average of three replicates. Each graph represents the results of two experiments. In these optimization series (FIG. 4A) the promoter driving the LbCpf1 nuclease expression pZmUbi1, was replaced with pBdUbi10 or pOsActin1 and their activities were compared at two targets crGEP5 and crGEP7 (cf. Table 1). Clearly pBdUbi10 outperformed the control pZmUbi1 at target crGEP5 while there was no difference in activity at target crGEP7. In the bottom graph (FIG. 4B), the promoter, pZmUbi1 driving the guide RNA expression from the ribozyme construct was swapped for pBdUbi10 and pOsActin1 and their activities were compared at two targets crGEP5 and crGEP7. Clearly pZmUbi1 outperformed the other two at target crGEP5 while there was no difference in activity at target crGEP7. For details, see Example 7 below.

In one embodiment, the codon-optimized LbCpf1 construct sequence may comprise two NLS sequences on both its 5' and 3'-ends and is flanked by a BdUbi10 promoter sequence, or a ZmUbi1 promoter sequence and a Nos terminator (NosT) sequence as further disclosed herein separately in the functional construct (SEQ ID NO: 37). This novel codon optimized sequence has shown high indel activities at multiple target sites when delivered together with a guide RNA delivery construct according to the prior art and according to the present invention. This effect can be attributed to the specific structure of the LbCpf1 sequence of the present invention and the optimized translation context. Furthermore, as detailed in Example 7 and FIG. 4 it could be systematically shown that the choice of the promoter for the LbCpf1 construct for use in plants can play a significant role.

In a further embodiment, the codon-optimized LbCpf1 construct sequence may comprise an additional (Zm)Ubi1 intron sequence of SEQ ID NO: 5 or 10, or a sequence having at least 90%, 91%, 92%, 93%, 94%, 95%, 96%, 97%, 98%, or 99% identity when compared over the whole length of the respective sequence of any one of SEQ ID NO: 5 or 10, to enhance expression.

In yet a further embodiment, the functional LbCpf1 construct may comprise a different promoter and/or terminator sequence in comparison to SEQ ID NO: 37 as further disclosed herein, or as known to the skilled person.

In one embodiment of the present invention, the construct for expression of a plant optimized LbCpf1 may be a sequence of SEQ ID NO: 37, or a sequence comprising the LbCpf1 sequence of SEQ ID NO: 13 or 14, or a sequence having at least 85%, 86%, 87%, 88%, 89%, 90%, 91%, 92%, 93%, 94%, 95%, 96%, 97%, 98%, or 99% identity over the whole length of the respective sequence of SEQ ID NO: 13 or 14.

The LbCpf1 nuclease requires a TTTV PAM sequence motif for target site recognition which potentially limits its usage in GC rich genomic regions. Thus, a further aspect of the present invention relates to the combination of codon-optimized LbCpf1 with several relaxed PAM sequence variants of LbCpf1 in order to broaden LbCpf1 recognition of target sites. In particular, two versions of the PAM motif, namely the G532R/K595R (RR) version and the G532R/K538V/Y542R (RVR) version, which have been shown to be active in mammalian cells but so far not in plant cells (Gao et al. (2017) Nat Biotechnol, 35(8): 789-792), were used in the present invention to broaden target specificity of LbCpf1 in plant cells. These modifications result in alternative PAM recognition sequences, namely TYCV and TATV. The present invention provides evidence that the use of these alternative PAM variants increases the range of target site recognition across diverse sequence loci in plant genomes (see FIG. 3B).

In one embodiment of the present invention, the construct for expression of a plant optimized LbCpf1 may be a sequence of SEQ ID NOs: 35, 36, or a sequence comprising the LbCpf1 sequence of SEQ ID NOs: 38 or 39, or a sequence having at least 85%, 86%, 87%, 88%, 89%, 90%, 91%, 92%, 93%, 94%, 95%, 96%, 97%, 98%, or 99% identity over the whole length of the respective sequence of SEQ ID NOs: 38 or 39, or the respective protein sequence encoded.

Furthermore, this invention thus relates to the combined use of a plant-optimized LbCpf1 enzyme, or an active fragment thereof, or of an alternative RR and RVR LbCpf1 with a specific Cpf1 guide RNA system comprising a ribozyme delivery system comprising plant-derived HDV sequences, and/or embedded within a non-coding region, preferably a 3' untranslated region (UTR), of a sequence encoding a frame sequence. This approach produces high rates of indel generation activity at various genomic loci.

In preferred embodiments of the various aspects of the present invention, the nucleic acid sequence encoding the Cpf1 enzyme or an active fragment thereof may be codon-optimized for expression in a plant or part of a plant.

In certain embodiments of the various aspects of the present invention, the nucleic acid sequence encoding the Cpf1 enzyme or an active fragment thereof of a plant delivery system of the present invention may be selected from SEQ ID NOs: 13, 14, 38, 39, 72, 73, 74, 75, 76, 157, or 158, or a sequence having at least 85%, 86%, 87%, 88%, 89%, 90%, 91%, 92%, 93%, 94%, 95%, 96%, 97%, 98%, or 99% identity over the whole length of the respective sequence of SEQ ID NOs: 13, 14, 38, 39, 72, 73, 74, 75, 76, 157, or 158.

In one embodiment of the various aspects of the present invention, the at least one construct of a plant delivery system comprises a promoter, wherein the at least one promoter may be independently selected from a (p)BdUbi10 promoter (SEQ ID NO: 1), a (p)ZmUbi1 promoter (SEQ ID NO: 2), a (p)OsActin promoter (SEQ ID NO: 3), and a single or double 35S promoter (SEQ ID NO: 4), optionally including an ZmUbi1 intron, an BdUbi10 intron and/or an Adh1 intron, (SEQ ID NOs: 5 to 10, or 67), or any combination thereof, or a sequence having at least 90%, 91%, 92%, 93%, 94%, 95%, 96%, 97%, 98%, or 99% identity when compared over the whole length of the respective sequence of any one of SEQ ID NOs: 1 to 10, or 67. Bd means originating from *Brachypodium distachyon*, Zm means originating from *Zea mays*, Adh1 means originating from alcohol dehydrogenase-1, and Os means originating from *Oryza sativa*.

As further disclosed herein, the choice of the promoter and the choice of different promoters for individual constructs may be crucial to obtain optimized expression of the respective effector sequences encoded by the constructs, or the plant delivery system (cf. Example 7).

Therefore, the present invention also provides for promoter optimization for Cpf1 nuclease and ribozyme-mediated gRNA expression. In particular, the present invention relates to the fine-tuning of the expression of a Cpf1 nuclease and a ribozyme-mediated gRNA delivery system. The invention relates to the use of different promoter sequences at different genomic loci in order to improve CRISPR/Cpf1 expression. In certain embodiments, the invention pertains to the use of highly constitutive promoters such as pZmUbi1, pBdUbi10, pOsActin and p2×35S+Adh1 intron as disclosed herein to drive high levels of synchronous expression of both Cpf1 nuclease and gRNA in plant cells.

Other suitable promoters may be selected from pNOS, pEF1-alphae, ubiquitin promoters from monocotyledonous and dicotyledonous plants, or a tubulin promoter. The sequences of said promoters are known to the skilled person and can be individually tested for their efficiency in the constructs of the present invention. As it is known to the skilled person, certain target cells will respond differently to a given promoter or terminator or any other regulatory sequence disclosed herein. Methods for replacing a regulatory sequence, including a promoter or terminator, are disclosed herein and rely on standard techniques of molecular cloning so that a suitable construct with a different regulatory sequence can be designed for a target cell, preferably a plant target cell of interest.

In certain embodiments, an inducible promoter, including a heat shock (e.g. HSP70 promoter like pZmERD2) or drought inducible promoter (e.g. Rab17 promoter), or a wound (e.g. Wun1 promoter) and/or pathogen inducible promoter may be used according to the present invention. Inducible promoters may have the advantage of a targeted switching on or off. In other embodiments, strong constitutively active promoter may be preferred to obtain a high level expression of a construct of interest.

In one embodiment, the first construct of a plant delivery system may comprise a first nucleotide molecule and the second construct of a plant delivery system may comprise a second nucleotide molecule comprising at least one terminator functional in a plant or part of a plant.

In one embodiment, the at least one terminator may be independently selected from a nopaline synthase terminator (NosT) (SEQ ID NO: 11), a 35S terminator (SEQ ID NO: 12), a Rbcs9 terminator, a *Arabidopsis* HSP terminator, Octopine Synthase terminator, an Ef1b terminator, a Tapal terminator, a Tapox3 terminator, a bvpa1 terminator, or a ZmEf terminator, or any combination thereof. Further terminators to be tested in accordance with the disclosure of the present invention for their suitability in the regulating termination in one of the individual constructs disclosed herein are available to the skilled person.

In certain embodiments, the scaffold RNA sequence, or a sequence encoding the same, of an LbCpf1 construct, or of a plant delivery system of the present invention may be selected from SEQ ID NO: 29 or 30, or a sequence having at least 95%, 96%, 97%, 98%, or 99% identity over the whole length of SEQ ID NO: 29 or 30. As it is known to the skilled person, scaffold sequences will inherently vary for individual Cpf1 effectors. Other scaffold sequences for other Cpf1 effectors in addition to *Lachnospiraceae bacterium* ND2006 (LbCpf1; pY016), including *Francisella tularensis* subsp. *Novicida* U112 (FnCpf1; pY004), *Lachnospiraceae bacterium* MC2017 (Lb3Cpf1; pY005), *Butyrivibrio proteoclasticus* (BpCpf1; pY006), *Peregrinibacteria bacterium* GW2011_GWA_33_10 (PeCpf1; pY007), *Parcubacteria bacterium* GWC2011_GWC2_44_17 (PbCpf1; pY008), *Smithella* sp. SC_K08D17 (SsCpf1; pY009), *Acidaminococcus* sp. BV3L6 (AsCpf1; pY010), *Lachnospiraceae bacterium* MA2020 (Lb2Cpf1; pY011), *Candidatus Methanoplasma termitum* (CMtCpf1; pY012), *Eubacterium eligens* (EeCpf1; pY013), *Moraxella bovoculi* 237 (MbCpf1; pY014), *Leptospira inadai* (LiCpf1; pY015), *Lachnospiraceae bacterium* ND2006 (LbCpf1; pY016), *Porphyromonas crevioricanis* (PcCpf1; pY017), *Prevotella disiens* (PdCpf1; pY018), or *Porphyromonas macacae* (PmCpf1; pY09), are known to the skilled person (cf. Zetsche et al., 2015, supra, FIG. 6B).

In one embodiment, a single scaffold RNA sequence, or a sequence encoding the same, may be used, for example, located in the 5' direction of a sequence encoding a gRNA or a crRNA, preferably in embodiments relying on the provision of embedded gRNA(s)/crRNA(s) of the present invention. In other embodiments, more than one scaffold RNA sequence, or a sequence encoding the same, may be used, e.g., for a multiplexing approach simultaneously targeting more than one target site and thus using more than one gRNA/crRNA. In this setting, each gRNA/crRNA encoding sequence will be preceded by a scaffold RNA sequence. In certain embodiments, the sequence encoding a gRNA/crRNA in a construct of the present invention may comprise at least one RNA scaffold sequence located in the 5' direction, and/or at least one additional RNA scaffold sequence located in the 3' direction. A "scaffold RNA sequence" in the context of at least one Cpf1 guide RNA system of the present invention thus implies a recognition sequence for a Cpf1 enzyme, or a catalytically active fragment thereof, which allows the activation of the inherent RNA processing function of a Cpf1 molecule further detailed below to excise at least one gRNA/crRNA from an embedded mRNA construct carrying at least one cognate scaffold RNA sequence of the Cpf1 enzyme, or the catalytically active fragment thereof (see FIG. 1C).

In one embodiment of the various aspects of the present invention, the at least one Cpf1 enzyme or an active fragment thereof, or a nucleic acid sequence encoding the same, is selected from any one of SEQ ID NOs: 13 to 16, or a sequence having at least 60%, 65%, 70%, 75%, 80%, 85%, 90%, 91%, 92%, 93%, 94%, 95%, 96%, 97%, 98%, 99% or more sequence identity over the whole length of the respective nucleic acid sequence of SEQ ID NOs: 13 or 14, or a sequence having at least 90%, 91%, 92%, 93%, 94%, 95%, 96%, 97%, 98%, or 99% identity over the whole length of the respective amino acid sequence of SEQ ID NOs: 15 or 16, respectively.

In further embodiments, another CRISPR effector nuclease, or the sequence encoding the same may be used. Sequences for further CRISPR effector nucleases can be obtained from publicly available databases (as permanent sequence links) *Francisella tularensis* subsp. *Novicida* U112 (FnCpf1; pY004)) benchling.com/s/0xgyNBMK/edit, *Lachnospiraceae bacterium* MC2017 (Lb3Cpf1; pY005) benchling.com/s/Oo2fP2pu/edit, *Butyrivibrio proteoclasticus* (BpCpf1; pY006) benchling.com/s/b9izZiQ3/edit, *Peregrinibacteria bacterium* GW2011_GWA_33_10 (PeCpf1; pY007) benchling.com/s/JcCPhiwB/edit, *Parcubacteria bacterium* GWC2011_GWC2_44_17 (PbCpf1; pY008) benchling.com/s/yAlizdZH/edit, *Smithella* sp. SC_K08D17 (SsCpf1; pY009) benchling.com/s/bUG7ykgA/edit, *Acidaminococcus* sp. BV3L6 (AsCpf1; pY010) benchling.com/s/wXO8WZJ7/edit, *Lachnospiraceae bacterium* MA2020 (Lb2Cpf1; pY011) benchling.com/s/R9H C1JbY/edit, *Candidatus Methanoplasma termitum* (CMtCpf1; pY012) benchling.com/s/ZC673QLc/edit, *Eubacterium eligens* (EeCpf1; pY013) benchling.com/s/0DPsrCES/edit, *Moraxella bovoculi* 237 (MbCpf1; pY014) benchling.com/s/bCMe5bII/edit, *Leptospira inadai* (LiCpf1; pY015) benchling.com/s/pqFOk5Rn/edit, *Lachnospiraceae bacterium* ND2006 (LbCpf1; pY016) benchling.com/s/HVIyGqQs/edit, *Porphyromonas crevioricanis* (PcCpf1; pY017) benchling.com/s/wDDn4cBS/edit, *Prevotella disiens* (PdCpf1; pY018) benchling.com/s/B8eGa0Ky/edit, *Porphyromonas macacae* (PmCpf1; pY09) benchling.com/s/NDZsqgFs/edit.

In a further embodiment of the various aspects disclosed herein, the at least one Cpf1 enzyme, or an active fragment thereof, or a nucleic acid sequence encoding the same, comprises at least one mutation in comparison to a wild-type sequence (SEQ ID NO: 16) resulting in an altered PAM recognition, preferably wherein the at least mutation is selected from G532R/K595R (cf. SEQ ID NO: 40), or G532R/K538V/Y542R (cf. SEQ ID NO: 41), or another Cpf1 sequence carrying the respective mutation in comparison to the wild-type sequence of SEQ ID NO: 16. As detailed above, PAM recognition by any naturally occurring or recombinant CRISPR system due to the interplay of a CRISPR effector and a tracr/crRNA or an artificial gRNA is crucial for the site-specificity of GE event effected. Therefore, altering PAM recognition properties of a CRISPR system is of high relevance to increase the targeting range of a recombinant CRISPR system.

Further mutations within various CRISPR effector nucleases may be selected from (data presented as "accession number", "organism name", "specific mutation") WP_013282991 *Butyrivibrio proteoclasticus* BpCpf1 R527 E535 N540 K590, WP_044910712 *Lachnospiraceae bacterium* MC2017 Lb3Cpf1 N520 E528 K533 K582, KKR91555 *Candidatus Falkowbacteria bacterium* GW2011_GWA2_41_14 E633 K639 Y643 G705, KKP36646 *Candidatus Peregrinibacteria bacterium* GW2011_GWA2_33_10 PeCpf1 G623 K629 N633 K703, KKQ36153 candidate division WS6 *bacterium* GW2011_GWA2_37_6 G568 Q574 K578 R619, EKE28449 uncultured *bacterium* (gcode 4) T552 K558 R562 R615, KKQ38174 *Candidatus Roizmanbacteria bacterium* GW2011_GWA2_37_7 N592 K598 N602 K660, KKT48220 *Parcubacteria* group *bacterium* GW2011_GWC2_44_17 PbCpf1 K624 K630 F634 R689, WP_005398606 *Helcococcus kunzii* D554 K560 N564 N614, WP_028830240 *Proteocatella sphenisci* K483 K489 N493 K551, WP_015504779 *Candidatus Methanomethylophilus alvus* D515 K521 N525 K577, CUP14506 *Lachnospira pectinoschiza* S548 K554 N558 K614, CUM80100 *Eubacterium rectale* D529 K535 N539 K594, WP_012739647 *Eubacterium eligens* EeCpf1 N535 K541 N545 K601, AIZ56868 *Candidatus Methanoplasma termitum* CMtCpf1 N528 K534 Y538 R591, WP_037975888 *Synergistes jonesfi* K539 K545 N549 K602, WP_021736722 *Acidaminococcus* sp. BV3L6 AsCpf1 S542 K548 N552 K607, WP_031492824 *Succinivibrio dextrinosolvens* E564 K570 C574 K629, WP_018359861 *Porphyromonas macacae* PmCpf1 S559 K565 N569 K623, WP_050786240 *Prevotella disiens* T588 N600 Y604 K674, WP_027407524 *Anaerovibrio* sp. RM50 A525 N531 N535 K594, KDN25524 *Moraxella bovoculi* 237 MbCpf1 N576 K582 N586 K637, AJ161006 *Francisella tularensis* subsp. *novicida* U112 FnCpf1 N607 K613 N617 K671, KUJ74576 *Thiomicrospira* sp. XS5 S575 K581 N585 K658, WP_051666128 *Lachnospiraceae bacterium* ND2006 (*) LbCpf1 G550 K556 Y560 K613, WP_027109509 *Lachnospiraceae bacterium* NC2008 G511 K517 C521 K574, WP_027216152 *Butyrivibrio fibrisolvens* D510 N516 Y520 N573, WP_028248456 *Pseudobutyrivibrio ruminis* N511 K517 N521 K574, WP_049895985 *Oribacterium* sp. NK2B42 D528 K534 N538 K591, WP_035798880 *Butyrivibrio* sp. NC3005 N512 K518 N522 K575, WP_044919442 *Lachnospiraceae bacterium* MA2020 Lb2Cpf1 N512 K518 N522 K575, WP_044910713 *Lachnospiraceae bacterium* MC2017 C537 K543 Y547 K599, WP_020988726 *Leptospira inadai* LiCpf1 K580 R586 N590 R644, WP_016301126 *Lachnospiraceae bacterium* COE1 D545 K551 N555 R608, KIE18657 *Smithella* sp. SC_K08D17 SsCpf1 G561 K567 N571 K625, WP_014085038 *Flavobacterium branchiophilum* N588 K594 Y598 K649, WP_045971446 *Flavobacterium* sp. 316 N586 K592 Y596 K647, KXB38146 *Bacteroidales bacterium* KA00251 A550 K556 N560 K613, WP_036890108 *Porphyromonas crevioricanis* PcCpf1 S575 K581 N585 K641, WP_044110123 *Prevotella brevis* D541 K547 N551 K603, WP_009217842 *Bacteroidetes oral taxon* 274 D564 K570 N574 K628, WP_006283774 *Prevotella bryantii* G566 K572 N576 K629, or WP_024988992 *Prevotella albensis* G561 K567 C571 K624 (cf. Gao et al., Nat. Biotech. doi:10.1038/nbt.3900).

In one embodiment of the present invention, the at least one Cpf1 enzyme, or an active fragment thereof, or a nucleic acid sequence encoding the same, may comprise at least one mutation in comparison to a wild-type sequence (SEQ ID NO: 16) resulting in an altered PAM recognition, wherein the altered PAM recognition is a recognition of a TYCV, or of a TATV PAM sequence. The present invention provides evidence that the use of these alternative PAM variants increases the range of target site recognition across diverse sequence loci in plant genomes (see FIG. 3 and SEQ ID NOs: 35, 36 and 38-41).

In one embodiment according to the various aspects of the present invention, the at least one Cpf1 enzyme or an active fragment thereof, or a nucleic acid sequence encoding the same, and/or the at least one Cpf1 guide RNA system, or a nucleic acid sequence encoding the same, may be provided as at least one vector construct, or they may be provided as at least one linear construct.

In a further embodiment according to the various aspects of the present invention, the at least one Cpf1 guide RNA system may comprises at least two guide RNAs, wherein the at least two guide RNAs are separated by a nucleotide sequence comprising direct repeats. Therefore, in one aspect, the present invention relates to the delivery of multiple Cpf1 gRNAs, e.g. using a ribozyme delivery system as disclosed herein. This aspect of the present invention combines the advantages of the ribozyme delivery system with the finding that Cpf1 is able to process its own gRNAs from an array format (Zetschke et al. Nat Biotechnol (2017) 35(1): 31-34) which was not previously shown to work in plant cells. Specifically, the invention relates to the delivery of at least two crRNAs in array format spaced by mature direct repeat sequences all of which are flanked by the HH and plant-derived HDR-like ribozyme sequences.

In a further embodiment according to the various aspects of the present invention, the at least one Cpf1 guide RNA system, preferably the guide RNA system of a plant delivery system, may comprise at least two Cpf1 guide RNAs, wherein the at least two Cpf1 guide RNAs are separated by a nucleotide sequence comprising direct repeats. This architecture may be specifically suitable for multiplexing approaches targeting more than one genomic target sequence of interest to be edited/modified. "Direct repeats" are a type of genetic sequence that consists of two or more repeats of a specific sequence. In other words, the direct repeats are nucleotide sequences present in multiple copies. Generally, a direct repeat occurs when a sequence is repeated with the same pattern downstream. There is no inversion and no reverse complement associated with a direct repeat. It may or may not have intervening nucleotides. In the constructs of the present invention, direct repeats may be used as spacers to link gRNA/crRNA encoding sequences in a construct of interest. In one embodiment of the present invention, the at least two gRNA/crRNA encoding sequences which are linked via direct repeats further comprise scaffold RNA sequences at their 5' ends which function as recognition sites for a Cpf1 enzyme. In a particular embodiment of the present invention, a LbCpf1 scaffold RNA sequence, or a sequence encoding the same, is set forth in SEQ ID NO: 29 or 30. This sequence may comprise variations in the non-repeat positions. The sequence may be different depending on the Cpf1 effector enzyme used. The sequence of SEQ ID NO: 29 or 30 has been successfully used for multiplexing experiments using either a ribozyme construct or an embedded mRNA construct of the present invention. In multiplexing experiments direct repeat sequences are used as spacer sequences for separating either individual crRNA encoding sequences (comprising at least one scaffold RNA sequence) from each other, or to separate a HH ribozyme encoding sequence from a crRNA encoding sequence (comprising at least one scaffold RNA sequence), or for separating a crRNA encoding sequence (comprising at least one scaffold RNA sequence) from any other element of a vector construct, e.g., a terminator or another regulatory sequence, or a nuclear localization signal, or from another coding sequence.

In one embodiment according to the various aspects of the present invention, at least one construct of a plant delivery system of the present invention will comprise at least one nuclear localization sequence (NLS). In embodiment, where at least two separate constructs are used, each construct will comprise at least one NLS. Suitable NLS sequences may be selected from a SV40 NLS (SEQ ID NO: 42), or a nucleoplasmin NLS (SEQ ID NO: 43). For example, a NLS may be placed 5', and another NLS may be placed 3' flanking the coding region of a Cpf1 gene, or a construct encoding at least one gRNA or crRNA of the present invention. The skilled person is aware of further NLS sequences which may be used in accordance with the teaching of the present invention.

The various modular plant delivery systems of the present invention can be particularly suitable for transient expression approaches in a plant cell or cellular system. Therefore, the elements of at least one vector construct will not be stably integrated into the genome of a cell of interest. This can be a huge advantage from a regulatory point of view, but additionally for practical reasons, as the transient expression allows much shorter turnaround cycles in product development to obtain successfully edited homozygous cells and plants being vector and backbone free.

In certain aspects, the present invention provides plant-derived Hepatitis Delta Virus (HDV)-like ribozyme sequences strongly improving the efficiency of CRISPR-based systems by providing a component for the delivery of a guide RNA system, e.g., a Cas or a Cpf1 guide RNA system, comprising at least one gRNA or crRNA.

Besides the improvement of Cpf1 nuclease delivery/activity, further aspects of the present invention relate to improved strategies of Cpf1 guide RNA (gRNA) delivery.

Cpf1 gRNA delivery strategies have shown very high indel activity at multiple target sites in corn cells (see e.g. Tang et al. (2017) Nature Plants 3, 17018). In this approach, the sequence of the target gRNA is cloned in between two autocatalytic ribozyme sequences, i.e. a Hammerhead ribozyme (HH) sequence on the 5'-end of the construct and a Hepatitis Delta virus (HDV) ribozyme sequence at the 3'-end of the construct. A prototypic HDV ribozyme sequence, or a sequence encoding the same, is shown in SEQ ID NO: 27 or 28, respectively. More than 10 genomic loci have been targeted using this strategy with high indel frequencies/activity. One major drawback of this technology, however, is the use of human pathogen-derived HDV ribozyme sequences that might hamper the development of agricultural and/or food products due to regulatory concerns.

It was surprisingly and in clear contrast to the teaching of the prior art found that a plant-derived HDV-like ribozyme sequence has activity of in vitro or in vivo when using a plant-derived HDV-like ribozyme in a recombinant way. The data presented herein indicate that plant-derived HDV-like ribozyme sequences could potentially replace the original HDV sequences in gRNA ribozyme delivery systems and beyond thereby avoiding the use of human pathogen-derived sequences and time consuming and expensive regulatory issues in product development in any CRISPR system relying on various effector nucleases to properly transport, transcribe and process gRNAs or, for Cpf1 systems, crRNAs.

The present invention thus provides, in one aspect, a ribozyme construct comprising at least one plant-derived Hepatitis Delta Virus (HDV)-like ribozyme sequence, or the sequence encoding the same. The plant-derived Hepatitis Delta Virus (HDV)-like ribozyme sequence can be used together with a plant delivery system of the present invention, or it can be used in a eukaryotic cell, going beyond the use as cargo for any gRNA or crRNA, particularly for applications where the use of a hepatitis virus derived ribozyme system might complicate regulatory procedures.

A "ribozyme" as used herein is an RNA molecule that—in its natural environment—catalyses the cleavage and/or ligation of another RNA molecules. This capacity of ribozymes has, for example, also huge applications for therapy for the inactivation of deleterious genes and the repair of mutated genes involved in many disease states.

Hepatitis delta virus (HDV) is a small, ~1,700-nucleotide (nt), single-stranded RNA virus first isolated from human hepatocytes infected with hepatitis B virus.1 HDV harbors two structurally related self-cleaving ribozymes in its genome, one in the genomic and one in the complementary, antigenomic strand. Like other small self-cleaving ribozymes, these RNAs catalyze a transesterification reaction, promoting a nucleophilic attack by a 2' hydroxyl on the adjacent phosphate and yield both a 2'-3' cyclic phosphate and a liberated 5' hydroxyl. The HDV antigenomic ribozyme was identified by in vitro transcription of cloned HDV genome (Sharmeen et al, 1988, J. Virol., 62:2674-9). The genomic RNA is a template for the synthesis of the concatemers of antigenomic RNA, which is then self-cleaved by its cis-ribozyme followed by host-aided ligation to generate circular, monomer length molecules. The circular "antigenomic" RNAs then serve as the templates for the genomic RNA synthesis followed by the similar self-cleaving and ligation processes.

The structures of the HDV ribozymes consist of five paired (P) regions that form two coaxial stacks (P1 stacks on P1.1 and P4, while P2 stacks on P3), which are linked by single-stranded joining (J) strands J1/2 and J4/2 (cf. Webb and Luptak, 2011, RNA biology, 8:5, 719-727). The genomic ribozyme was shown to self-cleave. The cleavage site for genomic ribozyme is between positions 685 and 686, whereas in the antigenomic RNA it is between positions 900 and 901.4 Both ribozymes require divalent metal ions, such as $Mg^{2+}$, $Mn^{2+}$ or $Ca^{2+}$, for efficient catalysis and exhibit a drastically lower activity in monovalent ions. The cleavage site of the antigenomic ribozyme is 33 nts downstream of the polyadenylation site of the mRNA that encodes HDV's only protein, the delta antigen (Webb and Luptak, 2011, supra).

HDV ribozymes can be converted into trans-active forms by bisection of the J1/2 and/or L4 regions to make those molecules available for applications in molecular biology. Although splitting the ribozymes in the L4 loop results in more extensive base pairing, which increases binding specificity and allows incorporation of modified nucleotides in the active site, the J1/2-bisected molecule preserves the ribozyme core and recognizes a target strand exclusive of any catalytic components. The design of J1/2-split HDV molecule has led to ribozymes that could cleave target RNAs in vitro and in vivo (Kawakami et al., 1996, FEBS Lett., 394:132-6). Still, HDV represents a ribozyme derived from a human pathogen so that there is a great need in identifying and optimizing ribozyme sequences originating from a non-pathogenic organism.

Based on excessive genome sequencing and structure-related searches, potential candidates for ribozymes suitable as recombinant molecular tools have been identified. Still, no ribozyme originating from a plant and having a high rate constant and specific activity in vitro and thus being suitable for recombinant trans-activating applications has been identified and optimized. Particularly, no plant-derived ribozyme has been recombinantly used for genome editing purposes in combination with a plant-optimized CRISPR system to synergistically increase the successful outcome of a GE event in a plant genome even at difficult to access target sites by constructing a complex vector relying on a plant-derived HDV like structure system for optimum performance in a plant cell.

In one embodiment of the various aspects of the present invention, there is provided a plant delivery system, wherein the Hammerhead ribozyme sequence, or a sequence encoding the same, of the Cpf1 guide RNA system may be selected from SEQ ID NO: 17 or 18, and/or wherein the plant-derived Hepatitis Delta Virus (HDV)-like ribozyme sequence, or a sequence encoding the same, is selected from any one of SEQ ID NOs: 19 to 26, or a sequence having at least 95%, 96%, 97%, 98%, or 99% identity over the whole length of any one of SEQ ID NOs: 17 to 26.

As demonstrated in Example 4 and FIG. 2, the plant-derived HDV like ribozymes of the present invention demonstrate high indel activities and are suitable to replace hepatitis delta virus derived sequences for constructing recombinant ribozyme systems. This make the plant-derived HDV like sequences of the present invention an attractive target for a variety of applications in molecular biology suitable for use in a variety of different cellular systems, comprising prokaryotic and eukaryotic cells or systems.

Figure 2A:
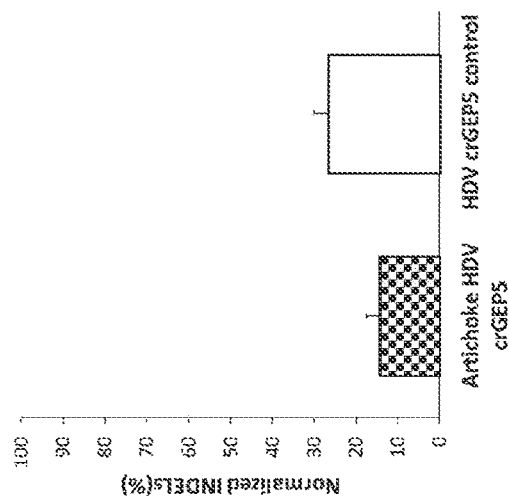
FIG. 2 (FIG. 2A to C) shows (FIG. 2A) an exemplary expression construct for a ribozyme-based RNA delivery system of the present invention. "HD" represent the HDV-like ribozyme portion, wherein this portion may be a plant-derived sequence as disclosed herein, e.g., being derived from rice, sunflower or artichoke. Notably, the LbCpf1 component and the ribozyme-based guide RNA (delivery) system can be used as single transcript system, or as two component system, wherein the LbCpf1 and the crRNA are delivered on two individual plasmids/constructs.
FIG. 2B and FIG. 2C show activity data obtain for the different ribozyme-based guide RNA system (cf. Example 5 below).
Figure 3A:
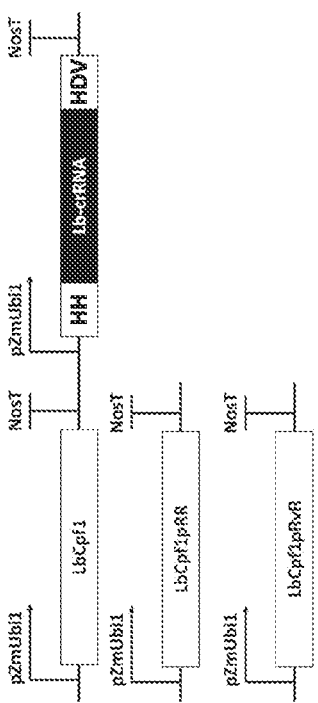
FIG. 3A shows another LbCpf1 variant, RVR, based expression construct (SEQ ID NO: 36).
Figure 3B:
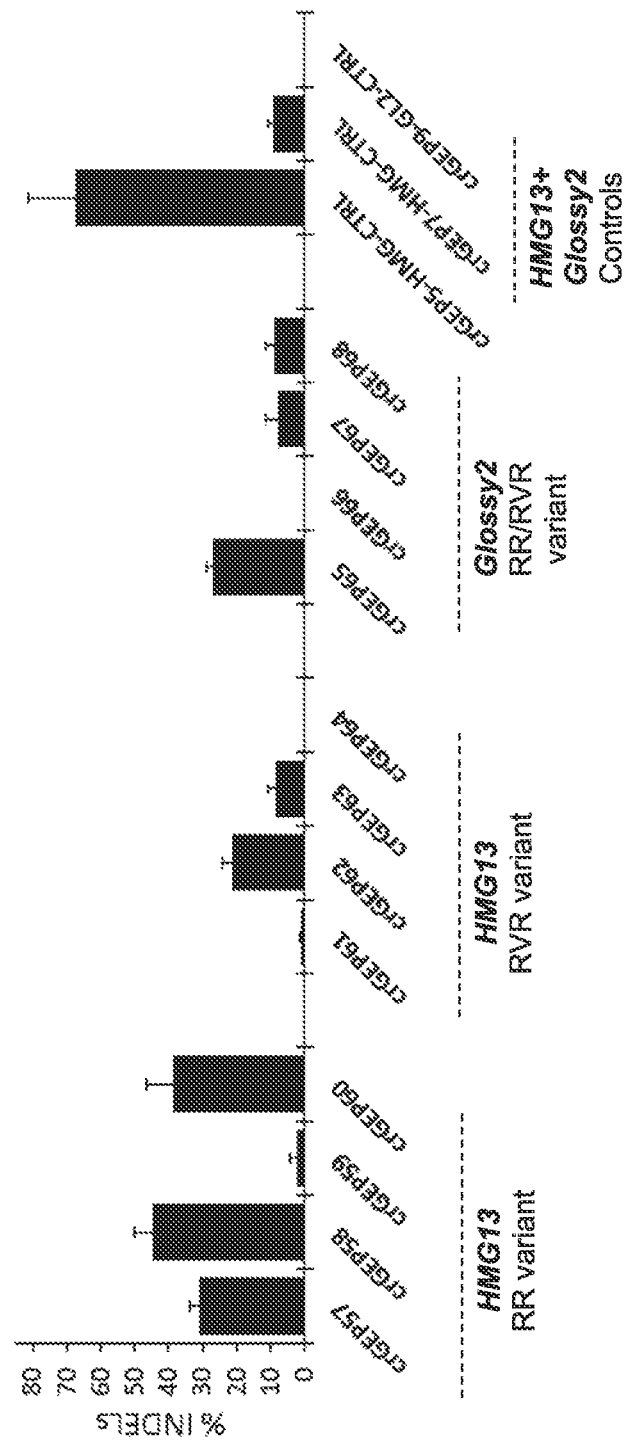
FIG. 3B shows the results of an experiment to test different PAM variants, i.e., a RR and RVR as detailed in Example 6 below.
Figure 5A:
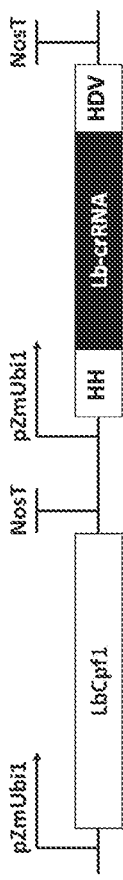
FIG. 5A an exemplary expression construct unit according to the present invention comprising an LbCpf1 unit and a ribozyme flanked LbCpf1 crRNA. Notably, the arrangement is an exemplary one. Promoters and/or terminators may be exchanged, the use of a single transcript unit or the use of two individual expression constructs, or the use of a specific plant-derived HDV-like sequence may be preferred according to the disclosure provided herein.

Furthermore, the plant-derived HDV like ribozymes can be advantageously used in a plant delivery system as disclosed herein. Suitably designed vector systems for providing a ribozyme flanked crRNA for a plant delivery system are provided in SEQ ID NOs: 45 to 48). SEQ ID NO: 44 further provides a ribozyme strategy vector comprising a conventional HDV ribozyme sequence, which was used as control herein. Notably, As it is known to the skilled person, certain variations of the vector backbones can be effected not influencing the coding sequence of a Cpf1 guide RNA system, or a nucleic acid sequence encoding the same, of the present invention. Such variations are encompassed by the sequences provided herein. As illustrated in Example 9 below, the plant-ribozyme based systems of the present invention are even suitable for multiplexing, i.e., the targeted modification of more than one genomic target site, preferably for a CRISPR-based site-directed GE approach, more preferably for Cpf1-based GE in a plant. FIGS. 2A, 3A and 5A show architectures for LbCpf1 genome editing constructs relying on a ribozyme Cpf1 guide RNA system of the present invention. Notably, the ribozyme system may be provided on a single transcript construct together with a CRISPR effector nuclease of interest. As further disclosed herein, it may be advantageous to provide a CRISPR effector nuclease and a guide RNA system, including a Cpf1 guide RNA system, on separate constructs under the control of separate regulatory elements to optimize the expression and thus the availability of the effector nuclease and the cognate gRNA. Providing separate constructs may allow a better fine-tuning of regulation of the plant delivery system. The various ribozyme constructs of the present invention, whether provided as single transcript unit, or as separate expression constructs together with further constructs, for example, encoding a CRISPR effector nuclease, including a Cas9 or a Cpf1 effector, have the advantage that they do not represent T-DNA vector, i.e., vectors for *Agrobacterium* mediated transformation comprising a right boarder and a left boarder sequence subject to regulatory hurdles.

In one embodiment of the present invention, to be used alone or preferably in combination in a plant delivery system of the present invention, there is provided a system, wherein the at least one Cpf1 guide RNA, or the nucleotide sequence encoding the same, which is (i) flanked by a Hammerhead ribozyme sequence at the 5' end and a plant-derived Hepatitis Delta Virus (HDV)-like ribozyme sequence at the 3' end, may further comprise a scaffold RNA sequence, or a sequence encoding the same, at the 5' end; and/or which is (ii) embedded within the non-coding region, preferably the 3' untranslated region (UTR), of the sequence encoding a frame sequence, may further comprise a scaffold RNA sequence, or a sequence encoding the same, at the 5' and 3'-end.

In one embodiment, the Hammerhead ribozyme sequence and/or the plant-derived Hepatitis Delta Virus (HDV)-like ribozyme sequence may be individually replaced against another HH or plant-derived HDV sequence.

Thus, a further aspect of the present invention relates to a guide RNA system, preferably a Cpf1 gRNA system, wherein the construct is flanked by autocatalytic ribozyme sequences in which the HDV ribozyme at the 3'-end of the construct is replaced with a plant-derived HDV-like ribozyme sequence. Three plant-derived HDV-like ribozyme sequences from Rice, Sunflower and Artichoke were identified and tested for their suitability as a HDV replacement. Surprisingly, it was found out that plant-derived HDV-like ribozymes, in particular Artichoke HDV-like ribozymes, as further detailed herein can replace HDV ribozyme sequences at the 3'-end of the construct to obtain indel activity similar to the ones observed with HDV ribozyme sequences (see FIG. 2) or even better than the prior art sequences. This was neither known nor expected from the known prior art so far not showing any activity of plant-derived HDV-like sequences.

In a further aspect, to be used alone or in combination in a plant delivery system of the present invention, there is provided a at least one Cpf1 guide RNA system, or a nucleic acid sequence encoding the same, the at least one Cpf1 guide RNA system comprising at least one Cpf1 guide RNA specific for a genomic target sequence of interest in a plant or part of a plant; wherein the at least one Cpf1 guide RNA, or the nucleic acid sequence encoding the same, may be embedded within a non-coding region, preferably a 3' untranslated region (UTR), of a sequence encoding a frame sequence.

To further improve gRNA delivery in a ribozyme-independent manner, for applications, where this might not represent a suitable strategy due to poor GE rates, an mRNA based expression system for gRNA/crRNA was established. Recently, it was shown that delivery of gRNA using an mRNA based system in mammalian cells could be used to improve gRNA delivery to the cells (Zhong et al. (2017) Nat Chem Biol. 13(8): 839-841). This report demonstrated indel activity from expression of multiple gRNAs embedded in an mRNA construct expressed from a Pol II promoter. Importantly, however, this system was so far not shown to work in plant cells.

According to a further aspect, the present invention therefore relates to at least one LbCpf1 gRNA/crRNA embedded in the 3' untranslated region of an mRNA construct and its use for improved delivery of gRNA at one or more genomic loci in plant cells. In particular, the present invention relates to embedding a CRISPR gRNA scaffold and target sequence within the 3' untranslated region of a reporter gene mRNA sequence in one construct, since it was shown that Cpf1 nuclease activity can process gRNA from mRNA constructs (Fonfara et al., 2016 Nature 532 7600; 517-21). The inventors surprisingly found out that the use of the mRNA delivery system could significantly improve the accessibility of genomic target sequences which are only poorly modified by using the ribozyme system (see FIG. 1, crGEP7 FIG. 1E). The mRNA based guide RNA delivery system therefore provides a novel approach to efficiently modify genomic target sequences in a plant cell which otherwise would be difficult to access, or not targetable at all. Notably, this aspect can be used alone for a variety of different genome editing purposes using a CRISPR effector nuclease, nickase or nuclease-dead variant of interest, as it serves the central purpose of embedding, transporting and providing at least one functional guide RNA suitable for any kind of CRISPR-based GE assay. The mRNA embedding as enclosed herein can be advantageously combined in a plant delivery system of the present invention.

The above aspect can be advantageously combined with the various aspects and embodiments relating to at least one Cpf1 enzyme or an active fragment thereof, or a nucleic acid sequence encoding the same, or relating to a plant delivery system of the present invention, and/or relating to at least one Cpf1 guide RNA system, to obtain a significantly enhanced efficiency rate of CRISPR/Cpf1 based genome editing (GE) in a plant, even when targeting difficult to access target sites, preferably in a plant genome. The gRNA embedding aspects as disclosed herein can, however, be used to deliver at least one or a multitude of gRNA(s)/cRNA(s) for optimizing gRNA/crRNA availability and in turn GE efficiency in any eukaryotic or prokaryotic genome using any CRISPR/Cpf1 based effector nuclease due to the inherent activity of Cpf1 to process precursor CRISPR RNA. I.e., the above aspect relies on the dual use of the Cpf1 capability to process its own crRNA and in turn to recognize and cleave a genomic target sequence of interest (cf. Fonfara et al., 2016, supra).

In one embodiment of the present invention, the sequence encoding a frame sequence may be selected from a translatable or non-translatable sequence being selected from a marker gene, including an antibiotic marker or a fluorescent marker, a gene encoding a structural protein, a gene encoding an RNA species, an internal ribosomal entry site (IRES) encoding sequence, or at least part of the aforementioned sequences. The term "frame sequence" according to the present disclosure may thus be construed broadly to comprise any naturally occurring or artificial sequence that is transcribable when introduced into a target cell or cellular system of interest. Marker genes, including fluorescent marker encoding genes, for example, tdTomato (e.g., comprised by SEQ ID NO: 33 or 31), mNeon Green (e.g., comprised by SEQ ID NO: 37), GFP or eGFP and variants thereof, luciferase and variants thereof, mOrange and variants thereof, mCherry or variants thereof, or any other commercially available marker gene, can have certain advantages as markers, as the activation of the embedded at least one gRNA/crRNA and/or a multitude of gRNA(s)/crRNA(s) can be monitored by quantifying the fluorescence in a target cell or cellular system of interest. In principal, without wishing to be bound by theory, any coding or non-coding RNA could serve as embedding tool for at least one gRNA/crRNA as long as the respective sequence is long enough to guarantee that it can be properly transcribed by RNA polymerase II and/or recognized by a Cpf1 enzyme of interest.

In one preferred embodiment, the at least one gRNA/crRNA may be embedded within a non-coding region, preferably a 3' untranslated region (UTR), or a 5' UTR, of the sequence encoding a frame sequence, the frame sequence per se being a coding or non-coding region.

In another embodiment, the at least one gRNA/crRNA may be embedded within a coding region, in case that the frame sequence represents a sequence encoding a RNA or protein.

In one embodiment, the sequence encoding a frame sequence may be thus selected from a gene, or part of a gene, encoding an RNA, for example an RNA taking a defined secondary or tertiary structure upon transcription.

In one embodiment, the sequence encoding a frame sequence may be selected from any one of SEQ ID NOs: 31, 32, 13, 14, 38, 39, 72, 73, 74, 75, 76, 157, or 158, or a sequence having at least 85%, 86%, 87%, 88%, 89%, 90%, 91%, 92%, 93%, 94%, 95%, 96%, 97%, 98%, or 99% identity over the whole length of the respective sequence of SEQ ID NOs: 31, 32, 13, 14, 38, 39, 72, 73, 74, 75, 76, 157, or 158.

In one particular embodiment, the sequence encoding a frame sequence may be selected from any one of SEQ ID NOs: 13 or 14, or a sequence having at least 85%, 86%, 87%, 88%, 89%, 90%, 91%, 92%, 93%, 94%, 95%, 96%, 97%, 98%, or 99% identity over the whole length of the respective sequence of SEQ ID NOs: 13 or 14, or a sequence portion of any one of SEQ ID NOs: 13 or 14 encoding an active fragment of an LbCpf1 enzyme of the present invention. In certain embodiments, the frame sequence may be selected from a sequence encoding a Cpf1 enzyme or an active fragment thereof. These embodiments using the effector nuclease itself as frame sequence can be particularly suitable to reduce the complexity of the systems and in turn to increase the success rate. The Cpf1 enzyme or the active fragment thereof will thus serve a dual function in (i) activiating its own at least one gRNA; (ii) interacting with the excised at least one gRNA to bind to a target sequence of interest to be cleaved and/or modified.

In one embodiment, the at least one Cpf1 guide RNA, or the nucleic acid sequence encoding the same, embedded within a coding or a non-coding region, preferably a 3' untranslated region (UTR), of a sequence encoding a frame sequence, may comprise at least one scaffold RNA sequence as detailed above in the context of a plant delivery system of the present invention. The scaffold sequence will allow the recognition of the provided, or the transcribed, mRNA construct by at least one Cpf1 enzyme, or a catalytically active fragment thereof, so that the at least one Cpf1 enzyme, or the catalytically active fragment thereof can process its gRNA/crRNA properly. In embodiments, where a multiplexing is envisaged, more than one gRNA/crRNA individually flanked by at least one scaffold RNA sequence may be present. An exemplary mRNA embedded construct comprising two scaffold regions is shown in FIG. 1A. Using a plant delivery construct relying on a construct as shown in FIG. 1A and further relying on a Cpf1 construct disclosed herein, on a separate construct, it could be demonstrated for the first time that a Cpf1 variant cleaves, processes and releases functional gRNA/crRNA in a plant cell from an embedded Cpf1 guide RNA system of the present invention which resulted in an unexpected high indel rate and thus GE efficiency (cf. Example 4 an FIG. 1D). Therefore, specifically combining a Cpf1 construct under the control of a suitable promoter and at least one Cpf1 guide RNA system, wherein the at least one Cpf1 guide RNA, or the nucleic acid sequence encoding the same, is embedded within a coding or a non-coding region, preferably a 3' untranslated region (UTR), of a sequence encoding a frame sequence in the form of a plant delivery system of the present invention targets crGEP5 and 7 (Table 1 and FIG. 1D) with equivalent or even improved activity compared to a conventional ribozyme-delivered guide RNA control from the prior art (Tang et al., 2017), even when targeting difficult to access sites like crGEP7. The non-mRNA embedded guides clearly show highly diminished activities at those two sites.

In one embodiment, at least one Cpf1 guide RNA system, or a nucleic acid sequence encoding the same, is provided, wherein the at least one Cpf1 guide RNA, or the nucleic acid sequence encoding the same, is embedded within a non-coding region, preferably a 3' untranslated region (UTR), of a sequence encoding a frame sequence, wherein the frame sequence is a sequence encoding a CRISPR nuclease enzyme, preferably a nucleic acid sequence encoding a Cpf1 enzyme or an active fragment thereof as disclosed herein. This arrangement may have the outstanding advantage of providing a CRISPR enzyme and the cognate at least one gRNA/crRNA on a single transcript for approaches, where the transformation or transfection of a single entity is favorable. Stability of the gRNA component is ensured by the fact that the gRNA/crRNA will only be activated as soon as the Cpf1 enzyme or the active fragment thereof will be available in a cell in functional form.

In a particular embodiment, a plant optimized promoter as disclosed above may be favorably used with the at least one Cpf1 guide RNA system, or a nucleic acid sequence encoding the same, embedded within a coding or within a non-coding region, preferably a 3' untranslated region (UTR), of a sequence encoding a frame sequence. This may allow optimized transcription of the construct, particularly in a plant system, where a polymerase II promoter may fail.

In one embodiment, the use of two construct requires to deliver them separately by two individual vectors like Agrbacterium cultures, a process that does not guarantee that you will be able to deliver both T-DNAs into the same cell making the construct encoding a Cpf1 enzyme or an active fragment thereof will be provided on two separate constructs. The two construct approach has been highly efficient as evidenced by sometimes 80-90% normalized INDEL efficiency. Another advantage is that, for example, T-DNA in a one construct *Agrobacterium* system is delivered in very low dosage into a cell (1-5 copies) while in the approach using separate construct it is possible to deliver more than 10-100 copies per cell, which leads to higher likelihood of activity at the target site. Also advantageous is the fact that in the system of the present invention INDEL (insertion/deletion) activity can be detected from transient expression of the delivered plasmids with no integration. With T-DNA based vectors, for example, the likelihood of T-DNA integration is extremely high. Furthermore, a two construct approach also allows the fine-tuning of the expression of the two components (Cpf1 and cognate gRNA/crRNA) to get the best possible outcome from the system at various target sites, as both Cpf1 representing a protein and the cognate RNA portion inherently have different turnover times and stabilities. This applies for any Cpf1 guide RNA system, or a nucleic acid sequence encoding the same, of the present invention.

In one embodiment of the various aspects provided herein, the part of a plant may be selected from the group consisting of a plant cell, a plant tissue and a plant organ. leaves, stems, roots, emerged radicles, flowers, flower parts, petals, fruits, pollen, pollen tubes, anther filaments, ovules, embryo sacs, egg cells, ovaries, zygotes, embryos, zygotic embryos, somatic embryos, apical meristems, vascular bundles, pericycles, seeds, roots, gametophytes, spores and cuttings.

In one specific embodiment, the plant or part of a plant may originate from a genus selected from the group consisting of *Hordeum, Sorghum, Saccharum, Zea, Setaria, Oryza, Triticum, Secale, Triticale, Malus, Brachypodium, Aegilops, Daucus, Beta, Eucalyptus, Nicotiana, Solanum, Coffea, Vitis, Erythrante, Genlisea, Cucumis, Marus, Arabidopsis, Crucihimalaya, Cardamine, Lepidium, Capsella, Olmarabidopsis, Arabis, Brassica, Eruca, Raphanus, Citrus, Jatropha, Populus, Medicago, Cicer, Cajanus, Phaseolus, Glycine, Gossypium, Astragalus, Lotus, Torenia, Allium,* or *Helianthus*. More preferably, the plant or part of a plant may originate from a species selected from the group consisting of *Hordeum vulgare, Hordeum bulbusom, Sorghum bicolor, Saccharum officinarium, Zea* spp., including *Zea mays, Setaria italica, Oryza minuta, Oryza sativa, Oryza australiensis, Oryza alta, Triticum aestivum, Triticum durum, Secale cereale, Triticale, Malus domestica, Brachypodium distachyon, Hordeum marinum, Aegilops tauschii, Daucus glochidiatus, Beta* spp., including *Beta vulgaris, Daucus pusillus, Daucus muricatus, Daucus carota, Eucalyptus grandis, Nicotiana sylvestris, Nicotiana tomentosiformis, Nicotiana tabacum, Nicotiana benthamiana, Solanum lycopersicum, Solanum tuberosum, Coffea canephora, Vitis vinifera, Erythrante guttata, Genlisea aurea, Cucumis sativus, Marus notabilis, Arabidopsis arenosa, Arabidopsis lyrata, Arabidopsis thaliana, Crucihimalaya himalaica, Crucihimalaya wallichii, Cardamine nexuosa, Lepidium virginicum, Capsella bursa pastoris, Olmarabidopsis pumila, Arabis hirsute, Brassica napus, Brassica oleracea, Brassica rapa, Raphanus sativus, Brassica juncacea, Brassica nigra, Eruca vesicaria subsp. sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanifolius, Cajanus scarabaeoides, Phaseolus vulgaris, Glycine max, Gossypium* sp., *Astragalus sinicus, Lotus japonicas, Torenia foumieri, Allium cepa, Allium fistulosum, Allium sativum, Helianthus annuus, Helianthus tuberosus* and/or *Allium tuberosum*. Particularly preferred are *Beta vulgaris, Zea mays, Triticum aestivum, Hordeum vulgare, Secale cereale, Helianthus annuus, Solanum tuberosum, Sorghum bicolor, Brassica rapa, Brassica napus, Brassica juncacea, Brassica oleracea, Raphanus sativus, Oryza sativa, Glycine max,* and/or *Gossypium* sp.

In one specific aspect of the present invention, there is provided a host cell, wherein the host cell may comprise any of the plant delivery system as disclosed herein. The plant delivery system may be introduced into the host cell by any technique as disclosed herein, or as known to the skilled person in the field of plant molecular biology.

In one aspect, there is provided a plant, or a plant cell, tissue, organ or material, or a derivative or progeny thereof, which may comprise at least one of the plant delivery systems as disclosed herein.

In one embodiment of the various aspects disclosed herein, the genomic target sequence of interest to be modified as disclosed herein may be a difficult to access target site. A "difficult to access target site" as used herein implies a target site, which is hard to be modified by genetic engineering and genome editing techniques. Such a "difficult to access target site" may occur, for example, in condensed chromatin, highly GC rich areas and areas with high methylation coverage in a complex eukaryotic genome. Using the example of target crGEP7 as disclosed herein which showed low INDEL activity using a common ribozyme system (under 10%), it was possible to obtain >40% activity using a plant delivery system comprising an embedded mRNA system of the present invention. It is speculated that the processing of the gRNA within the mRNA context of the various constructs disclosed herein results in more efficient processing and allows for better binding to the CRISPR Cpf1 nuclease versus at least a conventional ribozyme system, where the nuclease does not have to process the gRNA out of the larger RNA.

In a further aspect of the present invention, there is provided a method for modifying a genomic target sequence of interest in a plant or part of a plant, wherein the method may comprise the steps of: (a) providing at least one Cpf1 enzyme or an active fragment thereof, or a nucleic acid sequence encoding the same; preferably, wherein the at least one nucleic acid sequence encoding the Cpf1 enzyme or an active fragment thereof is codon-optimized for the expression in the plant or part of the plant; and (b) providing at least one Cpf1 guide RNA system, or a nucleic acid sequence encoding the same, the at least one Cpf1 guide RNA system comprising at least one Cpf1 guide RNA specific for a genomic target sequence of interest in the plant or part of the plant; wherein the at least one Cpf1 guide RNA, or the nucleic acid sequence encoding the same, is (i) flanked by a Hammerhead ribozyme sequence at the 5' and a plant-derived Hepatitis Delta Virus (HDV)-like ribozyme sequence at the 3'-end; and/or is (ii) embedded within a coding or within a non-coding region, preferably a 3' untranslated region (UTR), of a sequence encoding a frame sequence (c) optionally: providing at least one repair template nucleic acid sequence, wherein the at least one repair template nucleic acid sequence is preferably flanked by one or more homology sequence(s) complementary to one or both adjacent region(s) of the genomic sequence of interest in the plant or part of the plant; (d) introducing the at least one Cpf1 enzyme or an active fragment thereof, or a nucleic acid sequence encoding the same from step (a); and introducing the at least one Cpf1 guide RNA system, or a nucleic acid sequence encoding the same from step (b) and optionally: introducing the at least one repair template nucleic acid sequence from step (c) into the plant or part of the plant; and (e) obtaining a plant or part of a plant, or a progeny thereof, comprising a modification in the genomic target sequence of interest.

In eukaryotic cells, genome integrity is ensured by robust and partially redundant mechanisms for repairing DNA DSBs caused by environmental stresses and errors of cellular DNA processing machinery. In most eukaryotic cells and at most stages of the respective cell cycle, the non-homologous end-joining (NHEJ) DNA repair pathway is the highly dominant form of repair. A second pathway uses homologous recombination (HR) of similar DNA sequences to repair DSBs. This pathway can usually be used in the S and G2 stages of the cell cycle by templating from the duplicated homologous region of a paired chromosome to precisely repair the DSB. However, an artificially-provided repair template (RT) with homology to the target can also be used to repair the DSB, in a process known as homology-directed repair (HDR) or gene targeting. By this strategy it is possible to introduce very precise, targeted changes in the genomes of eukaryotic cells.

A "homology sequence", if present, may be part of the at least one RT of interest according to the various embodiments of the present invention, to be introduced to modify the genetic material of a cell or cellular system according to the present disclosure at a genomic target sequence or site of interest. Therefore, the at least one homology sequence is physically associated with the at least one RT within one molecule. As such, the homology sequence may be part of the at least one RT to be introduced and it may be positioned within the 5' and/or 3' position of the at least one RT of interest, optionally including at least one spacer nucleotide, or within the at least one RT sequence of interest to be introduced. As such, the homology sequence(s) serve as templates to mediate homology-directed repair by having complementarity to at least one region, the upstream and/or the downstream region, adjacent to the genomic target sequence or the predetermined location (said terms being used interchangeably herein) within the genetic material of a cell or cellular system to be modified. In certain embodiments, the RT may be further associated with another DNA and/or RNA sequence as mediated by complementary base pairing. In an alternative embodiment the RT may be associated with other sequence, for example, sequences of a vector, e.g., a plasmid vector, which vector can be used to amplify the RT prior to transformation. Furthermore, the RT may also be physically associated with at least part of an amino acid component, preferably a site-specific nuclease, more preferably a CRISPR nuclease, and most preferably a Cpf1 enzyme or an active fragment thereof. This configuration and association allows the availability of the RT in close physical proximity to the site of a DSB, i.e., exactly at the position a targeted GE event is to be effected to allow even higher efficiency rates. For example, the at least one RT may also be associated with at least one gRNA interacting with the at least one RT and further interacting with at least one portion of a CRISPR nuclease, e.g., a Cpf1 nuclease, as site-specific nuclease.

The one or more homology region(s) may each have a certain degree of complementarity to the respective region flanking the at least one predetermined location upstream and/or downstream of the double-strand break induced by the at least one site-specific nuclease, i.e., the upstream and downstream adjacent region, respectively. Preferably, the one or more homology region(s) will hybridize to the upstream and/or downstream adjacent region under conditions of high stringency. The longer the at least one homology region, the lower the degree of complementarity may be. The complementarity is usually calculated over the whole length of the respective region of homology. In case only one homology region is present, this single homology region will usually have a higher degree of complementarity to allow hybridization. Complementarity under stringent hybridization conditions will be at least 85%, at least 90%, at least 91%, at least 92%, at least 93%, at least 94%, at least 95%, at least 96%, and preferably at least 97%, at least 98%, at least 99%, or even 100%. At least in the region directly flanking a DSB induced (about 5 to 10 bp upstream and downstream of a DSB), complementarities of at least 98%, at least 99%, and preferably 100% should be present. Notably, as further disclosed herein below, the degree of complementarity can also be lower than 85%. This will largely depend on the target genetic material and the complexity of the genome it is derived from, the length of the nucleic acid sequence of interest to be introduced, the length and nature of the further homology arm or flanking region, the relative position and orientation of the flanking region in relation to the site at least one DSB is induced, and the like.

The term "adjacent" or "adjacent to" as used herein in the context of a predetermined location or a genomic target sequence of interest, and the one or more homology region(s) may comprise an upstream and a downstream adjacent region, or both. Therefore, the adjacent region is determined based on the genetic material of a cellular system to be modified, said material comprising the predetermined location.

There may be an upstream and/or downstream adjacent region near the predetermined location/the genomic target sequence of interest. For site-specific nucleases (SSNs), including CRISPR nucleases like Cpf1, Cas9, CasX or CasY, and variants thereof, leaving overhangs after double-strand break (DSB) induction, the predetermined location means the region between the cut in the 5' end on one strand and the 3'-end on the other strand. The adjacent regions in the case of sticky end SSNs thus may be calculated using the two different DNA strands as reference. The term "adjacent to a predetermined location" thus may imply the upstream and/or downstream nucleotide positions in a genetic material to be modified, wherein the adjacent region is defined based on the genetic material of a cellular system before inducing a DSB or modification.

If present, the upstream adjacent region defines the region directly upstream of the 5'-end of the cutting site of a CRISPR nuclease of interest, preferably a Cpf1 nuclease, with reference to a predetermined location before initiating a double-strand break, e.g., during targeted genome engineering. Correspondingly, a downstream adjacent region defines the region directly downstream of the 3'-end of the cutting site of a SSN of interest with reference to a predetermined location before initiating a double-strand break, e.g., during targeted genome engineering. The 5'-end and the 3'-end can be the same, depending on the site-specific nuclease of interest.

In certain embodiments, it may also be favorable to design at least one homology region in a distance away from the DSB to be induced, i.e., not directly flanking the predetermined location/the DSB site. In this scenario, the genomic sequence between the predetermined location and the homology sequence (the homology arm) would be "deleted" after homologous recombination had occurred, which may be preferred for certain strategies as this allows the targeted deletion of sequences near the DSB. Different kinds of RT configuration and design are thus contemplated according to the present invention for those embodiments relying on a RT. RTs may be used to introduce site-specific mutations, or RTs may be used for the site-specific integration of nucleic acid sequences of interest, or RTs may be used to assist a targeted deletion.

A "homology sequence(s)" introduced and the corresponding "adjacent region(s)" can each have varying and different length from about 15 bp to about 15.000 bp, i.e., an upstream homology region can have a different length in comparison to a downstream homology region. Only one homology region may be present. There is no real upper limit for the length of the homology region(s), which length is rather dictated by practical and technical issues. According to certain embodiments, depending on the nature of the RT and the targeted modification to be introduced, asymmetric homology regions may be preferred, i.e., homology regions, wherein the upstream and downstream flanking regions have varying length. In certain embodiments, only one upstream and downstream flanking region may be present.

In one embodiment of the above method of the present invention, the at least one Cpf1 enzyme or an active fragment thereof, or a nucleic acid sequence encoding the same, and the at least one Cpf1 guide RNA system, or a nucleic acid sequence encoding the same, and optionally the at least one repair template nucleic acid sequence, may be provided on separate constructs, wherein the at least two separate constructs are introduced simultaneously, or subsequently. The use of separate constructs, whether introduced simultaneously, or subsequently may have the advantage of a better regulation of the expression and thus the availability of the respective effector RNA (gRNA/crRNA), DNA (RT) and/or Cpf1 enzyme such encoded.

In another embodiment, the at least one Cpf1 enzyme or an active fragment thereof, or a nucleic acid sequence encoding the same, and the at least one Cpf1 guide RNA system, or a nucleic acid sequence encoding the same, may be provided on a single transcript construct. This setting may be particularly suitable, when *Agrobacterium* based transformation is intended.

In yet another embodiment, the at least one Cpf1 enzyme or an active fragment thereof, and the at least one Cpf1 guide RNA system, and optionally at least one RT, may be provided as an ex vivo synthesized and pre-assembled complex. This setting may be particularly suitable to transfect a cell, e.g., a cell recalcitrant to transformation in one shot with a pre-assembled and thus fully functional complex without the need of the cellular machinery to express at least one construct.

In still another embodiment, the at least one Cpf1 enzyme or an active fragment thereof, or a nucleic acid sequence encoding the same, and the at least one Cpf1 guide RNA system, or a nucleic acid sequence encoding the same, may be provided on a multiplexing construct. This approach is particularly suitable in case more than one genomic target sequence of interest is intended to be modified simultaneously using more than one gRNA/crRNA (cf. Example 9).

According to all of the above embodiments, the RT may be transformed as an individual construct, or it may be transfected as a separate construct, or it may be synthesized and assembled with at least one of the other components of a plant delivery system of the present invention ex vivo before introducing a complex into a cell of interest.

In one specific embodiment of the above method, the molecules of step (a), (b) and optionally of step (c) may thus be provided as a plant delivery system as disclosed herein, wherein the plant delivery system may comprise a first nucleotide molecule comprising a nucleic acid sequence encoding the at least one Cpf1 enzyme or an active fragment thereof, and a second nucleotide molecule comprising a nucleic acid sequence encoding the at least one Cpf1 guide RNA system, wherein the first and the second molecule are provided on separate constructs, or wherein the first and the second molecule are provided on a single transcript construct.

In one embodiment of the methods of the present invention, (i) the at least one nucleic acid sequence encoding the Cpf1 enzyme or an active fragment thereof, and the nucleic acid sequence encoding at least one Cpf1 guide RNA system; or (ii) the first construct comprising the first nucleotide molecule and the second construct comprising the second nucleotide molecule, may each comprise at least one promoter functional in a plant or part of a plant.

In one embodiment of the above methods, the at least one promoter may be independently selected from a (p)BdUbi10 promoter (SEQ ID NO: 1, a (p)ZmUbi1 promoter (SEQ ID NO: 2), a (p)OsActin promoter (SEQ ID NO: 3), and a single or double 35S promoter (SEQ ID NO: 4), optionally including an ZmUbi1 intron, an BdUbi10 intron and/or an Adh1 intron, (SEQ ID NOs: 5 to 10, or 67), or any combination thereof, or a sequence having at least 90%, 91%, 92%, 93%, 94%, 95%, 96%, 97%, 98%, or 99% identity when compared over the whole length of the respective sequence of any one of SEQ ID NOs: 1 to 10, or 67.

As further disclosed herein, the choice of the promoter and the choice of different promoters for individual constructs may be crucial to obtain optimized expression of the respective effector sequences encoded by the constructs, or the plant delivery system (cf. Example 7).

In yet a further embodiment of the above methods, (i) the at least one nucleic acid sequence encoding the Cpf1 enzyme or an active fragment thereof, and the nucleic acid sequence encoding at least one Cpf1 guide RNA system; or (ii) the first construct comprising the first nucleotide molecule and the second construct comprising the second nucleotide molecule; may comprise at least one terminator functional in a plant or part of a plant, preferably wherein the at least one terminator is independently selected from a nopaline synthase terminator (NosT) (SEQ ID NO: 11), or a 35S terminator (SEQ ID NO: 12) or any combination thereof, or a sequence having at least 90%, 91%, 92%, 93%, 94%, 95%, 96%, 97%, 98%, or 99% identity when compared over the whole length of the respective sequence of any one of SEQ ID NOs: 11 or 12. Further terminators to be tested in accordance with the disclosure of the present invention for their suitability in the regulating termination in one of the individual constructs disclosed herein are available to the skilled person.

In one embodiment of the methods of the present invention, the nucleic acid sequence encoding the Cpf1 enzyme or an active fragment thereof is codon-optimized for expression in a plant or part of a plant. Specific codon-optimization may significantly enhance the performance of a CRISPR-based nuclease naturally originating from non-plant organisms so that the CRISPR effector, preferably a Cpf1 effector, can be functionally transcribed and translated in a plant cell of interest.

In another embodiment of the methods of the present invention, the nucleic acid sequence encoding the Cpf1 enzyme or an active fragment thereof may be selected from SEQ ID NOs: 13 or 14, or a sequence having at least 85%, 86%, 87%, 88%, 89%, 90%, 91%, 92%, 93%, 94%, 95%, 96%, 97%, 98%, or 99% identity over the whole length of the respective sequence of SEQ ID NOs: 13 or 14.

In yet another embodiment of the methods of the present invention, the Hammerhead ribozyme sequence, or a sequence encoding the same, is selected from SEQ ID NO: 17 or 18, and/or wherein the plant-derived Hepatitis Delta Virus (HDV)-like ribozyme sequence, or a sequence encoding the same, is selected from any one of SEQ ID NOs: 19 to 26, or a sequence having at least 95%, 96%, 97%, 98%, or 99% identity over the whole length of any one of SEQ ID NOs: 17 to 26.

In another embodiment of the methods of the present invention, the at least one Cpf1 guide RNA, or the nucleotide sequence encoding the same, which is (i) flanked by the Hammerhead ribozyme sequence at the 5' and the plant-derived Hepatitis Delta Virus (HDV)-like ribozyme sequence at the 3' end, further comprises a scaffold RNA sequence, or a sequence encoding the same, at the 5' end; and/or which is (ii) embedded within the coding or within the non-coding region, preferably the 3' untranslated region (UTR), of the sequence encoding a frame sequence, further comprises a scaffold RNA sequence, or a sequence encoding the same, at the 5' and 3' end.

As detailed above for the embodiments directed to a plant delivery system, the at least one Cpf1 guide RNA may comprise at least one scaffold RNA sequence being specific for a cognate Cpf1 enzyme or an active fragment thereof. In embodiments of the methods disclosed herein relying on a ribozyme system, one scaffold RNA sequence, or the sequence encoding the same, may be used, wherein in embodiments relying on an embedded mRNA approach two scaffold RNA sequences, or the sequence encoding the same, may be used. As detailed above, more than one scaffold RNA sequence may be used, particularly, where a multiplex targeting in one experiment is envisaged. Usually, the at least one scaffold RNA sequence will be located directly adjacent to the 5' and/or 3'-end of a gRNA/crRNA of interest.

In one embodiment of the methods of the present invention, the scaffold RNA sequence, or a sequence encoding the same, may be selected from SEQ ID NO: 29 or 30, or a sequence having at least 95%, 96%, 97%, 98%, or 99% identity over the whole length of a SEQ ID NO: 29 or 30, or it may be selected from any further scaffold RNA sequence, or a DNA sequence encoding the same, as disclosed herein.

In one further embodiment of the methods of the present invention, the at least one Cpf1 enzyme or an active fragment thereof, or a nucleic acid sequence encoding the same, may be selected from any one of SEQ ID NOs: 13 to 16, or a sequence having at least 60%, 65%, 70%, 75%, 80%, 85%, 90%, 91%, 92%, 93%, 94%, 95%, 96%, 97%, 98%, 99% or more sequence identity over the whole length of the respective nucleic acid sequence of SEQ ID NOs: 13 or 14, or a sequence having at least 90%, 91%, 92%, 93%, 94%, 95%, 96%, 97%, 98%, or 99% identity over the whole length of the respective amino acid sequence of SEQ ID NOs: 15 or 16, respectively.

In one embodiment of the methods of the present invention, the at least one Cpf1 enzyme, or an active fragment thereof, or a nucleic acid sequence encoding the same, may comprise at least one mutation in comparison to a wild-type sequence (SEQ ID NO: 16) resulting in an altered PAM recognition, preferably wherein the at least one mutation is selected from G532R/K595R, or G532R/K538V/Y542R in comparison to the sequence of SEQ ID NO: 16.

In yet a further embodiment of the methods of the present invention, the at least one Cpf1 enzyme, or an active fragment thereof, or a nucleic acid sequence encoding the same, may comprise at least one mutation in comparison to a wild-type sequence (SEQ ID NO: 16) resulting in an altered PAM recognition, wherein the altered PAM recognition is a recognition of a TYCV, or of a TATV PAM sequence.

In certain embodiments, suitable Cpf1 mutant variants according to the present invention may be selected from any one of SEQ ID NOs: 38 to 41, or a sequence having at least 60%, 65%, 70%, 75%, 80%, 85%, 90%, 91%, 92%, 93%, 94%, 95%, 96%, 97%, 98%, 99% or more sequence identity over the whole length of the respective nucleic acid sequence of SEQ ID NOs: 38 or 39, or a sequence having at least 90%, 91%, 92%, 93%, 94%, 95%, 96%, 97%, 98%, or 99% identity over the whole length of the respective amino acid sequence of SEQ ID NOs: 40 and 41, respectively.

In another embodiment of the methods of the present invention, the at least one Cpf1 enzyme or an active fragment thereof, or a nucleic acid sequence encoding the same, and/or the at least one Cpf1 guide RNA system, or a nucleic acid sequence encoding the same, may be provided as at least one vector construct, or are provided as at least one linear construct.

In one embodiment of the methods of the present invention, the at least one Cpf1 guide RNA system comprises at least two guide RNAs, wherein the at least two guide RNAs may be separated by a nucleotide sequence comprising direct repeats, as disclosed herein above.

In one embodiment of the methods of the present invention, the sequence encoding a frame sequence is selected from a translatable or non-translatable sequence being selected from a marker gene, including an antibiotic marker or a fluorescent marker, a gene encoding a structural protein, a gene encoding an RNA species, an IRES encoding sequence. Further coding and non-coding sequences may serve the purpose of embedding and thus enhancing the efficiency and availability of at least one gRNA/crRNA as disclosed above for the at least one Cpf1 guide RNA system of the present invention, wherein the at least one gRNA/crRNA is embdedded into a coding or non-coding region, preferably a 3' untranslated region (UTR), of a sequence encoding a frame sequence.

In still another embodiment of the methods of the present invention, the sequence encoding a frame sequence may be selected from any one of SEQ ID NOs: 13, 14, 38, 39, 31, 32, 72, 73, 74, 75, 76, 157, or 158, or a sequence having at least 85%, 86%, 87%, 88%, 89%, 90%, 91%, 92%, 93%, 94%, 95%, 96%, 97%, 98%, or 99% identity over the whole length of the respective sequence of SEQ ID NOs: 13, 14, 38, 39, 31, 32, 72, 73, 74, 75, 76, 157, or 158.

In one embodiment of the methods of the present invention, the part of a plant may be selected from the group consisting of a plant cell, a plant tissue and a plant organ, preferably wherein the plant or a part of a plant may be selected from a genus selected from the group consisting of *Hordeum, Sorghum, Saccharum, Zea, Setaria, Oryza, Triticum, Secale, Triticale, Malus, Brachypodium, Aegilops, Daucus, Beta, Eucalyptus, Nicotiana, Solanum, Coffea, Vitis, Erythrante, Genlisea, Cucumis, Marus, Arabidopsis, Crucihimalaya, Cardamine, Lepidium, Capsella, Olmarabidopsis, Arabis, Brassica, Eruca, Raphanus, Citrus, Jatropha, Populus, Medicago, Cicer, Cajanus, Phaseolus, Glycine, Gossypium, Astragalus, Lotus, Torenia, Allium,* or *Helianthus*. More preferably, the plant or a part of a plant may be selected from a species selected from the group consisting of *Hordeum vulgare, Hordeum bulbusom, Sorghum bicolor, Saccharum officinarium, Zea* spp., including *Zea mays, Setaria italica, Oryza minuta, Oryza sativa, Oryza australiensis, Oryza alta, Triticum aestivum, Triticum durum, Secale cereale, Triticale, Malus domestica, Brachypodium distachyon, Hordeum marinum, Aegilops tauschii, Daucus glochidiatus, Beta* spp., including *Beta vulgaris, Daucus pusillus, Daucus muricatus, Daucus carota, Eucalyptus grandis, Nicotiana sylvestris, Nicotiana tomentosiformis, Nicotiana tabacum, Nicotiana benthamiana, Solanum lycopersicum, Solanum tuberosum, Coffea canephora, Vitis vinifera, Erythrante guttata, Genlisea aurea, Cucumis sativus, Marus notabilis, Arabidopsis arenosa, Arabidopsis lyrata, Arabidopsis thaliana, Crucihimalaya himalaica, Crucihimalaya wallichii, Cardamine nexuosa, Lepidium virginicum, Capsella bursa pastoris, Olmarabidopsis pumila, Arabis hirsute, Brassica napus, Brassica oleracea, Brassica rapa, Raphanus sativus, Brassica juncacea, Brassica nigra, Eruca vesicaria* subsp. *sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanifolius, Cajanus scarabaeoides, Phaseolus vulgaris, Glycine max, Gossypium* sp., *Astragalus sinicus, Lotus japonicas, Torenia foumieri, Allium cepa, Allium fistulosum, Allium sativum, Helianthus annuus, Helianthus tuberosus* and/or *Allium tuberosum*. Particularly preferred are *Beta vulgaris, Zea mays, Triticum aestivum, Hordeum vulgare, Secale cereale, Helianthus annuus, Solanum tuberosum, Sorghum bicolor, Brassica rapa, Brassica napus, Brassica juncacea, Brassica oleracea, Raphanus sativus, Oryza sativa, Glycine max*, and/or *Gossypium* sp.

In one specific embodiment of the methods of the present invention, the plant or part of the plant may be a monocotyledonous plant, preferably *Zea mays*.

In one aspect, there is provided a plant or a part of a plant, or a progeny thereof, which may be obtained, or which may be obtainable by any of the methods of the present invention.

In another aspect, there is provided a use of a plant delivery system of the present invention; or a use of a Cpf1 enzyme or an active fragment thereof, or of a nucleic acid sequence encoding the same of the present invention; and/or a use of at least one guide RNA system, or the nucleic acid sequence encoding the same of the present invention, in a method of modifying a genomic target sequence of interest in a plant or part of a plant.

In one embodiment of the above use, the genomic target sequence of interest is a difficult to access target site, i.e., a target site hard to modify by any genome editing methods due to the specific environment of the genomic target site of interest at a specific locus of a complex eukaryotic genome.

In another aspect, there is provided method for modifying a genomic target sequence of interest in a eukaryotic cell of interest, wherein the method may comprise the steps of: (a) providing at least one Cpf1 enzyme or an active fragment thereof, or a nucleic acid sequence encoding the same; preferably, wherein the at least one nucleic acid sequence encoding the Cpf1 enzyme or an active fragment thereof is codon-optimized for the expression in the eukaryotic cell of interest; and (b) providing at least one Cpf1 guide RNA system, or a nucleic acid sequence encoding the same, the at least one Cpf1 guide RNA system comprising at least one Cpf1 guide RNA specific for a genomic target sequence of interest in the eukaryotic cell of interest; wherein the at least one Cpf1 guide RNA, or the nucleic acid sequence encoding the same, is (i) flanked by a Hammerhead ribozyme sequence at the 5' and a plant-derived Hepatitis Delta Virus (HDV)-like ribozyme sequence at the 3'-end; and/or is (ii) embedded within a coding or non-coding region, preferably a 3' untranslated region (UTR), of a sequence encoding a frame sequence (c) optionally: providing at least one repair template nucleic acid sequence, wherein the at least one repair template nucleic acid sequence is preferably flanked by one or more homology sequence(s) complementary to one or both adjacent region(s) of the genomic sequence of interest in the eukaryotic cell of interest; (d) introducing the at least one Cpf1 enzyme or an active fragment thereof, or a nucleic acid sequence encoding the same from step (a); and introducing the at least one Cpf1 guide RNA system, or a nucleic acid sequence encoding the same from step (b) and optionally: introducing the at least one repair template nucleic acid sequence from step (c) into the eukaryotic cell of interest; and (e) obtaining a eukaryotic cell of interest, or a progeny thereof, comprising a modification in the genomic target sequence of interest.

The specific Cpf1 guide RNA systems of the present invention may be suitably used in any eukaryotic cell or cellular system of interest. Preferably, the sequence encoding a Cpf1 enzyme or an active fragment thereof will then be codon-optimized for the specific eukaryotic target cell of interest. Furthermore, suitable regulatory sequences may be chosen for the constructs to be used, wherein the regulatory sequences, including inter alia promoters and terminators, should be chosen to be functional in a eukaryotic target cell of interest. The skilled person is able to define suitable promoters, preferably strong promoters, either with inducible or constitutive expression, depending on a cellular system of interest. An example for a very strong constitutive promoter in the plant system, e.g., *Zea mays*, is BdUbi10. A weaker promoter would be the BdEF1 for example. Inducible plant promoters are the tetracycline-, the dexamethasone-, and salicylic acid inducible promoters. Other promoters suitable according to the present invention are a CaMV (Cauliflower mosaic virus) 35S or a double 35S promoter. Other constitutive eukaryotic promoters are CMV (Cytomegalovirus), EF1a, TEF1, SV40, PGK1 (human or mouse), Ubc (ubiquitin 1), human beta-actin, GDS, GAL1 or 2 (for a yeast system), CAG (comprising a CMV enhancer, chicken beta actin promoter, and rabbit beta-globin splice acceptor), H1, or U6. A variety of inducible promoters is known to the skilled person. Suitable terminators can likewise be determined by the skilled person and include, inter alia, a SV40 terminator, or a HGH terminator.

In particular at least one Cpf1 guide RNA system, or a nucleic acid sequence encoding the same, wherein the at least one Cpf1 guide RNA, or the nucleic acid sequence encoding the same, is (i) flanked by a Hammerhead ribozyme sequence at the 5'-end and by a plant-derived Hepatitis Delta Virus (HDV)-like ribozyme sequence at the 3'-end may be particularly suitable for any GE method in an animal cell, or a fungal cell, etc., as there is a great need in replacing virus-derived sequences by functional sequences from other non-human pathogenic organisms. The plant-derived HDV-like sequences of the present invention can thus substitute for the original HDV sequences in any ribozyme system, when used in a pre-transcribed form, or when provided on a construct optionally comprising codon-optimization and/or regulatory sequences functional in a eukaryotic target cell of interest.

Delivery and Analytical Methods:

According to the present disclosure, any suitable delivery method to introduce at least one plant delivery system, or a component thereof, or any other biomolecule into a cell or cellular system can be applied, depending on the cell or cellular system of interest. The term "introduction" as used herein thus implies a functional transport of a biomolecule or genetic construct (DNA, RNA, single- or double-stranded, protein, comprising natural and/or synthetic components, or a mixture thereof) into at least one cell or cellular system, which allows the transcription and/or translation and/or the catalytic activity and/or binding activity, including the binding of a nucleic acid molecule to another nucleic acid molecule, including DNA or RNA, or the binding of a protein to a target structure within the at least one cell or cellular system, and/or the catalytic activity of an enzyme such introduced, optionally after transcription and/or translation. Where pertinent, a functional integration of a genetic construct may take place in a certain cellular compartment of the at least one cell, including the nucleus, the cytosol, the mitochondrium, the chloroplast, the vacuole, the membrane, the cell wall and the like. Consequently, the term "functional integration" implies that a molecular complex of interest is introduced into the at least one cell or cellular system by any means of transformation, transfection or transduction by biological means, including *Agrobacterium* transformation, or physical means, including particle bombardment, as well as the subsequent step, wherein the molecular complex can exert its effect within or onto the at least one cell or cellular in which it was introduced regardless of whether the construct or complex is introduced in a stable or in a transient way.

According to the various embodiments, at least one plant delivery system according to the present invention may thus be provided in the form of at least one vector, e.g., a plasmid vector, as at least one linear molecule, or as at least one complex pre-assembled ex vivo.

Depending on the nature of the genetic construct or biomolecule to be introduced, said effect naturally can vary and including, alone or in combination, inter alia, the transcription of a DNA encoded by the genetic construct to a ribonucleic acid, the translation of an RNA to an amino acid sequence, the activity of an RNA molecule within a cell, comprising the activity of a guide RNA, a crRNA, a tracrRNA, or an miRNA or an siRNA for use in RNA interference, and/or a binding activity, including the binding of a nucleic acid molecule to another nucleic acid molecule, including DNA or RNA, or the binding of a protein to a target structure within the at least one cell, or including the integration of a sequence delivered via a vector or a genetic construct, either transiently or in a stable way. Said effect can also comprise the catalytic activity of an amino acid sequence representing an enzyme or a catalytically active portion thereof within the at least one cell and the like. Said effect achieved after functional integration of the molecular complex according to the present disclosure can depend on the presence of regulatory sequences or localization sequences which are comprised by the genetic construct of interest as it is known to the person skilled in the art.

A variety of suitable transient and stable delivery techniques suitable according to the methods of the present invention for introducing genetic material, biomolecules, including any kind of single-stranded and double-stranded DNA and/or RNA, or amino acids, synthetic or chemical substances, into a eukaryotic cell, preferably a plant cell, or into a cellular system comprising genetic material of interest, are known to the skilled person, and comprise inter alia choosing direct delivery techniques ranging from polyethylene glycol (PEG) treatment of protoplasts (Potrykus et al. 1985), procedures like electroporation (D'Halluin et al., 1992), microinjection (Neuhaus et al., 1987), silicon carbide fiber whisker technology (Kaeppler et al., 1992), viral vector mediated approaches (Gelvin, Nature Biotechnology 23, "Viral-mediated plant transformation gets a boost", 684-685 (2005)) and particle bombardment (see e.g. Sood et al., 2011, Biologic Plantarum, 55, 1-15). Transient transfection of mammalian cells with PEI is disclosed in Longo et al., Methods Enzymol., 2013, 529:227-240. Protocols for transformation of mammalian cells are disclosed in Methods in Molecular Biology, Nucleic Acids or Proteins, ed. John M. Walker, Springer Protocols.

For plant cells to be modified, despite transformation methods based on biological approaches, like *Agrobacterium* transformation or viral vector mediated plant transformation, and methods based on physical delivery methods, like particle bombardment or microinjection, have evolved as prominent techniques for introducing genetic material into a plant cell or tissue of interest. Helenius et al. ("Gene delivery into intact plants using the Helios™ Gene Gun", Plant Molecular Biology Reporter, 2000, 18 (3):287-288) discloses a particle bombardment as physical method for introducing material into a plant cell.

Currently, there thus exists a variety of plant transformation or transfection methods to introduce genetic material in the form of a genetic construct into a plant cell or cellular system of interest, comprising biological and physical means known to the skilled person on the field of plant biotechnology which are applicable to the various introduction techniques of biomolecules or complexes thereof according to the present invention. Notably, said delivery methods for transformation and transfection can be applied to introduce the tools of the present invention simultaneously. A common biological means is transformation with *Agrobacterium* spp. which has been used for decades for a variety of different plant materials. Viral vector mediated plant transformation represents a further strategy for introducing genetic material into a cell of interest. Physical means finding application in plant biology are particle bombardment, also named biolistic transfection or microparticle-mediated gene transfer, which refers to a physical delivery method for transferring a coated microparticle or nanoparticle comprising a nucleic acid or a genetic construct of interest into a target cell or tissue. Physical introduction means are suitable to introduce nucleic acids, i.e., RNA and/or DNA, and proteins. Likewise, specific transformation or transfection methods exist for specifically introducing a nucleic acid or an amino acid construct of interest into a plant cell, including electroporation, microinjection, nanoparticles, and cell-penetrating peptides (CPPs). Furthermore, chemical-based transfection methods exist to introduce genetic constructs and/or nucleic acids and/or proteins, comprising inter alia transfection with calcium phosphate, transfection using liposomes, e.g., cationic liposomes, or transfection with cationic polymers, including DEAD-dextran or polyethylenimine, or combinations thereof. Said delivery methods and delivery vehicles or cargos thus inherently differ from delivery tools as used for other eukaryotic cells, including animal and mammalian cells and every delivery method may have to be specifically fine-tuned and optimized for a construct of interest for introducing and/or modifying the genetic material of at least one cellular system, plant cell, tissue, organ, or whole plant; and/or can be introduced into a specific compartment of a target cell of interest in a fully functional and active way.

The above delivery techniques, alone or in combination, can be used for in vivo (in planta) or in vitro approaches. According to the various embodiments of the present invention, different delivery techniques may be combined with each other, simultaneously or subsequently, for example, using a chemical transfection for the at least synthetic transcription factor, or the sequence encoding the same, one site-specific nuclease, or a mRNA or DNA encoding the same, and optionally further molecules, for example, a gRNA, whereas this is combined with the transient provision of the (partial) inactivation(s) using an *Agrobacterium* based technique.

A plant delivery system, or a sub-component thereof, of the present invention may thus be introduced together with, before, or subsequently to the transformation and/or transfection of relevant tools for inducing a targeted genomic edit.

Likewise, methods for analyzing a successful transformation or transfection event according to the present invention are known to the person skilled in the art and comprise, but are not limited to polymerase chain reaction (PCR), including inter alia real time quantitative PCR, multiplex PCR, RT-PCR, nested PCR, analytical PCR and the like, microscopy, including bright and dark field microscopy, dispersion staining, phase contrast, fluorescence, confocal, differential interference contrast, deconvolution, electron microscopy, UV microscopy, IR microscopy, scanning probe microscopy, the analysis of plant or plant cell metabolites, RNA analysis, proteome analysis, functional assays for determining a functional integration, e.g. of a marker gene or a transgene of interest, or of a knock-out, Southern-Blot analysis, sequencing, including next generation sequencing, including deep sequencing or multiplex sequencing and the like, and combinations thereof.

In yet another embodiment of the above aspect according to the present invention, the introduction of a construct of interest is conducted using physical and/or biological means selected from the group consisting of a device suitable for particle bombardment, including a gene gun, including a hand-held gene gun (e.g. Helios® Gene Gun System, BIO-RAD) or a stationary gene gun, transformation, including transformation using *Agrobacterium* spp. or using a viral vector, microinjection, electroporation, whisker technology, including silicon carbide whisker technology, and transfection, or a combination thereof.

The practice of the disclosed methods employs, unless otherwise indicated, conventional techniques in molecular biology, biochemistry, genetics, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989; Ausubel et al., CURRENT PROTOCOLS IN MOLECULAR BIOLOGY, John Wiley & Sons, New York, 1987 and periodic updates; and the series METHODS IN ENZYMOLOGY, Academic Press, San Diego.

The present invention is further described with reference to the following non-limiting examples.

EXAMPLES

Example 1: Target Sequences

A variety of different gene editing plasmids (GEPs) was designed and used for the purpose of the present analysis. As shown below, Table 1 provides the internal name (crGEP) of the different gene editing plasmids (left column), information about the targeted gene (middle column), as well as the respective target site of selected crRNAs or sgRNAs (right column). The target sites represent the actual binding sites in a genomic target region or gene of interest.

TABLE 1

| crGEP | Gene information | Target sequence in gene |
|---|---|---|
| crGEP5 | HMG13 intron 3 near sgGEP8 | CTCGTCACGATTCCCCTCTCCTGG (SEQ ID NO: 49) |
| crGEP6 | HMG13 intron 3 near sgGEP9 | CCCACCTGAAAAGTTCGACCAGGA (SEQ ID NO: 50) |

TABLE 1-continued

| crGEP | Gene information | Target sequence in gene |
|---|---|---|
| crGEP7 | HMG13 exon 7 near gRNA-18 | TGTGTGGTCACACTTGCCAGCAG (SEQ ID NO: 51) |
| crGEP9 | Glossy 2 (Gl 2) intron 1 near exon 1 | GTGGTCGGATTTCTGGCATCGCTG (SEQ ID NO: 52) |
| crGEP43 | ZM-GLYK autoinhibitor | GTCTATGTCGATGACCAGCAGAT (SEQ ID NO: 53) |
| crGEP57 | HMG13 (for RR LbCpf1 PAM Variant) near crGEP5 | CCTCTCCTGGTCGAACTTTTCAGG (SEQ ID NO: 54) |
| crGEP58 | HMG13 (for RR LbCpf1 PAM Variant) near crGEP5 | ACCAGGAGAGGGGAATCGTGACGA (SEQ ID NO: 55) |
| crGEP59 | HMG13 (for RR LbCpf1 PAM Variant) near crGEP7 | TTATAGCACGACAAAAGTAAAAAT (SEQ ID NO: 56) |
| crGEP60 | HMG13 (for RR LbCpf1 PAM Variant) near crGEP7 | ATTGTCGTCATCATCGGCTAACAT (SEQ ID NO: 57) |
| crGEP61 | HMG13 (for RVR LbCpf1 PAM Variant) near crGEP5 | TACTTTGACTTTTCCCTTAATGAC (SEQ ID NO: 58) |
| crGEP62 | HMG13 (for RVR LbCpf1 PAM Variant) near crGEP5 | GGGCCGGTCATAAAGCAGCTCTCA (SEQ ID NO: 59) |
| crGEP63 | HMG13 (for RVR LbCpf1 PAM Variant) near crGEP7 | ACGGATAGCGCTCCTCGTTGGCGC (SEQ ID NO: 60) |
| crGEP64 | HMG13 (for RVR LbCpf1 PAM Variant) near crGEP7 | ACAATGTTAGCCGATGATGACGAC (SEQ ID NO: 61) |
| crGEP65 | Glossy2 (for RR LbCpf1 PAM Variant) near sgGEP14 | GGTAACCGTCCTCCGTACGTCGTC (SEQ ID NO: 62) |
| crGEP66 | Glossy2 (for RR LbCpf1 PAM Variant) near sgGEP14 | CCTCTCTACGACGACGTACGGAGG (SEQ ID NO: 63) |
| crGEP67 | Glossy2 (for RVR LbCpf1 PAM Variant) near sgGEP14 | GTTACGGGCAGTGCAGTTGAGCAA (SEQ ID NO: 64) |
| crGEP68 | Glossy2 (for RVR LbCpf1 PAM Variant) near sgGEP14 | CTGACTGTCCAGTGGCCACCTAGA (SEQ ID NO: 65) |
| crGEP52 | Wheat TDF (For RR LbCpf1 PAM variant) | CAGCATGGCATGGAGGGTGACGAT (SEQ ID NO: 77) |
| crGEP53 | Wheat TDF (For RR LbCpf1 PAM variant) | AGCATGGCATGGAGGGTGACGATG (SEQ ID NO: 78) |
| crGEP54 | Wheat TDF (For RR LbCpf1 PAM variant) | CGCAGGAGGAGGAGGAGCTCATCG (SEQ ID NO: 79) |
| crGEP55 | Wheat TDF (For RR LbCpf1 PAM variant) | CGCACCGCTTCAGCCCTGCAGCAC (SEQ ID NO: 80) |
| crGEP56 | Wheat TDF (For RR LbCpf1 PAM variant) | GCACCGCTTCAGCCCTGCAGCACG (SEQ ID NO: 81) |
| crGEP26 | Sugar beet ALS | GCTGCTAAACAATCAACATTT (SEQ ID NO: 82) |
| crGEP27 | Sugar beet ALS | TAAACAATCAACATTTAGGTA (SEQ ID NO: 83) |
| crGEP28 | Sugar beet ALS | ATTTAGGTATGGTTGTCCAA (SEQ ID NO: 84) |
| crGEP29 | Sugar beet ALS | TTTAGCAGCATTATCTTAAC (SEQ ID NO: 85) |
| crGEP30 | Sugar beet ALS | TATAGAACCTATCTTCCCAT (SEQ ID NO: 86) |

Example 2: Plant Protoplast Transfection

Whenever a plant protoplast transfection was used for the purpose of the experiments disclosed herein, protocols known in the art were used relying on the following steps:

The buffers and solutions used were an enzyme solution, an enzyme wash solution, an enzyme wash buffer (EWB), an MMG (glycol-mannitol magensium) buffer, e.g., containing 0.1 to 0.5 M mannitol, 15 mM to 20 mM magnesium chloride and 4 mM MES (pH10 to 40% PEG (polyethylene glycol) calcium, a stop buffer, and a W5 buffer (e.g., comprising 154 mM NaCl, 125 mM $CaCl_2$), 5 mM KCl, 2 mM MES (pH 5.7), with or without glucose).

First 20 μg (or unless otherwise specified) plasmid DNA were added to 2 ml tubes place at 4° C. Next, leaves were harvested from greenhouse of first and/or second fully expanded true leaves from 10-14 day old etiolated seedlings, and they were placed in a bag with wet paper towels. The leaves were cut into fine strips and weigh out 4.5 g. They were placed into a deep petri dish with 30 ml of enzyme solution and then into vacuum at 714 mbar for 30 minutes. Digestion was continued for 2.5 more hours on a rocker (40 rpm (between 1 and 2) at 28° C. in an incubator. During the last 5 minutes, the rocker was set to 80 rpm. Equal amounts (30 ml) of EWB were added and the mixture was mixed by gentle swirling. In a hood, a 40 Um cell strainer was pre-wetted with ~2 ml of EWB in a 50 ml conical tube. The tube was holded at angle and the protoplast solution was gently put through the filter so that the cells could run down the side of the tube. The resulting material was split into two tubes with 30 ml per tube.

Next, the cells were pelleted at 70 g for 5 minutes at RT (room temperature) and as much supernatant as possible was removed. The material was resuspended in 20 ml EWB, by letting it fall down the side of the tube and it was mixed by gentle rocking. Next, the material was centrifuged at 70 g for 5 minutes at RT. Supernatant was removed followed by a resuspension in 5 ml of EWB. It may be rocked gently to break up clumps. Cells were allowed to settle for 30 minutes. Then, cells were counted by adding 10 μl of one tube to a hemacytometer. The cells within the small squares on both sides were counted. Calculation was performed by: number of protoplasts×10^4×5 ml, for example 158 cells×10^4×5 ml=7925000.

The pellet was respuspended in 7.925 ml MMG for 10^6 cells per ml. Supernatant from settled cells was removed and the pellet was resuspended in a calculated amount of MMG. Cells should not be left in MMG for longer than 15 minutes. Next, 200 μl of resuspended protoplasts were added to each tube with DNA. 220 μl of 40% $PEG-CaCl_2$) buffer were added and it was mixed by tapping. Incubation time: for 5-10 minutes. The transfection was stopped with 880 μl of stop buffer and the mixture was mixed by gently inverting. Next, a centrifugation at 70 g for 5 minutes at RT was done and the supernatant was removed. Cells were resuspended in 1 ml of W5 buffer. 1 ml of W5 buffer was added to 6-well plate and the 1 ml of cells was added to the plate for a total of 2 ml. The cells were placed in dark cabinet for 24 hours.

Analysis was performed by taking pictures on the inverted scope, (Brightfield and either Green or Red). Place all 2 ml into a 2 ml tube and flow 1,000 cells. Spin at 70 g for 5 minutes. Finally, the supernatant was removed and the pellet was frozen.

Suitable variations of the above protocol for different target cells, plants or cellular systems are known to the skilled person. Protocols, including transient expression assays for monocot and dicot plant cells, can be obtained from Sheen, J. 2002, A transient expression assay using Arabidopsis mesophyll protoplasts, genetics.mgh.harvard.edu/sheenweb/; Yanagisawa et al., 2003, Nature 425: 521-525; Asai et al., 2002, Nature 415: 977-983; Sheen, 2001, Plant Physiol. 127:1466-1475; Hwang & Sheen, 2001, Nature 413: 383-389; Kovtun et al., 2000, PNAS 97: 2940-2945; Abel & Theologis, 1994, Plant J. 5: 421-427; Masson & Paszkowski, 1992, Plant J. 2: 829-833; Damm et al., 1989, MGG 217: 6-12; or Negrutiu et al., 1987, Plant Mol Biol 8:363-373.

Example 3: Next Generation Sequencing (NGS) Protocol

Whenever NGS was used for the experiments, the following protocol was followed: Library preparation: Libraries were prepared by two PCR steps to amplify target region and add sequencing adaptors. Barcodes were designed with the primers and added during $1^{st}$ PCR step for sample differentiating. Adaptors were added during $2^{nd}$ PCR for sequencing. Next generation sequencing (NGS): Amplicons were sequenced with Illumina Miseq 150 PEplatform. Protoplast populations were sequenced with 100,000× coverage, immature embryo and callus, agrobacteria transformed leaf samples and bombardment wheat leaf samples were sequenced with 250,000×, 300,000× and 50,000× coverage respectively. Data were analyzed using FastQC+Jemultiplexer+Trimmomatic for reads QC and demultiplexing, CRISPResso for Indel identification at the targets, and in house bash customer script for editing events calling. The whole analysis pipeline was used automatically using an in-house bash customer script.

Figure 1C:
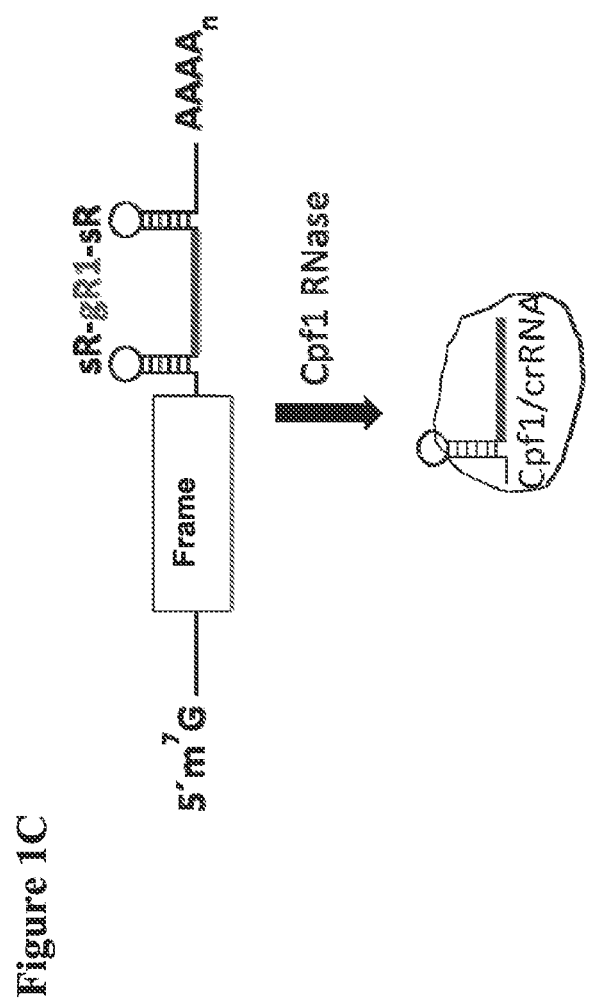
FIG. 1C shows the functional mechanism underlying the process underlying the excision of gRNA/crRNA excision from an mRNA construct by a Cpf1 enzyme. An mRNA encoding a suitable frame sequence (Frame) with two scaffold RNA sequences (sR) separated by a gRNA/crRNA in its 3' UTR (frame-sR-gR-sR) can be cleaved by a Cpf1 enzyme. If both sRs are cleaved, a functional gRNA/crRNA can be produced and loaded into a Cpf1 enzyme to perform genome editing.
Figure 1D:
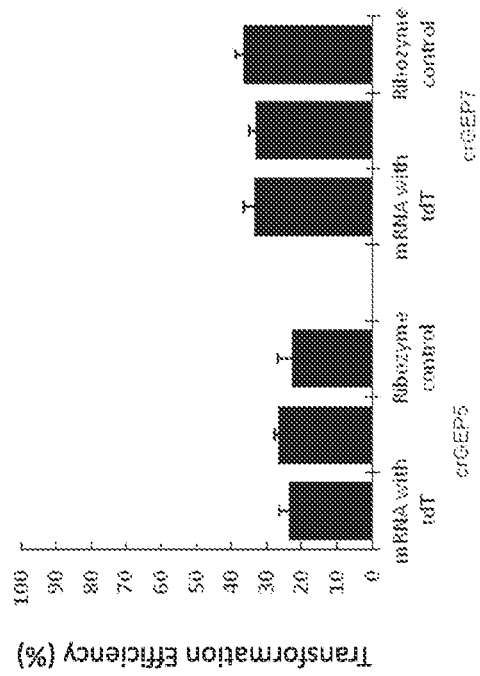
FIG. 1D shows the advantages of the embedded constructs of the present invention in comparison to a ribozyme control system when targeting two different loci of interest (cf. Example 4 below). The ribozyme control used in these experiments is a conventional ribozyme two component system (Cpf1 and crRNA provided on different expression constructs) having the HH and the HDV ribozyme sequences published by Tang et al., 2017 ("A CRISPR-Cpf1 system for efficient genome editing and transcriptional repression in plants." *Nat Plants* 3: 17018.). This experiment was done by co-delivering an LbCpf1 plasmid and the mRNA/non-mRNA embedded guide RNA into protoplasts of corn leaf cells and after 24 hrs cells are counted in a flow cytometer using reporter gene fluorescence. After genomic DNA isolation from these cells, the target sites are amplified and the PCR products get sequenced through NGS. The indel frequency seen from the samples are then normalized against the protoplast transformation efficiency seen from the flow cytometer as shown in FIG. 1E showing a graph of the protoplast transformation efficiency for each sample, in triplicate. The y-axis shown the transformation efficiency in %.
Figure 1E:
FIG. 1 (FIG. 1A to 1E) shows (FIG. 1A) an example of an embedded gRNA construct of the present invention. In this setting (on the top) the construct comprises a BdUbi10 promoter, a tdTomato (tdT) sequence as frame sequence and two scaffold regions (SC) for a cognate Cpf1 enzyme. The gRNA/crRNA is located between the two scaffold sequences. The construct further comprises a NosT terminator. The sequence on the bottom is a control construct not comprising the tdT sequence as frame sequence. Corresponding sequences are provided with SEQ ID NO: 33 and SEQ ID NO: 34, respectively.

Example 4: mRNA Embedded Cpf1 Guide RNA Delivery is a Viable Option to Replace Ribozyme Based Delivery Systems in Plant Cells This experiment was performed to compare gRNA induced indel activity from mRNA-embedded gRNA with the indel activity of gRNAs delivered by the ribozyme system. The data clearly show equivalent or even improved indel activity for mRNA embedded gRNA compared to gRNAs delivered by the ribozyme system for target gRNAs crGEP5 (easily to access target site, cf. Table 1 above) and crGEP7 (difficult to access target site, cf. Table 1 above). In contrast, the non-mRNA embedded guides clearly show highly diminished activities at those two target sites (FIG. 1C). The data provide evidence that an mRNA delivery system when properly configured is a potent tool in order to improve modification of genomic target sequences which are hardly accessible by conventional CRISPR/Cpf1 delivery systems.

The experiment was performed by co-delivery of the LbCpf1 plasmid (SEQ ID NO: 37) and the mRNA/non-mRNA embedded guide RNAs into protoplasts of corn leaf cells. Exemplary sequences of the concept vectors are shown in SEQ ID Nos: 33 and 34, respectively. A conventional ribozyme control vector is shown in SEQ ID NO: 44. Different fluorescent markers and crRNA repeats (cf. Table 1 above) were cloned into the basic vector to test the general applicability of the technique and to evaluate the efficiency for different target sites in different settings. After 24 hrs, cells were counted in a flow cytometer using reporter gene fluorescence. After DNA isolation from these cells, the target sites were amplified and the obtained PCR products were sequenced using NGS technology. The indel frequency observed for the different samples were then normalized against the protoplast transformation efficiency seen from the flow cytometer (data not shown).

To test whether mRNA embedded gRNAs and/or gRNAs deliverered in the ribozyme system result in InDel activity at target genomic loci in plants of the species Beta vulgaris, the following experiment was performed.

Figure 8A:
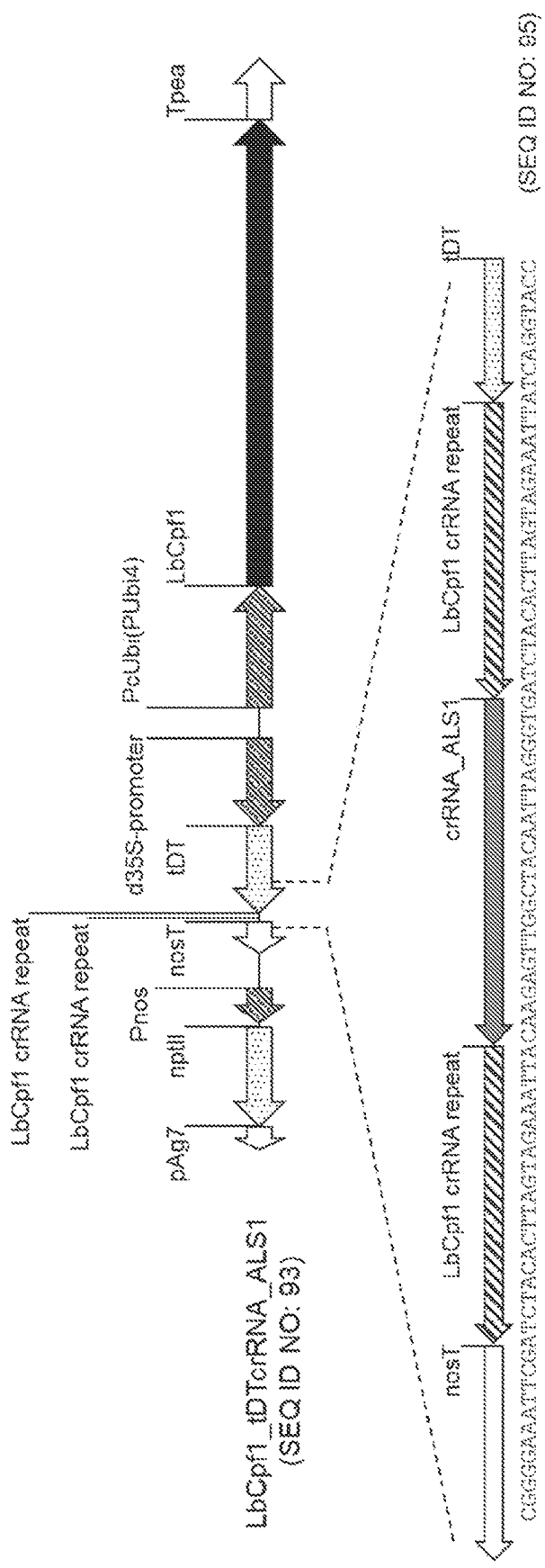
FIG. 8 (FIGS. 8A and B) shows the design of the binary vectors used for in planta proof of LbCpf1 mediated genome editing. The LbCpf1_JDTcrRNA_ALS #1 construct harbors expression cassettes for nptII, LbCpf1 and crRNA_ALS #1, which is directed to the target BvALS #1. The crRNA is embedded in a Pol II-driven RNA transcript as described before in Zhong et al., 2017 (FIG. 8A). The binary vector in FIG. 8B shows expression cassettes for nptII, LbCpf1 and crRNA_ALS1, to the BvALS1 sequence (flanked by the HH and HDV ribozymes). This system of expression of crRNA is known from Tang et al. (2017).

Binary vectors were created, which harbor (i) an nptII resistance cassette for in planta selection, (ii) a PcUbi4::Cpf1 expression cassette and (iii) a crRNA, which targets one of five different target regions within the target gene BvALS (Table 2). For each of the five protospacer two different crRNA versions were tested. In a first version (tDTcrRNA_ALS1-ALS5) the crRNA is embedded in a Pol II-driven RNA transcript as described before in Zhong et al., 2017 (Zhong, G., et al. (2017). "Cpf1 proteins excise CRISPR RNAs from mRNA transcripts in mammalian cells." Nat Chem Biol 13(8): 839-841). This transcript includes an mRNA encoding the fluorescent protein tDT (FIG. 8A).

Figure 8B:
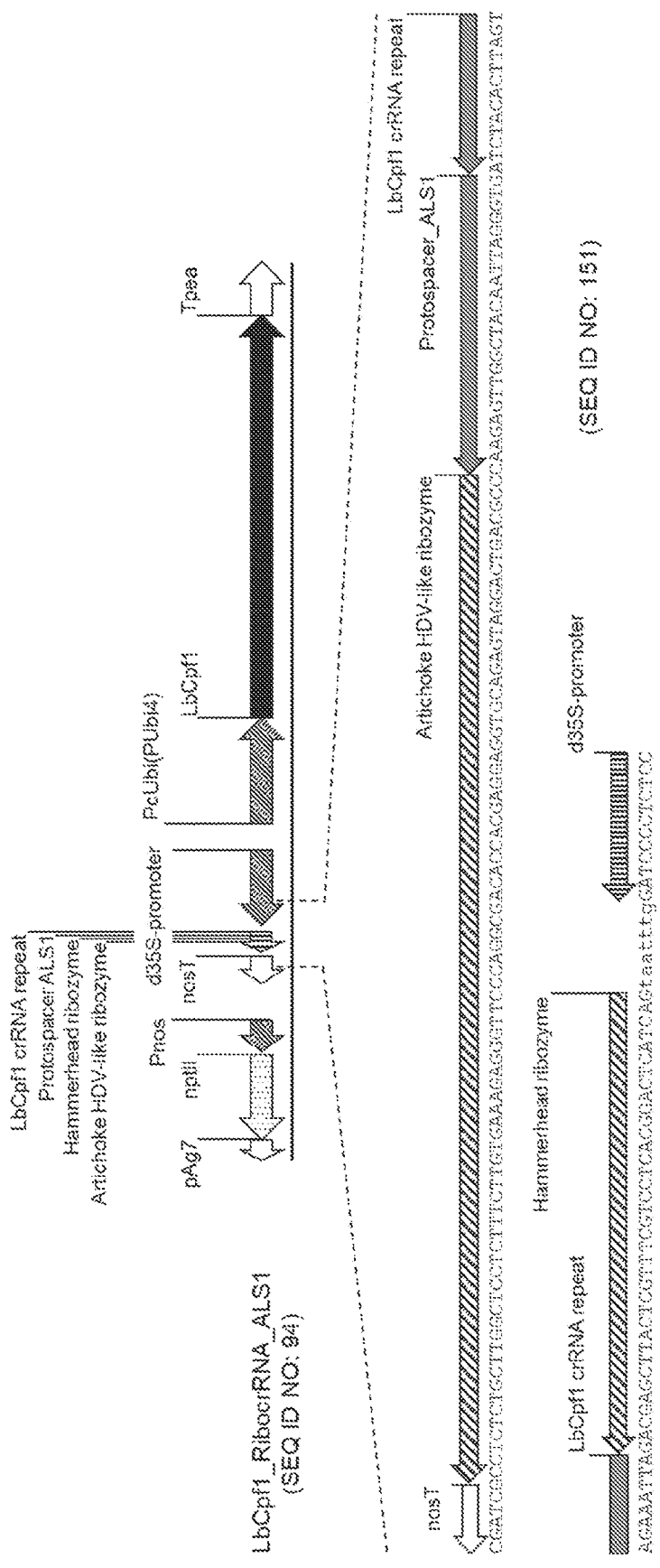

The second crRNA version (RibocrRNA_ALS1-ALS5) produces the crRNA from a Pol II promoter using the ribozyme-based strategy described in He et al., 2017 (He, Y., et al. (2017). "Self-cleaving ribozymes enable the production of guide RNAs from unlimited choices of promoters for CRISPR/Cas9 mediated genome editing." J Genet Genomics 44(9): 469-472). Thereby, the crRNA production unit is composed of three parts: the 5'-end encoding the Hammerhead (HH) ribozyme, the middle part encoding the crRNA, and the 3'-end encoding the Artichoke HDV-like ribozyme (FIG. 8B). The primary transcripts will undergo self-cleavage catalyzed by the intrinsic nuclease activities of the ribozymes to release the mature and desired crRNA.

TABLE 2

Selected PAM plus protospacer within the target gene BvALS and nomenclature of the corresponding crRNAs.

| crRNA | PAM | Protosparer | |
|---|---|---|---|
| crRNA_ALS #1 | TTCT | CACCCTAATTGTAGCCAACTCTTG | SEQ ID NO: 146 |
| crRNA_ALS #2 | TTTA | GCAGCATTATCTTAACTGGGAGAT | SEQ ID NO: 147 |
| crRNA_ALS #3 | TTTA | GGTATGGTTGTCCAATGGGAAGAT | SEQ ID NO: 148 |
| crRNA_ALS #4 | TTTC | CAAGGTATGTATGTGCCCGGTTAG | SEQ ID NO: 149 |
| crRNA_ALS #5 | TTTG | GAAGGGTTTCCAAGGTATGTATGT | SEQ ID NO: 150 |

The binary vectors were transformed into Agrobacteria strain AGL1-1. AGL-1 harbouring the genome editing constructs were cultivated in medium A, supplemented with 100 mg/l Carbenicillin, 100 mg/l Rifampicin, 50 mg/l Spectinomycin and 25 mg/l Streptomycin for cultivation. Afterwards, Agrobacterium was suspended in medium B at OD600=0.8 and used for vacuum infiltration of 5×5 mm large leaf explants from three weeks old in vitro shoots of the genotype S706. Co-Cultivation was done on Medium C at 21° C. in the dark. Three days after infiltration explants were transferred to Medium D containing 500 mg/l Timentin. Sampling of the infiltrated leaf explants for subsequent DNA extraction and NGS analysis was done 10 days after infiltration. For each infiltrated construct two times 15 leaf explants were pooled for DNA extraction and handled as two biological replicates.

For detailed medium composition see table 3.

Figure 9:
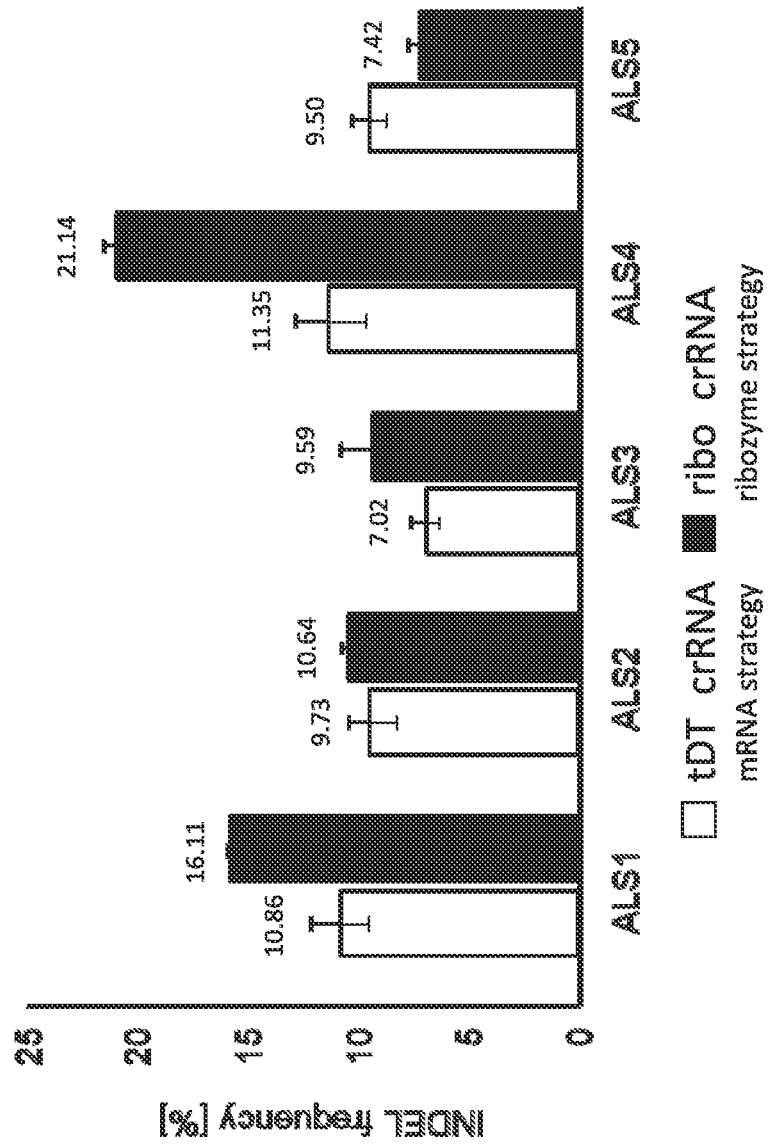
FIG. 9 (FIG. 9) shows the results of Cpf1-mediated InDel frequencies in five different target regions (ALS #1-5) of BvALS. For each target region two different crRNA versions (tDT_crRNA [mRNA strategy] or Ribo_crRNA [ribozyme strategy]) were tested. Bars represent mean value of two biological replicates. Error bars represent the standard deviation error.

Vaccum infiltrated sugar beet leaf explants were analyzed via NGS to determine the LbCpf1-mediated INDEL frequency within the target gene BvALS (FIG. 9). Over all, InDel frequencies between 7% and 21% were observed. With one exemption, direct comparison of the two crRNA versions (tDTcrRNA vs. RibocrRNA) revealed higher InDel frequencies of the crRNAs, which are produced via the ribozyme strategy.

TABLE 3

Medium composition.

| Medium | Composition |
|---|---|
| Medium A | 5 g/l tryptone + 2.5 g/l yeast extract + 1 g/l NaCl + 5 g/l mannitol + 0.1 g/l MgSO$_4$x7H2O + 0.25 g/l KH$_2$PO$_4$ + 1 g/l glutamic acid, pH 7.0, pH 7.0 |
| Medium B | 440 mg/l CaCl$_2$x2H$_2$O + 170 mg/l KH$_2$PO$_4$ + 1.9 g/l KNO$_3$ + 180.7 mg/l MgSO$_4$ + 1.65 g/l NH$_4$NO$_3$ + 2 mg/l BAP + 40 µg/ml Acetosyringone + 20 g/l sucrose + 2 g/l glucose, pH 6.0 |
| Medium C | 440 mg/l CaCl$_2$x2H$_2$O + 170 mg/l KH$_2$PO$_4$ + 1.9 g/l KNO$_3$ + 180.7 mg/l MgSO$_4$ + 1.65 g/l NH$_4$NO$_3$ + 2 mg/l BAP + 40 µg/ml Acetosyringone + 20 g/l sucrose + 2 g/l glucose + 10 g/l agar, pH 6.0 |
| Medium D | MS salts + 15 g/l sucrose + 2 mg/l BAP + 8 g/l agar, pH 6. |
| Medium E | MS salts + 30 g/l sucrose + 0.25 mg/l benzyladenine (BAP) + 10 g/l agar, pH 6.0 |
| Medium F | MS salts + 30 g/l sucrose + 1 mg/l GA3 + 1 mg/l Thidiazuron (TDZ) + 10 g/l agar, pH 6.0 |
| Medium G | MS salts + 30 g/l sucrose + 1 mg/l GA3 + 1 mg/l TDZ + 500 mg/l Timentin + 10 g/l agar, pH 6.0 |
| Medium H | MS salts + 30 g/l sucrose + 1 mg/l GA3 + 1 mg/l TDZ + 500 mg/l Timentin + 100 mg/l paromomycin + 10 g/l agar, pH 6.0 |
| Medium I | MS salts + 30 g/l sucrose + 0.25 mg/l benzyladenine (BAP) + 100 mg/l kanamycin + 10 g/l agar, pH 6.0 |
| Medium J | MS salts + 30 g/l sucrose + 6.25 mg/l NAA + 10 g/l agar, pH 6.0 |

Example 5: HDV-Like Plant-Derived Ribozymes Show High Indel Activity and are Suitable as HDV Replacements This experiment was performed in order to test the activity of specific plant-derived autocatalytic ribozymes and their suitability to replace HDV ribozymes. Therefore, plant-derived HDV-like sequences from Rice, Sunflower and Artichoke were identified, cloned and specifically tested for their ability to replace the original HDV ribozyme sequence of Hepatitis-delta virus. Specifically, the constructs with plant-derived HDV ribozyme sequences were tested for their indel activity at two previously validated targets sites (cf. Table 1 above) using the crGEP5 and crGEP6 gRNAs flanked by the HH ribozyme at the 3'-end (see SEQ ID NOs: 17 and 45, 46 and 48) and the respective plant-derived HDV-like ribozyme at the 5'-end (SEQ ID NOs: 19, 21 and 25 and 45, 46 and 48). Further, a specific strategy vector was constructed comprising a HH and a conventional HDV ribozyme sequence, a LbCpf1 RNA scaffold sequence, and suitable regulatory elements and a beta-lactamase encoding gene (SEQ ID NO: 44). Sequences of interest, in particular suitable gRNAs/crRNAs can be easily cloned into this vector. Plasmid cloning vectors suitable to insert a coding sequence of interest were constructed for the HDV-like ribozymes characterized, i.e., for rice-, sunflower- and artichoke-derived HDV sequences (see SEQ ID NOs: 45, 46 and 48).

Figure 2B:
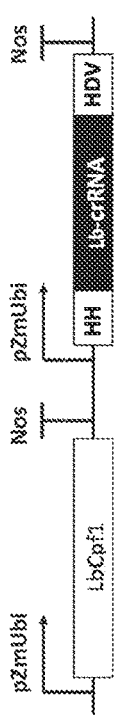
Figure 2C:
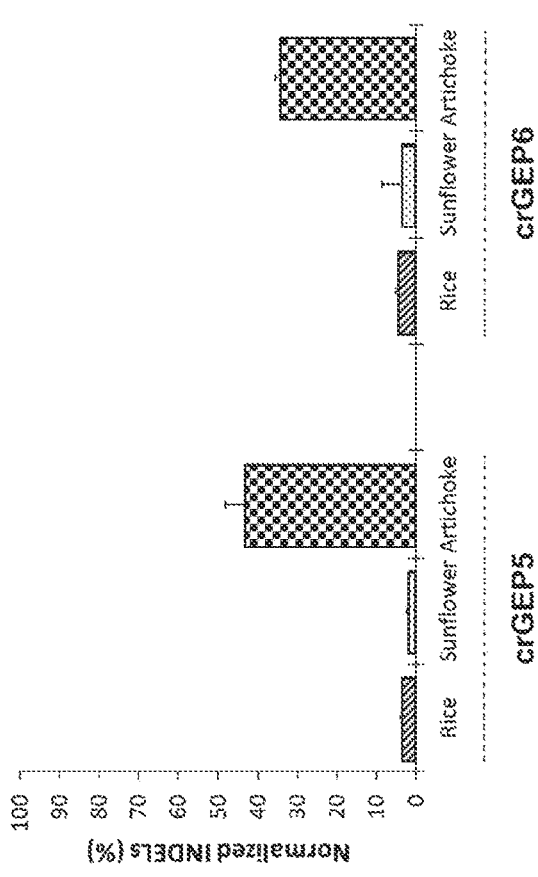

As can be seen from the results shown in FIG. 2B, the HDV-like sequence derived from Artichoke showed significant indel activity at both target sites (crGEP5 and crGEP6, see also Table 1), while the Rice and Sunflower derived sequences showed poor indel activity. Furthermore, the activity of the Artichoke derived sequence was compared with the activity of the HDV ribozyme sequence. The data indicate that the Artichoke derived sequence results in up to 50-60% indel activity (2-5% indel activity for Rice and Sunflower sequences) compared to the original HDV sequence (FIG. 2C).

This surprising observation is in clear contrast to the teaching of the prior art which could not present evidence for the activity of a plant-derived HDV-like ribozyme sequence in vitro or in vivo when using a plant-derived HDV-like ribozyme in a recombinant way. The data of the present experiment therefore indicate that plant-derived HDV-like ribozyme sequences could potentially replace the original HDV sequences in gRNA ribozyme delivery systems thereby avoiding the use human pathogen-derived sequences and time consuming and expensive deregulation processes in product development in biotechnology.

The above described experiment was performed in the same manner as outlined in Examples 2 and 3 above. Constructs were introduced into protoplasts, and indel activity from the action of the RR or RVR versions was determined by NGS.

The sunflower HDV-like ribozyme sequence is highly homologous to the HDV-like ribozyme sequence derived from artichoke. Due to the accidental usage of a truncated sunflower HDV-like sequence (SEQ ID NO: 22) which showed low indel activity, it was further tested whether the correct full-length sunflower HDV-like ribozyme sequence (SEQ ID NO: 24) results in increased indel activity comparable to the indel activity observed for the artichoke HDV-like ribozyme sequence. Therefore, the indel activity at two target sites crGEP7 and crGEP43 was investigated using delivery by either the HDV ribozyme sequence (SEQ ID NO: 28) or the full-length sunflower HDV-like ribozyme sequence (SEQ ID NO: 24) in the expression plasmids. These constructs were co-delivered into protoplasts along with the LbCpf1 nuclease and samples were collected after 24 hrs for analysis after flow cytometry was carried out for transformation efficiency. The NGS analysis of target sites gave % raw indels which were multiplied by each samples' % protoplast transformation efficiency to give % indel formation, normalized to the protoplast trabsformation efficiciency.

Figure 10:
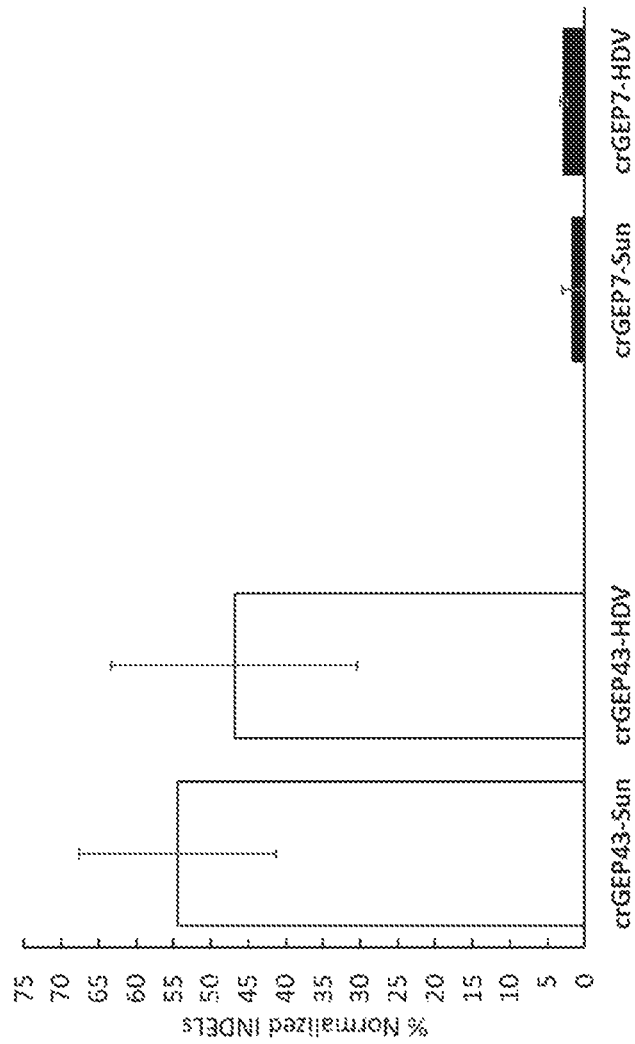
FIG. 10 (FIG. 10): Comparison of activity of Sunflower-HDV like sequence to the original HDV sequence in the ribozyme-mediated delivery of guide RNA to two targets in a protoplast assay. Using constructs expressing LbCpf1 and guide RNAs flanked by either HH and HDV or HH and Sunflower HDV sequence, the normalized INDELs [%] seen at either target 43 and 7 are equivalent, suggesting that these two sequences are equally active in their function.

The results are summarized in FIG. 10 and indicate that the % indel activity of full-length sunflower HDV-like ribozyme sequence is equivalent or even greater than the indel activity of the original HDV ribozyme sequence confirming previous data obtained for the artichoke HDV-like ribozyme sequence. The herein presented data therefore strengthens the hypothesis that plant-derived HDV-like ribozyme sequences could potentially replace the original HDV sequences in a gRNA ribozyme delivery systems, making the use of human pathogen-derived sequences superfluous.

Example 6: LbCpf1 PAM Variants RR and RVR Show Activity at Multiple Target Sites, Including Difficult to Access Genomic Loci The experiment was performed to test different PAM variants (i.e. a RR and RVR versions previously described for the mammalian cell system (Gao et al. (2017) Nat Biotechnol, 35(8): 789-792)). Those PAM variants (SEQ ID NOs: 35, 36, 38 and 39) were specifically codon-optimized in contrast to the variants available. Specifically, the PAM variants were tested against targets in the neighborhood of the control target sites of crGEP5, crGEP7 and sgGEP14, and crGEP9 in the HMG13 and Glossy2 genes (cf. Table 1 above). Based on this data the inventors were able to identify multiple target sites at which the RR PAM motif shows more than 50% indel activity compared to the wildtype control PAM sequences of LbCpf1 (SEQ ID NO: 16). Based on this data the authors further concluded that previously difficult-to-cut-target sites like glossy2 (due to their GC-rich sequences), are now accessible by using modified PAM sequences like the RR PAM motif. This motif resulted in 30% indel activity rates compared to 0.36% of the original PAM sequence (control) (see FIG. 3B). The data indicate that the expanded PAM repertoire can be a promising alternative to target genomic sequences which would be otherwise not accessible by using the wildtype Cpf1 PAM sequences (SEQ ID NO: 16). The experiment was performed in the same manner as described in Examples 2 and 3 above.

The above results were also confirmed by post-published data which show that Cpf1 PAM variants RR and RVR are able to recognize difficult to access genomic loci (Zhong Z. et al. (2018), Plant genome editing using FnCpf1 and LbCpf1 nucleases at redefined and altered PAM sites, Molecular Plant 11, 7:999-1002; and Li S. et al. (2018), Expanding the scope of CRISPR/Cpf1-mediated genome editing in rice, Molecular Plant 11, 7:995-998).

Example 7: Promoter Swaps on Cpf1 and crRNA Modules to Identify Best Expression Strategy This experiment was performed in order to validate different promoter sequences and their ability to induce expression and indel activity of nuclease and/or ribozyme constructs (see FIGS. 4A and 4B). As can be seen from the respective data, highest expression and/or activity of the Cpf1 nuclease construct was observed for the expression under the control of the promoter pBdUbi10 (SEQ ID NO: 1), whereas highest activity for the gRNA/ribozyme construct was observed for the expression under the control of the pZmUbi1 promoter sequence (SEQ ID NO: 2).

The effect of different promoter sequences on LbCpf1 nuclease expression was tested by validating their indel activity at the two target sites crGEP5 and crGEP7 (cf. Table 1 above). The results in FIG. 4A indicate that replacement of the promoter pZmUbi1 for the LbCpf1 construct (cf. SEQ ID NO: 37 with the promoter sequence pBdUbi10 significantly improves nuclease expression and indel activity compared to pZmUbi1, whereas the use of pOsActin1 (SEQ ID NO: 3) does not improve the expression and/or indel activity of the nuclease construct. The data therefore clearly indicate that the promoter pBdUbi10 is a promising alternative to replace the promoter pZmUbi1 in the respective construct in order to increase LbCpf1 expression and indel activity at the tested target sites.

Figure 4B:
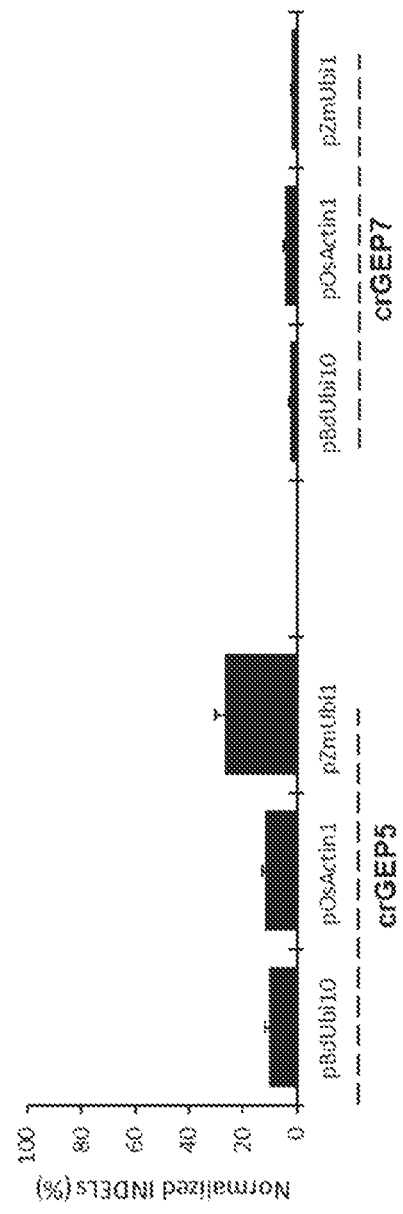

Similar experiments were performed for gRNA/ribozyme constructs by replacing the ZmUbi1 promoter in pGEP296 with either the BdUbi10 promoter or the OsActin promoter (FIG. 4B). Here, the data indicate that best expression and indel activity was obtained for the promoter sequence pZmUbi1.

In summary, the data provide evidence that the expression and indel activity of the CRISPR/Cpf1 system can be fine-tuned by the use of specific promoter sequences for the different expression constructs needed to provide a functional CRISPR system.

Example 8: Head to Head Comparison of pUbi1 vs pBdUbi10 Activity Driving Either RR or RVR Version of LbCpf1 Across Target Sites in HMG13 or G12

This experiment was performed to test the promoter strength to drive expression of RR (cf. SEQ ID NOs: 35 and 38) or RVR (SEQ ID NOs: 36 and 39) version of LbCpf1. The promoters pZmUbi1 versus pBdUbi10 were tested for their capability to drive nuclease expression in a targeted way by also testing activity at the same targets for both constructs. The data indicate that the BdUbi10 promoter clearly outperformed the ZmUbi2 promoter at each target, further bolstering the results that the pBdUbi10 promoter is superior in driving nuclease expression in the plant system (cf. FIG. 6, Table 1).

Figure 5B:
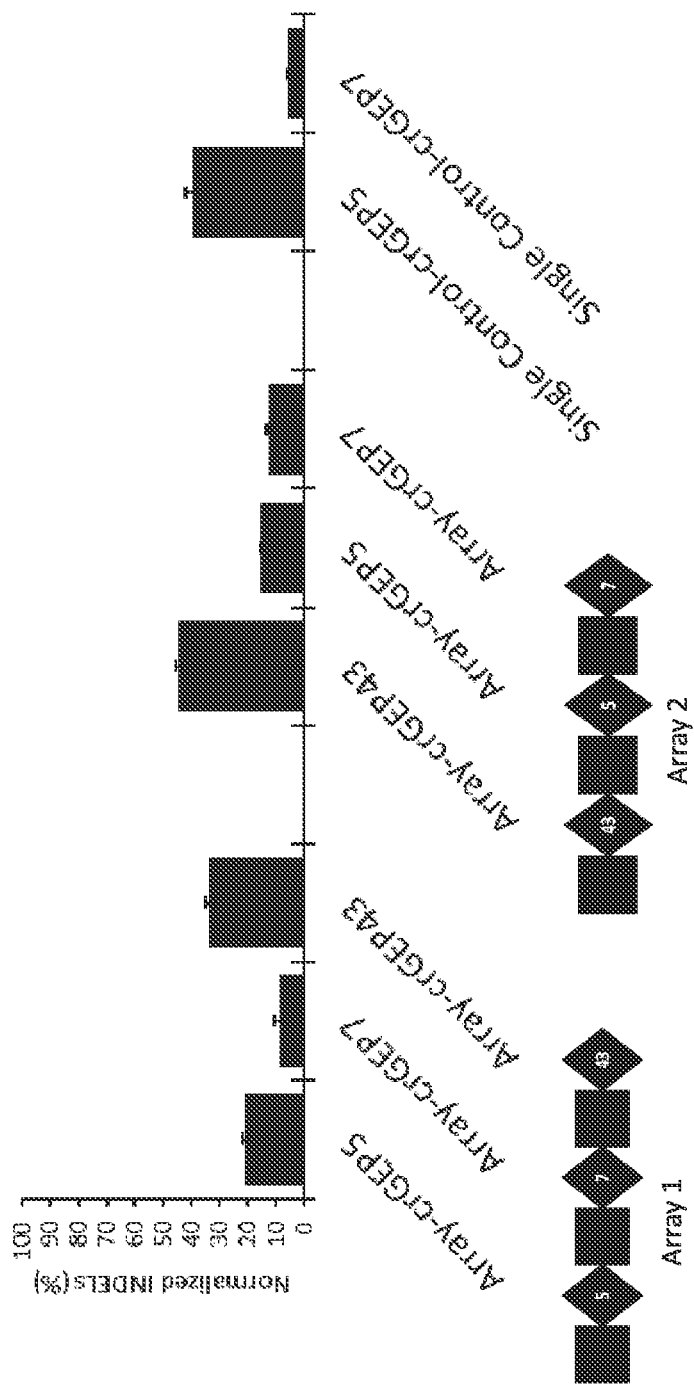
FIG. 5B shows the results on an experiment, wherein the ability of the ribozyme system to disrupt more than one target simultaneously was tested by expressing three guides, crGEP5, crGEP7 and crGEP43 (cf. Table 1 below) from an array format. A second array with the three guides in the order 43, 5 and 7 was also tested. Based on these results, the indel activity at each guide in decreasing order remained the same irrespective of its position in the array. Further details can be found in Example 9 below.
Figure 5C:
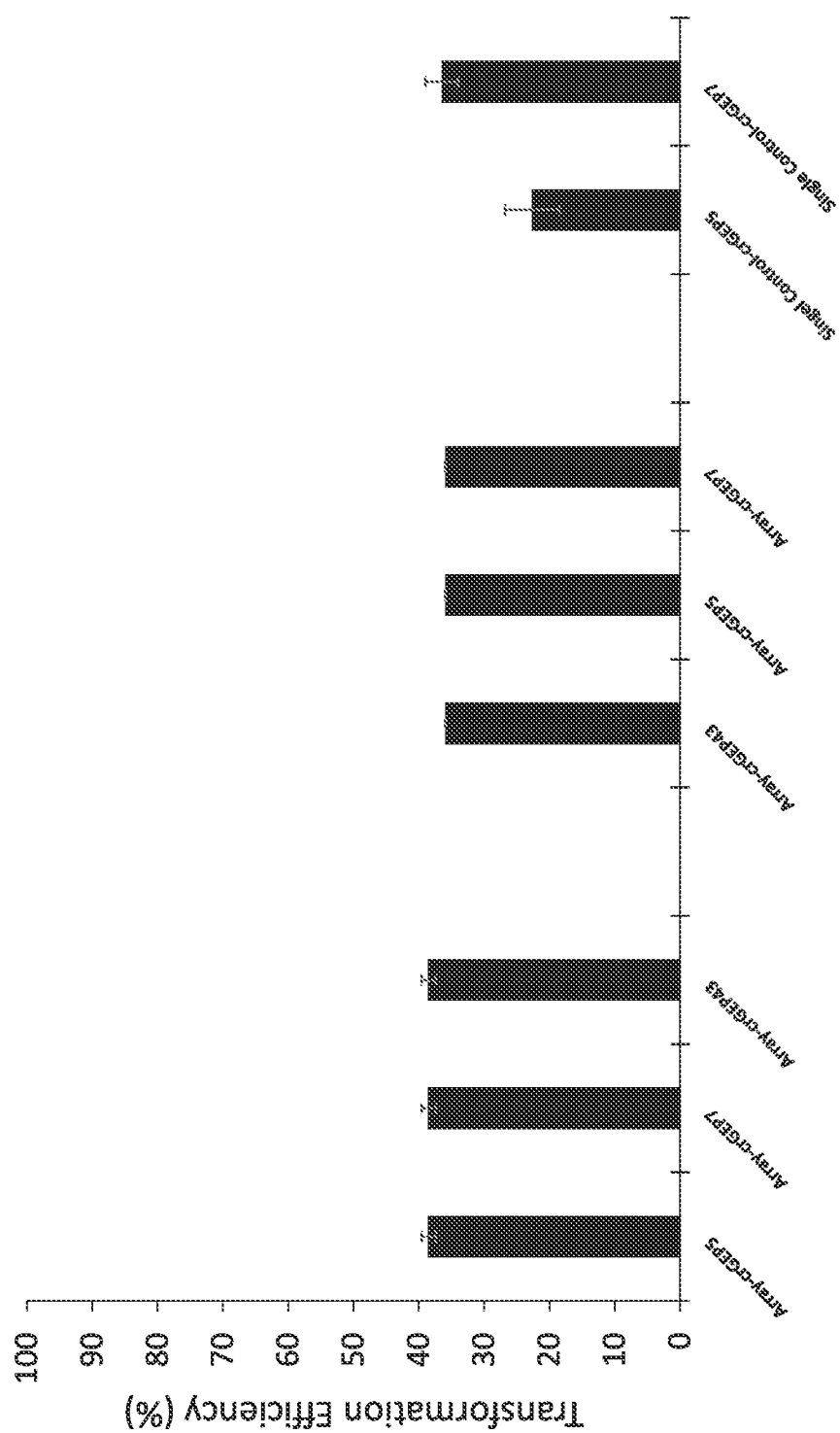
FIG. 5C shows, as a control, the transformation efficiency of the various arrays presented in FIG. 5B.

Example 9: Multiplexing—Ribozyme-Based gRNA Arrays Efficiently Disrupt Multiple Target Sites This experiment was performed in order to test the ability of the gRNA/ribozyme system to disrupt more than one target simultaneously by the expression of three gRNAs, namely crGEP5, crGEP7 and crGEP43 from an array format (cf. Table 1). Based on the data shown in FIG. 5B, the authors concluded that the indel activity for each gRNA remains unchanged irrespective of its position in the array (see indel activity for array 1 compared to the indel activity of array 2). Although the activity of gRNAs tested in the arrays were slightly lower and/or comparable to the activity of the respective gRNA when expressed in isolation, the data nevertheless indicate that gRNA arrays can be used to simultaneously target multiple genomic sequences in plant cells. The activity from the arrays was lower or comparable than control single guides and this experiment thus provided a proof of concept for multiplex targeting using the Ribozyme strategy.

Figure 7:
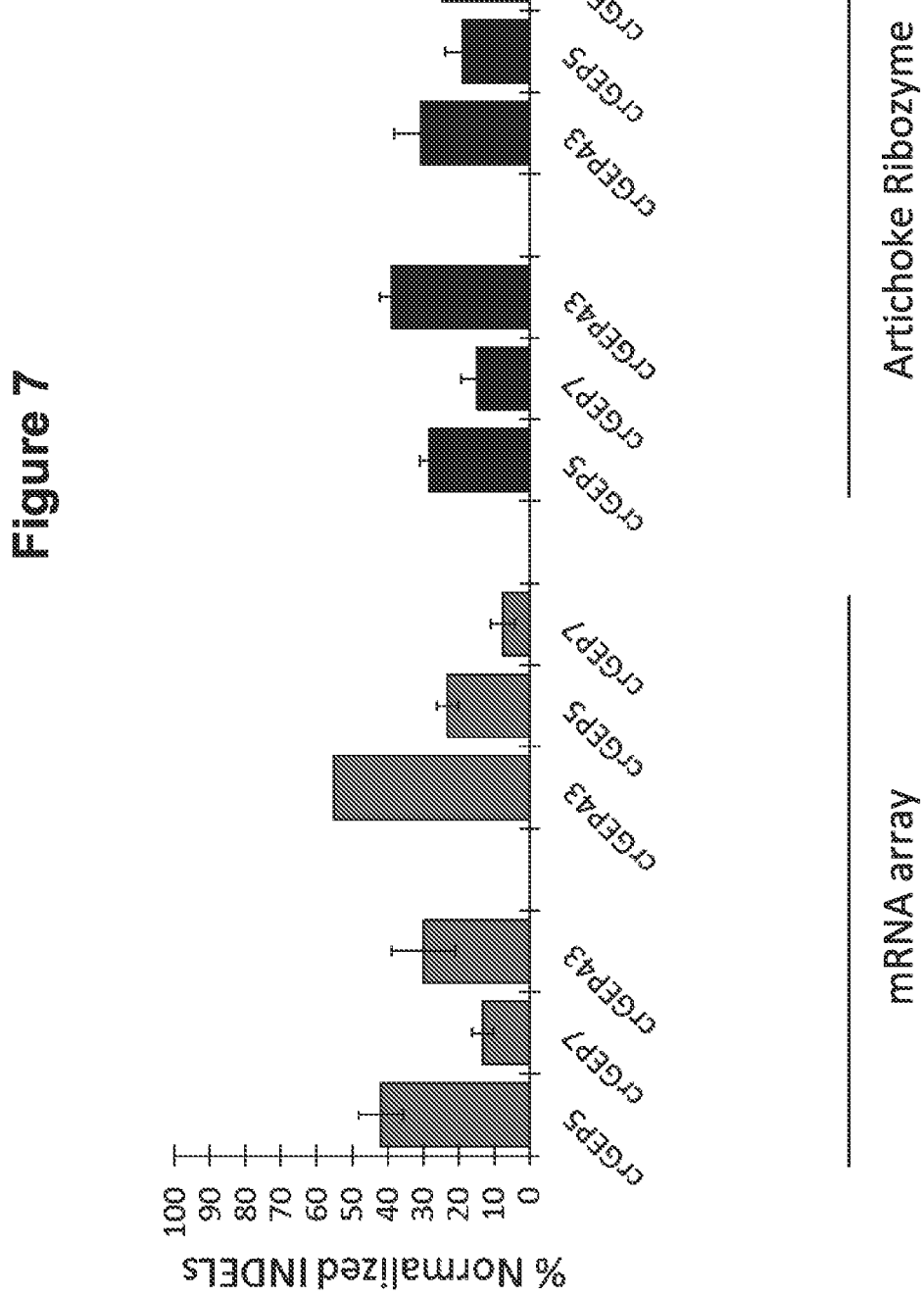
FIG. 7 (FIG. 7) shows the targeted comparison of two arrays with three targets in different order across the two systems of the present invention, the mRNA embedded delivery system and the Artichoke Ribozyme based array, respectively. For further details, see Table 1 and Example 10 below.

Example 10: mRNA-Based Guide Arrays and Artichoke Ribozyme-Based Arrays do Show Activities at Individual Sites Comparable or Better than Control Single Guides In this experiment two arrays with three targets (Table 1 and FIG. 7) in different order across the two systems analyzed herein, the mRNA embedded delivery system carrying the corresponding LbCpf1 crRNA as detailed in Table1 and the Artichoke Ribozyme based array carrying the corresponding LbCpf1 crRNA as detailed in Table1, were extensively compared. Results are shown in FIG. 7. The controls are the single targets in the HDV ribozyme version. Clearly both systems work well. In the artichoke array the target crGEP43 is best performing irrespective of its position while in the mRNA array the first crRNA in the in the array performs the best. Both systems seem to show activity at least comparable to, or even better than single guide RNAs.

The array systems were introduced into base vectors pGEP424 for mRNA array or pGEP376 for Artichoke based array. The array sequences sequence of crGEPs 5/7/43 and crGEPs 43/5/7 correspond to the same sequence as described above. The vector sequences used in the mRNA arrays (i.e. for vectors pGEP471 and pGEP472) and the vector sequences used for the artichoke arrays (i.e. for vectors pGEP473 and pGEP474) are set forth in SEQ ID NO: 68 to 71.

Example 11: An Optimized Cpf1 Nuclease System for Corn and Wheat Cells

To proof functionality of the Cpf1 system in corn, corn ears were harvested at 9-10 days post pollination and immature embryos (IE) were extracted from individual kernels. The embryos were placed on culture medium containing 2,4 D and cultured 2 days in preparation for transformation by particle bombardment. On the day of transformation the IE were transferred to another medium with high osmotic potential at least 4 hrs prior to particle bombardment to further prepare them. Following the 4 hrs pretreatment, the IE were bombarded 2× with 0.6 µM gold particles coated with the nuclease plasmid and crRNA plasmid. The day after bombardment, embryos were transferred off of the osmotic medium and then cultured for 3 days. During this process, the fluorescent marker was expressed and seen as distinct fluorescent spots on the surface of the treated IE. Excess IE explants are bombarded and then a subset of the explants were selected based on having the highest number of fluorescent cells. Approximately half of the bombarded explants are added together as a pooled sample for DNA extraction and then submitted for amplicon deep sequencing via the NGS process. After bombardment of these explants the nuclease and crRNAs are expressed in the cells where DNA was delivered and provided the activity needed for genome editing (SDN-1 approach). This activity was detected using amplicon deep sequencing despite the dominant presence of wild type cells without editing.

FIG. 11 shows a number of high efficiency targets based on protoplast data. In IE tissue, the highest values that have been observed for transient activity are between 0.2 to 0.3%. In this experiment the inventors had two samples, one with crGEP75 and one with crGEP77, that were approaching 0.1% activity at their respective target sites. The sequence data shows the highest numbers of sequence reads and are demonstrating that the deletions are in the expected region of the proto-spacer.

Furthermore, it was tested whether a wheat protoplast system can be used to identify best guides for a given target locus. Therefore, five guides for Cpf1 (RR variant) were designed at the TaTDF locus in the same vicinity of an efficient Cas9 guide location. Each of these guides were cloned into the ribozyme delivery base vector and co-delivered with the RRLbCp1 nuclease into wheat protoplasts by PEG transformation. 24 hrs later, samples were collected and after flow cytometry were analysed for transformation efficiency. NGS analysis for target sites gave % raw InDels which were multiplied by each samples % protoplast transformation efficiency to give the normalized InDel efficiency. From the NGS data it was evident that guide crGEP56 was the most efficiently cut target in all three genomes of wheat (see FIG. 12).

Furthermore, five additional Cpf1 genes (SEQ ID NO: 72-76) encoding the same protein have been designed and generated and are currently tested in monocots for their gene editing efficiency. The five variants of LbCpf1 that have been synthesized are sequences generated as codon-optimized variants from three vendors or a published version from Tang et al 2017, Nature Plants 3:17018.

Example 12: The Cpf1 Nuclease can be Used to Generate Heritable Edits in Corn Plants To test whether the Cpf1 nuclease can be used to generate heritable edits in corn plants high type II immature embryos were co-bombarded with 2 constructs and 15 ng per shot with the chemical compound Trichostatin A (TSA), which was included to stimulate cell division and/or gene editing events. The constructs encoded the genes needed to obtain SDN-1 events at the HMG13 gene locus in corn. The first construct comprises a ZmUbi1 promoter controlling the expression of LbCpf1 gene and a separate fluorescent marker gene under control of the 2XCaMV35S promoter. The second plasmid encodes the crRNA gene under control of a ZmUbi1 promoter. The constructs were bombarded to either transiently or stably express the LbCpf1 gene and the crRNA in order to obtain SDN-1 edits early in the cell culture process that could later be captured in regenerated plants from cultures. Regenerated $T_0$ plants were moved to phyta-trays and placed in the growth chamber for continued growth and recovery. Until sufficient amount of plants of the $T_0$ population had grown, plants were sampled to detect SDN-1 events by capillary electrophoresis (CE) assay. The CE assay was developed to identify insertions and deletions (InDels) in amplicon pools generated by PCR amplification of a selected Cpf1 target locus. Pooled leaf tip samples were taken from each individual plant to facilitate detection of SDN-1 events even if the pants were chimeric for the editing event. Positive $T_0$ plants were moved to soil in flats within approximately 3 weeks of sampling to ensure the recovery of viable plants to the greenhouse. Once the plants were established in soil, a second round of analysis was initiated consisting of repeating the capillary electrophoresis with a new leaf sample and later as the plant was developing, additional samples for PCR and sequence analysis were collected. By this approach, plants which were chimeric for the SDN-1 edit were easier to detect.

Following molecular confirmation of SDN-1 in plants and their sufficient growth in flats, plants were transferred to pots for growth to fertility and seed recovery. SDN-1 and wild type A188 plants were used in reciprocal crosses to insure good pollination and to better insure the recovery of the SDN-1 event in the next generation (Hill X A188, A188 X Hill). Approximately 15-20 days after pollination, one ear was harvested and surface sterilized for immature embryo extraction. Immature embryos were extracted from kernels and placed embryo axis side down on a basic MS based embryo culture medium and cultured for 3 days in the dark which initiated radicle and plumule development. Next, they were transferred to the light for normal plant development and once the plants were of sufficient size they were sampled for detection of the edit to confirm transmission to the $T_1$ generation.

Figure 13:
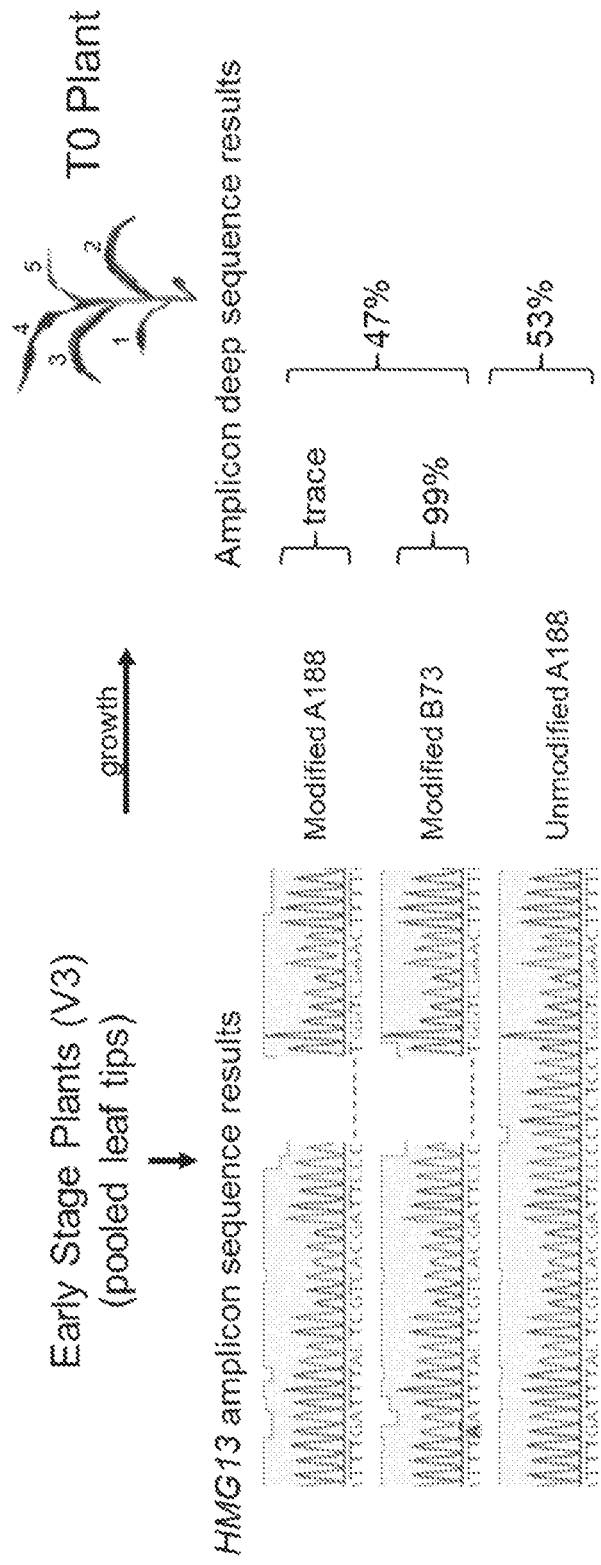
FIG. 13 (FIG. 13): Demonstration of Cpf1 editing and transmission of the edit in whole plants. T0 plants were screened by Cappillary Electrophoresis (CE) for editing leading to identification of three clonal plants with same 6 bp edit at the V3 leaf stage. New leaf growth to v5 leaf stage was checked by CE and showed presence of same amplicon. NGS sequencing of pooled leaves showed presence of the same edits with half traces of wildtype sequence and half traces showing edits conforming a heterozygous plant. T1 progeny was also sequenced shown to contain the edit segregating in a mendelian fashion.

The obtained data confirmed SDN-1 edits and inheritance of two InDel events generated by Cpf1 in corn embryos which regenerated into whole plants (FIG. 13 and Table 4). Approxiamtley 185 high type II immature embryos were co-bombarded with the constructs described for SDN-1 at the HMG13 targte site. The Cpf1 gene construct also carried a constitutive red fluorescent marker gene (tdTomato). Embryos were cultured to induce type II callus and calli were analyzed for the expression of the red fluorescent marker gene. Approximately 1100 $T_0$ plants were regenerated and transferred to phyta-trays for additional growth and recovery. Pooled leaf tip samples were taken from each plant or small plant cluster for DNA extraction in multi-well plates. Genomic DNA was extracted and submitted for the capillary electrophoresis assay. One event had 5 regenerated shoots and each of the 5 demonstrated the presence of the same 6 bp deletion in the amplicon (FIG. 13). These plants were introduced into the plant recovery process and 3/5 were able to be recovered to the greenhouse. Following transplant to soil and establishment of the plants by demonstration of new growth, new pooled leaf tip samples were taken for the CE assay and used to confirm that the deletion was still detectable in the growing $T_0$ plants at the V4 to V7 stage. Individual leaf samples were taken following additional plant growth and transplant to pots. PCR was used to generate amplicons from each individual leaf sample and then individual amplicons were sequenced by first capturing them in a plasmid and then cloning them for sequencing. The inventors were able to show that all of the amplicons shared the same InDel sequence and it appeard that the plants were not chimeric for the genome edit. These same DNA samples were submitted to an NGS process based on amplicon deep sequencing. The results shown in FIG. 13 demonstrate that approximately 53% of the samples was unmodified at the target site and 47% was modified with the 6 bp deletion. Although there was a trace amount of this deletion detected in the A188 genome, most was in the B73 genome as was evident by the presence of a G to A single nucleotide polymorphism (SNP).

Next, plants were grown to feritility and then pollinated. In the Fi generation, 160 plants were recovered from extracted 180 kernels. Individual leaf samples were taken from these plants and submitted for the CE assay. The assay was positive for 63 of 160 of these samples thereby confirming transmission of the InDel to the next generation.

In a second experiment, five Hi-II $T_0$ plants were found to contain KO mutations in the crGEP5 target which were then transferred to soil. PCR and sequence analysis of DNA showed a bi-allelic deletion profile with a 5 bp deletion in the B73 chromosome and a 32 bp deletion in the A188 chromosome. $T_1$ transmisson was confirmed by PCR and sequence analysis according to the pattern shown in the following table:

TABLE 4

Cpf1 causes heritable edits in corn plants.

| T0 genotype | Crosses | Number of Sequence-confirmed T1 plants | T1 genotypes |
|---|---|---|---|
| 5 bp/32 bp bi-allelic KO | KO × A188 | 36 | 31/33 heterozygous KO |
| 5 bp/32 bp bi-allelic KO | KO × A188 | 36 | 23/23 heterozygous KO |
| 5 bp/32 bp bi-allelic KO | KO × KO (self) | 36 | 33 homozygous KO |
| 5 bp/32 bp bi-allelic KO | KO × A188 | 36 | 32/32 heterozygous KO |
| wt Control | A188 × A188 (control) | 18 | 18/18 A188 wt |

Figure 14:
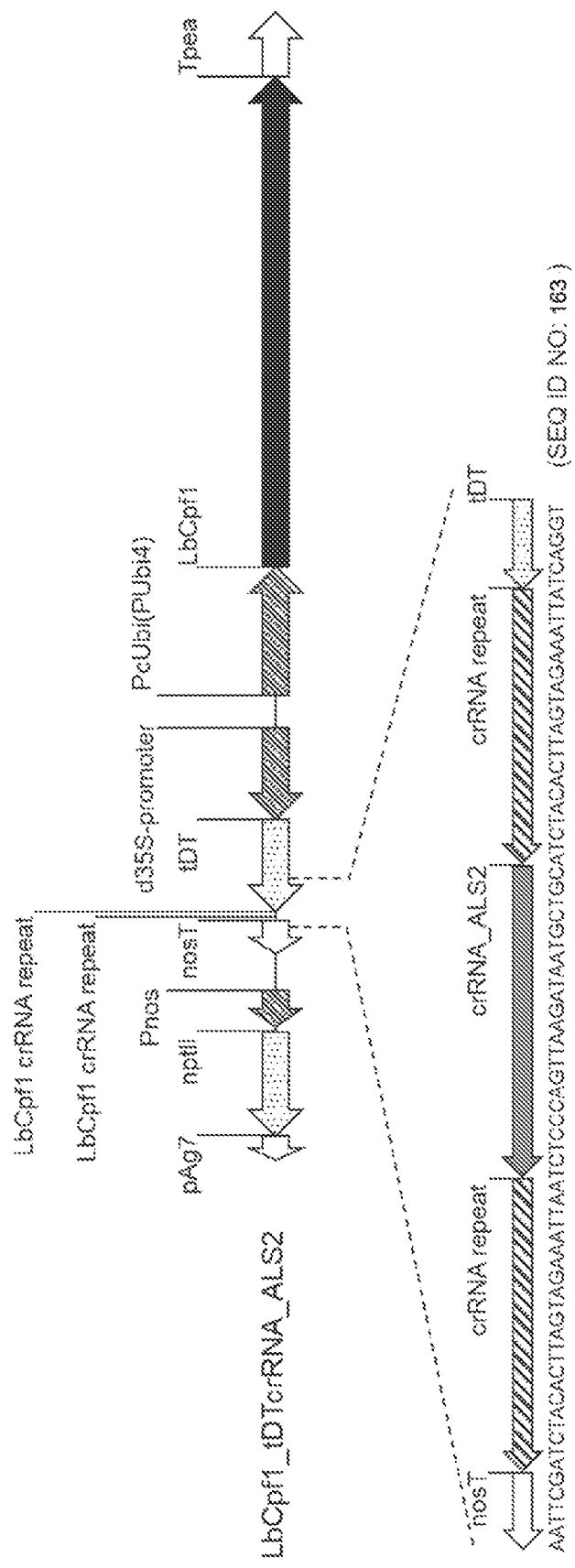
FIG. 14 (FIG. 14) shows the design of the binary vector construct LbCpf1-tDTcrRNA ALS2, which was used for stable transformation of sugar beet. The LbCpf1 tDTcrRNA ALS2 construct harbors expression cassettes for nptII, LbCpf1, and crRNA ALS2, which is directed against the target region BvALS2. The crRNA is embedded in a Pol II-driven RNA transcript as described before in Zhong et al., 2017. Terminators: pAG7, nosT, Tpea, PolII promoters: Pnos, PcUbi4. nptII =neomycin phosphotransferase.

Example 13: Demonstration of Efficient Cpf1-Mediated Editing in T0 Sugar Beet Plants To test whether the herein described Cpf1 systems can be used to generate edits in T0 sugar beet plants, the following experiments were performed. For stable transformation of sugar beet plants the binary vector construct LbCpf1_JDTcrRNA_ALS #2 was used (FIG. 14). This construct includes (i) an nptII resistance cassette for in planta selection (ii) the PcUbi4::Cpf1 expression cassette and (iii) a crRNA, which is directed against target region BvALS #2 within the target gene BvALS. The crRNA is embedded in a Pol II-driven RNA transcript as described before in Zhong et al., 2017. This transcript includes an mRNA encoding the fluorescent protein tDT.

The stable callus transformation method described below is based on the method published by Kishchenko et al, 2005 (Kishchenko, E. M., et al. (2005). "Production of transgenetic sugarbeet (Beta vulgaris L.) plants resistant to phosphinothricin." Cell Biology International 29(1): 15-19).

Micropropagated shoots of the genotype S706 were used as starting material. Shoots were multiplied in medium E. To induce friable callus, leaf explants were incubated in medium D at 28° C. for 7-8 weeks. Friable calli were harvested in medium F and kept for 1 week in the dark at 24° C. Agrobacterium AGL-1 harbouring the binary vector of interest was grown in medium A supplemented with the appropriate antibiotics at 28° C. for 24 h. Calli were inoculated with Agrobacterium suspension prepared in medium B at an OD600 of 0.6-0.8. The co-culture of the callus tissue and the Agrobacterium was done in medium C at 21° C. for three days in the dark. Calli were sub-cultured to medium G and incubated in the dark at 24° C. for one week. For the selection of transgenic cells, calli were transferred to medium H and incubated at 24° C. in the light (16 h) for three weeks. Transgenic calli were selected and sub-cultured for several times in the same medium and conditions. Regenerating shoots were isolated and propagated in medium I. Selected shoots were rooted in medium J and transferred to the green house for seed production.

Callus transformation of sugar beet using the construct LbCpf1_tDTcrRNA_ALS #2 resulted in 115 regenerated shoots, which were analyzed for presence of Cpf1 and SDN-1 genome editing. The results of this analysis are summarized in Table 5. 22.6% (26/115) of the regenerated shoots have been positively tested for the presence of LbCpf1 using qPCR. Those shoots are termed "transgenic". 73.1% (19/26) of the transgenic shoots have been positively tested for the presence of SDN-1 editing events (INDELS) via sequencing and/or capillary electrophoresis of the amplified target region. This ratio of 73.1% therefore corresponds to the LbCpf1 editing efficiency. In addition to the 19 stably transformed edited shoots, we obtained three shoots, which do not have LbCpf1 stably integrated but harbour SDN-1 events in the desired target location within BvALS. Those shoots represent transient editing events (Table 5).

Figure 15:
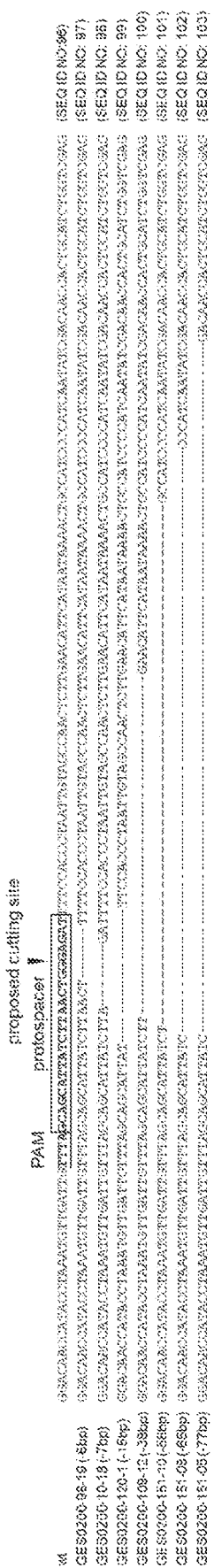
FIG. 15 (FIG. 15) shows a sequence alignment of the BvALS target regions in different edited shoots, which were regenerated after stable callus transformation. In the wild-type sequence of the BvALS gene PAM and protospacer are indicated. The triangle marks the proposed cutting site.

A selection of edited shoots was analyzed in detail by performing sequencing of the amplified BvALS target region. This analysis revealed the presence of varying deletions (−6 bp to −77 bp) in the different analyzed shoots (FIG. 15). No insertions or substitutions were identified.

TABLE 5

Callus transformation of sugar beet using the construct LbCpf1_tDTcrRNA_ALS#2 resulted in 115 regenerated shoots, which were analyzed for the presence of Cpf1 and SDN-1 genome editing.

| | |
|---|---|
| total number of shoots analyzed | 115 |
| transgenic | 26 |
| edited (transgenic) | 19 |
| non-edited (transgenic) | 7 |
| Cpf1 efficiency (transgenic) | 73.08% |
| Edited non-transgenic | 3 |

Figure 16:
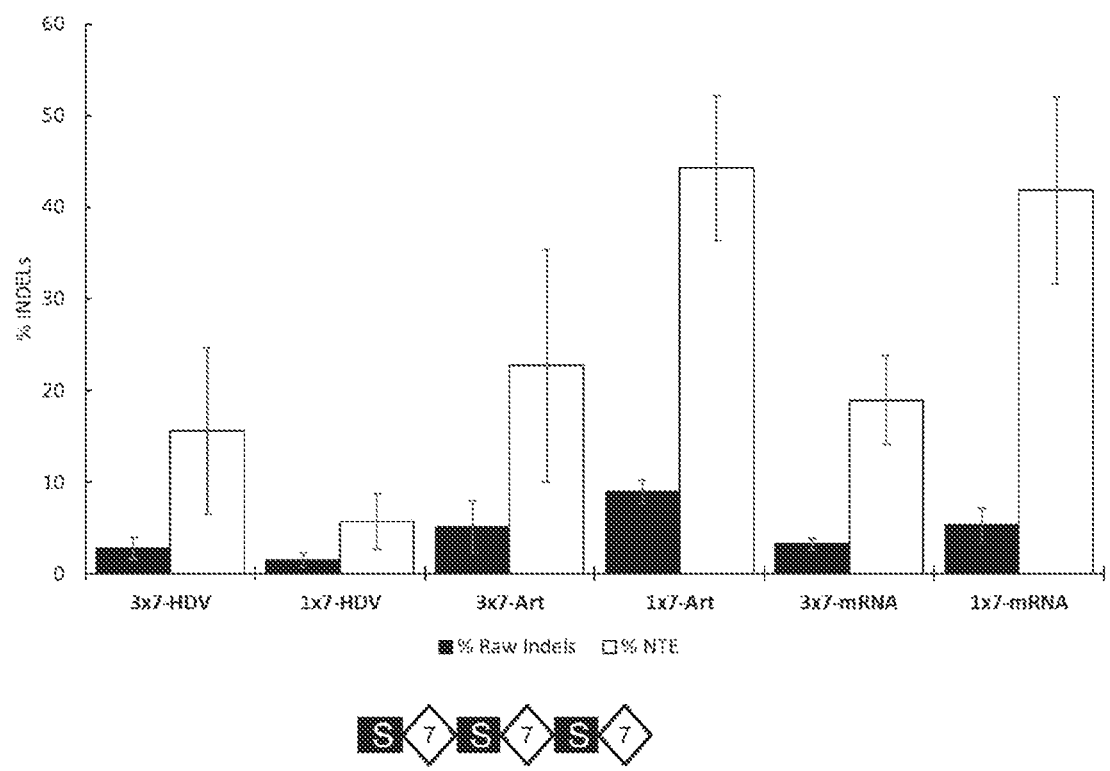
FIG. 16 (FIG. 16): Demonstration of increased activity through a multiplexed guide RNA module. Constructs containing a repeat of a module containing the LbCpf1 scaffold (S) and guide RNA sequence (in this case crGEP7 (7)) were tested for increased INDEL activity in protoplast via delivery through HDV Riobzyme system (HDV) or Artichoke Ribozyme system (Art) or mRNA delivery system (mRNA). As demonstrated here, for target 7 increased delivery through a 3×7-HDV module showed approximately three times higher INDEL activity over a 1×7-HDV module. With the Atichoke ribozyme system (Art) and mRNA delivery system (mRNA) the 3×7 module showed only 50% activity compared to the 1×7 module. NTE=normalized to transformation efficiency.

Example 14: Guide RNA Abundance can be Modulated by Repeated Arrays of the Same crRNA Sequence The intention was to test whether an increased dosage of target crRNA could lead to increased InDel events at a given target site. Target crGEP7 in gene HMG13 always gives low InDel % using a HDV ribozyme system. To test whether an array of 3 guide RNAs could increase activity at target site locus, a 3x scaffold (s) and target 7 guide module was cloned into constructs which are base vectors for HDV, Artichoke ribozyme and mRNA delivery systems (FIG. 16). The control was the 1xcrGEP7 vector for each delivery system. Each construct was co-transformed into protoplasts with the LbCpf1 nuclease vector and samples collected at 24 hrs for analysis after flow cytometry was carried out for transformation efficiency. NGS analysis of target site crGEP7 gave us 7% raw InDels which were multiplied by each samples % protoplast tramsformation efficiency to give the 5 NTE. FIG. 16 shows that the 3x guide delivery system seems to be beneficial for HDV delivered target sites but not for the other delivery methods.

Example 15: Modifying the Relative Dosage of the Cpf1 Protein and crRNA Modulates the Editing Efficiency in Plant Cells Maize A188 protoplast were transfected with different molar ratios of 2 plasmids to examine the effect on cutting efficiency. One of these plasmids has a plant gene cassette including the Cpf1 nuclease gene plus a fluorescent marker gene and the second plasmid has a similar cassette with one of two crRNA in Rm-HMG13, crGEP5 or crGEP7. Typically, these plasmid are transfected at a 1:1 molar ratio while holding the overall DNA quantity for transfection constant at 20 μg per transfection. In order to hold the DNA concentration constant in these experiments while increasing the crRNA plasmid amount, the nuclease gene plasmid concentration, was dropped as the crRNA plasmid concentration increased incrementally. Following transfection and a standard culture time for protoplasts, the cells exhibiting a fluorescent phenotype were counted using a flow cytometer to measure the transformation frequency. The recovered cells were pelleted and frozen in preparation for genomic DNA extraction. DNA was extracted and submitted for the NGS process, better described as amplicon deep sequencing, to measure the presence of insertions and deletions (InDels) at the expected target site. Amplicons with InDels were counted using NGS and reported as a percentage of total amplicon reads (short bars in FIG. 17). These values were finally reported as a function of the protoplast transformation frequency (taller bars in FIG. 17).

Figure 17A:
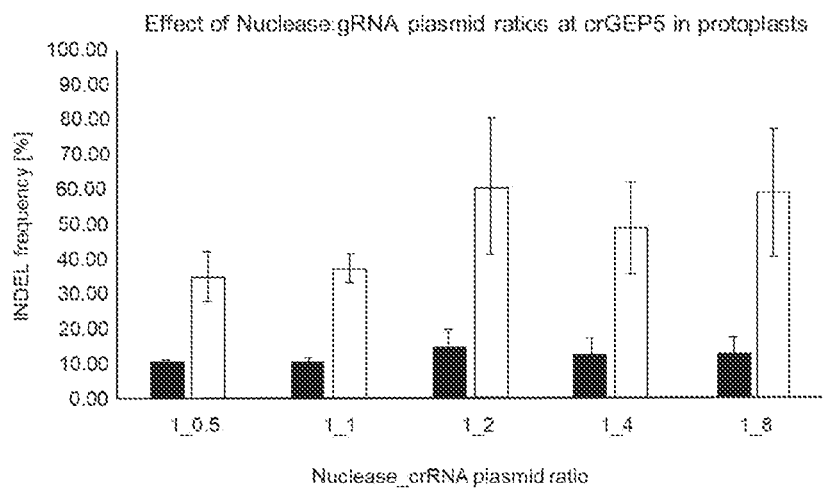
FIG. 17 (FIGS. 17A, B and C) Modifying the relative dosage of the Cpf1 protein and crRNA modulates the editing efficiency in plant cells (A, B). Adjusting the molar ratios (from 1:0.5 [1_0.5]-1:8 [1_8]) of the nuclease and crRNA constructs shows a demonstrable increase in INDEL activity at targets crGEP5 and crGEP7 in a protoplast assay. (C) Continuing the nuclease:crRNA ratio comparison for target cr7 in B which showed an upward trend from 1:1 [1_1] to a 1:32 [1_32] ratio. NTE=normalized to transformation efficiency.
Figure 17B:
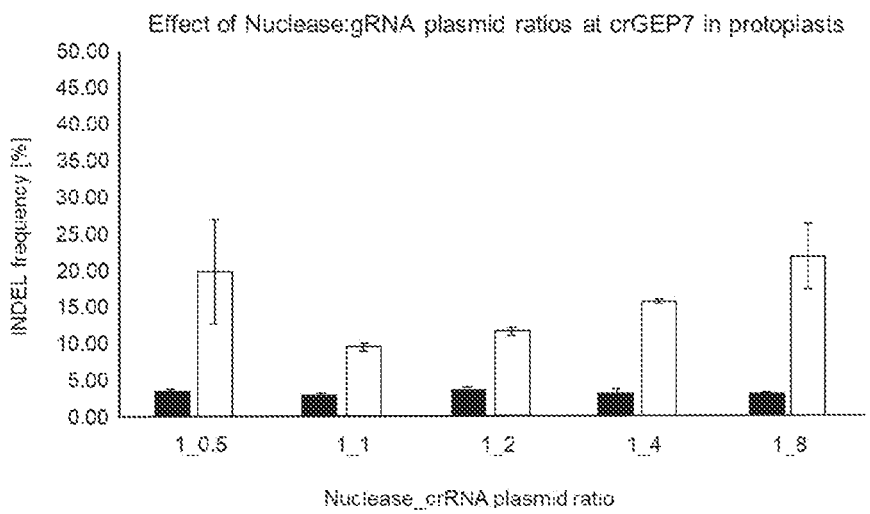
Figure 17C:
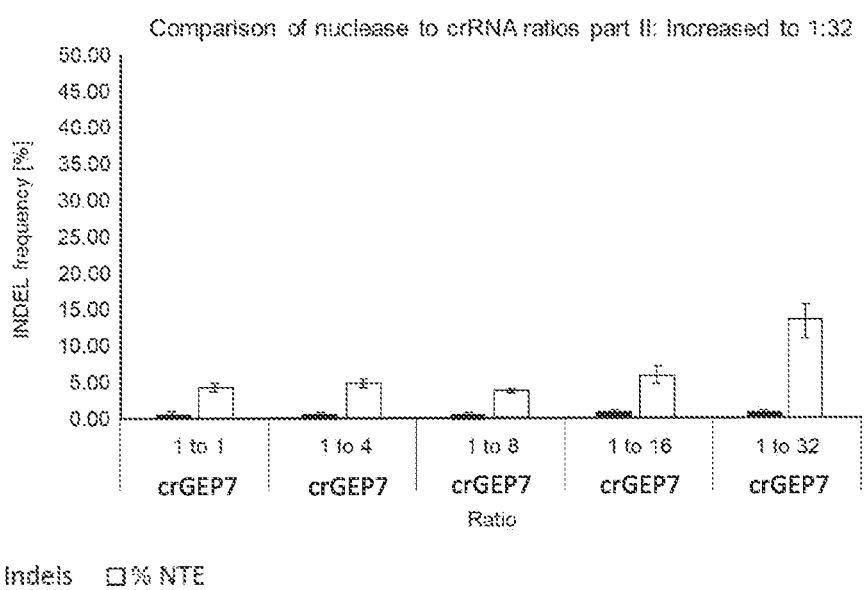

The experiments involved two genomic target sites, crGEP5 (FIG. 17) and crGEP7 (FIGS. 17 B and C), that had previously been characterized as having high and low activity, respectively. The previous characterization experiments also used maize A188 protoplasts and a 1:1 molar ratio of nuclease to crRNA plasmids. The variation in target site activity was of interest in these tests to determine if there would be different responses. The higher active site, target crGEP5 did not show a significant difference in activity with increasing crRNA plasmid concentrations (FIG. 17 A). There might be an increase of approximately 30% when increasing the ratio from 1:1 to 1:2 but no further increase from 1:4 and 1:8 ratios. Interestingly, there was no significant difference in InDel frequency when half the crRNA quantity was used (FIG. 17 A, 1_0.05). In contrast, the low efficiency target crGEP7 showed incremental increases with each increase in the crRNA concentration (FIG. 17 B) ending at the 1:8 ratio which had about twice the activity of the 1:1 ratio. FIG. 17 C represents an experiment which was designed to extend the quantity of the crRNA even higher compared to that shown in FIG. 17 B.

Figure 18:
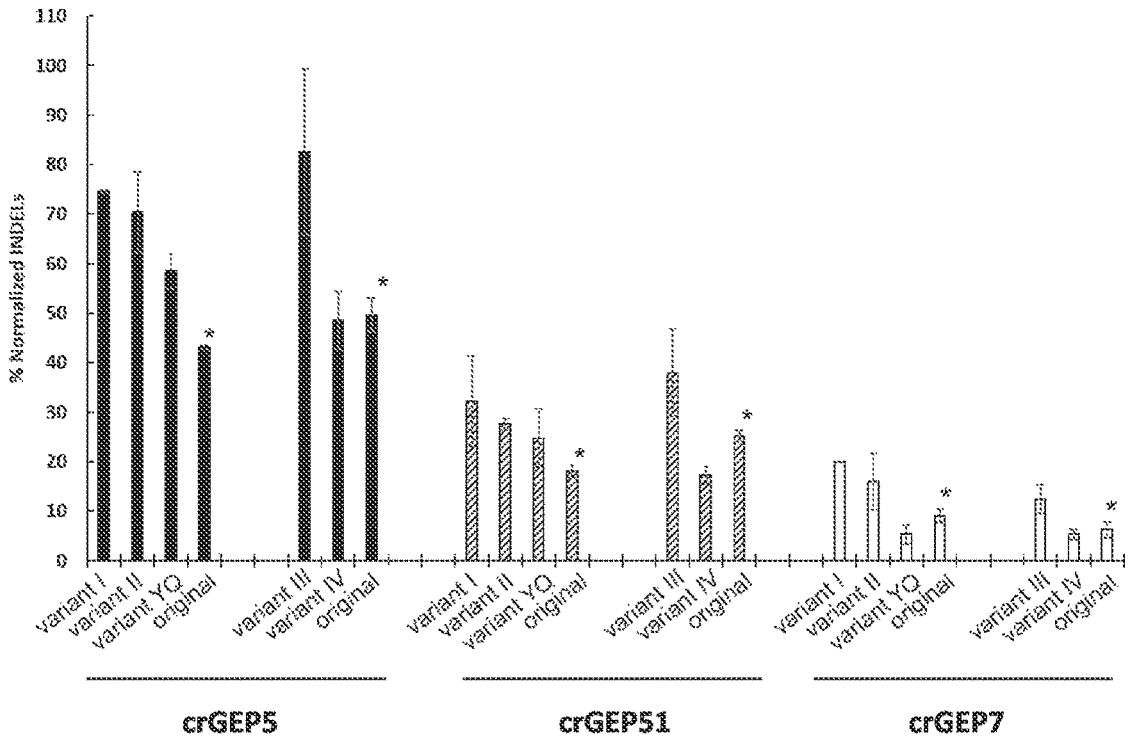
FIG. 18 (FIG. 18) shows the performance of Cpf1 variants compared to original Cpf1 version in protoplast assays. Four designed versions ordered at commercial sequence providers (variants I (SEQ ID NO: 72), II (SEQ ID NO: 73), III (SEQ ID NO: 75) and IV (SEQ ID NO: 76)) and one published version from Yiping Qi's group (Tang et al., 2017 Nature Plants 3:17018) (variant YQ (SEQ ID NO: 74)). Each block of bars represents a separate experiment wherein the variants were compared to the original version (*). Black bars=Target crGEP5; striped bars=Target crGEP51 and white bars=Target crGEP7. Target INDEL quantification done by ddPCR to get Raw INDELs and the normalized INDEL score was obtained by multiplying raw score with transformation efficiency %. In particular variants I and III outperform the original Cpf1 version.

Example 16: Codon Optimized Variants of LbCpf1 Show Enhanced Activity at Target Sites in Corn Leaf Protoplasts or Non-Dividing Cells Five Codon optimized variants of LbCpf1 were made and tested across three target sites in a protoplast assay. Four designed versions ordered at commercial sequence providers (variants I (SEQ ID NO: 72), II (SEQ ID NO: 73), III (SEQ ID NO: 75) and IV (SEQ ID NO: 76)) and one published version from Yiping Qi's group (Tang et al., 2017 Nature Plants 3:17018) (variant YQ (SEQ ID NO: 74)). A total of 15 µg of Nuclease plasmid and 8 µg of target guide plasmid were transformed into corn leaf protoplasts by PEG method and reporter gene expression from nuclease vector was quantified by flow cytometry for transformation efficiency. Protoplast samples were collected at 24 hrs and INDEL activity from the LbCpf1 variants was compared to the original version of LbCpf1 (see FIG. 18).

In Each experiment the results show that that multiple variants show activity equal to or even better than the original LbCpf1 version. Based on these results two variants I and III showed consistent enhanced activity against all three targets over the other variants.

Figure 19:
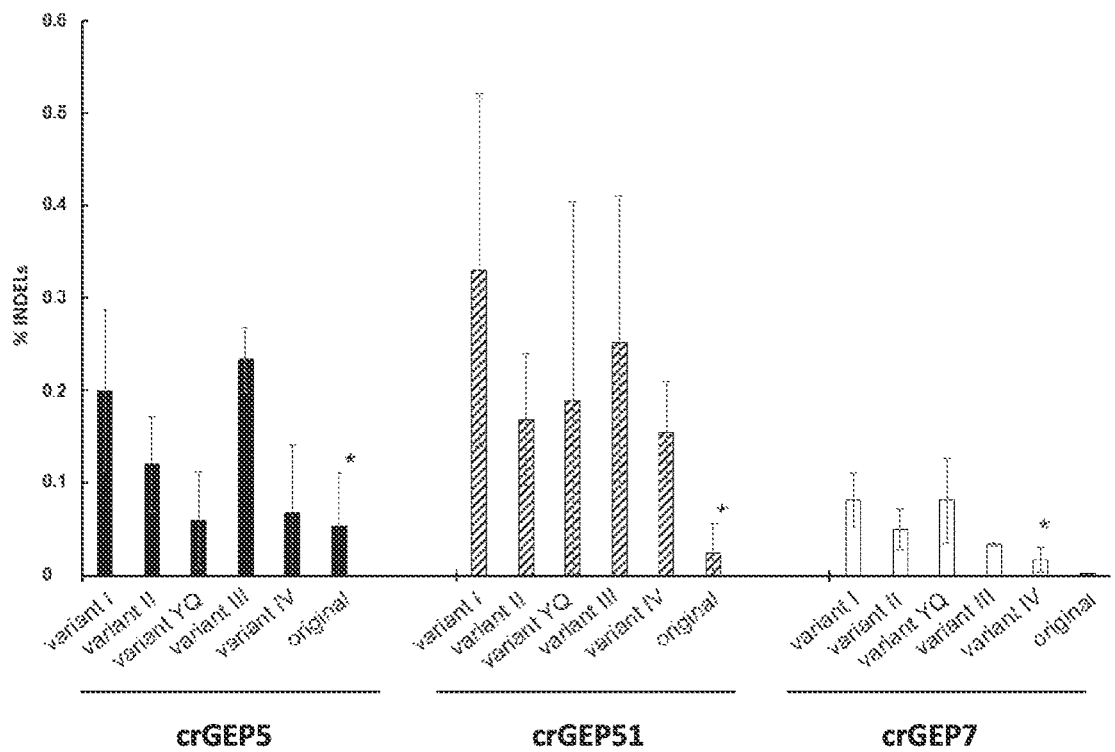
FIG. 19 (FIG. 19) shows the performance of Cpf1 variants compared to original Cpf1 version in corn Immature Embryos bombardment assay. Four designed versions ordered at commercial sequence providers (variants I (SEQ ID NO: 72), II (SEQ ID NO: 73), III (SEQ ID NO: 75) and IV (SEQ ID NO: 76)) and one published version from Yiping Qi's group (Tang et al., 2017 Nature Plants 3:17018) (variant YQ (SEQ ID NO: 74)). Each block of bars represents a separate experiment wherein the variants were compared to the original version (*). Black bars=Target crGEP5; striped bars=Target crGEP51 and white bars=Target crGEP7. Target INDEL quantification done by NGS to get INDELs %.

Example 17: Codon Optimized Variants of LbCpf1 Show Enhanced Activity at Target Sites in Corn Immature Embryos (IE) or Dividing Cells The five Codon optimized variants of LbCpf1 of example 16 were tested also across three target sites in corn IEs. A total of 100 ng of Nuclease plasmid and 150 ng of target guide plasmid were bombarded into corn IE (9 days after pollination) and reporter gene expression from nuclease vector was observed by microscopy for transformation efficiency. Samples were collected at 48 hrs and INDEL activity from the LbCpf1 variants was compared to the original version of LbCpf1 (see FIG. 19).

In Each experiment the results show that that multiple variants show activity equal to or better than the original LbCpf1 version. Like in experiment 16 the results showed that the two variants I and III consistently enhance the activity against all three targets over the other variants.

Example 18: Intron-Sequence Containing Cpf1 Variants Show Improved INDEL Activity Compared to Intron-Less Versions To prevent sequence rearrangement in *Agrobacterium* T-DNA vectors due to expression of the Cpf1 (lacking intron to prevent bacterial expression) we constructed Intron containing Cpf1 variants of the two best versions (variants I and III; SEQ ID NOs: 157 and 158) as described in the experiments 16 and 17 and compared them to the LbCpf1 original version (without intron) in protoplast assays. A total of 15 µg of Nuclease plasmid and 8 µg of Target guide plasmid were transformed into corn leaf protoplasts by PEG method and reporter gene expression from nuclease vector was quantified by flow cytometry for transformation efficiency. Protoplast samples were collected at 24 hrs and INDEL activity from the LbCpf1 variants was compared to the original version (see FIG. 20).

It is evident that the intron-containing Cpf1 variants show lesser activity than the control intron-less versions of themselves but still show higher activity over the original version of LbCpf1 (intron-free). These results indicate that these intron containing variants still outperform the original Cpf1 and can be used to make stable *Agrobacterium* T-DNA vectors.

The invention claimed is:

1. A plant delivery system, the delivery system comprising
   (a) at least one Cpf1 enzyme or an active fragment thereof, or a nucleic acid sequence encoding the same, wherein the at least one nucleic acid sequence encoding the Cpf1 enzyme or an active fragment thereof is codon-optimized for the expression in the plant or part of the plant; and
   (b) at least one Cpf1 guide RNA system, or a nucleic acid sequence encoding the same, the at least one Cpf1 guide RNA system comprising at least one Cpf1 guide RNA specific for a genomic target sequence of interest in a plant or part of a plant;
wherein the at least one Cpf1 guide RNA, or the nucleic acid sequence encoding the same, is
   (i) flanked by a Hammerhead ribozyme sequence at the 5'-end and by a plant-derived Hepatitis Delta Virus (HDV)-like ribozyme sequence at the 3'-end, wherein the plant-derived HDV-like ribozyme sequence, or a sequence encoding the same, is selected from any one of SEQ ID NOs: 19, 21, 25, and sequences having at least 95% identity over the whole length of any one of SEQ ID NOs: 19, 21, or 25; and is
   (ii) embedded within a 3' untranslated region (UTR) of a sequence encoding a frame sequence.

2. The plant delivery system of claim 1, wherein the plant delivery system comprises a first nucleotide molecule comprising a nucleic acid sequence encoding the at least one Cpf1 enzyme or an active fragment thereof, and a second nucleotide molecule comprising a nucleic acid sequence encoding the at least one Cpf1 guide RNA system, wherein the first and the second molecule are provided on separate constructs.

3. The plant delivery system according to claim 2, wherein the first nucleotide molecule and the second nucleotide molecule are delivered in a ratio selected from the group consisting of: 1.0 to 0.5; 1.0 to 01.0; 1.0 to 1.5; 1.0 to 2.0; 1.0 to 2.5; 1.0 to 3.0; 1.0 to 3.5; 1.0 to 4.0; 1.0 to 4.5; 1.0 to 5.0; 1.0 to 5.5; 1.0 to 6.0; 1.0 to 6.5; 1.0 to 7.0; 1.0 to 7.5; and 1.0 to 8.0.

4. The plant delivery system of claim 3, wherein the at least one nucleic acid sequence encoding the Cpf1 enzyme or an active fragment thereof, and the nucleic acid sequence encoding at least one Cpf1 guide RNA system each comprise at least one promoter functional in a plant selected from SEQ ID NOs: 1 to 10, 67, and any combination thereof, and sequences having at least 95% identity when compared over the whole length of the respective sequence of any one of SEQ ID NOs: 1 to 10 or 67.

5. The plant delivery system of claim 1, wherein the first construct comprising the first nucleotide molecule and the second construct comprising the second nucleotide molecule comprise at least one terminator functional in a plant or part of a plant.

6. The plant delivery system of claim 5, wherein the at least one terminator is selected from SEQ ID NO: 11, SEQ ID NO: 12, and any combination thereof, and a sequence having at least 95% identity when compared over the whole length of the respective sequence of any one of SEQ ID NOs: 11 or 12.

7. The plant delivery system of claim 1, wherein the nucleic acid sequence encoding the Cpf1 enzyme or an active fragment thereof is selected from SEQ ID NOs: 13 and 14, and sequences having at least 95% identity over the whole length of the respective sequence of SEQ ID NOs: 13 or 14.

8. The plant delivery system of claim 1, wherein the Hammerhead ribozyme sequence, or a sequence encoding the same, is selected from SEQ ID NO: 17 and 18, and sequences having at least 95% identity over the whole length of any one of SEQ ID NOs: 17 or 18.

9. The plant delivery system of claim 1, wherein the at least one Cpf1 guide RNA, or the nucleotide sequence encoding the same
further comprises a scaffold RNA sequence, or a sequence encoding the same, at the 5'-end
or at the 5' and 3' ends.

10. The plant delivery system of claim 8, wherein the scaffold RNA sequence, or a sequence encoding the same, is selected from SEQ ID NO: 29 and 30, and sequences having at least 95% identity over the whole length of SEQ ID NO: 29 or 30.

11. The plant delivery system of claim 1, wherein the at least one Cpf1 enzyme or an active fragment thereof, or a nucleic acid sequence encoding the same, is selected from any one of SEQ ID NOs: 13 to 16, 38 to 41, 72 to 76, and 152 to 158, and sequences having at least 95% or more sequence identity over the whole length of the respective nucleic acid sequence of SEQ ID NOs: 13, 14, 38, 39, 72, 73, 74, 75, 76, 157, or 158, and sequences having at least 95% identity over the whole length of the respective amino acid sequence of SEQ ID NOs: 15, 16, 40, 41, 152, 153, 154, 155, or 156, respectively.

12. The plant delivery system of claim 1, wherein the at least one Cpf1 enzyme, or an active fragment thereof, or a nucleic acid sequence encoding the same, comprises at least one mutation in comparison to a wild-type sequence resulting in an altered PAM recognition, wherein the at least mutation is selected from G532R/K595R, or G532R/K538V/Y542R in comparison to the sequence of SEQ ID NO: 16.

13. The plant delivery system of claim 1, wherein the at least one Cpf1 enzyme, or an active fragment thereof, or a nucleic acid sequence encoding the same, comprises at least one mutation in comparison to a wild-type sequence resulting in an altered PAM recognition, wherein the altered PAM recognition is a recognition of a TYCV or of a TATV PAM sequence.

14. The plant delivery system of claim 1, wherein the at least one Cpf1 enzyme or an active fragment thereof, or a nucleic acid sequence encoding the same, and/or the at least one Cpf1 guide RNA system, or a nucleic acid sequence encoding the same, are provided as at least one vector construct, or are provided as at least one linear construct.

15. The plant delivery system of claim 1, wherein the at least one Cpf1 guide RNA system comprises at least two guide RNAs, wherein the at least two guide RNAs are separated by a nucleotide sequence comprising direct repeats.

16. The plant delivery system of claim 1, wherein the sequence encoding a frame sequence is selected from a sequence comprising a marker gene, including an antibiotic marker or a fluorescent marker, and a gene encoding a structural protein.

17. The plant delivery system of claim 16, wherein the sequence encoding a frame sequence is selected from any one of SEQ ID NOs: 13 14 31, 32, 38, 39, 72, 73, 74, 75, 76, 157, and 158, and sequences having at least 95% identity over the whole length of the respective sequence of SEQ ID NOs: 13 14 31, 32, 38, 39, 72, 73, 74, 75, 76, 157, or 158.

18. A host cell comprising the plant delivery system of claim 1.

19. A plant, or a plant cell, tissue, organ or material, or a derivative or progeny thereof, comprising the plant delivery system of claim 1.

20. A method for modifying a genomic target sequence of interest in a plant or part of a plant, wherein the method comprises the steps of:
(a) providing at least one Cpf1 enzyme or an active fragment thereof, or a nucleic acid sequence encoding the same, wherein the at least one nucleic acid sequence encoding the Cpf1 enzyme or an active fragment thereof is codon-optimized for the expression in the plant or part of the plant; and
(b) providing at least one Cpf1 guide RNA system, or a nucleic acid sequence encoding the same, the at least one Cpf1 guide RNA system comprising at least one Cpf1 guide RNA specific for a genomic target sequence of interest in the plant or part of the plant;
wherein
(i) the at least one Cpf1 guide RNA, or the nucleic acid sequence encoding the same, is flanked by a Hammerhead ribozyme sequence at the 5' and a plant-derived Hepatitis Delta Virus (HDV)-like ribozyme sequence at the 3'-end, wherein the plant-derived HDV-like ribozyme sequence, or a sequence encoding the same, is selected from any one of SEQ ID NOs: 19, 21, and 25, and sequences having at least 95% identity over the whole length of any one of SEQ ID NOs: 19, 21, or 25; and
(ii) the at least one Cpf1 guide RNA, or the nucleic acid sequence encoding the same, is embedded within a 3' untranslated region (UTR) of a sequence encoding a frame sequence;
(c) optionally: providing at least one repair template nucleic acid sequence, wherein the at least one repair template nucleic acid sequence is flanked by one or more homology sequence(s) complementary to one or both adjacent region(s) of the genomic sequence of interest in the plant or part of the plant;
(d) introducing the at least one Cpf1 enzyme or an active fragment thereof, or a nucleic acid sequence encoding the same from step (a); and introducing the at least one Cpf1 guide RNA system, or a nucleic acid sequence encoding the same from step (b) and optionally: introducing the at least one repair template nucleic acid sequence from step (c) into the plant or part of the plant; and
(e) obtaining a plant or part of a plant, or a progeny thereof, comprising a modification in the genomic target sequence of interest.

21. The method of claim 20, wherein the at least one Cpf1 enzyme or an active fragment thereof, or a nucleic acid sequence encoding the same, and the at least one Cpf1 guide RNA system, or a nucleic acid sequence encoding the same, and optionally wherein the at least one repair template nucleic acid sequence, are provided on separate constructs, wherein the at least two separate constructs are introduced simultaneously or consecutively.

22. The method of claim 20, wherein the at least one Cpf1 enzyme or an active fragment thereof, or a nucleic acid sequence encoding the same, and the at least one Cpf1 guide RNA system, or a nucleic acid sequence encoding the same, are provided on a single transcript construct.

23. The method of claim 20, wherein the at least one Cpf1 enzyme or an active fragment thereof, or a nucleic acid sequence encoding the same, and at least two Cpf1 guide RNA systems, or a nucleic acid sequence encoding the same, are provided on a multiplexed guide RNA construct to simultaneously target more than one target site.

24. The method of claim 20, wherein the molecules of step (a), (b) and optionally of step (c) are provided as a plant delivery system, wherein the plant delivery system comprises:
   (a) a first nucleotide molecule comprising a nucleic acid sequence encoding at least one Cpf1 enzyme or an active fragment thereof, and
   (b) a second nucleotide molecule comprising a nucleic acid sequence encoding at least one Cpf1 guide RNA system,
   wherein the first and the second molecule are provided on separate constructs.

25. The method of claim 24, wherein the first nucleotide molecule and the second nucleotide molecule are delivered in a ratio selected from the group consisting of: 1.0 to 0.5; 1.0 to 01.0; 1.0 to 1.5; 1.0 to 2.0; 1.0 to 2.5; 1.0 to 3.0; 1.0 to 3.5; 1.0 to 4.0; 1.0 to 4.5; 1.0 to 5.0; 1.0 to 5.5; 1.0 to 6.0; 1.0 to 6.5; 1.0 to 7.0; 1.0 to 7.5; and 1.0 to 8.0.

26. The method of claim 20, wherein the at least one nucleic acid sequence encoding the Cpf1 enzyme or an active fragment thereof, and the nucleic acid sequence encoding at least one Cpf1 guide RNA system each comprise at least one promoter functional in a plant selected from SEQ ID NOs: 1 to 10, 67, and any combination thereof, and sequences having at least 95% identity when compared over the whole length of the respective sequence of any one of SEQ ID NOs: 1 to 10 or 67.

27. The method of claim 20, wherein the at least one nucleic acid sequence encoding the Cpf1 enzyme or an active fragment thereof, and the nucleic acid sequence encoding at least one Cpf1 guide RNA system each comprise at least one terminator functional in a plant or part of a plant.

28. The method of claim 27, wherein the at least one terminator is selected from SEQ ID NO: 11, SEQ ID NO: 12, and any combination thereof, and sequences having at least 95% identity when compared over the whole length of the respective sequence of any one of SEQ ID NOs: 11 or 12.

29. The method of claim 20, wherein the nucleic acid sequence encoding the Cpf1 enzyme or an active fragment thereof is selected from SEQ ID NOs: 13, 14, 38, 39, 72, 73, 74, 75, 76, 157, 158, and sequences having at least 95% identity over the whole length of the respective sequence of SEQ ID NOs: 13, 14, 38, 39, 72, 73, 74, 75, 76, 157, or 158.

30. The method of claim 20, wherein the Hammerhead ribozyme sequence, or a sequence encoding the same, is selected from SEQ ID NO: 17, 18, and sequences having at least 95% identity over the whole length of any one of SEQ ID NOs: 17 or 18.

31. The method of claim 20, wherein the at least one Cpf1 guide RNA, or the nucleotide sequence encoding the same further comprises a scaffold RNA sequence, or a sequence encoding the same, at the 5' end or at the 5' and 3'-end.

32. The method of claim 31, wherein the scaffold RNA sequence, or a sequence encoding the same, is selected from SEQ ID NO: 29, 30, and sequences having at least 95% identity over the whole length of any one of SEQ ID NOs: 29 or 30.

33. The method of claim 20, wherein the at least one Cpf1 enzyme or an active fragment thereof, or a nucleic acid sequence encoding the same, is selected from any one of SEQ ID NOs: 13 to 16, 38 to 41, 72 to 76, 152 to 158, and sequences having at least 95% or more sequence identity over the whole length of the respective nucleic acid sequence of SEQ ID NOs: 13, 14, 38, 39, 72, 73, 74, 75, 76, 157, or 158, and sequences having at least 95% identity over the whole length of the respective amino acid sequence of SEQ ID NOs: 15, 16, 40, 41, 152, 153, 154, 155, or 156, respectively.

34. The method of claim 20, wherein the at least one Cpf1 enzyme, or an active fragment thereof, or a nucleic acid sequence encoding the same, comprises at least one mutation in comparison to a wild-type sequence resulting in an altered PAM recognition.

35. The method of claim 20, wherein the at least one Cpf1 enzyme, or an active fragment thereof, or a nucleic acid sequence encoding the same, comprises at least one mutation in comparison to a wild-type sequence resulting in an altered PAM recognition, wherein the altered PAM recognition is a recognition of a TYCV or of a TATV PAM sequence.

36. The method of claim 20, wherein the at least one Cpf1 enzyme or an active fragment thereof, or a nucleic acid sequence encoding the same, and/or the at least one Cpf1 guide RNA system, or a nucleic acid sequence encoding the same, are provided as at least one vector construct, or are provided as at least one linear construct.

37. The method of claim 20, wherein the at least one Cpf1 guide RNA system comprises at least two guide RNAs, wherein the at least two guide RNAs are separated by a nucleotide sequence comprising direct repeats.

38. The method of claim 20, wherein the sequence encoding the frame sequence is selected from a sequence comprising a marker gene, an antibiotic marker or a fluorescent marker, and a gene encoding a structural protein.

39. The method of claim 38, wherein the sequence encoding the frame sequence is selected from any one of SEQ ID NOs: 31, 32, 13, 14, 38, 39, 72, 73, 74, 75, 76, 157, 158, and sequences having at least 95% identity over the whole length of the respective sequence of SEQ ID NOs: 31, 32, 13, 14, 38, 39, 72, 73, 74, 75, 76, 157, or 158.

40. The method of claim 20, wherein the part of a plant is selected from the group consisting of a plant cell, a plant tissue and a plant organ.

41. The method of claim 20, wherein the plant or a part of a plant originates from a genus selected from the group consisting of *Hordeum, Sorghum, Saccharum, Zea, Setaria, Oryza, Triticum, Secale, Triticale, Malta, Brachypodium, Aegilops, Daucus, Beta, Eucalyptus, Nicotiana, Solanum, Coffea, Vitis, Erythrante, Genlisea, Cucumis, Marta, Arabidopsis, Crucihimalaya, Cardamine, Lepidium, Capsella, Olmarabidopsis, Arabis, Brassica, Eruca, Raphanus, Citrus, Jatropha, Populus, Medicago, Cicer, Cajanus, Phaseolus, Glycine, Gossypium, Astragalus, Lotus, Torenia, Allium,* or *Helianthus*.

42. The method of claim 20, wherein the plant or part of the plant is a *Zea mays* plant.

43. The method of claim 34, wherein the at least one mutation is selected from G532R/K595R, or G532R/K538V/Y542R in comparison to the sequence of SEQ ID NO: 16.

44. The method of claim 20, wherein the plant or a part of a plant is selected from the group consisting of *Beta vulgaris, Zea mays, Triticum aestivum, Hordeum vulgare, Secale cereale, Helianthus annuus, Solanum tuberosum, Sorghum bicolor, Brassica rapa, Brassica napus, Brassica juncea, Brassica oleracea, Raphanus sativus, Oryza sativa, Glycine max,* and/or *Gossypium* sp.

* * * * *

SEQUENCE LISTING

<160> NUMBER OF SEQ ID NOS: 163

<210> SEQ ID NO 1
<211> LENGTH: 1413
<212> TYPE: DNA
<213> ORGANISM: Brachypodium distachyon

<400> SEQUENCE: 1

```
ggagaagaac tcgagaggga attgcagatc atgaggcaga tggctatttt tgtgtcacat      60
atgcgcaaaa agagaggcta tatttgtgtc cctaggttct tcgttgtatt gcagtttcca     120
tatcaatctg acttggtcgc atgagaaatt gatggtaaa taatttgaat ctctcatgta      180
gtatcaacta ttagatatta ttttcaccaa atatatttcc atcggagaag aagaggctac     240
agaggaagca gaagagaggg gtgggagaat ttttacactt ttgtacaccc acttaaacag     300
caaaatccgt atgaaaacag gcccaccaaa acaatgccac gataacaatc cgtagaaaca     360
aaagcttcat ttaacagcgg cgcaacaaag cacgcttatc catggtagtt gtagtccgta     420
tgcgatccaa agatcacgat tcacgcgtga cggacggacg acgcgtgcca caccacaact     480
aacggcatcc atggtagttg tagtccgtat gcgatccaaa gatcacgatt cacgcgtgac     540
ggacggacga cgcgcgccac accacaacta acagcgtgag ccagcgtcca aactccggat     600
ggcaacgggg acgaaacccg tcgggtagtc actgcccaaa cccgtccccg caaccttcat     660
```

```
cccaaacccg tcccgtttc cggtcgcggg tttcagtttt ctaccagacc cgtccccatc    720 gggttttca tcccgtcgg gaaatccgaa cccgccagca tttcagcacc aagccaaagt    780
tgcagcagca acatgaataa aaaacaaccc gtttcaacac caagataaaa caaaacatta    840
taatttagac aacatttcac acgtataaca ataacatata gttctcacat ataacaacac    900
catttcacac ataaaacaac accatttggg ataaaaatat gggctatatc aggccatttt    960
tatgggccat attgagtttt cgtgggtttc acaggtaccg gatttgtaga atgctgaacc    1020
gggtttgaac cgtaaaatcc gcgggtattg aatttgaccc aatcccgtcg tccctggtg    1080 gggtaaaaac accatcttga gtccaaacgg ccaccaacca aactccgacg gcaacaaaca    1140
aacggcgttg ctttgctcct cggtatctcc gtgaccgctc aatctcccgg ctgtttcccc    1200
ggaattgcgt ggactctctc atccacacgc aaaccgcctc tccctcctct ctcgtcctat    1260
ccgccccggt gccgtagcct cacgggactc ttcttcctcc cttgctataa aatccccgcc    1320
ccctcccgtc tcctctccac acatccaaac tctcaatcgc accgagaaaa atcctctagc    1380
gatcgaagcg aagcctctcc cgatcctctc aag                                 1413

<210> SEQ ID NO 2
<211> LENGTH: 981
<212> TYPE: DNA
<213> ORGANISM: Zea mays

<400> SEQUENCE: 2
tgcagcgtga cccggtcgtg cccctctcta gagataatga gcattgcatg tctaagttat     60
aaaaaattac cacatatttt ttttgtcaca cttgtttgaa gtgcagtttta tctatcttta    120 tacatatatt taaactttac tctacgaata atataatcta tagtactaca ataatatcag    180
tgttttagag aatcatataa atgaacagtt agacatggtc taaggacaa ttgagtattt    240 tgacaacagg actctacagt tttatctttt tagtgtgcat gtgttctcct ttttttttgc    300
aaatagcttc acctatataa tacttcatcc attttattag tacatccatt tagggtttag    360
ggttaatggt ttttatagac taattttttt agtacatcta ttttattcta ttttagcctc    420
taaattaaga aaactaaaac tctattttag ttttttatt taataattta gatataaaat    480
agaataaaat aaagtgacta aaattaaac aaataccctt taagaaatta aaaaaactaa    540
ggaaacattt ttcttgtttc gagtagataa tgccagcctg ttaaacgccg tcgatcgacg    600
agtctaacgg acaccaacca gcgaaccagc agcgtcgcgt cgggccaagc gaagcagacg    660
gcacggcatc tctgtcgctg cctctggacc cctctcgaga gttccgctcc accgttggac    720
ttgctccgct gtcggcatcc agaaattgcg tggcggagcg gcagacgtga gccggcacgg    780
caggcggcct cctcctcctc tcacggcacc ggcagctacg ggggattcct ttcccaccgc    840
tccttcgctt tcccttcctc gcccgccgta ataaatagac ccccctcca cacctctttt    900 ccccaacctc gtgttgttcg gagcgcacac acacaacc agatctcccc caaatccacc    960
cgtcggcacc tccgcttcaa g                                               981

<210> SEQ ID NO 3
<211> LENGTH: 1247
<212> TYPE: DNA
<213> ORGANISM: Oryza sativa

<400> SEQUENCE: 3
tagctagcat actcgaggtc attcatatgc ttgagaagag agtcgggata gtccaaaata    60
```

```
aaacaaaggt aagattacct ggtcaaaagt gaaaacatca gttaaaaggt ggtataagta      120
aaatatcggt aataaaaggt ggcccaaagt gaaatttact cttttctact attataaaaa      180
ttgaggatgt tttgtcggta ctttgatacg tcattttgt atgaattggt ttttaagttt       240
attcgcgatt tggaaatgca tatctgtatt tgagtcggtt tttaagttcg ttgcttttgt      300
aaatacagag ggatttgtat aagaaatatc tttaaaaaac ccatatgcta atttgacata      360 attttgaga aaaatatata ttcaggcgaa ttccacaatg aacaataata agattaaaat       420
agcttgcccc cgttgcagcg atgggtattt tttctagtaa aataaaagat aaacttagac      480
tcaaaacatt tacaaaaaca acccctaaag tcctaaagcc caaagtgcta tgcacgatcc      540
atagcaagcc cagcccaacc caacccaacc caacccaccc cagtgcagcc aactggcaaa      600
tagtctccac ccccggcact atcaccgtga gttgtccgca ccaccgcacg actcgcagcc      660
aaaaaaaaaa aagaaagaa aaaaagaaa agaaaaaca gcagctgggt ccgggtcgtg         720
ggggccggaa aagcgaggag gatcgcgagc agcgacgagg cccggccctc cctccgcttc      780
caaagaaacg ccccccatcg ccactatata catacccccc cctctcctcc catccccca       840 accctaccac caccaccacc accacctcct cccccctcgc tgccggacga cgagctcctc      900 cccccctcccc ctccgccgcc gccggtaacc accccgcccc tctcctctttt ctttctccgt   960 tttttttttc gtcacggtct cgatctttgg ccttggtagt ttgggtgggc gagagcggct     1020
tcgtcgccca gatcggtgcg cgggagggc gggatctcgc ggctggcgac tccgggcgtg     1080
agtcggcccg gatcctcgcg gggaatgggg ctctcggatg tagatcttct ttctttcttc    1140
tttttgtggt agaatttgaa tccctcagca ttgttcatcg gtagttttc ttttcatgat     1200 ttgtgacaaa tgcagcctcg tgcggagctt ttttgtaggc ctagaag                  1247

<210> SEQ ID NO 4
<211> LENGTH: 691
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: p35S promoter sequence

<400> SEQUENCE: 4
gttcagaaga ccagagggct attgagactt ttcaacaaag gtaatatcg ggaaacctcc       60 tcggattcca ttgcccagct atctgtcact tcatcgaaag gacagtagaa aaggaagatg     120
gcttctacaa atgccatcat tgcgataaag gaaaggctat cgttcaagat gcctctaccg    180
acagtggtcc caaagatgga ccccacccca cgaggaacat cgtggaaaaa gaagacgttc   240
caaccacgtc ttcaaagcaa gtggattgat gtgatacatg gtggagcacg acactctcgt   300
ctactccaag aatatcaaag atacagtctc agaagaccag agggctattg agacttttca   360 acaagggta atatcgggaa acctcctcgg attccattgc ccagctatct gtcacttcat    420
cgaaaggaca gtagaaaagg aagatggctt ctacaaatgc catcattgcg ataaaggaaa    480
ggctatcgtt caagatgcct ctaccgacag tggtcccaaa gatggacccc acccacgag     540 gaacatcgtg gaaaaagaag acgttccaac cacgtcttca aagcaagtgg attgatgtga    600
tatctccact gacgtaaggg atgacgcaca atcccactat ccttcgcaag accctcctc     660 tatataagga agttcatttc atttggagag g                                    691

<210> SEQ ID NO 5
```

<211> LENGTH: 519
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
gtacgccgct cgtcctcccc cccccccctc tctaccttct ctagatcggc gttccggtcc    60
atggttaggg cccggtagtt ctacttctgt tcatgtttgt gttagatccg tgtttgtgtt   120
agatccgtgc tgctagcgtt cgtacacgga tgcgacctgt acgtcagaca cgttctgatt   180
gctaacttgc cagtgtttct ctttggggaa tcctgggatg gctctagccg ttccgcagac   240
gggatcgatc taggataggt atacatgttg atgtgggttt tactgatgca tatacatgat   300
ggcatatgca gcatctattc atatgctcta accttgagta cctatctatt ataataaaca   360
agtatgtttt ataattattt tgatcttgat atacttggat gatggcatat gcagcagcta   420
tatgtggatt tttttagccc tgccttcata cgctatttat ttgcttggta ctgtttcttt   480
tgtcgatgct caccctgttg tttggtgtta cttctgcag                          519
```

<210> SEQ ID NO 6
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pZmUbi1+Ubi1 intron promoter sequence

<400> SEQUENCE: 6

```
tgcagcgtga cccggtcgtg cccctctcta gagataatga gcattgcatg tctaagttat    60
aaaaaattac cacatatttt ttttgtcaca cttgtttgaa gtgcagttta tctatcttta   120
tacatatatt taaactttac tctacgaata atataatcta tagtactaca ataatatcag   180
tgttttagag aatcatataa atgaacagtt agacatggtc taaaggacaa ttgagtattt   240
tgacaacagg actctacagt tttatctttt tagtgtgcat gtgttctcct ttttttttgc   300
aaatagcttc acctatataa tacttcatcc attttattag tacatccatt tagggtttag   360
ggttaatggt ttttatagac taattttttt agtacatcta ttttattcta ttttagcctc   420
taaattaaga aaactaaaac tctattttag ttttttatt taataattta gatataaaat   480
agaataaaat aaagtgacta aaattaaac aaatacccctt taagaaatta aaaaactaa   540
ggaaacattt ttcttgtttc gagtagataa tgccagcctg ttaaacgccg tcgatcgacg   600
agtctaacgg acaccaacca gcgaaccagc agcgtcgcgt cgggccaagc gaagcagacg   660
gcacggcatc tctgtcgctg cctctggacc cctctcgaga gttccgctcc accgttggac   720
ttgctccgct gtcggcatcc agaaattgcg tggcggagcg gcagacgtga gccggcacgg   780
caggcggcct cctcctcctc tcacggcacc ggcagctacg ggggattcct ttcccaccgc   840
tccttcgctt tcccttcctc gcccgccgta ataaatagac ccccctcca caccctcttt   900
ccccaacctc gtgttgttcg gagcgcacac acacacaacc agatctcccc caaatccacc   960
cgtcggcacc tccgcttcaa ggtacgccgc tcgtcctccc ccccccccct ctctaccttc  1020
tctagatcgg cgttccggtc catggttagg gcccggtagt tctacttctg ttcatgtttg  1080
tgttagatcc gtgtttgtgt tagatccgtg ctgctagcgt tcgtacacgg atgcgaccctg  1140
tacgtcagac acgttctgat tgctaacttg ccagtgtttc tctttgggga atcctgggat  1200
```

-continued

```
ggctctagcc gttccgcaga cgggatcgat ctaggatagg tatacatgtt gatgtgggtt    1260
ttactgatgc atatacatga tggcatatgc agcatctatt catatgctct aaccttgagt    1320
acctatctat tataataaac aagtatgttt tataattatt ttgatcttga tatacttgga    1380
tgatggcata tgcagcagct atatgtggat ttttttagcc ctgccttcat acgctattta    1440
tttgcttggt actgtttctt ttgtcgatgc tcaccctgtt gtttggtgtt acttctgcag    1500
```

<210> SEQ ID NO 7
<211> LENGTH: 2503
<212> TYPE: DNA
<213> ORGANISM: Brachypodium distachyon

<400> SEQUENCE: 7

```
ggagaagaac tcgagaggga attgcagatc atgaggcaga tggctatttt tgtgtcacat      60
atgcgcaaaa agagaggcta tatttgtgtc cctaggttct tcgttgtatt gcagtttcca     120
tatcaatctg acttggtcgc atgagaaatt gatggttaaa taatttgaat ctctcatgta     180
gtatcaacta ttagatatta ttttcaccaa atatatttcc atcggagaag aagaggctac     240
agaggaagca aagagaggg gtgggagaat ttttacactt ttgtacaccc acttaaacag     300
caaaatccgt atgaaaacag gcccaccaaa acaatgccac gataacaatc cgtagaaaca     360
aaagcttcat ttaacagcgg cgcaacaaag cacgcttatc catggtagtt gtagtccgta     420
tgcgatccaa agatcacgat tcacgcgtga cggacggacg acgcgtgcca caccacaact     480
aacggcatcc atggtagttg tagtccgtat gcgatccaaa gatcacgatt cacgcgtgac     540
ggacggacga cgcgcgccac accacaacta acagcgtgag ccagcgtcca aactccggat     600
ggcaacgggg acgaaacccg tcgggtagtc actgcccaaa cccgtccccg caaccttcat     660
cccaaacccg tccccgtttc cggtcgcggg tttcagtttt ctaccagacc cgtcccatc     720 gggttttca tccccgtcgg gaaatccgaa cccgccagca tttcagcacc aagccaaagt     780
tgcagcagca acatgaataa aaaacaaccc gtttcaacac caagataaaa caaaacatta     840
taatttagac aacatttcac acgtataaca ataacatata gttctcacat ataacaacac     900
catttcacac ataaaacaac accatttggg ataaaaatat gggctatatc aggccatttt     960
tatgggccat attgagtttt cgtgggtttc acaggtaccg gatttgtaga atgctgaacc    1020
gggtttgaac cgtaaaatcc gcgggtattg aatttgaccc aatcccgtcg tccctggtg    1080 gggtaaaaac accatcttga gtccaaacgg ccaccaacca aactccgacg gcaacaaaca    1140
aacggcgttg ctttgctcct cggtatctcc gtgaccgctc aatctcccgg ctgtttcccc    1200
ggaattgcgt ggactctctc atccacacgc aaaccgcctc tccctcctct ctcgtcctat    1260 ccgcccggt gccgtagcct cacgggactc ttcttcctcc cttgctataa aatccccgcc    1320
ccctcccgtc tcctctccac acatccaaac tctcaatcgc accgagaaaa atctcctagc    1380
gatcgaagcg aagcctctcc cgatcctctc aaggtacgcc cgtttcccgt cgatcctcct    1440
ccttccgttc gtgttctgta gccgatcgat tcgattccct tacacccgtt cgtgttctct    1500
cgtggatcga tcgattgttt gttgctagaa ggaactcgta gatctggcgt ttatgaactg    1560
tgattcgggt tagtccagat cgattcaggt cggtcgtcgt tgagcctctc ggctatgtct    1620
ggattatcgt gtagatctgc tggttcagtt gattatgttc ttctaggagt aatttcgttg    1680
ggtcagcgcg atttctgctt aatctatgct gcttattgcg cctgtaccta tctactaagc    1740
tatgtgcacc tgtaatttg ctagattatt cgttcatcct cgtagttggt ttgtcacagt    1800
```

```
aatccgtatg ggttctgacg atgttattgt tggtcatacc taggcttctc cagattttat    1860
tttgttaaaa ttggatagat ctgctactga tagttgatga tggaatttgg tgctgaatct    1920
atgctattta ttgcgcctat acctgatcta tcgggctatg tacggctgta gtttactgga    1980
ttattcgttc atcctcggta gttggttcat cgtttgggtt ctgacgataa tattgttgat    2040
tatgcgtagg cttctgcaga ttgttgttaa aattggatac atcggttact gatggttgat    2100
gatagatttg tgctgaacct atctgtttat tgctcctata cctgatctat agggctatgt    2160
atgcctgtaa tttaccagat tattcgttca tcctcgtagt tggttcatct ctataattcg    2220
tatgggttct tatgatgtta tcgttgatta tgcctagtct tatacagatt attgtgtcaa    2280
gattgaatat acctgctact gatcggtgat aatttggtta gtagtttgca atctgctagg    2340
aacacgttac cactgtaatc tgtaaacatg gtttgccaga gtagtttgtt ctactactct    2400
tgatatggtt gctgatttta gtcgcctcct ttggatcat gtattgatgt ccttgcagat    2460
ttccgtgtac ttaccccggc ttttgtgtac ttcgtgttaa cag                      2503

<210> SEQ ID NO 8
<211> LENGTH: 535
<212> TYPE: DNA
<213> ORGANISM: Zea mays

<400> SEQUENCE: 8
gtccgccttg tttctcctct gtctcttgat ctgactaatc ttggtttatg attcgttgag      60
taattttggg gaaagcttcg tccacagttt tttttcgatg aacagtgccg cagtggcgct     120
gatcttgtat gctatcctgc aatcgtggtg aacttattc ttttatatcc tttactccca     180
tgaaaaggct agtaatcttt ctcgatgtaa catcgtccag cactgctatt accgtgtggt     240
ccatccgaca gtctggctga acacatcata cgatctatgg agcaaaaatc tatcttccct     300
gttctttaat gaaggacgtc attttcatta gtatgatcta ggaatgttgc aacttgcaag     360
gaggcgtttc tttctttgaa tttaactaac tcgttgagtg gccctgtttc tcggacgtaa     420
ggcctttgct gctccacaca tgtccattcg aattttaccg tgtttagcaa gggcgaaaag     480
tttgcatctt gatgatttag cttgactatg cgattgcttt cctggacccg tgcag         535

<210> SEQ ID NO 9
<211> LENGTH: 1090
<212> TYPE: DNA
<213> ORGANISM: Brachypodium distachyon

<400> SEQUENCE: 9
gtacgcccgt ttcccgtcga tcctcctcct tccgttcgtg ttctgtagcc gatcgattcg      60
attcccttac acccgttcgt gttctctcgt ggatcgatcg attgtttgtt gctagaagga     120
actcgtagat ctggcgttta tgaactgtga ttcgggttag tccagatcga ttcaggtcgg     180
tcgtcgttga gcctctcggc tatgtctgga ttatcgtgta gatctgctgg ttcagttgat     240
tatgttcttc taggagtaat ttcgttgggt cagcgcgatt tctgcttaat ctatgctgct     300
tattgcgcct gtacctatct actaagctat gtgcacctgt aattttgcta gattattcgt     360
tcatcctcgt agttggtttg tcacagtaat ccgtatgggt tctgacgatg ttattgttgg     420
tcatacctag gcttctccag attttatttt gttaaaattg gatagatctg ctactgatag     480
ttgatgatgg aatttggtgc tgaatctatg ctatttattg cgcctatacc tgatctatcg     540
ggctatgtac ggctgtagtt tactggatta ttcgttcatc ctcggtagtt ggttcatcgt     600
ttgggttctg acgataatat tgttgattat gcgtaggctt ctgcagattg ttgttaaaat     660
```

```
tggatacatc ggttactgat ggttgatgat agatttgtgc tgaacctatc tgtttattgc    720
tcctataccT gatctatagg gctatgtatg cctgtaattt accagattat tcgttcatcc    780
tcgtagttgg ttcatctcta taattcgtat gggttcttat gatgttatcg ttgattatgc    840
ctagtcttat acagattatt gtgtcaagat tgaatatacc tgctactgat cggtgataat    900
ttggttagta gtttgcaatc tgctaggaac acgttaccac tgtaatctgt aaacatggtt    960
tgccagagta gtttgttcta ctactcttga tatggttgct gattttagtc gcctcctttt   1020
ggatcatgta ttgatgtcct tgcagatttc cgtgtactta ccccggcttt tgtgtacttc   1080
gtgttaacag                                                          1090

<210> SEQ ID NO 10
<211> LENGTH: 517
<212> TYPE: DNA
<213> ORGANISM: Zea mays

<400> SEQUENCE: 10
gtacgccgct cgtcctcccc cccccctctc taccttctct agatcggcgt tccggtccat     60
ggttagggcc cggtagttct acttctgttc atgtttgtgt tagatccgtg tttgtgttag    120
atccgtgctg ctagcgttcg tacacggatg cgacctgtac gtcagacacg ttctgattgc    180
taacttgcca gtgtttctct ttggggaatc ctgggatggc tctagccgtt ccgcagacgg    240
gatcgatcta ggataggtat acatgttgat gtgggtttta ctgatgcata tacatgatgg    300
catatgcagc atctattcat atgctctaac cttgagtacc tatctattat aataaacaag    360
tatgttttat aattatttTg atcttgatat acttggatga tggcatatgc agcagctata    420
tgtggatttt tttagccctg ccttcatacg ctatttattt gcttggtact gtttcttttg    480
tcgatgctca ccctgttgtt tggtgttact tctgcag                             517

<210> SEQ ID NO 11
<211> LENGTH: 258
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: NosT terminator sequence

<400> SEQUENCE: 11
cgatcgttca acatttggc aataaagttt cttaagattg aatcctgttg ccggtcttgc      60
gatgattatc atataatttc tgttgaatta cgttaagcat gtaataatta acatgtaatg    120
catgacgtta tttatgagat gggtttttat gattagagtc ccgcaattat acatttaata    180
cgcgataaga acaaaatat agcgcgcaaa ctaggataaa ttatcgcgcg cggtgtcatc    240
tatgttacta gatcgatc                                                 258

<210> SEQ ID NO 12
<211> LENGTH: 204
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 35S terminator sequence

<400> SEQUENCE: 12
```

```
gtcgatcgac aagctcgagt tctccataa taatgtgtga gtagttccca gataagggaa    60
ttagggttcc tatagggttt cgctcatgtg ttgagcatat aagaaaccct tagtatgtat   120
ttgtatttgt aaaatacttc tatcaataaa atttctaatt cctaaaacca aaatccagta   180
ctaaaatcca gatcccccga atta                                          204

<210> SEQ ID NO 13
<211> LENGTH: 3771
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: codon optimized polynulceotide

<400> SEQUENCE: 13
atggcatcta gcatggcacc aaagaaaaaa aggaaagttt ccaaacttga aaatttaca    60 aactgctact ccctttccaa gacgcttagg tttaaagcga tccccgttgg caagacccaa   120
gagaatatcg ataacaaaag acttctggtc gaagatgaaa aagggccga agactacaag   180 ggggtcaaga agttgctcga tcgctattat ctttccttta tcaacgatgt gcttcattca   240
atcaaactga agaacttgaa taactacatt agccttttca gaaagaaaac gaggactgaa   300
aaggagaaca aggaacttga gaatcttgaa ataaaccttc gcaaagaaat tgcaaaagcc   360
ttcaagggga acgaaggata taaatctctt ttcaaaaaag acattataga aacaattttg   420
cctgagtttc ttgacgacaa ggatgaaatt gcgctcgtca atagctttaa cggatttaca   480
actgccttca cagggttctt cgacaatagg gagaatatgt ttagcgagga ggcaaaaagc   540
acatccatcg cattcagatg catcaatgaa atcttaccc ggtacatatc gaatatggac   600
atatttgaaa aagtggatgc aatattcgat aagcacgaag tccaggagat aaaggaaaag   660
atactgaata gcgactatga tgtcgaagat ttttcgaag gtgagttctt caactttgtc   720
ctgactcaag aaggcattga tgtctataat gcaataattg gaggttttgt gactgagtct   780
ggcgagaaga taagggctt gaacgagtat atcaatctct acaaccagaa gactaagcaa   840
aagttgccta aatttaaacc gctttacaag caagttttga gcgaccggga aagcctttcc   900
ttttacggtg aaggatacac gagcgatgaa gaagtcctcg aagtcttccg caacacactc   960
aacaagaact cagaaatctt ttcctcaatt aaaaaattgg agaagctttt caagaacttc  1020
gatgaatact cttcggcggg gattttgtg aagaacggcc cggcaatttc cacaatatct  1080
aaagacattt tcgagaatg gaacgtgata gagacaagt ggaatgcgga gtatgatgac  1140
atacacctga gaagaaggc agttgtgact gaaaaatacg aagatgacag gagaaaaagc  1200
tttaaaaaga tcgggtcctt ttcactgaa cagctgcagg agtatgccga cgccgatctt  1260
tcggttgtcg aaaagctcaa agaataatt atccagaagg tcgatgaaat ctacaaggtg  1320
tacggctcaa gcgagaagct ctttgatgct gacttcgtgt tggagaagtc tcttaaaaaa  1380
aacgacgcag tcgtcgcgat aatgaaagat ttgctggatt cagtgaaatc cttcgagaat  1440
tatatcaaag ccttcttcgg cgaggggaag gagacaaaca gggatgagtc cttctatgga  1500
gacttcgttc tggcttacga catccttctt aaggtcgacc acatctatga cgcaattcgg  1560
aactatgtga cgcagaagcc gtattcgaaa gataagttca gctctatttt ccaaaaccct  1620
caatttatgg gtgggtggga taagacaaa gagaccgatt accgggcaac aattttgcgg  1680
tacgggtcta atattaccct cgctataatg gataagaaat acgctaaatg tctccagaaa  1740
```

```
attgacaaag atgacgtcaa cggcaattat gaaaaaatca attataaact ccttcctggc    1800
ccaaataaaa tgctcccgaa ggtgttttt tccaaaaagt ggatggccta ttataatcca    1860
tcagaggata ttcagaaaat ctataaaaat gggacctta agaagggtga catgtttaac    1920
ctgaacgatt gccacaagct tatagatttt ttcaaagact ctattagccg ctatcccaaa    1980
tggtctaatg cttatgattt caacttctct gaaactgaaa agtacaaaga tattgcagga    2040
ttctaccgcg aagttgaaga acaaggttat aaggtttcct ttgagtctgc gtccaagaaa    2100
gaggtcgata agttggtcga agaagggaaa ttgtatatgt ttcaaattta caataaagac    2160
ttttccgaca gtcccatgg tacacctaat ctgcatacca tgtacttcaa actgctgttc    2220
gatgagaata atcacggtca gattcgcctg agcggagggg cggaactctt catgaggaga    2280
gcatcgttga aaaagagga gctcgtcgtg catccggcta acagccccat tgctaacaag    2340
aatccggata atccaaagaa gactactacc ctctcctatg acgtctataa ggataagaga    2400
ttctctgagg accagtacga gttgcacatc cctattgcga taaataaatg ccctaagaac    2460
atctttaaaa tcaatactga ggtcagagtc ctgcttaagc acgacgacaa cccgtatgtg    2520
atcgggattg ataggggtga aaggaacttg ctttatattg tggttgtcga tggaaaaggt    2580
aatatagtgg aacaatactc tctgaatgaa attatcaaca acttcaatgg cattaggatc    2640
aagaccgact atcattctct gttggacaag aaagagaaag agcgcttcga ggcacggcaa    2700
aactggacgt ctattgagaa catcaaggag cttaaggctg ttacatttc tcaggttgtg    2760
cacaaaattt gcgaactggt cgagaaatat gatgccgtta tcgcacttga agatctcaac    2820
agcggattta agaattctcg ggtgaaagtc gaaaaacagg tgtatcaaaa attcgaaaag    2880
atgctgatcg acaagctcaa ttatatggtt gataaaaaga gcaacccatg cgccacgggg    2940
ggtgcgctta agggctatca gattacgaac aaatttgaat ccttcaagtc aatgtcgacg    3000
caaaatgggt ttatattcta tataccggcg tggcttacat ctaaaataga tcctagcact    3060
gggttcgtga acctgctgaa aaccaagtac acttcaatcg cagattctaa aaaatttata    3120
agcagcttcg acagaatcat gtatgtgccc gaggaagacc tcttcgagtt tgcccttgat    3180
tacaaaaatt tctcaagaac ggatgcagac tacataaaga agtggaagct gtactcttat    3240
gggaaccgga ttcggatatt cagaaatccg aaaaaaaaca atgtctttga ttgggaggaa    3300
gtttgtctta cctctgctta caagagctg ttcaataaat atggcattaa ttaccagcaa    3360
ggtgatatcc gggcgctcct tgcgaacag tctgacaaag cttctattc ttcatttatg    3420
gcgctcatgt cattgatgct gcagatgagg aatagcatta cggggaggac tgatgttgac    3480
tttctgatct cgcccgtgaa aaattctgat ggaatcttct acgattccag gaattatgag    3540
gcccaggaaa atgctatcct tcccaagaac gcagacgcaa atggcgcgta caatatagct    3600
cgcaaggttt tgtgggctat aggccaattc aagaaagccg aagacgaaaa gctggacaaa    3660
gttaagattg ctatatctaa caaagagtgg cttgagtatg cgcaaacatc tgttaaacac    3720
aaacgccccg cggctacaaa gaaggctggc caggcaaaga agaagaagtg a             3771
```

<210> SEQ ID NO 14
<211> LENGTH: 3684
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: codon optimized polynucleotide

```
<400> SEQUENCE: 14
atgtccaaac ttgaaaaatt tacaaactgc tactcccttt ccaagacgct taggtttaaa     60
gcgatccccg ttggcaagac ccaagagaat atcgataaca aaagacttct ggtcgaagat    120
gaaaaaaggg ccgaagacta caggggggtc aagaagttgc tcgatcgcta ttatctttcc    180
tttatcaacg atgtgcttca ttcaatcaaa ctgaagaact tgaataacta cattagcctt    240
ttcagaaaga aaacgaggac tgaaaaggag aacaaggaac ttgagaatct tgaaataaac    300
cttcgcaaag aaattgcaaa agccttcaag gggaacgaag gatataaatc tcttttcaaa    360
aaagacatta tagaaacaat tttgcctgag tttcttgacg acaaggatga aattgcgctc    420
gtcaatagct ttaacggatt tacaactgcc ttcacagggt tcttcgacaa tagggagaat    480
atgtttagcg aggaggcaaa aagcacatcc atcgcattca gatgcatcaa tgaaaatctt    540
acccggtaca tatcgaatat ggacatattt gaaaaagtgg atgcaatatt cgataagcac    600
gaagtccagg agataaagga aaagatactg aatagcgact atgatgtcga agatttttc     660 gaaggtgagt tcttcaactt tgtcctgact caagaaggca ttgatgtcta taatgcaata    720
attggaggtt ttgtgactga gtctggcgag aagataaagg gcttgaacga gtatatcaat    780
ctctacaacc agaagactaa gcaaaagttg cctaaattta aaccgcttta caagcaagtt    840
ttgagcgacc gggaaagcct ttccttttac ggtgaaggat acacgagcga tgaagaagtc    900
ctcgaagtct tccgcaacac actcaacaag aactcagaaa tcttttcctc aattaaaaaa    960
ttggagaagc ttttcaagaa cttcgatgaa tactcttcgg cggggatttt tgtgaagaac   1020
ggcccggcaa tttccacaat atctaaagac attttcggag aatggaacgt gataagagac   1080
aagtggaatg cggagtatga tgacatacac ctgaagaaga aggcagttgt gactgaaaaa   1140
tacgaagatg acaggagaaa aagctttaaa agatcgggt cctttcact ggaacagctg     1200 caggagtatg ccgacgccga tctttcggtt gtcgaaaagc tcaaagaaat aattatccag   1260
aaggtcgatg aaatctacaa ggtgtacggc tcaagcgaga gctctttga tgctgacttc    1320 gtgttggaga agtctcttaa aaaaaacgac gcagtcgtcg cgataatgaa agatttgctg   1380
gattcagtga aatccttcga gaattatatc aaagccttct tcggcgaggg gaaggagaca   1440
aacagggatg agtccttcta tggagacttc gttctggctt acgacatcct tcttaaggtc   1500
gaccacatct atgacgcaat tcggaactat gtgacgcaga agccgtattc gaaagataag   1560
ttcaagctct atttccaaaa ccctcaattt atgggtgggt gggataaaga caaagagacc   1620
gattaccggg caacaatttt gcggtacggg tctaaatatt acctcgctat aatggataag   1680
aaatacgcta atgtctcca gaaaattgac aaagatgacg tcaacggcaa ttatgaaaaa    1740
atcaattata aactccttcc tggcccaaat aaaatgctcc cgaaggtgtt tttttccaaa    1800
aagtggatgg cctattataa tccatcagag gatattcaga aaatctataa aaatgggacc   1860
tttaagaagg gtgacatgtt taacctgaac gattgccaca agcttataga tttttcaaa    1920 gactctatta gccgctatcc caaatggtct aatgcttatg atttcaactt ctctgaaact   1980
gaaaagtaca agatattgc aggattctac cgcgaagttg aagaacaagg ttataaggtt    2040
tcctttgagt ctgcgtccaa gaaagaggtc gataagttgg tcgaagaagg gaaattgtat   2100
atgtttcaaa tttacaataa agacttttcc gacaagtccc atggtacacc taatctgcat   2160
accatgtact tcaaactgct gttcgatgag aataatcacg gtcagattcg cctgagcgga   2220
ggggcggaac tcttcatgag gagagcatcg ttgaaaaaag aggagctcgt cgtgcatccg   2280
gctaacagcc ccattgctaa caagaatccg gataatccaa agaagactac taccctctcc   2340
```

```
tatgacgtct ataaggataa gagattctct gaggaccagt acgagttgca catccctatt    2400
gcgataaata aatgccctaa gaacatcttt aaaatcaata ctgaggtcag agtcctgctt    2460
aagcacgacg acaacccgta tgtgatcggg attgataggg gtgaaaggaa cttgctttat    2520
attgtggttg tcgatggaaa aggtaatata gtggaacaat actctctgaa tgaaattatc    2580
aacaacttca atggcattag gatcaagacc gactatcatt ctctgttgga caagaaagag    2640
aaagagcgct tcgaggcacg gcaaaactgg acgtctattg agaacatcaa ggagcttaag    2700
gctggttaca tttctcaggt tgtgcacaaa atttgcgaac tggtcgagaa atatgatgcc    2760
gttatcgcac ttgaagatct caacagcgga tttaagaatt ctcgggtgaa agtcgaaaaa    2820
caggtgtatc aaaaattcga aagatgctg atcgacaagc tcaattatat ggttgataaa    2880
aagagcaacc catgcgccac gggggtgcg cttaagggct atcagattac gaacaaattt    2940
gaatccttca gtcaatgtc gacgcaaaat gggtttatat tctatatacc ggcgtggctt    3000
acatctaaaa tagatcctag cactgggttc gtgaacctgc tgaaaaccaa gtacacttca    3060
atcgcagatt ctaaaaaatt tataagcagc ttcgacagaa tcatgtatgt gcccgaggaa    3120
gacctcttcg agtttgccct tgattacaaa aatttctcaa gaacggatgc agactacata    3180
aagaagtgga agctgtactc ttatgggaac cggattcgga tattcagaaa tccgaaaaaa    3240
aacaatgtct tgattggga ggaagtttgt cttacctctg cttacaaaga gctgttcaat    3300
aaatatggca ttaattacca gcaaggtgat atccgggcgc tcctttgcga acagtctgac    3360 aaagcttct attcttcatt tatggcgctc atgtcattga tgctgcagat gaggaatagc    3420
attacgggga ggactgatgt tgactttctg atctcgcccg tgaaaaattc tgatggaatc    3480
ttctacgatt ccaggaatta tgaggcccag gaaaatgcta tccttcccaa gaacgcagac    3540
gcaaatggcg cgtacaatat agctcgcaag gttttgtggg ctataggcca attcaagaaa    3600
gccgaagacg aaaagctgga caaagttaag attgctatat ctaacaaaga gtggcttgag    3660
tatgcgcaaa catctgttaa acac                                          3684
```

<210> SEQ ID NO 15
<211> LENGTH: 1255
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: codon optimized polypeptide

<400> SEQUENCE: 15

```
Met Ala Ser Ser Met Ala Pro Lys Lys Arg Lys Val Ser Lys Leu
1               5                   10                  15

Glu Lys Phe Thr Asn Cys Tyr Ser Leu Ser Lys Thr Leu Arg Phe Lys
            20                  25                  30

Ala Ile Pro Val Gly Lys Thr Gln Glu Asn Ile Asp Asn Lys Arg Leu
        35                  40                  45

Leu Val Glu Asp Glu Lys Arg Ala Glu Asp Tyr Lys Gly Val Lys Lys
    50                  55                  60

Leu Leu Asp Arg Tyr Tyr Leu Ser Phe Ile Asn Asp Val Leu His Ser
65                  70                  75                  80

Ile Lys Leu Lys Asn Leu Asn Asn Tyr Ile Ser Leu Phe Arg Lys Lys
                85                  90                  95

Thr Arg Thr Glu Lys Glu Asn Lys Glu Leu Glu Asn Leu Glu Ile Asn
```

```
                100                 105                 110
Leu Arg Lys Glu Ile Ala Lys Ala Phe Lys Gly Asn Glu Gly Tyr Lys
                115                 120                 125
Ser Leu Phe Lys Lys Asp Ile Ile Glu Thr Ile Leu Pro Glu Phe Leu
            130                 135                 140
Asp Asp Lys Asp Glu Ile Ala Leu Val Asn Ser Phe Asn Gly Phe Thr
145                 150                 155                 160
Thr Ala Phe Thr Gly Phe Phe Asp Asn Arg Glu Asn Met Phe Ser Glu
                165                 170                 175
Glu Ala Lys Ser Thr Ser Ile Ala Phe Arg Cys Ile Asn Glu Asn Leu
            180                 185                 190
Thr Arg Tyr Ile Ser Asn Met Asp Ile Phe Glu Lys Val Asp Ala Ile
        195                 200                 205
Phe Asp Lys His Glu Val Gln Glu Ile Lys Glu Lys Ile Leu Asn Ser
        210                 215                 220
Asp Tyr Asp Val Glu Asp Phe Phe Glu Gly Glu Phe Phe Asn Phe Val
225                 230                 235                 240
Leu Thr Gln Glu Gly Ile Asp Val Tyr Asn Ala Ile Ile Gly Gly Phe
                245                 250                 255
Val Thr Glu Ser Gly Glu Lys Ile Lys Gly Leu Asn Glu Tyr Ile Asn
            260                 265                 270
Leu Tyr Asn Gln Lys Thr Lys Gln Lys Leu Pro Lys Phe Lys Pro Leu
        275                 280                 285
Tyr Lys Gln Val Leu Ser Asp Arg Glu Ser Leu Ser Phe Tyr Gly Glu
        290                 295                 300
Gly Tyr Thr Ser Asp Glu Glu Val Leu Glu Val Phe Arg Asn Thr Leu
305                 310                 315                 320
Asn Lys Asn Ser Glu Ile Phe Ser Ser Ile Lys Lys Leu Glu Lys Leu
                325                 330                 335
Phe Lys Asn Phe Asp Glu Tyr Ser Ser Ala Gly Ile Phe Val Lys Asn
            340                 345                 350
Gly Pro Ala Ile Ser Thr Ile Ser Lys Asp Ile Phe Gly Glu Trp Asn
        355                 360                 365
Val Ile Arg Asp Lys Trp Asn Ala Glu Tyr Asp Asp Ile His Leu Lys
        370                 375                 380
Lys Lys Ala Val Val Thr Glu Lys Tyr Glu Asp Asp Arg Arg Lys Ser
385                 390                 395                 400
Phe Lys Lys Ile Gly Ser Phe Ser Leu Glu Gln Leu Gln Glu Tyr Ala
                405                 410                 415
Asp Ala Asp Leu Ser Val Val Glu Lys Leu Lys Glu Ile Ile Ile Gln
            420                 425                 430
Lys Val Asp Glu Ile Tyr Lys Val Tyr Gly Ser Ser Glu Lys Leu Phe
        435                 440                 445
Asp Ala Asp Phe Val Leu Glu Lys Ser Leu Lys Lys Asn Asp Ala Val
        450                 455                 460
Val Ala Ile Met Lys Asp Leu Leu Asp Ser Val Lys Ser Phe Glu Asn
465                 470                 475                 480
Tyr Ile Lys Ala Phe Phe Gly Glu Gly Lys Glu Thr Asn Arg Asp Glu
                485                 490                 495
Ser Phe Tyr Gly Asp Phe Val Leu Ala Tyr Asp Ile Leu Leu Lys Val
            500                 505                 510
Asp His Ile Tyr Asp Ala Ile Arg Asn Tyr Val Thr Gln Lys Pro Tyr
        515                 520                 525
```

```
Ser Lys Asp Lys Phe Lys Leu Tyr Phe Gln Asn Pro Gln Phe Met Gly
    530                 535                 540

Gly Trp Asp Lys Asp Lys Glu Thr Asp Tyr Arg Ala Thr Ile Leu Arg
545                 550                 555                 560

Tyr Gly Ser Lys Tyr Tyr Leu Ala Ile Met Asp Lys Lys Tyr Ala Lys
                565                 570                 575

Cys Leu Gln Lys Ile Asp Lys Asp Val Asn Gly Asn Tyr Glu Lys
                580                 585                 590

Ile Asn Tyr Lys Leu Leu Pro Gly Pro Asn Lys Met Leu Pro Lys Val
            595                 600                 605

Phe Phe Ser Lys Lys Trp Met Ala Tyr Asn Pro Ser Glu Asp Ile
    610                 615                 620

Gln Lys Ile Tyr Lys Asn Gly Thr Phe Lys Lys Gly Asp Met Phe Asn
625                 630                 635                 640

Leu Asn Asp Cys His Lys Leu Ile Asp Phe Phe Lys Asp Ser Ile Ser
                645                 650                 655

Arg Tyr Pro Lys Trp Ser Asn Ala Tyr Asp Phe Asn Phe Ser Glu Thr
                660                 665                 670

Glu Lys Tyr Lys Asp Ile Ala Gly Phe Tyr Arg Glu Val Glu Glu Gln
                675                 680                 685

Gly Tyr Lys Val Ser Phe Glu Ser Ala Ser Lys Lys Glu Val Asp Lys
690                 695                 700

Leu Val Glu Glu Gly Lys Leu Tyr Met Phe Gln Ile Tyr Asn Lys Asp
705                 710                 715                 720

Phe Ser Asp Lys Ser His Gly Thr Pro Asn Leu His Thr Met Tyr Phe
                725                 730                 735

Lys Leu Leu Phe Asp Glu Asn Asn His Gly Gln Ile Arg Leu Ser Gly
                740                 745                 750

Gly Ala Glu Leu Phe Met Arg Arg Ala Ser Leu Lys Lys Glu Glu Leu
            755                 760                 765

Val Val His Pro Ala Asn Ser Pro Ile Ala Asn Lys Asn Pro Asp Asn
    770                 775                 780

Pro Lys Lys Thr Thr Leu Ser Tyr Asp Val Tyr Lys Asp Lys Arg
785                 790                 795                 800

Phe Ser Glu Asp Gln Tyr Glu Leu His Ile Pro Ile Ala Ile Asn Lys
                805                 810                 815

Cys Pro Lys Asn Ile Phe Lys Ile Asn Thr Glu Val Arg Val Leu Leu
                820                 825                 830

Lys His Asp Asp Asn Pro Tyr Val Ile Gly Ile Asp Arg Gly Glu Arg
                835                 840                 845

Asn Leu Leu Tyr Ile Val Val Val Asp Gly Lys Gly Asn Ile Val Glu
                850                 855                 860

Gln Tyr Ser Leu Asn Glu Ile Ile Asn Asn Phe Asn Gly Ile Arg Ile
865                 870                 875                 880

Lys Thr Asp Tyr His Ser Leu Leu Asp Lys Lys Glu Lys Glu Arg Phe
                885                 890                 895

Glu Ala Arg Gln Asn Trp Thr Ser Ile Glu Asn Ile Lys Glu Leu Lys
                900                 905                 910

Ala Gly Tyr Ile Ser Gln Val Val His Lys Ile Cys Glu Leu Val Glu
            915                 920                 925

Lys Tyr Asp Ala Val Ile Ala Leu Glu Asp Leu Asn Ser Gly Phe Lys
930                 935                 940
```

```
Asn Ser Arg Val Lys Val Glu Lys Gln Val Tyr Gln Lys Phe Glu Lys
945                 950                 955                 960

Met Leu Ile Asp Lys Leu Asn Tyr Met Val Asp Lys Ser Asn Pro
            965                 970                 975

Cys Ala Thr Gly Gly Ala Leu Lys Gly Tyr Gln Ile Thr Asn Lys Phe
            980                 985                 990

Glu Ser Phe Lys Ser Met Ser Thr Gln Asn Gly Phe Ile Phe Tyr Ile
        995                 1000                1005

Pro Ala Trp Leu Thr Ser Lys Ile Asp Pro Ser Thr Gly Phe Val
    1010                1015                1020

Asn Leu Leu Lys Thr Lys Tyr Thr Ser Ile Ala Asp Ser Lys Lys
    1025                1030                1035

Phe Ile Ser Ser Phe Asp Arg Ile Met Tyr Val Pro Glu Glu Asp
    1040                1045                1050

Leu Phe Glu Phe Ala Leu Asp Tyr Lys Asn Phe Ser Arg Thr Asp
    1055                1060                1065

Ala Asp Tyr Ile Lys Lys Trp Lys Leu Tyr Ser Tyr Gly Asn Arg
    1070                1075                1080

Ile Arg Ile Phe Arg Asn Pro Lys Lys Asn Asn Val Phe Asp Trp
    1085                1090                1095

Glu Glu Val Cys Leu Thr Ser Ala Tyr Lys Glu Leu Phe Asn Lys
    1100                1105                1110

Tyr Gly Ile Asn Tyr Gln Gln Gly Asp Ile Arg Ala Leu Leu Cys
    1115                1120                1125

Glu Gln Ser Asp Lys Ala Phe Tyr Ser Ser Phe Met Ala Leu Met
    1130                1135                1140

Ser Leu Met Leu Gln Met Arg Asn Ser Ile Thr Gly Arg Thr Asp
    1145                1150                1155

Val Asp Phe Leu Ile Ser Pro Val Lys Asn Ser Asp Gly Ile Phe
    1160                1165                1170

Tyr Asp Ser Arg Asn Tyr Glu Ala Gln Glu Asn Ala Ile Leu Pro
    1175                1180                1185

Lys Asn Ala Asp Ala Asn Gly Ala Tyr Asn Ile Ala Arg Lys Val
    1190                1195                1200

Leu Trp Ala Ile Gly Gln Phe Lys Lys Ala Glu Asp Glu Lys Leu
    1205                1210                1215

Asp Lys Val Lys Ile Ala Ile Ser Asn Lys Glu Trp Leu Glu Tyr
    1220                1225                1230

Ala Gln Thr Ser Val Lys His Lys Arg Pro Ala Ala Thr Lys Lys
    1235                1240                1245

Ala Gly Gln Ala Lys Lys Lys
    1250                1255

<210> SEQ ID NO 16
<211> LENGTH: 1228
<212> TYPE: PRT
<213> ORGANISM: Unknown
<220> FEATURE:
<223> OTHER INFORMATION: Description of Unknown:
      Lachnospiraceae bacterium sequence

<400> SEQUENCE: 16

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30
```

```
Asn Lys Arg Leu Leu Val Glu Asp Glu Lys Arg Ala Glu Asp Tyr Lys
    35                  40                  45

Gly Val Lys Lys Leu Leu Asp Arg Tyr Tyr Leu Ser Phe Ile Asn Asp
50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445
```

```
Asn Asp Ala Val Val Ala Ile Met Lys Asp Leu Leu Asp Ser Val Lys
            450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
            515                 520                 525

Gln Phe Met Gly Gly Trp Asp Lys Asp Lys Glu Thr Asp Tyr Arg Ala
530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
            595                 600                 605

Ser Glu Asp Ile Gln Lys Ile Tyr Lys Asn Gly Thr Phe Lys Lys Gly
            610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
            675                 680                 685

Glu Val Asp Lys Leu Val Glu Glu Gly Lys Leu Tyr Met Phe Gln Ile
            690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
            755                 760                 765

Asn Pro Asp Asn Pro Lys Lys Thr Thr Thr Leu Ser Tyr Asp Val Tyr
770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
            820                 825                 830

Arg Gly Glu Arg Asn Leu Leu Tyr Ile Val Val Asp Gly Lys Gly
            835                 840                 845

Asn Ile Val Glu Gln Tyr Ser Leu Asn Glu Ile Asn Asn Phe Asn
850                 855                 860

Gly Ile Arg Ile Lys Thr Asp Tyr His Ser Leu Leu Asp Lys Lys Glu
```

```
                865                 870                 875                 880
Lys Glu Arg Phe Glu Ala Arg Gln Asn Trp Thr Ser Ile Glu Asn Ile
                885                 890                 895
Lys Glu Leu Lys Ala Gly Tyr Ile Ser Gln Val Val His Lys Ile Cys
                900                 905                 910
Glu Leu Val Glu Lys Tyr Asp Ala Val Ile Ala Leu Glu Asp Leu Asn
                915                 920                 925
Ser Gly Phe Lys Asn Ser Arg Val Lys Val Lys Gln Val Tyr Gln
                930                 935                 940
Lys Phe Glu Lys Met Leu Ile Asp Lys Leu Asn Tyr Met Val Asp Lys
945                 950                 955                 960
Lys Ser Asn Pro Cys Ala Thr Gly Gly Ala Leu Lys Gly Tyr Gln Ile
                965                 970                 975
Thr Asn Lys Phe Glu Ser Phe Lys Ser Met Ser Thr Asn Gly Phe
                980                 985                 990
Ile Phe Tyr Ile Pro Ala Trp Leu Thr Ser Lys Ile Asp Pro Ser Thr
                995                 1000                1005
Gly Phe Val Asn Leu Leu Lys Thr Lys Tyr Thr Ser Ile Ala Asp
    1010                1015                1020
Ser Lys Lys Phe Ile Ser Ser Phe Asp Arg Ile Met Tyr Val Pro
    1025                1030                1035
Glu Glu Asp Leu Phe Glu Phe Ala Leu Asp Tyr Lys Asn Phe Ser
    1040                1045                1050
Arg Thr Asp Ala Asp Tyr Ile Lys Lys Trp Lys Leu Tyr Ser Tyr
    1055                1060                1065
Gly Asn Arg Ile Arg Ile Phe Arg Asn Pro Lys Lys Asn Asn Val
    1070                1075                1080
Phe Asp Trp Glu Glu Val Cys Leu Thr Ser Ala Tyr Lys Glu Leu
    1085                1090                1095
Phe Asn Lys Tyr Gly Ile Asn Tyr Gln Gln Gly Asp Ile Arg Ala
    1100                1105                1110
Leu Leu Cys Glu Gln Ser Asp Lys Ala Phe Tyr Ser Ser Phe Met
    1115                1120                1125
Ala Leu Met Ser Leu Met Leu Gln Met Arg Asn Ser Ile Thr Gly
    1130                1135                1140
Arg Thr Asp Val Asp Phe Leu Ile Ser Pro Val Lys Asn Ser Asp
    1145                1150                1155
Gly Ile Phe Tyr Asp Ser Arg Asn Tyr Glu Ala Gln Glu Asn Ala
    1160                1165                1170
Ile Leu Pro Lys Asn Ala Asp Ala Asn Gly Ala Tyr Asn Ile Ala
    1175                1180                1185
Arg Lys Val Leu Trp Ala Ile Gly Gln Phe Lys Lys Ala Glu Asp
    1190                1195                1200
Glu Lys Leu Asp Lys Val Lys Ile Ala Ile Ser Asn Lys Glu Trp
    1205                1210                1215
Leu Glu Tyr Ala Gln Thr Ser Val Lys His
    1220                1225
```

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

```
<220> FEATURE:
<223> OTHER INFORMATION: HH ribozyme encoding sequence

<400> SEQUENCE: 17
ctgatgagtc cgtgaggacg aaacgagtaa gctcgtc                              37

<210> SEQ ID NO 18
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HH ribozyme sequence

<400> SEQUENCE: 18
cugaugaguc cgugaggacg aaacgaguaa gcucguc                              37

<210> SEQ ID NO 19
<211> LENGTH: 53
<212> TYPE: DNA
<213> ORGANISM: Oryza sativa

<400> SEQUENCE: 19
ccgccaacac tgccaatgcc ggtcccaagc ccggataaaa gtggaggggg cgg            53

<210> SEQ ID NO 20
<211> LENGTH: 53
<212> TYPE: RNA
<213> ORGANISM: Oryza sativa

<400> SEQUENCE: 20
ccgccaacac ugccaaugcc ggucccaagc ccggauaaaa guggaggggg cgg            53

<210> SEQ ID NO 21
<211> LENGTH: 63
<212> TYPE: DNA
<213> ORGANISM: Helianthus annuus

<400> SEQUENCE: 21 gcgggggggcg tcagtcctac tctgcacctc ctcgtggtgt cgcctgggaa ccctctttcg    60
caa                                                                   63

<210> SEQ ID NO 22
<211> LENGTH: 63
<212> TYPE: RNA
<213> ORGANISM: Helianthus annuus

<400> SEQUENCE: 22 gcgggggggcg ucaguccuac ucugcaccuc cucguggugu cgccugggaa cccucuuucg    60
caa                                                                   63

<210> SEQ ID NO 23
<211> LENGTH: 86
<212> TYPE: DNA
<213> ORGANISM: Helianthus annuus

<400> SEQUENCE: 23 gcgggggggcg tcagtcctac tctgcacctc ctcgtggtgt cgcctgggaa ccctctttcg    60
caagaaagag gagccaagca gagagg                                          86
```

```
<210> SEQ ID NO 24
<211> LENGTH: 86
<212> TYPE: RNA
<213> ORGANISM: Helianthus annuus

<400> SEQUENCE: 24 gcgggggcg ucaguccuac ucugcaccuc cucguggugu cgccugggaa cccucuuucg      60
caagaaagag gagccaagca gagagg                                         86

<210> SEQ ID NO 25
<211> LENGTH: 80
<212> TYPE: DNA
<213> ORGANISM: Cynara scolymus

<400> SEQUENCE: 25
ggcgtcagtc ctactctgca cctcctcgtg gtgtcgcctg ggaaccctct ttcacaagaa      60
agaggagcca agcagagagg                                                80

<210> SEQ ID NO 26
<211> LENGTH: 80
<212> TYPE: RNA
<213> ORGANISM: Cynara scolymus

<400> SEQUENCE: 26
ggcgucaguc cuacucugca ccuccucgug gugucgccug ggaacccucu uucacaagaa      60
agaggagcca agcagagagg                                                80

<210> SEQ ID NO 27
<211> LENGTH: 68
<212> TYPE: DNA
<213> ORGANISM: Hepatitis Delta Virus

<400> SEQUENCE: 27
ggccggcatg gtcccagcct cctcgctggc gccggctggg caacatgctt cggcatggcg      60
aatgggac                                                             68

<210> SEQ ID NO 28
<211> LENGTH: 68
<212> TYPE: RNA
<213> ORGANISM: Hepatitis Delta Virus

<400> SEQUENCE: 28
ggccggcaug gucccagccu ccucgcuggc gccggcuggg caacaugcuu cggcauggcg      60
aaugggac                                                             68

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: scaffold RNA encoding sequnece

<400> SEQUENCE: 29
taatttctac taagtgtaga t                                              21

<210> SEQ ID NO 30
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: scaffold RNA sequence

<400> SEQUENCE: 30
uaauuucuac uaaguguaga u                                              21

<210> SEQ ID NO 31
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: tdTomato polynucleotide

<400> SEQUENCE: 31
atggtgagca agggcgagga ggtcatcaaa gagttcatgc gcttcaaggt gcgcatggag      60
ggctccatga acgccacga gttcgagatc gagggcgagg gcgagggccg ccctacgag      120 ggcacccaga ccgccaagct gaaggtgacc aagggcggcc cctgcccctt cgcctgggac    180
atcctgtccc cccagttcat gtacggctcc aaggcgtacg tgaagcaccc cgccgacatc    240
cccgattaca gaagctgtc cttccccgag ggcttcaagt gggagcgcgt gatgaacttc     300
gaggacggcg gtctggtgac cgtgacccag gactcctccc tgcaggacgg cacgctgatc    360
tacaaggtga agatgcgcgg caccaacttc ccccccgacg gccccgtaat gcagaagaag    420
accatgggct gggaggcctc caccgagcgc ctgtaccccc gcgacggcgt gctgaagggc    480
gagatccacc aggccctgaa gctgaaggac ggcggccact acctggtgga gttcaagacc    540
atctacatgg ccaagaagcc cgtgcaactg cccggctact actacgtgga caccaagctg    600
gacatcaccT cccacaacga ggactacacc atcgtggaac agtacgagcg ctccgagggc    660
cgccaccacc tgttcctgta cggcatggac gagctgtaca gtctagagg tacctga        717

<210> SEQ ID NO 32
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: mNeoGreen polynucleotide

<400> SEQUENCE: 32
atggcgtcct ccgtgagtaa aggagaagaa gataacatgg cttcgcttcc agccacacat      60
gagcttcaca tcttcggttc catcaacggc gttgacttcg atatggtcgg acaaggcact     120 gggaaccccta atgacggata cgaagagctg aaccttcaaga gcaccaaagg tgatcttcag   180
ttttctccat ggattctggt gccacacatt ggctacggat ccatcaata ccttccatac     240 cctgacggaa tgagtccatt ccaagcagcc atggttgatg ctccggata ccaagtccac     300 aggacaatgc agtttgagga cggtgcttcg ctcaccgtca actaccgtta cacttacgaa   360
gggagccaca tcaaaggaga agcccaagtg aaggggacag gctttcctgc tgatggacct    420
gtcatgacca actccttaac tgccgctgat tggtgccggt ccaagaaaac ctaccctaac    480
gacaagacca tcattagtac cttcaaatgg tcttacacca caggcaatgg caagagatat    540
cgctctacag ccaggactac ctacacattc gctaaaccaa tggccgctaa ctaccttaag    600
```

```
aaccaaccca tgtacgtgtt ccgtaagact gagttgaaac attccaagac cgaacttaac    660
ttcaaggagt ggcagaaggc atttaccgac gtaatgggca tggatgaact atacaaataa    720

<210> SEQ ID NO 33
<211> LENGTH: 5693
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pGEP424 tdT embedded gRNA delivery vector

<400> SEQUENCE: 33
ctgacgcgcc ctgtagcggc acgtcacctg catcaggaat tcaggagaag aactcgagag     60
ggaattgcag atcatgaggc agatggctat ttttgtgtca catatgcgca aaagagagg    120 ctatatttgt gtccctaggt tcttcgttgt attgcagttt ccatatcaat ctgacttggt    180
cgcatgagaa attgatggtt aaataatttg aatctctcat gtagtatcaa ctattagata    240
ttattttcac caaatatatt tccatcggag aagaagaggc tacagaggaa gcagaagaga    300
ggggtgggag aattttttaca ctttttgtaca cccacttaaa cagcaaaatc cgtatgaaaa    360
caggcccacc aaaacaatgc cacgataaca atccgtagaa acaaaagctt catttaacag    420
cggcgcaaca aagcacgctt atccatggta gttgtagtcc gtatgcgatc caaagatcac    480
gattcacgcg tgacggacgg acgacgcgtg ccacaccaca actaacggca tccatggtag    540
ttgtagtccg tatgcgatcc aaagatcacg attcacgcgt gacggacgga cgacgcgcgc    600
cacaccacaa ctaacagcgt gagccagcgt ccaaactccg gatggcaacg gggacgaaac    660
ccgtcgggta gtcactgccc aaacccgtcc ccgcaacctt catcccaaac ccgtccccgt    720
ttccggtcgc gggtttcagt tttctaccag acccgtcccc atcgggtttt tcatccccgt    780
cgggaaatcc gaacccgcca gcatttcagc accaagccaa agttcagca gcaacatgaa    840 taaaaaacaa cccgtttcaa caccaagata aaacaaaaca ttataattta gacaacattt    900
cacacgtata acaataacat atagttctca catataacaa caccatttca cacataaaac    960
aacaccattt gggataaaaa tatgggctat atcaggccat ttttatgggc catattgagt   1020
tttcgtgggt ttcacaggta ccggatttgt agaatgctga accgggtttg aaccgtaaaa   1080
tccgcgggta ttgaatttga cccaatcccg tcgtccctg gtggggtaaa aacaccatct   1140
tgagtccaaa cggccaccaa ccaaactccg acggcaacaa acaaacggcg ttgctttgct   1200
cctcggtatc tccgtgaccg ctcaatctcc cggctgtttc cccggaattg cgtggactct   1260
ctcatccaca cgcaaaccgc ctctccctcc tctctcgtcc tatccgcccc ggtgccgtag   1320
cctcacggga ctcttcttcc tcccttgcta taaaatcccc gcccctcct gtctcctctc   1380 cacacatcca aactctcaat cgcaccgaga aaaatctcct agcgatcgaa gcgaagcctc   1440
tcccgatcct ctcaaggtac gcccgtttcc cgtcgatcct cctccttccg ttcgtgttct   1500
gtagccgatc gattcgattc ccttacaccc gttcgtgttc tctcgtggat cgatcgattg   1560
tttgttgcta gaaggaactc gtagatctgg cgttttatgaa ctgtgattcg ggttagtcca   1620
gatcgattca ggtcggtcgt cgttgagcct ctcggctatg tctggattat cgtgtagatc   1680
tgctggttca gttgattatg ttcttctagg agtaatttcg ttgggtcagc gcgatttctg   1740
cttaatctat gctgcttatt gcgcctgtac ctatctcta agctatgtgc acctgtaatt   1800
ttgctagatt attcgttcat cctcgtagtt ggtttgtcac agtaatccgt atgggttctg   1860
```

```
acgatgttat tgttggtcat acctaggctt ctccagattt tattttgtta aaattggata    1920
gatctgctac tgatagttga tgatggaatt tggtgctgaa tctatgctat ttattgcgcc    1980
tatacctgat ctatcgggct atgtacggct gtagtttact ggattattcg ttcatcctcg    2040
gtagttggtt catcgtttgg gttctgacga taatattgtt gattatgcgt aggcttctgc    2100
agattgttgt taaaattgga tacatcggtt actgatggtt gatgatagat ttgtgctgaa    2160
cctatctgtt tattgctcct atacctgatc tatagggcta tgtatgcctg taatttacca    2220
gattattcgt tcatcctcgt agttggttca tctctataat tcgtatgggt tcttatgatg    2280
ttatcgttga ttatgcctag tcttatacag attattgtgt caagattgaa tatacctgct    2340
actgatcggt gataatttgg ttagtagttt gcaatctgct aggaacacgt taccactgta    2400
atctgtaaac atggtttgcc agagtagttt gttctactac tcttgatatg gttgctgatt    2460
ttagtcgcct ccttttggat catgtattga tgtccttgca gatttccgtg tacttaccccc   2520
ggcttttgtg tacttcgtgt taacagctct agaggatcct ctcaacacaa catatacaaa    2580
acaaacgaat ctcaagcaat caagcattct acttctattg cagcaattta aatcatttct    2640
tttaaagcaa aagcaatttt ctgaaaattt tcaccattta cgaacgatag ggcgcgatcc    2700
cgccaccatg gtgagcaagg gcgaggaggt catcaaagag ttcatgcgct tcaaggtgcg    2760
catggagggc tccatgaacg gccacgagtt cgagatcgag ggcgagggcg agggccgccc    2820
ctacgagggc acccagaccg ccaagctgaa ggtgaccaag ggcggccccc tgcccttcgc    2880
ctgggacatc ctgtcccccc agttcatgta cggctccaag gcgtacgtga agcaccccgc    2940
cgacatcccc gattacaaga agctgtcctt ccccgagggc ttcaagtggg agcgcgtgat    3000
gaacttcgag gacggcggtc tggtgaccgt gacccaggac tcctccctgc aggacggcac    3060
gctgatctac aaggtgaaga tgcgcggcac caacttcccc cccgacggcc ccgtaatgca    3120
gaagaagacc atgggctggg aggcctccac cgagcgcctg tacccccgcg acggcgtgct    3180
gaagggcgag atccaccagg ccctgaagct gaaggacggg ggccactacc tggtggagtt    3240
caagaccatc tacatggcca agaagcccgt gcaactgccc ggctactact acgtggacac    3300
caagctggac atcacctccc acaacgagga ctacaccatc gtggaacagt acgagcgctc    3360
cgagggccgc caccacctgt tcctgtacgg catggacgag ctgtacaagt ctagaggtac    3420
ctgataattt ctactaagtg tagatgagac ggagctcagt ctgaccgcgg cgtctcttaa    3480
tttctactaa gtgtagatcg aatttccccg atcgttcaaa catttggcaa taaagtttct    3540
taagattgaa tcctgttgcc ggtcttgcga tgattatcat ataatttctg ttgaattacg    3600
ttaagcatgt aataattaac atgtaatgca tgacgttatt tatgagatgg gttttttatga   3660
ttagagtccc gcaattatac atttaatacg cgatagaaaa caaatatag cgcgcaaact    3720
aggataaatt atcgcgcgcg gtgtcatcta tgttactaga tcgctcgacg cggccgccat    3780
ggcctctagt ggatcaggtg tcgttcggct gcggcgagcg gtatcagctc actcaaaggc    3840
ggtaatacgg ttatccacag aatcagggga taacgcagga agaacatgt gagcaaaagg    3900
ccagcaaaag gccaggaacc gtaaaaaggc cgcgttgctg gcgttttttcc ataggctccg    3960
ccccccctgac gagcatcaca aaaatcgacg ctcaagtcag aggtggcgaa acccgacagg    4020
actataaaga taccaggcgt ttccccctgg aagctccctc gtgcgctctc ctgttccgac    4080
cctgccgctt accggatacc tgtccgcctt tctcccttcg ggaagcgtgg cgctttctca    4140
tagctcacgc tgtaggtatc tcagttcggt gtaggtcgtt cgctccaagc tgggctgtgt    4200
```

| | |
|---|---:|
| gcacgaaccc cccgttcagc ccgaccgctg cgccttatcc ggtaactatc gtcttgagtc | 4260 |
| caacccggta agacacgact tatcgccact ggcagcagcc actggtaaca ggattagcag | 4320 |
| agcgaggtat gtaggcggtg ctacagagtt cttgaagtgg tggcctaact acggctacac | 4380 |
| tagaaggaca gtatttggta tctgcgctct gctgaagcca gttaccttcg gaaaaagagt | 4440 |
| tggtagctct tgatccggca aacaaaccac cgctggtagc ggtggttttt ttgtttgcaa | 4500 |
| gcagcagatt acgcgcagaa aaaaggatc tcaagaagat cctttgatct tttctacggg | 4560 |
| gtctgacgct cagtggaacg aaaactcacg ttaagggatt ttggtcatga gattatcaaa | 4620 |
| aaggatcttc acctagatcc ttttaaatta aaaatgaagt tttaaatcaa tctaaagtat | 4680 |
| atatgagtaa acttggtctg acagttacca atgcttaatc agtgaggcac ctatctcagc | 4740 |
| gatctgtcta tttcgttcat ccatagttgc ctgactcccc gtcgtgtaga taactacgat | 4800 |
| acgggagggc ttaccatctg gccccagtgc tgcaatgata ccgcgagacc cacgctcacc | 4860 |
| ggctccagat ttatcagcaa taaaccagcc agccggaagg gccgagcgca gaagtggtcc | 4920 |
| tgcaacttta tccgcctcca tccagtctat taattgttgc cgggaagcta gagtaagtag | 4980 |
| ttcgccagtt aatagtttgc gcaacgttgt tgccattgct acaggcatcg tggtgtcacg | 5040 |
| ctcgtcgttt ggtatggctt cattcagctc cggttcccaa cgatcaaggc gagttacatg | 5100 |
| atcccccatg ttgtgcaaaa aagcggttag ctccttcggt cctccgatcg ttgtcagaag | 5160 |
| taagttggcc gcagtgttat cactcatggt tatggcagca ctgcataatt ctcttactgt | 5220 |
| catgccatcc gtaagatgct tttctgtgac tggtgagtac tcaaccaagt cattctgaga | 5280 |
| atagtgtatg cggcgaccga gttgctcttg cccggcgtca atacgggata ataccgcgcc | 5340 |
| acatagcaga actttaaaag tgctcatcat tggaaaacgt tcttcggggc gaaaactctc | 5400 |
| aaggatctta ccgctgttga gatccagttc gatgtaaccc actcgtgcac ccaactgatc | 5460 |
| ttcagcatct tttactttca ccagcgtttc tgggtgagca aaaacaggaa ggcaaaatgc | 5520 |
| cgcaaaaaag gaataaggg cgacacggaa atgttgaata ctcatactct tcctttttca | 5580 |
| atattattga agcatttatc agggttattg tctcatgagc ggatacatat ttgaatgtat | 5640 |
| ttagaaaaat aaacaaatag gggttccgcg cacatttccc cgaaaagtgc cac | 5693 |

<210> SEQ ID NO 34
<211> LENGTH: 4959
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pGEP425 vector control guide RNA delivery
      without tdT

<400> SEQUENCE: 34

| | |
|---|---:|
| ctgacgcgcc ctgtagcggc acgtcacctg catcaggaat tcaggagaag aactcgagag | 60 |
| ggaattgcag atcatgaggc agatggctat ttttgtgtca catatgcgca aaagagagg | 120 |
| ctatatttgt gtccctaggt tcttcgttgt attgcagttt ccatatcaat ctgacttggt | 180 |
| cgcatgagaa attgatggtt aaataatttg aatctctcat gtagtatcaa ctattagata | 240 |
| ttattttcac caaatatatt tccatcggag aagaagaggc tacagaggaa gcagaagaga | 300 |
| ggggtgggag aattttttaca cttttgtaca cccacttaaa cagcaaaatc cgtatgaaaa | 360 |
| caggcccacc aaaacaatgc cacgataaca atccgtagaa acaaaagctt catttaacag | 420 |
| cggcgcaaca aagcacgctt atccatggta gttgtagtcc gtatgcgatc caaagatcac | 480 |

-continued

```
gattcacgcg tgacggacgg acgacgcgtg ccacaccaca actaacggca tccatggtag    540
ttgtagtccg tatgcgatcc aaagatcacg attcacgcgt gacggacgga cgacgcgcgc    600
cacaccacaa ctaacagcgt gagccagcgt ccaaactccg gatggcaacg gggacgaaac    660
ccgtcgggta gtcactgccc aaacccgtcc ccgcaacctt catcccaaac ccgtccccgt    720
ttccggtcgc gggtttcagt tttctaccag acccgtcccc atcgggtttt tcatccccgt    780
cgggaaatcc gaacccgcca gcatttcagc accaagccaa agttgcagca gcaacatgaa    840
taaaaaacaa cccgtttcaa caccaagata aaacaaaaca ttataattta gacaacattt    900
cacacgtata acaataacat atagttctca catataacaa caccatttca cacataaaac    960
aacaccattt gggataaaaa tatgggctat atcaggccat ttttatgggc catattgagt   1020
tttcgtgggt ttcacaggta ccggatttgt agaatgctga accgggtttg aaccgtaaaa   1080
tccgcgggta ttgaatttga cccaatcccg tcgtcccctg gtggggtaaa aacaccatct   1140
tgagtccaaa cggccaccaa ccaaactccg acggcaacaa acaaacggcg ttgctttgct   1200
cctcggtatc tccgtgaccg ctcaatctcc cggctgtttc cccggaattg cgtggactct   1260
ctcatccaca cgcaaaccgc ctctccctcc tctctcgtcc tatccgcccc ggtgccgtag   1320
cctcacggga ctcttcttcc tcccttgcta taaaatcccc gcccctcct gtctcctctc    1380 cacacatcca aactctcaat cgcaccgaga aaaatctcct agcgatcgaa gcgaagcctc   1440
tcccgatcct ctcaaggtac gcccgtttcc cgtcgatcct cctccttccg ttcgtgttct   1500
gtagccgatc gattcgattc ccttacaccc gttcgtgttc tctcgtggat cgatcgattg   1560
tttgttgcta gaaggaactc gtagatctgg cgtttatgaa ctgtgattcg ggttagtcca   1620
gatcgattca ggtcggtcgt cgttgagcct ctcggctatg tctggattat cgtgtagatc   1680
tgctggttca gttgattatg ttcttctagg agtaatttcg ttgggtcagc gcgatttctg   1740
cttaatctat gctgcttatt gcgcctgtac ctatctacta agctatgtgc acctgtaatt   1800
ttgctagatt attcgttcat cctcgtagtt ggtttgtcac agtaatccgt atgggttctg   1860
acgatgttat tgttggtcat acctaggctt ctccagattt tattttgtta aaattggata   1920
gatctgctac tgatagttga tgatggaatt tggtgctgaa tctatgctat ttattgcgcc   1980
tatacctgat ctatcgggct atgtacggct gtagtttact ggattattcg ttcatcctcg   2040
gtagttggtt catcgtttgg gttctgacga taatattgtt gattatgcgt aggcttctgc   2100
agattgttgt taaaattgga tacatcggtt actgatggtt gatgatagat ttgtgctgaa   2160
cctatctgtt tattgctcct atacctgatc tatagggcta tgtatgcctg taatttacca   2220
gattattcgt tcatcctcgt agttggttca tctctataat tcgtatgggt tcttatgatg   2280
ttatcgttga ttatgcctag tcttatacag attattgtgt caagattgaa tatacctgct   2340
actgatcggt gataatttgg ttagtagttt gcaatctgct aggaacacgt taccactgta   2400
atctgtaaac atggtttgcc agagtagttt gttctactac tcttgatatg gttgctgatt   2460
ttagtcgcct ccttttggat catgtattga tgtccttgca gatttccgtg tacttacccc   2520
ggcttttgtg tacttcgtgt taacagctct agaggatcct ctcaacacaa catatacaaa   2580
acaaacgaat ctcaagcaat caagcattct acttctattg cagcaattta aatcatttct   2640
tttaaagcaa aagcaatttt ctgaaaattt tcaccattta cgaacgatag taatttctac   2700
taagtgtaga tgagacggag ctcagtctga ccgcggcgtc tcttaatttc tactaagtgt   2760
agatcgaatt tccccgatcg ttcaaacatt tggcaataaa gtttcttaag attgaatcct   2820
```

```
gttgccggtc ttgcgatgat tatcatataa tttctgttga attacgttaa gcatgtaata    2880
attaacatgt aatgcatgac gttatttatg agatgggttt ttatgattag agtcccgcaa    2940
ttatacattt aatacgcgat agaaaacaaa atatagcgcg caaactagga taaattatcg    3000
cgcgcggtgt catctatgtt actagatcgc tcgacgcggc cgccatggcc tctagtggat    3060
caggtgtcgt tcggctgcgg cgagcggtat cagctcactc aaaggcggta atacggttat    3120
ccacagaatc aggggataac gcaggaaaga acatgtgagc aaaaggccag caaaaggcca    3180
ggaaccgtaa aaaggccgcg ttgctggcgt ttttccatag gctccgcccc cctgacgagc    3240
atcacaaaaa tcgacgctca agtcagaggt ggcgaaaccc gacaggacta taaagatacc    3300
aggcgtttcc ccctggaagc tccctcgtgc gctctcctgt tccgaccctg ccgcttaccg    3360
gatacctgtc cgcctttctc ccttcgggaa gcgtggcgct ttctcatagc tcacgctgta    3420
ggtatctcag ttcggtgtag gtcgttcgct ccaagctggg ctgtgtgcac gaaccccccg    3480
ttcagcccga ccgctgcgcc ttatccggta actatcgtct tgagtccaac ccggtaagac    3540
acgacttatc gccactggca gcagccactg gtaacaggat tagcagagcg aggtatgtag    3600
gcggtgctac agagttcttg aagtggtggc ctaactacgg ctacactaga aggacagtat    3660
ttggtatctg cgctctgctg aagccagtta ccttcggaaa aagagttggt agctcttgat    3720
ccggcaaaca aaccaccgct ggtagcggtg gtttttttgt ttgcaagcag cagattacgc    3780
gcagaaaaaa aggatctcaa gaagatcctt tgatctttc tacggggtct gacgctcagt    3840
ggaacgaaaa ctcacgttaa gggattttgg tcatgagatt atcaaaaagg atcttcacct    3900
agatcctttt aaattaaaaa tgaagtttta aatcaatcta agtatatat gagtaaactt    3960 ggtctgacag ttaccaatgc ttaatcagtg aggcacctat ctcagcgatc tgtctatttc    4020
gttcatccat agttgcctga ctccccgtcg tgtagataac tacgatacgg agggcttac    4080 catctggccc cagtgctgca atgataccgc gagacccacg ctcaccggct ccagatttat    4140
cagcaataaa ccagccagcc ggaagggccg agcgcagaag tggtcctgca actttatccg    4200
cctccatcca gtctattaat tgttgccggg aagctagagt aagtagttcg ccagttaata    4260
gtttgcgcaa cgttgttgcc attgctacag gcatcgtggt gtcacgctcg tcgtttggta    4320
tggcttcatt cagctccggt tcccaacgat caaggcgagt tacatgatcc cccatgttgt    4380
gcaaaaaagc ggttagctcc ttcggtcctc cgatcgttgt cagaagtaag ttggccgcag    4440
tgttatcact catggttatg gcagcactgc ataattctct tactgtcatg ccatccgtaa    4500
gatgcttttc tgtgactggt gagtactcaa ccaagtcatt ctgagaatag tgtatgcggc    4560
gaccgagttg ctcttgcccg gcgtcaatac gggataatac cgcgccacat agcagaactt    4620
taaaagtgct catcattgga aaacgttctt cggggcgaaa actctcaagg atcttaccgc    4680
tgttgagatc cagttcgatg taacccactc gtgcacccaa ctgatcttca gcatctttta    4740
ctttcaccag cgtttctggg tgagcaaaaa caggaaggca aaatgccgca aaaagggaa    4800 taagggcgac acggaaatgt tgaatactca tactcttcct ttttcaatat tattgaagca    4860
tttatcaggg ttattgtctc atgagcggat acatatttga atgtatttag aaaaataaac    4920
aaataggggt tccgcgcaca tttccccgaa aagtgccac                           4959
```

<210> SEQ ID NO 35
<211> LENGTH: 10434
<212> TYPE: DNA
<213> ORGANISM: Artificial Sequence
<220> FEATURE:
<223> OTHER INFORMATION: Description of Artificial Sequence: Synthetic

```
        polynucleotide
<220> FEATURE:
<223> OTHER INFORMATION: pGEP372 LbCpf1 RR construct

<400> SEQUENCE: 35
actgctgcag tgcagcgtga cccggtcgtg cccctctcta gagataatga gcattgcatg      60
tctaagttat aaaaaattac cacatatttt ttttgtcaca cttgtttgaa gtgcagttta     120
tctatcttta tacatatatt taaactttac tctacgaata atataatcta tagtactaca     180
ataatatcag tgttttagag aatcatataa atgaacagtt agacatggtc taaaggacaa     240
ttgagtattt tgacaacagg actctacagt tttatctttt tagtgtgcat gtgttctcct     300 tttttttgc aaatagcttc acctatataa tacttcatcc attttattag tacatccatt     360
tagggtttag ggttaatggt ttttatagac taattttttt agtacatcta ttttattcta     420
ttttagcctc taaattaaga aaactaaaac tctattttag tttttttatt taataattta     480
gatataaaat agaataaaat aaagtgacta aaaattaaac aaatacccctt taagaaatta     540 aaaaaactaa ggaaacattt ttcttgtttc gagtagataa tgccagcctg ttaaacgccg     600
tcgatcgacg agtctaacgg acaccaacca gcgaaccagc agcgtcgcgt cgggccaagc     660
gaagcagacg gcacggcatc tctgtcgctg cctctggacc cctctcgaga gttccgctcc     720
accgttggac ttgctccgct gtcggcatcc agaaattgcg tggcggagcg gcagacgtga     780
gccggcacgg caggcggcct cctcctcctc tcacggcacc ggcagctacg ggggattcct     840
ttcccaccgc tccttcgctt tcccttcctc gcccgccgta ataaatagac ccccctcca     900 caccctcttt ccccaacctc gtgttgttcg gagcgcacac acacacaacc agatctcccc     960
caaatccacc cgtcggcacc tccgcttcaa ggtacgccgc tcgtcctccc cccccccccc    1020
tctctacctt ctctagatcg gcgttccggt ccatggttag ggcccggtag ttctacttct    1080
gttcatgttt gtgttagatc cgtgtttgtg ttagatccgt gctgctagcg ttcgtacacg    1140
gatgcgacct gtacgtcaga cacgttctga ttgctaactt gccagtgttt ctctttgggg    1200
aatcctggga tggctctagc cgttccgcag acgggatcga tctaggatag gtatacatgt    1260
tgatgtgggt tttactgatg catatacatg atggcatatg cagcatctat tcatatgctc    1320
taaccttgag tacctatcta ttataataaa caagtatgtt ttataattat tttgatcttg    1380
atatacttgg atgatggcat atgcagcagc tatatgtgga ttttttttagc cctgccttca    1440 tacgctattt atttgcttgg tactgtttct tttgtcgatg ctcaccctgt tgtttggtgt    1500
tacttctgca ggtcgaagct tgaagcaaac atggcatcta gcatggcacc aaagaaaaaa    1560
aggaaagttt ccaaacttga aaaatttaca aactgctact cccttttccaa gacgcttagg    1620 tttaaagcga tccccgttgg caagacccaa gagaatatcg ataacaaaag acttctggtc    1680
gaagatgaaa aagggccga agactacaag ggggtcaaga agttgctcga tcgctattat    1740 ctttcctta tcaacgatgt gcttcattca atcaaactga gaacttgaa taactacatt    1800 agccttttca gaaagaaaac gaggactgaa aaggagaaca aggaacttga gatcttgaa    1860 ataaaccttc gcaaagaaat tgcaaaagcc ttcaagggga acgaaggata taaatctctt    1920
ttcaaaaaag acattataga aacaattttg cctgagtttc ttgacgacaa ggatgaaatt    1980
gcgctcgtca atagctttaa cggatttaca actgccttca cagggttctt cgacaatagg    2040
gagaatatgt ttagcgagga ggcaaaaagc acatccatcg cattcagatg catcaatgaa    2100
aatcttaccc ggtacatatc gaatatggac atatttgaaa aagtggatgc aatattcgat    2160
aagcacgaag tccaggagat aaaggaaaag atactgaata gcgactatga tgtcgaagat    2220
```

| | |
|---|---|
| tttttcgaag gtgagttctt caactttgtc ctgactcaag aaggcattga tgtctataat | 2280 |
| gcaataattg gaggttttgt gactgagtct ggcgagaaga taaagggctt gaacgagtat | 2340 |
| atcaatctct acaaccagaa gactaagcaa aagttgccta aatttaaacc gctttacaag | 2400 |
| caagttttga gcgaccggga aagcctttcc ttttacggtg aaggatacac gagcgatgaa | 2460 |
| gaagtcctcg aagtcttccg caacacactc aacaagaact cagaaatctt ttcctcaatt | 2520 |
| aaaaaattgg agaagctttt caagaacttc gatgaatact cttcggcggg gattttttgtg | 2580 |
| aagaacggcc cggcaatttc cacaatatct aaagacattt cggagaatg aacgtgata | 2640 |
| agagacaagt ggaatgcgga gtatgatgac atacacctga agaagaaggc agttgtgact | 2700 |
| gaaaaatacg aagatgacag gagaaaaagc tttaaaaaga tcgggtcctt ttcactggaa | 2760 |
| cagctgcagg agtatgccga cgccgatctt tcggttgtcg aaaagctcaa agaataatt | 2820 |
| atccagaagg tcgatgaaat ctacaaggtg tacggctcaa gcgagaagct ctttgatgct | 2880 |
| gacttcgtgt tggagaagtc tcttaaaaaa acgacgcag tcgtcgcgat aatgaaagat | 2940 |
| ttgctggatt cagtgaaatc cttcgagaat tatatcaaag ccttcttcgg cgaggggaag | 3000 |
| gagacaaaca gggatgagtc cttctatgga gacttcgttc tggcttacga catccttctt | 3060 |
| aaggtcgacc acatctatga cgcaattcgg aactatgtga cgcagaagcc gtattcgaaa | 3120 |
| gataagttca agctctattt ccaaaaccct caatttatgc gtgggtggga taagacaaaa | 3180 |
| gagaccgatt accgggcaac aattttgcgg tacgggtcta atattaccct cgctataatg | 3240 |
| gataagaaat acgctaaatg tctccagaaa attgacaaag atgacgtcaa cggcaattat | 3300 |
| gaaaaaatca attataaact ccttcctggc ccaaataaaa tgctcccgag ggtgtttttt | 3360 |
| tccaaaaagt ggatggccta ttataatcca tcagaggata ttcagaaaat ctataaaaat | 3420 |
| gggacccttta agaagggtga catgtttaac ctgaacgatt gccacaagct tatagatttt | 3480 |
| ttcaaagact ctattagccg ctatcccaaa tggtctaatg cttatgattt caacttctct | 3540 |
| gaaactgaaa agtacaaaga tattgcagga ttctaccgcg aagttgaaga acaaggttat | 3600 |
| aaggtttcct tgagtctgc gtccaagaaa gaggtcgata agttggtcga agaagggaaa | 3660 |
| ttgtatatgt ttcaaattta caataaagac ttttccgaca agtcccatgg tacacctaat | 3720 |
| ctgcatacca tgtacttcaa actgctgttc gatgagaata atcacggtca gattcgcctg | 3780 |
| agcggagggg cggaactctt catgaggaga gcatcgttga aaaagagga gctcgtcgtg | 3840 |
| catccggcta acagccccat tgctaacaag aatccggata atccaaagaa gactactacc | 3900 |
| ctctcctatg acgtctataa ggataagaga ttctctgagg accagtacga gttgcacatc | 3960 |
| cctattgcga taaataaatg ccctaagaac atctttaaaa tcaatactga ggtcagagtc | 4020 |
| ctgcttaagc acgacgacaa cccgtatgtg atcgggattg atagggtgta aaggaacttg | 4080 |
| ctttatattg tggttgtcga tggaaaaggt aatatagtgg aacaatactc tctgaatgaa | 4140 |
| attatcaaca acttcaatgg cattaggatc aagaccgact atcattctct gttggacaag | 4200 |
| aaagagaaag agcgcttcga ggcacggcaa aactggacgt ctattgagaa catcaaggag | 4260 |
| cttaaggctg gttacatttc tcaggttgtg cacaaaattt gcgaactggt cgagaaatat | 4320 |
| gatgccgtta tcgcacttga agatctcaac agcggattta agaattctcg ggtgaaagtc | 4380 |
| gaaaaacagg tgtatcaaaa attcgaaaag atgctgatcg acaagctcaa ttatatggtt | 4440 |
| gataaaaaga gcaacccatg cgccacgggg ggtgcgctta agggctatca gattacgaac | 4500 |
| aaatttgaat ccttcaagtc aatgtcgacg caaaatgggt ttatattcta tataccggcg | 4560 |

```
tggcttacat ctaaaataga tcctagcact gggttcgtga acctgctgaa aaccaagtac    4620
acttcaatcg cagattctaa aaaatttata agcagcttcg acagaatcat gtatgtgccc    4680
gaggaagacc tcttcgagtt tgcccttgat tacaaaaatt tctcaagaac ggatgcagac    4740
tacataaaga agtggaagct gtactcttat gggaaccgga ttcggatatt cagaaatccg    4800
aaaaaaaaca atgtctttga ttgggaggaa gtttgtctta cctctgctta caagagctg     4860 ttcaataaat atggcattaa ttaccagcaa ggtgatatcc gggcgctcct ttgcgaacag    4920
tctgacaaag ctttctattc ttcatttatg gcgctcatgt cattgatgct gcagatgagg    4980
aatagcatta cggggaggac tgatgttgac tttctgatct cgcccgtgaa aaattctgat    5040
ggaatcttct acgattccag gaattatgag gcccaggaaa atgctatcct tcccaagaac    5100
gcagacgcaa atggcgcgta caatatagct cgcaaggttt tgtgggctat aggccaattc    5160
aagaaagccg aagacgaaaa gctggacaaa gttaagattg ctatatctaa caagagtgg    5220 cttgagtatg cgcaaacatc tgttaaacac aaacgccccg cggctacaaa gaaggctggc    5280
caggcaaaga agaagaagtg agtcgaccga tcgttcaaac atttggcaat aaagtttctt    5340
aagattgaat cctgttgccg gtcttgcgat gattatcata taatttctgt tgaattacgt    5400
taagcatgta ataattaaca tgtaatgcat gacgttattt atgagatggg ttttatgat     5460 tagagtcccg caattataca tttaatacgc gatagaaaac aaaatatagc gcgcaaacta    5520
ggataaatta tcgcgcgcgg tgtcatctat gttactagat cgatcccggg atatcgcggc    5580
cgcgtcgttc ggctgcggcg agcggtatca gctcactcaa aggcggtaat acggttatcc    5640
acagaatcag gggataacgc aggaaagaac atgtgagcaa aaggccagca aaaggccagg    5700
aaccgtaaaa aggccgcgtt gctggcgttt ttccataggc tccgcccccc tgacgagcat    5760
cacaaaaatc gacgctcaag tcagaggtgg cgaaacccga caggactata agataccag     5820 gcgtttcccc ctggaagctc cctcgtgcgc tctcctgttc cgaccctgcc gcttaccgga    5880
tacctgtccg cctttctccc ttcgggaagc gtggcgcttt ctcatagctc acgctgtagg    5940
tatctcagtt cggtgtaggt cgttcgctcc aagctgggct gtgtgcacga accccccgtt    6000
cagcccgacc gctgcgcctt atccggtaac tatcgtcttg agtccaaccc ggtaagacac    6060
gacttatcgc cactggcagc agccactggt aacaggatta gcagagcgag gtatgtaggc    6120
ggtgctacag agttcttgaa gtggtggcct aactacggct acactagaag gacagtattt    6180
ggtatctgcg ctctgctgaa gccagttacc ttcggaaaaa gagttggtag ctcttgatcc    6240
ggcaaacaaa ccaccgctgg tagcggtggt ttttttgttt gcaagcagca gattacgcgc    6300
agaaaaaaag gatctcaaga agatcctttg atcttttcta cggggtctga cgctcagtgg    6360
aacgaaaact cacgttaagg gattttggtc atgagattat caaaaaggat cttcacctag    6420
atccttttaa attaaaaatg aagttttaaa tcaatctaaa gtatatatga gtaaacttgg    6480
tctgacagtt accaatgctt aatcagtgag gcacctatct cagcgatctg tctatttcgt    6540
tcatccatag ttgcctgact ccccgtcgtg tagataacta cgatacggga gggcttacca    6600
tctggcccca gtgctgcaat gataccgcga gacccacgct caccggctcc agatttatca    6660
gcaataaacc agccagccgg aagggccgag cgcagaagtg gtcctgcaac tttatccgcc    6720
tccatccagt ctattaattg ttgccgggaa gctagagtaa gtagttcgcc agttaatagt    6780
ttgcgcaacg ttgttgccat tgctacaggc atcgtggtgt cacgctcgtc gtttggtatg    6840
gcttcattca gctccggttc ccaacgatca aggcgagtta catgatcccc catgttgtgc    6900
aaaaaagcgg ttagctcctt cggtcctccg atcgttgtca gaagtaagtt ggccgcagtg    6960
```

```
ttatcactca tggttatggc agcactgcat aattctctta ctgtcatgcc atccgtaaga    7020
tgcttttctg tgactggtga gtactcaacc aagtcattct gagaatagtg tatgcggcga    7080
ccgagttgct cttgcccggc gtcaatacgg gataataccg cgccacatag cagaacttta    7140
aaagtgctca tcattggaaa acgttcttcg gggcgaaaac tctcaaggat cttaccgctg    7200
ttgagatcca gttcgatgta acccactcgt gcacccaact gatcttcagc atcttttact    7260
ttcaccagcg tttctgggtg agcaaaaaca ggaaggcaaa atgccgcaaa aaagggaata    7320
agggcgacac ggaaatgttg aatactcata ctcttccttt ttcaatatta ttgaagcatt    7380
tatcagggtt attgtctcat gagcggatac atatttgaat gtatttagaa aaataaacaa    7440
ataggggttc cgcgcacatt tccccgaaaa gtgccacctg acgcgccctg tagcggcacg    7500
tctaattcgg gggatctgga ttttagtact ggattttggt tttaggaatt agaaatttta    7560
ttgatagaag tattttacaa atacaaatac atactaaggg tttcttatat gctcaacaca    7620
tgagcgaaac cctataggaa ccctaattcc cttatctggg aactactcac acattattat    7680
ggagaaactc gagcttgtcg atcgacatga tcagggagct ctagattatt tgtatagttc    7740
atccatgccc attacgtcgg taaatgcctt ctgccactcc ttgaagttaa gttcggtctt    7800
ggaatgtttc aactcagtct tacggaacac gtacatgggt tggttcttaa ggtagttagc    7860
ggccattggt ttagcgaatg tgtaggtagt cctggctgta gagcgatatc tcttgccatt    7920
gcctgtggtg taagaccatt tgaaggtact aatgatggtc ttgtcgttag ggtaggtttt    7980
cttggaccgg caccaatcag cggcagttaa ggagttggtc atgacaggtc catcagcagg    8040
aaagcctgtc cccttcactt gggcttctcc tttgatgtgg ctcccttcgt aagtgtaacg    8100
gtagttgacg gtgagcgaag caccgtcctc aaactgcatt gtcctgtgga cttggtatcc    8160
ggagccatca accatggctg cttggaatgg actcattccg tcagggtatg gaaggtattg    8220
atggaatccg tagccaatgt gtggcaccag aatccatgga gaaaactgaa gatcaccttt    8280
ggtgctcttg aggttcagct cttcgtatcc gtcattaggg ttcccagtgc cttgtccgac    8340
catatcgaag tcaacgccgt tgatggaacc gaagatgtga agctcatgtg tggctggaag    8400
cgaagccatg ttatcttctt ctcctttact cacggaggac gccatggtgg cgggatcgcg    8460
ccctatcgtt cgtaaatggt gaaaattttc agaaaattgc ttttgcttta aagaaaatga    8520
tttaaattgc tgcaatagaa gtagaatgct tgattgcttg agattcgttt gttttgtata    8580
tgttgtgttg agaggatcct caagcttcga cctgcagaag taacaccaaa caacagggtg    8640
agcatcgaca aaagaaacag taccaagcaa ataaatagcg tatgaaggca gggctaaaaa    8700
aatccacata tagctgctgc atatgccatc atccaagtat atcaagatca aaataattat    8760
aaaacatact tgtttattat aatagatagg tactcaaggt tagagcatat gaatagatgc    8820
tgcatatgcc atcatgtata tgcatcagta aaacccacat caacatgtat acctatccta    8880
gatcgatatt tccatccatc ttaaactcgt aactatgaag atgtatgaca cacacataca    8940
gttccaaaat taataaatac accaggtagt ttgaaacagt attctactcc gatctagaac    9000
gaatgaacga ccgcccaacc acaccacatc atcacaacca agcgaacaaa agcatctctg    9060
tatatgcatc agtaaaaccc gcatcaacat gtatacctat cctagatcga tatttccatc    9120
catcatcttc aattcgtaac tatgaatatg tatggcacac acatacagat ccaaaattaa    9180
taaatccacc aggtagtttg aaacagaatt ctactccgat ctagaacgac cgcccaacca    9240
gaccacatca tcacaaccaa gacaaaaaaa agcatgaaaa gatgacccga caacaagtg    9300
```

```
cacggcatat attgaaataa aggaaaaggg caaaccaaac cctatgcaac gaaacaaaaa    9360
aaatcatgaa atcgatcccg tctgcggaac ggctagagcc atcccaggat tccccaaaga    9420
gaaacactgg caagttagca atcagaacgt gtctgacgta caggtcgcat ccgtgtacga    9480
acgctagcag cacggatcta acacaaacac ggatctaaca caaacatgaa cagaagtaga    9540
actaccgggc cctaaccatg gaccggaacg ccgatctaga gaaggtagag aggggggggg    9600
aggacgagcg gcgtaccttg aagcggaggt gccgacgggt ggatttgggg gagatccact    9660
agttctagag cggccgccac cgcggtggaa ttctcgaggt cctctccaaa tgaaatgaac    9720
ttccttatat agaggaaggg tcttgcgaag gatagtggga ttgtgcgtca tcccttacgt    9780
cagtggagat atcacatcaa tccacttgct ttgaagacgt ggttggaacg tcttcttttt    9840
ccacgatgct cctcgtgggt gggggtccat ctttgggacc actgtcggca gaggcatctt    9900
gaacgatagc ctttccttta tcgcaatgat ggcatttgta ggtgccacct tcctttttcta   9960 ctgtcctttt gatcaagtga ccgatagctg ggcaatggaa tccgaggagg tttcccgata    10020
ttaccctttg ttgaaaagtc tcaatagccc tttggtcttc tgagactgta tctttgatat    10080
tcttggagta gacgagagtg tcgtgctcca ccatgttatc acatcaattc acttgctttg    10140
aagacgtggt tggaacgtct tcttttttcca cgatgctcct cgtgggtggg ggtccatctt    10200
tgggaccact gtcggcagag gcatcttgaa cgatagcctt tcctttatcg caatgatggc    10260
atttgtaggt gccaccttcc ttttctactg tcctttttgat caagtgacag atagctgggc    10320
aatggaatcc gaggaggttt cccgatatta cccttgttg aaaagtctca atagcccttt    10380
ggtcttctga gacttgcagg caagcaagca tgaatgcctg ggcgcgccga tatc          10434
```

<210> SEQ ID NO 36
<211> LENGTH: 10434
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pGEP373 LbCpf1 RVR construct

<400> SEQUENCE: 36

```
actgctgcag tgcagcgtga cccggtcgtg cccctctcta gagataatga gcattgcatg    60
tctaagttat aaaaaattac cacatatttt ttttgtcaca cttgtttgaa gtgcagttta   120
tctatcttta tacatatatt taaactttac tctacgaata atataatcta tagtactaca   180
ataatatcag tgtttttagag aatcatataa atgaacagtt agacatggtc taaaggacaa   240
ttgagtattt tgacaacagg actctacagt tttatctttt tagtgtgcat gtgttctcct   300
ttttttttgc aaatagcttc acctatataa tacttcatcc atttttattag tacatccatt   360 tagggtttag ggttaatggt ttttatagac taattttttt agtacatcta ttttattcta   420
ttttagcctc taaattaaga aaactaaaac tctatttttag tttttttttatt taataattta   480 gatataaaat agaataaaat aaagtgacta aaaattaaac aaatacccttt taagaaatta   540 aaaaaactaa ggaaacattt tcttgtttc gagtagataa tgccagcctg ttaaacgccg    600
tcgatcgacg agtctaacgg acaccaacca gcgaaccagc agcgtcgcgt cgggccaagc   660
gaagcagacg gcacggcatc tctgtcgctg cctctggacc cctctcgaga gttccgctcc   720
accgttggac ttgctccgct gtcggcatcc agaaattgcg tggcggagcg gcagacgtga   780
gccggcacgg caggcggcct cctcctcctc tcacggcacc ggcagctacg ggggattcct   840
```

```
ttcccaccgc tccttcgctt tcccttcctc gcccgccgta ataaatagac accccctcca    900
caccctcttt ccccaacctc gtgttgttcg gagcgcacac acacacaacc agatctcccc    960
caaatccacc cgtcggcacc tccgcttcaa ggtacgccgc tcgtcctccc ccccccccc    1020
tctctacctt ctctagatcg gcgttccggt ccatggttag ggcccggtag ttctacttct   1080
gttcatgttt gtgttagatc cgtgtttgtg ttagatccgt gctgctagcg ttcgtacacg   1140
gatgcgacct gtacgtcaga cacgttctga ttgctaactt gccagtgttt ctctttgggg   1200
aatcctggga tggctctagc cgttccgcag acgggatcga tctaggatag gtatacatgt   1260
tgatgtgggt tttactgatg catatacatg atggcatatg cagcatctat tcatatgctc   1320
taaccttgag tacctatcta ttataataaa caagtatgtt ttataattat tttgatcttg   1380
atatacttgg atgatggcat atgcagcagc tatatgtgga tttttttagc cctgccttca   1440
tacgctattt atttgcttgg tactgtttct tttgtcgatg ctcaccctgt tgtttggtgt   1500
tacttctgca ggtcgaagct tgaagcaaac atggcatcta gcatggcacc aaagaaaaaa   1560
aggaaagttt ccaaacttga aaaatttaca aactgctact cccttccaa dacgcttagg    1620
tttaaagcga tccccgttgg caagacccaa gagaatatcg ataacaaaag acttctggtc   1680
gaagatgaaa aaagggccga agactacaag ggggtcaaga agttgctcga tcgctattat   1740
ctttcctttta tcaacgatgt gcttcattca atcaaactga gaacttgaa taactacatt    1800
agcctttcca gaaagaaaac gaggactgaa aaggagaaca aggaacttga gaatcttgaa   1860
ataaaccttc gcaaagaaat tgcaaaagcc ttcagggga acgaaggata taaatctctt    1920
ttcaaaaaag acattataga aacaattttg cctgagtttc ttgacgacaa ggatgaaatt   1980
gcgctcgtca atagctttaa cggatttaca actgccttca cagggttctt cgacaatagg   2040
gagaatatgt ttagcgagga ggcaaaaagc acatccatcg cattcagatg catcaatgaa   2100
aatcttaccc ggtacatatc gaatatggac atatttgaaa aagtggatgc aatattcgat   2160
aagcacgaag tccaggagat aaaggaaaag atactgaata gcgactatga tgtcgaagat   2220
ttttcgaag gtgagttctt caactttgtc ctgactcaag aaggcattga tgtctataat    2280
gcaataattg gaggttttgt gactgagtct ggcgagaaga taaagggctt gaacgagtat   2340
atcaatctct acaaccagaa gactaagcaa aagttgccta aatttaaacc gctttacaag   2400
caagttttga gcgaccggga aagccttttcc ttttacggtg aaggatacac gagcgatgaa   2460
gaagtcctcg aagtcttccg caacacactc aacaagaact cagaaatctt ttcctcaatt   2520
aaaaaattgg agaagctttt caagaacttc gatgaatact cttcggcggg gattttgtg    2580
aagaacggcc cggcaatttc cacaatatct aaagacattt tcggagaatg gaacgtgata   2640
agagacaagt ggaatgcgga gtatgatgac atacacctga gaagaaggc agttgtgact    2700
gaaaaatacg aagatgacag gagaaaaagc tttaaaaaga tcgggtcctt ttcactggaa   2760
cagctgcagg agtatgccga cgccgatctt tcggttgtcg aaaagctcaa agaaataatt   2820
atccagaagg tcgatgaaat ctacaaggtg tacggctcaa gcgagaagct ctttgatgct   2880
gacttcgtgt tggagaagtc tcttaaaaaa aacgacgcag tcgtcgcgat aatgaaagat   2940
ttgctggatt cagtgaaatc cttcgagaat tatatcaaag ccttcttcgg cgaggggaag   3000
gagacaaaca gggatgagtc cttctatgga gacttcgttc tggcttacga catccttctt   3060
aaggtcgacc acatctatga cgcaattcgg aactatgtga cgcagaagcc gtattcgaaa   3120
gataagttca agctctattt ccaaaaccct caatttatgc gtgggtggga taagacgta    3180
gagaccgatc gccgggcaac aattttgcgg tacgggtcta atattaccct cgctataatg   3240
```

```
gataagaaat acgctaaatg tctccagaaa attgacaaag atgacgtcaa cggcaattat    3300
gaaaaaatca attataaact ccttcctggc ccaaataaaa tgctcccgaa ggtgtttttt    3360
tccaaaaagt ggatggccta ttataatcca tcagaggata ttcagaaaat ctataaaaat    3420 gggacccttta agaagggtga catgtttaac ctgaacgatt gccacaagct tatagatttt    3480
ttcaaagact ctattagccg ctatcccaaa tggtctaatg cttatgattt caacttctct    3540
gaaactgaaa agtacaaaga tattgcagga ttctaccgcg aagttgaaga acaaggttat    3600
aaggtttcct ttgagtctgc gtccaagaaa gaggtcgata agttggtcga agaagggaaa    3660
ttgtatatgt ttcaaattta caataaagac ttttccgaca gtcccatgg tacacctaat    3720 ctgcatacca tgtacttcaa actgctgttc gatgagaata atcacggtca gattcgcctg    3780
agcggagggg cggaactctt catgaggaga gcatcgttga aaaagagga gctcgtcgtg    3840 catccggcta acagccccat tgctaacaag aatccggata atccaaagaa gactactacc    3900
ctctcctatg acgtctataa ggataagaga ttctctgagg accagtacga gttgcacatc    3960
cctattgcga taaataaatg ccctaagaac atctttaaaa tcaatactga ggtcagagtc    4020
ctgcttaagc acgacgacaa cccgtatgtg atcgggattg atagggtga aaggaacttg    4080 ctttatattg tggttgtcga tggaaaaggt aatatagtgg aacaatactc tctgaatgaa    4140
attatcaaca acttcaatgg cattaggatc aagaccgact atcattctct gttgacaag    4200 aaagagaaag agcgcttcga ggcacggcaa aactggacgt ctattgagaa catcaaggag    4260
cttaaggctg gttacatttc tcaggttgtg cacaaaattt gcgaactggt cgagaaatat    4320
gatgccgtta tcgcacttga agatctcaac agcggattta agaattctcg ggtgaaagtc    4380
gaaaaacagg tgtatcaaaa attcgaaaag atgctgatcg acaagctcaa ttatatggtt    4440
gataaaaaga gcaaccccatg cgccacgggg ggtgcgctta agggctatca gattacgaac    4500
aaatttgaat ccttcaagtc aatgtcgacg caaaatgggt ttatattcta tataccggcg    4560
tggcttacat ctaaaataga tcctagcact gggttcgtga acctgctgaa aaccaagtac    4620
acttcaatcg cagattctaa aaaatttata agcagcttcg acagaatcat gtatgtgccc    4680
gaggaagacc tcttcgagtt tgcccttgat tacaaaaatt tctcaagaac ggatgcagac    4740
tacataaaga agtggaagct gtactcttat gggaaccgga ttcggatatt cagaaatccg    4800
aaaaaaaaca atgtctttga ttgggaggaa gtttgtctta cctctgctta caaagagctg    4860
ttcaataaat atggcattaa ttaccagcaa ggtgatatcc gggcgctcct ttgcgaacag    4920
tctgacaaag ctttctattc ttcatttatg gcgctcatgt cattgatgct gcagatgagg    4980
aatagcatta cggggaggac tgatgttgac tttctgatct cgcccgtgaa aaattctgat    5040
ggaatcttct acgattccag gaattatgag gcccaggaaa atgctatcct tcccaagaac    5100
gcagacgcaa atggcgcgta caatatagct cgcaaggttt tgtgggctat aggccaattc    5160
aagaaagccg aagacgaaaa gctggacaaa gttaagattg ctatatctaa caagagtgg    5220 cttgagtatg cgcaaacatc tgttaaacac aaacgccccg cggctacaaa gaaggctggc    5280
caggcaaaga agaagaagtg agtcgaccga tcgttcaaac attggcaat aaagtttctt    5340 aagattgaat cctgttgccg gtcttgcgat gattatcata taatttctgt tgaattacgt    5400
taagcatgta ataattaaca tgtaatgcat gacgttattt atgagatggg ttttatgat    5460 tagagtcccg caattataca tttaatacgc gatagaaaac aaaatatagc gcgcaaacta    5520
ggataaatta tcgcgcgcgg tgtcatctat gttactagat cgatcccggg atatcgcggc    5580
```

```
cgcgtcgttc ggctgcggcg agcggtatca gctcactcaa aggcggtaat acggttatcc     5640
acagaatcag gggataacgc aggaaagaac atgtgagcaa aaggccagca aaaggccagg     5700
aaccgtaaaa aggccgcgtt gctggcgttt ttccataggc tccgcccccc tgacgagcat     5760
cacaaaaatc gacgctcaag tcagaggtgg cgaaacccga caggactata agataccag     5820 gcgtttcccc ctggaagctc cctcgtgcgc tctcctgttc cgaccctgcc gcttaccgga     5880
tacctgtccg cctttctccc ttcgggaagc gtggcgcttt ctcatagctc acgctgtagg     5940
tatctcagtt cggtgtaggt cgttcgctcc aagctgggct gtgtgcacga accccccgtt     6000
cagcccgacc gctgcgcctt atccggtaac tatcgtcttg agtccaaccc ggtaagacac     6060
gacttatcgc cactggcagc agccactggt aacaggatta gcagagcgag gtatgtaggc     6120
ggtgctacag agttcttgaa gtggtggcct aactacggct acactagaag gacagtattt     6180
ggtatctgcg ctctgctgaa gccagttacc ttcggaaaaa gagttggtag ctcttgatcc     6240
ggcaaacaaa ccaccgctgg tagcggtggt ttttttgttt gcaagcagca gattacgcgc     6300
agaaaaaaag gatctcaaga agatcctttg atcttttcta cggggtctga cgctcagtgg     6360
aacgaaaact cacgttaagg gattttggtc atgagattat caaaaaggat cttcacctag     6420
atccttttaa attaaaaatg aagttttaaa tcaatctaaa gtatatatga gtaaacttgg     6480
tctgacagtt accaatgctt aatcagtgag gcacctatct cagcgatctg tctatttcgt     6540
tcatccatag ttgcctgact ccccgtcgtg tagataacta cgatacggga gggcttacca     6600
tctggcccca gtgctgcaat gataccgcga gacccacgct caccggctcc agatttatca     6660
gcaataaacc agccagccgg aagggccgag cgcagaagtg gtcctgcaac tttatccgcc     6720
tccatccagt ctattaattg ttgccgggaa gctagagtaa gtagttcgcc agttaatagt     6780
ttgcgcaacg ttgttgccat tgctacaggc atcgtggtgt cacgctcgtc gtttggtatg     6840
gcttcattca gctccggttc ccaacgatca aggcgagtta catgatcccc catgttgtgc     6900
aaaaaagcgg ttagctcctt cggtcctccg atcgttgtca gaagtaagtt ggccgcagtg     6960
ttatcactca tggttatggc agcactgcat aattctctta ctgtcatgcc atccgtaaga     7020
tgcttttctg tgactggtga gtactcaacc aagtcattct gagaatagtg tatgcggcga     7080
ccgagttgct cttgcccggc gtcaatacgg gataataccg cgccacatag cagaacttta     7140
aaagtgctca tcattggaaa acgttcttcg gggcgaaaac tctcaaggat cttaccgctg     7200
ttgagatcca gttcgatgta acccactcgt gcacccaact gatcttcagc atcttttact     7260
ttcaccagcg tttctgggtg agcaaaaaca ggaaggcaaa atgccgcaaa aagggaata     7320 agggcgacac ggaaatgttg aatactcata ctcttccttt ttcaatatta ttgaagcatt     7380
tatcagggtt attgtctcat gagcggatac atatttgaat gtatttagaa aaataaacaa     7440
ataggggttc cgcgcacatt tccccgaaaa gtgccacctg acgcgcctg tagcggcacg     7500 tctaattcgg gggatctgga ttttagtact ggattttggt tttaggaatt agaaatttta     7560
ttgatagaag tattttacaa atacaaatac atactaaggg tttcttatat gctcaacaca     7620
tgagcgaaac cctataggaa ccctaattcc cttatctggg aactactcac acattattat     7680
ggagaaactc gagcttgtcg atcgacatga tcagggagct ctagattatt tgtatagttc     7740
atccatgccc attacgtcgg taaatgcctt ctgccactcc ttgaagttaa gttcggtctt     7800
ggaatgtttc aactcagtct tacgaacac gtacatgggt tggttcttaa ggtagttagc     7860
ggccattggt ttagcgaatg tgtaggtagt cctggctgta gagcgatatc tcttgccatt     7920
gcctgtggtg taagaccatt tgaaggtact aatgatggtc ttgtcgttag ggtaggtttt     7980
```

```
cttggaccgg caccaatcag cggcagttaa ggagttggtc atgacaggtc catcagcagg    8040
aaagcctgtc cccttcactt gggcttctcc tttgatgtgg ctcccttcgt aagtgtaacg    8100
gtagttgacg gtgagcgaag caccgtcctc aaactgcatt gtcctgtgga cttggtatcc    8160
ggagccatca accatggctg cttggaatgg actcattccg tcagggtatg gaaggtattg    8220
atggaatccg tagccaatgt gtggcaccag aatccatgga gaaaactgaa gatcaccttt    8280
ggtgctcttg aggttcagct cttcgtatcc gtcattaggg ttcccagtgc cttgtccgac    8340
catatcgaag tcaacgccgt tgatggaacc gaagatgtga agctcatgtg tggctggaag    8400
cgaagccatg ttatcttctt ctcctttact cacggaggac gccatggtgg cgggatcgcg    8460
ccctatcgtt cgtaaatggt gaaaattttc agaaaattgc ttttgcttta aagaaaatga    8520
tttaaattgc tgcaatagaa gtagaatgct tgattgcttg agattcgttt gttttgtata    8580
tgttgtgttg agaggatcct caagcttcga cctgcagaag taacaccaaa caacagggtg    8640
agcatcgaca aaagaaacag taccaagcaa ataaatagcg tatgaaggca gggctaaaaa    8700
aatccacata tagctgctgc atatgccatc atccaagtat atcaagatca aataattat    8760 aaaacatact tgtttattat aatagatagg tactcaaggt tagagcatat gaatagatgc    8820
tgcatatgcc atcatgtata tgcatcagta aaacccacat caacatgtat acctatccta    8880
gatcgatatt tccatccatc ttaaactcgt aactatgaag atgtatgaca cacatacca    8940 gttccaaaat taataaatac accaggtagt ttgaaacagt attctactcc gatctagaac    9000
gaatgaacga ccgcccaacc acaccacatc atcacaacca agcgaacaaa agcatctctg    9060
tatatgcatc agtaaaaccc gcatcaacat gtataccat cctagatcga tatttccatc    9120
catcatcttc aattcgtaac tatgaatatg tatggcacac acatacagat ccaaaattaa    9180
taaatccacc aggtagtttg aaacagaatt ctactccgat ctagaacgac cgcccaacca    9240
gaccacatca tcacaaccaa gacaaaaaaa agcatgaaaa gatgacccga caaacaagtg    9300
cacggcatat attgaaataa aggaaagggg caaaccaaac cctatgcaac gaaacaaaaa    9360
aaatcatgaa atcgatcccg tctgcggaac ggctagagcc atcccaggat tccccaaaga    9420
gaaacactgg caagttagca atcagaacgt gtctgacgta caggtcgcat ccgtgtacga    9480
acgctagcag cacggatcta acacaaacac ggatctaaca caaacatgaa cagaagtaga    9540
actaccgggc cctaaccatg gaccggaacg ccgatctaga gaaggtagag aggggggggg    9600
aggacgagcg gcgtaccttg aagcggaggt gccgacgggt ggatttgggg gagatccact    9660
agttctagag cggccgccac cgcggtggaa ttctcgaggt cctctccaaa tgaaatgaac    9720
ttccttatat agaggaaggg tcttgcgaag gatagtggga ttgtgcgtca tcccttacgt    9780
cagtggagat atcacatcaa tccacttgct ttgaagacgt ggttggaacg tcttctttt    9840 ccacgatgct cctcgtgggt gggggtccat cttgggacc actgtcggca gaggcatctt    9900
gaacgatagc ctttccttta tcgcaatgat ggcatttgta ggtgccacct tccttttcta    9960
ctgtcctttt gatcaagtga ccgatagctg ggcaatggaa tccgaggagg tttcccgata   10020
ttaccctttg ttgaaaagtc tcaatagccc tttggtcttc tgagactgta tctttgatat   10080
tcttggagta gacgagagtg tcgtgctcca ccatgttatc acatcaattc acttgctttg   10140
aagacgtggt tggaacgtct tcttttttcca cgatgctcct cgtgggtggg ggtccatctt   10200
tgggaccact gtcggcagag gcatcttgaa cgatagcctt tccttatcg caatgatggc   10260 atttgtaggt gccaccttcc ttttctactg tccttttgat caagtgacag atagctgggc   10320
```
aatggaatcc gaggaggttt cccgatatta ccctttgttg aaaagtctca atagcccttt    10380
ggtcttctga gacttgcagg caagcaagca tgaatgcctg ggcgcgccga tatc           10434

<210> SEQ ID NO 37
<211> LENGTH: 10432
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pGEP315 Corn strategy LbCpf1 vector

<400> SEQUENCE: 37
actgctgcag tgcagcgtga cccggtcgtg cccctctcta gagataatga gcattgcatg      60
tctaagttat aaaaaattac cacatatttt ttttgtcaca cttgtttgaa gtgcagttta    120
tctatcttta tacatatatt taaactttac tctacgaata atataatcta tagtactaca    180
ataatatcag tgttttagag aatcatataa atgaacagtt agacatggtc taaaggacaa    240
ttgagtattt tgacaacagg actctacagt tttatctttt tagtgtgcat gtgttctcct    300
ttttttttgc aaatagcttc acctatataa tacttcatcc attttattag tacatccatt    360
tagggtttag ggttaatggt tttatagac taattttttt agtacatcta ttttattcta    420
ttttagcctc taaattaaga aaactaaaac tctattttag ttttttttatt taataattta    480 gatataaaat agaataaaat aaagtgacta aaaattaaac aaataccctt taagaaatta    540
aaaaaactaa ggaaacattt ttcttgtttc gagtagataa tgccagcctg ttaaacgccg    600
tcgatcgacg agtctaacgg acaccaacca gcgaaccagc agcgtcgcgt cgggccaagc    660
gaagcagacg gcacggcatc tctgtcgctg cctctggacc cctctcgaga gttccgctcc    720
accgttggac ttgctccgct gtcggcatcc agaaattgcg tggcggagcg gcagacgtga    780
gccggcacgg caggcggcct cctcctcctc tcacggcacc ggcagctacg ggggattcct    840
ttcccaccgc tccttcgctt tcccttcctc gcccgccgta ataaatagac accccctcca    900
caccctcttt ccccaacctc gtgttgttcg gagcgcacac acacacaacc agatctcccc    960
caaatccacc cgtcggcacc tccgcttcaa ggtacgccgc tcgtcctccc ccccccctct   1020
ctaccttctc tagatcggcg ttccggtcca tggttagggc ccggtagttc tacttctgtt   1080
catgtttgtg ttagatccgt gtttgtgtta gatccgtgct gctagcgttc gtacacggat   1140
gcgacctgta cgtcagacac gttctgattg ctaacttgcc agtgtttctc tttggggaat   1200
cctgggatgg ctctagccgt tccgcagacg ggatcgatct aggataggta tacatgttga   1260
tgtgggtttt actgatgcat atacatgatg gcatatgcag catctattca tatgctctaa   1320
ccttgagtac ctatctatta taataaacaa gtatgtttta taattatttt gatcttgata   1380
tacttggatg atggcatatg cagcagctat atgtggattt ttttagccct gccttcatac   1440
gctatttatt tgcttggtac tgtttctttt gtcgatgctc accctgttgt ttggtgttac   1500
ttctgcaggt cgaagcttga agcaaacatg gcatctagca tggcaccaaa gaaaaaaagg   1560
aaagtttcca aacttgaaaa atttacaaac tgctactccc tttccaagac gcttaggttt   1620
aaagcgatcc ccgttggcaa gacccaagag aatatcgata caaaagact tctggtcgaa   1680 gatgaaaaaa gggccgaaga ctacaagggg gtcaagaagt tgctcgatcg ctattatctt   1740
tcctttatca acgatgtgct tcattcaatc aaactgaaga acttgaataa ctacattagc   1800
cttttcagaa agaaaacgag gactgaaaag gagaacaagg aacttgagaa tcttgaaata   1860

```
aaccttcgca aagaaattgc aaaagccttc aaggggaacg aaggatataa atctcttttc    1920
aaaaaagaca ttatagaaac aatttttgcct gagtttcttg acgacaagga tgaaattgcg   1980
ctcgtcaata gctttaacgg atttacaact gccttcacag ggttcttcga caatagggag    2040
aatatgttta gcgaggaggc aaaaagcaca tccatcgcat tcagatgcat caatgaaaat    2100
cttacccggt acatatcgaa tatggacata tttgaaaaag tggatgcaat attcgataag    2160
cacgaagtcc aggagataaa ggaaaagata ctgaatagcg actatgatgt cgaagatttt    2220
ttcgaaggtg agttcttcaa ctttgtcctg actcaagaag gcattgatgt ctataatgca    2280
ataattggag ttttgtgac tgagtctggc gagaagataa agggcttgaa cgagtatatc     2340
aatctctaca accagaagac taagcaaaag ttgcctaaat ttaaaccgct ttacaagcaa    2400
gttttgagcg accgggaaag ccttttccttt tacggtgaag gatacacgag cgatgaagaa   2460
gtcctcgaag tcttccgcaa cacactcaac aagaactcag aaatcttttc ctcaattaaa    2520
aaattggaga gcttttcaa gaacttcgat gaatactctt cggcggggat ttttgtgaag     2580
aacggcccgg caatttccac aatatctaaa gacatttcg gagaatggaa cgtgataaga    2640
gacaagtgga atgcggagta tgatgacata cacctgaaga agaaggcagt tgtgactgaa   2700
aaatacgaag atgacaggag aaaaagcttt aaaaagatcg gtccttttc actggaacag    2760 ctgcaggagt atgccgacgc cgatctttcg gttgtcgaaa agctcaaaga aataattatc    2820
cagaaggtcg atgaaatcta caaggtgtac ggctcaagcg agaagctctt tgatgctgac    2880
ttcgtgttgg agaagtctct taaaaaaaac gacgcagtcg tcgcgataat gaaagatttg    2940
ctggattcag tgaaatcctt cgagaattat atcaaagcct tcttcggcga ggggaaggag    3000
acaaacaggg atgagtcctt ctatggagac ttcgttctgg cttacgacat ccttcttaag    3060
gtcgaccaca tctatgacgc aattcggaac tatgtgacgc agaagccgta ttcgaaagat    3120
aagttcaagc tctatttcca aaaccctcaa tttatgggtg ggtgggataa agacaaagag   3180
accgattacc gggcaacaat tttgcggtac gggtctaaat attacctcgc tataatggat    3240
aagaaatacg ctaaatgtct ccagaaaatt gacaaagatg acgtcaacgg caattatgaa    3300
aaaatcaatt ataaactcct tcctggccca aataaaaatgc tcccgaaggt gtttttttcc    3360
aaaaagtgga tggcctatta taatccatca gaggatattc agaaaatcta taaaatggg    3420 acctttaaga agggtgacat gtttaacctg aacgattgcc acaagcttat agattttttc    3480
aaagactcta ttagccgcta tcccaaatgg tctaatgctt atgatttcaa cttctctgaa    3540
actgaaaagt acaaagatat tgcaggattc taccgcgaag ttgaagaaca aggttataag    3600
gtttcctttg agtctgcgtc caagaaagag gtcgataagt tggtcgaaga agggaaattg    3660
tatatgtttc aaatttacaa taagactttt ccgacaagt cccatggtac acctaatctg     3720
cataccatgt acttcaaact gctgttcgat gagaataatc acggtcagat cgcctgagc    3780 ggagggcgg aactcttcat gaggagagca tcgttgaaaa aagaggagct cgtcgtgcat     3840
ccggctaaca gccccattgc taacaagaat ccggataatc aaagaagac tactaccctc    3900 tcctatgacg tctataagga taagagattc tctgaggacc agtacgagtt gcacatccct    3960
attgcgataa ataaatgccc taagaacatc tttaaaatca atactgaggt cagagtcctg    4020
cttaagcacg acgacaaccc gtatgtgatc gggattgata gggtgaaag gaacttgctt    4080 tatattgtgg ttgtcgatgg aaaaggtaat atagtggaac aatactctct gaatgaaatt    4140
atcaacaact tcaatggcat taggatcaag accgactatc attctctgtt ggacaagaaa    4200
gagaaagagc gcttcgaggc acggcaaaac tggacgtcta ttgagaacat caaggagctt    4260
```

```
aaggctggtt acatttctca ggttgtgcac aaaatttgcg aactggtcga gaaatatgat    4320
gccgttatcg cacttgaaga tctcaacagc ggatttaaga attctcgggt gaaagtcgaa    4380
aaacaggtgt atcaaaaatt cgaaaagatg ctgatcgaca agctcaatta tatggttgat    4440
aaaaagagca acccatgcgc cacgggggt gcgcttaagg gctatcagat tacgaacaaa     4500
tttgaatcct tcaagtcaat gtcgacgcaa aatgggttta tattctatat accggcgtgg    4560
cttacatcta aaatagatcc tagcactggg ttcgtgaacc tgctgaaaac caagtacact    4620
tcaatcgcag attctaaaaa atttataagc agcttcgaca gaatcatgta tgtgcccgag    4680
gaagacctct tcgagtttgc ccttgattac aaaaatttct caagaacgga tgcagactac    4740
ataaagaagt ggaagctgta ctcttatggg aaccggattc ggatattcag aaatccgaaa    4800
aaaaacaatg tctttgattg ggaggaagtt tgtcttacct ctgcttacaa agagctgttc    4860
aataaatatg gcattaatta ccagcaaggt gatatccggg cgctcctttg cgaacagtct    4920
gacaaagctt tctattcttc atttatggcg ctcatgtcat tgatgctgca gatgaggaat    4980
agcattacgg ggaggactga tgttgacttt ctgatctcgc ccgtgaaaaa ttctgatgga    5040
atcttctacg attccaggaa ttatgaggcc caggaaaatg ctatccttcc caagaacgca    5100
gacgcaaatg gcgcgtacaa tatagctcgc aaggttttgt gggctatagg ccaattcaag    5160
aaagccgaag acgaaaagct ggacaaagtt aagattgcta tatctaacaa agagtggctt    5220
gagtatgcgc aaacatctgt taaacacaaa cgccccgcgg ctacaaagaa ggctggccag    5280
gcaaagaaga gaagtgagt cgaccgatcg ttcaaacatt tggcaataaa gtttcttaag    5340
attgaatcct gttgccggtc ttgcgatgat tatcatataa tttctgttga attacgttaa    5400
gcatgtaata attaacatgt aatgcatgac gttatttatg agatgggttt ttatgattag    5460
agtcccgcaa ttatacattt aatacgcgat agaaaacaaa atatagcgcg caaactagga    5520
taaattatcg cgcgcggtgt catctatgtt actagatcga tcccgggata tcgcggccgg    5580
tcgttcggct gcggcgagcg gtatcagctc actcaaaggc ggtaatacgg ttatccacag    5640
aatcagggga taacgcagga agaacatgt gagcaaaagg ccagcaaaag gccaggaacc    5700
gtaaaaaggc cgcgttgctg gcgttttcc ataggctccg ccccctgac gagcatcaca    5760
aaaatcgacg ctcaagtcag aggtggcgaa acccgacagg actataaaga taccaggcgt    5820
ttccccctgg aagctccctc gtgcgctctc ctgttccgac cctgccgctt accggatacc    5880
tgtccgcctt tctcccttcg ggaagcgtgg cgctttctca tagctcacgc tgtaggtatc    5940
tcagttcggt gtaggtcgtt cgctccaagc tgggctgtgt gcacgaaccc cccgttcagc    6000
ccgaccgctg cgccttatcc ggtaactatc gtcttgagtc aacccggta agacacgact    6060
tatcgccact ggcagcagcc actggtaaca ggattagcag agcgaggtat gtaggcggtg    6120
ctacagagtt cttgaagtgg tggcctaact acggctacac tagaagaaca gtatttggta    6180
tctgcgctct gctgaagcca gttaccttcg gaaaaagagt tggtagctct tgatccggca    6240
aacaaaccac cgctggtagc ggtggttttt tgtttgcaa gcagcagatt acgcgcagaa    6300
aaaaaggatc tcaagaagat cctttgatct tttctacggg gtctgacgct cagtggaacg    6360
aaaactcacg ttaagggatt ttggtcatga gattatcaaa aaggatcttc acctagatcc    6420
ttttaaatta aaaatgaagt tttaaatcaa tctaaagtat atatgagtaa acttggtctg    6480
acagttacca atgcttaatc agtgaggcac ctatctcagc gatctgtcta tttcgttcat    6540
ccatagttgc ctgactcccc gtcgtgtaga taactacgat acgggagggc ttaccatctg    6600
```

```
gccccagtgc tgcaatgata ccgcgagacc cacgctcacc ggctccagat ttatcagcaa    6660
taaaccagcc agccggaagg gccgagcgca gaagtggtcc tgcaacttta tccgcctcca    6720
tccagtctat taattgttgc cgggaagcta gagtaagtag ttcgccagtt aatagtttgc    6780
gcaacgttgt tgccattgct acaggcatcg tggtgtcacg ctcgtcgttt ggtatggctt    6840
cattcagctc cggttcccaa cgatcaaggc gagttacatg atcccccatg ttgtgcaaaa    6900
aagcggttag ctccttcggt cctccgatcg ttgtcagaag taagttggcc gcagtgttat    6960
cactcatggt tatggcagca ctgcataatt ctcttactgt catgccatcc gtaagatgct    7020
tttctgtgac tggtgagtac tcaaccaagt cattctgaga atagtgtatg cggcgaccga    7080
gttgctcttg cccggcgtca atacgggata taccgcgcc acatagcaga actttaaaag     7140
tgctcatcat tggaaaacgt tcttcggggc gaaaactctc aaggatctta ccgctgttga    7200
gatccagttc gatgtaaccc actcgtgcac ccaactgatc ttcagcatct tttactttca    7260
ccagcgtttc tgggtgagca aaaacaggaa ggcaaaatgc cgcaaaaaag gaataaggg     7320 cgacacggaa atgttgaata ctcatactct tcctttttca atattattga agcatttatc    7380
agggttattg tctcatgagc ggatacatat ttgaatgtat ttagaaaaat aaacaaatag    7440
gggttccgcg cacatttccc cgaaaagtgc cacctgacgc gccctgtatc ggcacgtcta    7500
attcggggga tctggatttt agtactggat tttggtttta ggaattagaa attttattga    7560
tagaagtatt ttacaaatac aaatacatac taagggtttc ttatatgctc aacacatgag    7620 cgaaaccta ggaaccct aattcccttta tctgggaact actcacacat tattatggag      7680
aaactcgagc ttgtcgatcg acatgatcag ggagccctag attatttgta tagttcatcc    7740
atgcccatta cgtcggtaaa tgccttctgc cactccttga agttaagttc ggtcttggaa    7800
tgtttcaact cagtcttacg gaacacgtac atgggttggt tcttaaggta gttagcggcc    7860
attggtttag cgaatgtgta ggtagtcctg gctgtagagc gatatctctt gccattgcct    7920
gtggtgtaag accatttgaa ggtactaatg atggtcttgt cgttagggta ggttttcttg    7980
gaccggcacc aatcagcggc agttaaggag ttggtcatga caggtccatc agcaggaaag    8040
cctgtcccct tcacttgggc ttctcctttg atgtggctcc cttcgtaagt gtaacggtag    8100
ttgacggtga gcgaagcacc gtcctcaaac tgcattgtcc tgtggacttg gtatccggag    8160
ccatcaacca tggctgcttg gaatggactc attccgtcag ggtatggaag gtattgatgg    8220
aatccgtagc caatgtgtgg caccagaatc catggagaaa actgaagatc accctttggtg   8280 ctcttgaggt tcagctcttc gtatccgtca ttagggttcc cagtgccttg tccgaccata    8340
tcgaagtcaa cgccgttgat ggaaccgaag atgtgaagct catgtgtggc tggaagcgaa    8400
gccatgttat cttcttctcc tttactcacg gaggacgcca tggtggcggg atcgcgccct    8460
atcgttcgta aatggtgaaa attttcagaa aattgctttt gctttaaaag aaatgattta    8520
aattgctgca atagaagtag aatgcttgat tgcttgagat tcgtttgttt tgtatatgtt    8580
gtgttgagag gatcctcaag cttcgacctg cagaagtaac accaaacaac agggtgagca    8640
tcgacaaaag aaacagtacc aagcaaataa atagcgtatg aaggcagggc taaaaaaatc    8700
cacatatagc tgctgcatat gccatcatcc aagtatatca agatcaaaat aattataaaa    8760
catacttgtt tattataata gataggtact caaggttaga gcatatgaat agatgctgca    8820
tatgccatca tgtatatgca tcagtaaaac ccacatcaac atgtataccgt atcctagatc    8880 gatatttcca tccatcttaa actcgtaact atgaagatgt atgacacaca catacagttc    8940
caaaattaat aaatacacca ggtagtttga aacagtattc tactccgatc tagaacgaat    9000
```

```
gaacgaccgc caaccacac cacatcatca caaccaagcg aacaaaaagc atctctgtat    9060
atgcatcagt aaaacccgca tcaacatgta tacctatcct agatcgatat ttccatccat    9120
catcttcaat tcgtaactat gaatatgtat ggcacacaca tacagatcca aaattaataa    9180
atccaccagg tagtttgaaa cagaattcta ctccgatcta gaacgaccgc ccaaccagac    9240
cacatcatca caaccaagac aaaaaaaagc atgaaaagat gacccgacaa acaagtgcac    9300
ggcatatatt gaaataaagg aaagggcaa accaaaccct atgcaacgaa acaaaaaaaa    9360
tcatgaaatc gatcccgtct gcggaacggc tagagccatc ccaggattcc ccaaagagaa    9420
acactggcaa gttagcaatc agaacgtgtc tgacgtacag gtcgcatccg tgtacgaacg    9480
ctagcagcac ggatctaaca caaacacgga tctaacacaa acatgaacag aagtagaact    9540
accgggccct aaccatggac cggaacgccg atctagagaa ggtagagagg ggggggggg    9600 aggacgagcg gcgtaccttg aagcggaggt gccgacgggt ggatttgggg gagatccact    9660
agttctagag cggccgccac cgcggtgaa ttctcgaggt cctctccaaa tgaaatgaac    9720
ttccttatat agaggaaggg tcttgcgaag gatagtggga ttgtgcgtca tcccttacgt    9780
cagtggagat atcacatcaa tccacttgct ttgaagacgt ggttggaacg tcttcttttt    9840
ccacgatgtt cctcgtgggt ggggtccat cttgggacc actgtcggta gaggcatctt    9900
gaacgatagc ctttccttta tcgcaatgat ggcatttgta gaagccatct tccttttcta    9960
ctgtcctttc gatgaagtga cagatagctg ggcaatggaa tccgaggagg tttcccgata   10020
ttaccctttg ttgaaaagtc tcaatagccc tctggtcttc tgagactgta tctttgatat   10080
tcttggagta gacgagagtg tcgtgctcca ccatgtatca catcaatcca cttgctttga   10140
agacgtggtt ggaacgtctt cttttccac gatgttcctc gtgggtgggg gtccatcttt   10200
gggaccactg tcggtagagg catcttgaac gatagccttt cctttatcgc aatgatggca   10260
tttgtagaag ccatcttcct tttctactgt cctttcgatg aagtgacaga tagctgggca   10320
atggaatccg aggaggtttc ccgatattac cctttgttga aaagtctcaa tagccctctg   10380
gtcttctgaa cctgcaggca agcaagcatg aatgcctggg cgcgccgata tc           10432
```

<210> SEQ ID NO 38
<211> LENGTH: 3684
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: LbCpf1 RR coding sequence codon optimized

<400> SEQUENCE: 38

```
atgtccaaac ttgaaaaatt tacaaactgc tactcccttt ccaagacgct taggtttaaa      60
gcgatccccg ttggcaagac ccaagagaat atcgataaca aaagacttct ggtcgaagat     120 gaaaaaggg ccgaagacta caggggggtc aagaagttgc tcgatcgcta ttatctttcc     180
tttatcaacg atgtgcttca ttcaatcaaa ctgaagaact tgaataacta cattagcctt     240
ttcagaaaga aaacgaggac tgaaaaggag aacaaggaac ttgagaatct tgaaataaac    300
cttcgcaaag aaattgcaaa agccttcaag gggaacgaag gatataaatc tctttttcaaa    360 aaagacatta tagaaacaat tttgcctgag tttcttgacg acaaggatga aattgcgctc     420
gtcaatagct ttaacggatt tacaactgcc ttcacagggt tcttcgacaa tagggagaat     480
atgtttagcg aggaggcaaa aagcacatcc atcgcattca gatgcatcaa tgaaaatctt     540
```

-continued

```
acccggtaca tatcgaatat ggacatattt gaaaaagtgg atgcaatatt cgataagcac    600
gaagtccagg agataaagga aaagatactg aatagcgact atgatgtcga agatttttc     660 gaaggtgagt tcttcaactt tgtcctgact caagaaggca ttgatgtcta taatgcaata    720
attggaggtt ttgtgactga gtctggcgag aagataaagg gcttgaacga gtatatcaat    780
ctctacaacc agaagactaa gcaaaagttg cctaaattta aaccgcttta caagcaagtt    840
ttgagcgacc gggaaagcct ttccttttac ggtgaaggat acacgagcga tgaagaagtc    900
ctcgaagtct tccgcaacac actcaacaag aactcagaaa tcttttcctc aattaaaaaa    960
ttggagaagc ttttcaagaa cttcgatgaa tactcttcgg cggggatttt tgtgaagaac   1020
ggcccggcaa tttccacaat atctaaagac attttcggag aatggaacgt gataagagac   1080
aagtggaatg cggagtatga tgacatacac ctgaagaaga aggcagttgt gactgaaaaa   1140
tacgaagatg acaggagaaa aagctttaaa aagatcgggt ccttttcact ggaacagctg   1200
caggagtatg ccgacgccga tctttcggtt gtcgaaaagc tcaaagaaat aattatccag   1260
aaggtcgatg aaatctacaa ggtgtacggc tcaagcgaga agctctttga tgctgacttc   1320
gtgttggaga agtctcttaa aaaaaacgac gcagtcgtcg cgataatgaa agatttgctg   1380
gattcagtga atccttcga gaattatatc aaagccttct tcggcgaggg gaaggagaca    1440
aacagggatg agtccttcta tggagacttc gttctggctt acgacatcct tcttaaggtc   1500
gaccacatct atgacgcaat tcggaactat gtgacgcaga agccgtattc gaaagataag   1560
ttcaagctct atttccaaaa ccctcaattt atgcgtgggt gggataaaga caaagagacc   1620
gattaccggg caacaatttt gcggtacggg tctaaatatt acctcgctat aatggataag   1680
aaatacgcta atgtctcca gaaaattgac aaagatgacg tcaacggcaa ttatgaaaaa   1740
atcaattata aactccttcc tggcccaaat aaaatgctcc cgagggtgtt ttttttccaaa   1800 aagtggatgg cctattataa tccatcagag gatattcaga aaatctataa aaatgggacc   1860
tttaagaagg gtgacatgtt taacctgaac gattgccaca agcttataga ttttttcaaa   1920
gactctatta gccgctatcc caaatggtct aatgcttatg atttcaactt ctctgaaact   1980
gaaaagtaca agatattgc aggattctac cgcgaagttg aagaacaagg ttataaggtt    2040
tcctttgagt ctgcgtccaa gaaagaggtc gataagttgg tcgaagaagg gaaattgtat   2100
atgtttcaaa tttacaataa agacttttcc gacaagtccc atggtacacc taatctgcat   2160
accatgtact tcaaactgct gttcgatgag aataatcacg gtcagattcg cctgagcgga   2220
ggggcggaac tcttcatgag gagagcatcg ttgaaaaaag aggagctcgt cgtgcatccg   2280
gctaacagcc ccattgctaa caagaatccg gataatccaa agaagactac taccctctcc   2340
tatgacgtct ataaggataa agattctct gaggaccagt acgagttgca catccctatt    2400
gcgataaata aatgccctaa gaacatcttt aaaatcaata ctgaggtcag agtcctgctt   2460
aagcacgacg acaacccgta tgtgatcggg attgataggg gtgaaaggaa cttgcttat    2520 attgtggttg tcgatggaaa aggtaatata gtggaacaat actctctgaa tgaaattatc   2580
aacaacttca atggcattag gatcaagacc gactatcatt ctctgttgga caagaaagag   2640 aaaagagcgct tcgaggcacg gcaaaactgg acgtctattg agaacatcaa ggagcttaag   2700
gctggttaca tttctcaggt tgtgcacaaa atttgcgaac tggtcgagaa atatgatgcc   2760
gttatcgcac ttgaagatct caacagcgga tttaagaatt ctcgggtgaa agtcgaaaaa   2820
caggtgtatc aaaaattcga aaagatgctg atcgacaagc tcaattatat ggttgataaa   2880
```

| | |
|---|---|
| aagagcaacc catgcgccac gggggtgcg cttaagggct atcagattac gaacaaattt | 2940 |
| gaatccttca agtcaatgtc gacgcaaaat gggtttatat tctatatacc ggcgtggctt | 3000 |
| acatctaaaa tagatcctag cactgggttc gtgaacctgc tgaaaaccaa gtacacttca | 3060 |
| atcgcagatt ctaaaaaatt tataagcagc ttcgacagaa tcatgtatgt gcccgaggaa | 3120 |
| gacctcttcg agtttgccct tgattacaaa aatttctcaa gaacggatgc agactacata | 3180 |
| aagaagtgga agctgtactc ttatgggaac cggattcgga tattcagaaa tccgaaaaaa | 3240 |
| aacaatgtct ttgattggga ggaagtttgt cttacctctg cttacaaaga gctgttcaat | 3300 |
| aaatatggca ttaattacca gcaaggtgat atccgggcgc tccttttgcga acagtctgac | 3360 |
| aaagctttct attcttcatt tatggcgctc atgtcattga tgctgcagat gaggaatagc | 3420 |
| attacgggga ggactgatgt tgactttctg atctcgcccg tgaaaaattc tgatggaatc | 3480 |
| ttctacgatt ccaggaatta tgaggcccag gaaaatgcta tccttcccaa gaacgcagac | 3540 |
| gcaaatggcg cgtacaatat agctcgcaag gttttgtggg ctataggcca attcaagaaa | 3600 |
| gccgaagacg aaaagctgga caaagttaag attgctatat ctaacaaaga gtggcttgag | 3660 |
| tatgcgcaaa catctgttaa acac | 3684 |

<210> SEQ ID NO 39
<211> LENGTH: 3684
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: LbCpf1 RVR coding sequence codon optimized

<400> SEQUENCE: 39

| | |
|---|---|
| atgtccaaac ttgaaaaatt tacaaactgc tactcccttt ccaagacgct taggtttaaa | 60 |
| gcgatccccg ttggcaagac ccaagagaat atcgataaca aaagacttct ggtcgaagat | 120 |
| gaaaaaggg ccgaagacta aaggggggtc aagaagttgc tcgatcgcta ttatctttcc | 180 |
| tttatcaacg atgtgcttca ttcaatcaaa ctgaagaact tgaataacta cattagcctt | 240 |
| ttcagaaaga aaacgaggac tgaaaaggag aacaaggaac ttgagaatct tgaaataaac | 300 |
| cttcgcaaag aaattgcaaa agccttcaag gggaacgaag gatataaaatc tcttttcaaa | 360 |
| aaagacatta tagaaacaat tttgcctgag tttcttgacg acaaggatga aattgcgctc | 420 |
| gtcaatagct ttaacggatt tacaactgcc ttcacagggt tcttcgacaa tagggagaat | 480 |
| atgtttagca aggaggcaaa aagcacatcc atcgcattca gatgcatcaa tgaaaatctt | 540 |
| acccggtaca tatcgaatat ggacatattt gaaaaagtgg atgcaatatt cgataagcac | 600 |
| gaagtccaga gataaaagga aaagatactg aatagcgact atgatgtcga agattttttc | 660 |
| gaaggtgagt tcttcaactt tgtcctgact caagaaggca ttgatgtcta taatgcaata | 720 |
| attggaggtt ttgtgactga gtctggcgag aagataaagg gcttgaacga gtatatcaat | 780 |
| ctctacaacc agaagactaa gcaaaagttg cctaaattta accgcttta caagcaagtt | 840 |
| ttgagcgacc gggaaagcct ttcctttttac ggtgaaggat acacgagcga tgaagaagtc | 900 |
| ctcgaagtct tccgcaacac actcaacaag aactcagaaa tcttttcctc aattaaaaaa | 960 |
| ttggagaagc tttcaagaa cttcgatgaa tactcttcgg cggggatttt tgtgaagaac | 1020 |
| ggcccggcaa tttccacaat atctaaagac attttcggag aatggaacgt gataagagac | 1080 |
| aagtggaatg cggagtatga tgacatacac ctgaagaaga aggcagttgt gactgaaaaa | 1140 |

```
tacgaagatg acaggagaaa aagctttaaa aagatcgggt ccttttcact ggaacagctg    1200
caggagtatg ccgacgccga tctttcggtt gtcgaaaagc tcaaagaaat aattatccag    1260
aaggtcgatg aaatctacaa ggtgtacggc tcaagcgaga agctctttga tgctgacttc    1320
gtgttggaga agtctcttaa aaaaaacgac gcagtcgtcg cgataatgaa agatttgctg    1380
gattcagtga atccttcga gaattatatc aaagccttct tcggcgaggg gaaggagaca    1440
aacagggatg agtccttcta tggagacttc gttctggctt acgacatcct tcttaaggtc    1500
gaccacatct atgacgcaat tcggaactat gtgacgcaga agccgtattc gaaagataag    1560
ttcaagctct atttccaaaa ccctcaattt atgcgtgggt gggataaaga cgtagagacc    1620
gatcgccggg caacaatttt gcggtacggg tctaaatatt acctcgctat aatggataag    1680
aaatacgcta atgtctcca gaaaattgac aaagatgacg tcaacggcaa ttatgaaaaa    1740
atcaattata aactccttcc tggcccaaat aaaatgctcc cgaaggtgtt tttttccaaa    1800
aagtggatgg cctattataa tccatcagag gatattcaga aaatctataa aaatgggacc    1860
tttaagaagg gtgacatgtt taacctgaac gattgccaca agcttataga tttttttcaaa    1920 gactctatta gccgctatcc caaatggtct aatgcttatg atttcaactt ctctgaaact    1980
gaaaagtaca aagatattgc aggattctac cgcgaagttg aagaacaagg ttataaggtt    2040
tcctttgagt ctgcgtccaa gaaagaggtc gataagttgg tcgaagaagg gaaattgtat    2100
atgtttcaaa tttacaataa agacttttcc gacaagtccc atggtacacc taatctgcat    2160
accatgtact tcaaactgct gttcgatgag aataatcacg gtcagattcg cctgagcgga    2220 gggcggaac tcttcatgag gagagcatcg ttgaaaaaag aggagctcgt cgtgcatccg    2280
gctaacagcc ccattgctaa caagaatccg gataatccaa agaagactac taccctctcc    2340
tatgacgtct ataaggataa gagattctct gaggaccagt acgagttgca catccctatt    2400
gcgataaata aatgccctaa gaacatcttt aaaatcaata ctgaggtcag agtcctgctt    2460
aagcacgacg acaacccgta tgtgatcggg attgatagg gtgaaaggaa cttgctttat    2520
attgtggttg tcgatggaaa aggtaatata gtggaacaat actctctgaa tgaaattatc    2580
aacaacttca atggcattag gatcaagacc gactatcatt ctctgttgga caagaaagag    2640
aaagagcgct tcgaggcacg gcaaaactgg acgtctattg agaacatcaa ggagcttaag    2700
gctggttaca tttctcaggt tgtgcacaaa atttgcgaac tggtcgagaa atatgatgcc    2760
gttatcgcac ttgaagatct caacagcgga tttaagaatt ctcgggtgaa agtcgaaaaa    2820
caggtgtatc aaaaattcga aaagatgctg atcgacaagc tcaattatat ggttgataaa    2880
aagagcaacc catgcgccac ggggggtgcg cttaagggct atcagattac gaacaaattt    2940
gaatccttca gtcaatgtc gacgcaaaat gggtttatat tctatatacc ggcgtggctt    3000
acatctaaaa tagatcctag cactgggttc gtgaacctgc tgaaaaccaa gtacacttca    3060
atcgcagatt ctaaaaaatt tataagcagc ttcgacagaa tcatgtatgt gcccgaggaa    3120
gacctcttcg agtttgccct tgattacaaa aatttctcaa gaacggatgc agactacata    3180
aagaagtgga agctgtactc ttatgggaac cggattcgga tattcagaaa tccgaaaaaa    3240
aacaatgtct ttgattggga ggaagttttgt cttacctctg cttacaaaga gctgttcaat    3300
aaatatggca ttaattacca gcaaggtgat atccgggcgc tcctttgcga acagtctgac    3360
aaagctttct attcttcatt tatggcgctc atgtcattga tgctgcagat gaggaatagc    3420
attacggggA ggactgatgt tgactttctg atctcgcccg tgaaaaattc tgatggaatc    3480
ttctacgatt ccaggaatta tgaggcccag gaaaatgcta tccttcccaa gaacgcagac    3540
```

```
gcaaatggcg cgtacaatat agctcgcaag gttttgtggg ctataggcca attcaagaaa    3600
gccgaagacg aaaagctgga caaagttaag attgctatat ctaacaaaga gtggcttgag    3660
tatgcgcaaa catctgttaa acac                                           3684
```

<210> SEQ ID NO 40
<211> LENGTH: 1228
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: LbCpf1 RR polypeptide

<400> SEQUENCE: 40

```
Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320
```

```
Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
                340                 345                 350

Gly Glu Trp Asn Val Ile Arg Asp Lys Trp Asn Ala Glu Tyr Asp Asp
            355                 360                 365

Ile His Leu Lys Lys Lys Ala Val Val Thr Glu Lys Tyr Glu Asp Asp
        370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
                420                 425                 430

Glu Lys Leu Phe Asp Ala Asp Phe Val Leu Glu Lys Ser Leu Lys Lys
                435                 440                 445

Asn Asp Ala Val Val Ala Ile Met Lys Asp Leu Leu Asp Ser Val Lys
                450                 455                 460

Ser Phe Glu Asn Tyr Ile Lys Ala Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
                500                 505                 510

Gln Lys Pro Tyr Ser Lys Asp Lys Phe Lys Leu Tyr Phe Gln Asn Pro
                515                 520                 525

Gln Phe Met Arg Gly Trp Asp Lys Asp Lys Glu Thr Asp Tyr Arg Ala
                530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Val Asn Gly
                565                 570                 575

Asn Tyr Glu Lys Ile Asn Tyr Lys Leu Leu Pro Gly Pro Asn Lys Met
                580                 585                 590

Leu Pro Arg Val Phe Phe Ser Lys Lys Trp Met Ala Tyr Tyr Asn Pro
                595                 600                 605

Ser Glu Asp Ile Gln Lys Ile Tyr Lys Asn Gly Thr Phe Lys Lys Gly
                610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
                660                 665                 670

Val Glu Glu Gln Gly Tyr Lys Val Ser Phe Glu Ser Ala Ser Lys Lys
                675                 680                 685

Glu Val Asp Lys Leu Val Glu Glu Gly Lys Leu Tyr Met Phe Gln Ile
                690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735
```

-continued

Arg Leu Ser Gly Gly Ala Glu Leu Phe Met Arg Arg Ala Ser Leu Lys
             740                 745                 750

Lys Glu Glu Leu Val Val His Pro Ala Asn Ser Pro Ile Ala Asn Lys
         755                 760                 765

Asn Pro Asp Asn Pro Lys Lys Thr Thr Thr Leu Ser Tyr Asp Val Tyr
     770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                 805                 810                 815

Arg Val Leu Leu Lys His Asp Asp Asn Pro Tyr Val Ile Gly Ile Asp
             820                 825                 830

Arg Gly Glu Arg Asn Leu Leu Tyr Ile Val Val Val Asp Gly Lys Gly
         835                 840                 845

Asn Ile Val Glu Gln Tyr Ser Leu Asn Glu Ile Ile Asn Asn Phe Asn
850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                 885                 890                 895

Lys Glu Leu Lys Ala Gly Tyr Ile Ser Gln Val Val His Lys Ile Cys
             900                 905                 910

Glu Leu Val Glu Lys Tyr Asp Ala Val Ile Ala Leu Glu Asp Leu Asn
             915                 920                 925

Ser Gly Phe Lys Asn Ser Arg Val Lys Val Glu Lys Gln Val Tyr Gln
         930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                 965                 970                 975

Thr Asn Lys Phe Glu Ser Phe Lys Ser Met Ser Thr Gln Asn Gly Phe
             980                 985                 990

Ile Phe Tyr Ile Pro Ala Trp Leu Thr Ser Lys Ile Asp Pro Ser Thr
         995                 1000                1005

Gly Phe Val Asn Leu Leu Lys Thr Lys Tyr Thr Ser Ile Ala Asp
     1010                1015                1020

Ser Lys Lys Phe Ile Ser Ser Phe Asp Arg Ile Met Tyr Val Pro
     1025                1030                1035

Glu Glu Asp Leu Phe Glu Phe Ala Leu Asp Tyr Lys Asn Phe Ser
     1040                1045                1050

Arg Thr Asp Ala Asp Tyr Ile Lys Lys Trp Lys Leu Tyr Ser Tyr
     1055                1060                1065

Gly Asn Arg Ile Arg Ile Phe Arg Asn Pro Lys Lys Asn Asn Val
     1070                1075                1080

Phe Asp Trp Glu Glu Val Cys Leu Thr Ser Ala Tyr Lys Glu Leu
     1085                1090                1095

Phe Asn Lys Tyr Gly Ile Asn Tyr Gln Gln Gly Asp Ile Arg Ala
     1100                1105                1110

Leu Leu Cys Glu Gln Ser Asp Lys Ala Phe Tyr Ser Ser Phe Met
     1115                1120                1125

Ala Leu Met Ser Leu Met Leu Gln Met Arg Asn Ser Ile Thr Gly
     1130                1135                1140

Arg Thr Asp Val Asp Phe Leu Ile Ser Pro Val Lys Asn Ser Asp

```
                1145                1150                1155
Gly Ile  Phe Tyr Asp Ser Arg  Asn Tyr Glu Ala Gln  Glu Asn Ala
            1160                1165                1170

Ile Leu  Pro Lys Asn Ala Asp  Ala Asn Gly Ala Tyr  Asn Ile Ala
            1175                1180                1185

Arg Lys  Val Leu Trp Ala Ile  Gly Gln Phe Lys Lys  Ala Glu Asp
            1190                1195                1200

Glu Lys  Leu Asp Lys Val Lys  Ile Ala Ile Ser Asn  Lys Glu Trp
            1205                1210                1215

Leu Glu  Tyr Ala Gln Thr Ser  Val Lys His
            1220                1225

<210> SEQ ID NO 41
<211> LENGTH: 1228
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: LbCpf1 RVR polypeptide

<400> SEQUENCE: 41

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
```

```
            260                 265                 270
Phe Lys Pro Leu Tyr Lys Gln Val Leu Ser Asp Arg Glu Ser Leu Ser
            275                 280                 285

Phe Tyr Gly Glu Gly Tyr Thr Ser Asp Glu Val Leu Glu Val Phe
        290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
            370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
            435                 440                 445

Asn Asp Ala Val Val Ala Ile Met Lys Asp Leu Leu Asp Ser Val Lys
        450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
            515                 520                 525

Gln Phe Met Arg Gly Trp Asp Lys Asp Val Glu Thr Asp Arg Arg Ala
        530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
            595                 600                 605

Ser Glu Asp Ile Gln Lys Ile Tyr Lys Asn Gly Thr Phe Lys Lys Gly
        610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
            675                 680                 685
```

```
Glu Val Asp Lys Leu Val Glu Gly Lys Leu Tyr Met Phe Gln Ile
    690             695             700

Tyr Asn Lys Asp Phe Ser Asp Lys Ser His Gly Thr Pro Asn Leu His
705             710             715                         720

Thr Met Tyr Phe Lys Leu Leu Phe Asp Glu Asn Asn His Gly Gln Ile
                725             730             735

Arg Leu Ser Gly Gly Ala Glu Leu Phe Met Arg Arg Ala Ser Leu Lys
            740             745             750

Lys Glu Glu Leu Val Val His Pro Ala Asn Ser Pro Ile Ala Asn Lys
        755             760             765

Asn Pro Asp Asn Pro Lys Lys Thr Thr Thr Leu Ser Tyr Asp Val Tyr
770             775             780

Lys Asp Lys Arg Phe Ser Glu Asp Gln Tyr Glu Leu His Ile Pro Ile
785             790             795                         800

Ala Ile Asn Lys Cys Pro Lys Asn Ile Phe Lys Ile Asn Thr Glu Val
            805             810             815

Arg Val Leu Leu Lys His Asp Asp Asn Pro Tyr Val Ile Gly Ile Asp
            820             825             830

Arg Gly Glu Arg Asn Leu Leu Tyr Ile Val Val Asp Gly Lys Gly
    835             840             845

Asn Ile Val Glu Gln Tyr Ser Leu Asn Glu Ile Ile Asn Asn Phe Asn
850             855             860

Gly Ile Arg Ile Lys Thr Asp Tyr His Ser Leu Leu Asp Lys Lys Glu
865             870             875             880

Lys Glu Arg Phe Glu Ala Arg Gln Asn Trp Thr Ser Ile Glu Asn Ile
            885             890             895

Lys Glu Leu Lys Ala Gly Tyr Ile Ser Gln Val Val His Lys Ile Cys
        900             905             910

Glu Leu Val Glu Lys Tyr Asp Ala Val Ile Ala Leu Glu Asp Leu Asn
        915             920             925

Ser Gly Phe Lys Asn Ser Arg Val Lys Val Glu Lys Gln Val Tyr Gln
930             935             940

Lys Phe Glu Lys Met Leu Ile Asp Lys Leu Asn Tyr Met Val Asp Lys
945             950             955             960

Lys Ser Asn Pro Cys Ala Thr Gly Gly Ala Leu Lys Gly Tyr Gln Ile
            965             970             975

Thr Asn Lys Phe Glu Ser Phe Lys Ser Met Ser Thr Gln Asn Gly Phe
            980             985             990

Ile Phe Tyr Ile Pro Ala Trp Leu Thr Ser Lys Ile Asp Pro Ser Thr
            995             1000            1005

Gly Phe Val Asn Leu Leu Lys Thr Lys Tyr Thr Ser Ile Ala Asp
    1010            1015            1020

Ser Lys Lys Phe Ile Ser Ser Phe Asp Arg Ile Met Tyr Val Pro
    1025            1030            1035

Glu Glu Asp Leu Phe Glu Phe Ala Leu Asp Tyr Lys Asn Phe Ser
    1040            1045            1050

Arg Thr Asp Ala Asp Tyr Ile Lys Lys Trp Lys Leu Tyr Ser Tyr
    1055            1060            1065

Gly Asn Arg Ile Arg Ile Phe Arg Asn Pro Lys Lys Asn Asn Val
    1070            1075            1080

Phe Asp Trp Glu Glu Val Cys Leu Thr Ser Ala Tyr Lys Glu Leu
    1085            1090            1095
```

-continued

```
Phe Asn Lys Tyr Gly Ile Asn Tyr Gln Gln Gly Asp Ile Arg Ala
    1100                1105                1110

Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

Arg Thr Asp Val Asp Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

Ile Leu Pro Lys Asn Ala Asp Ala Asn Gly Ala Tyr Asn Ile Ala
    1175                1180                1185

Arg Lys Val Leu Trp Ala Ile Gly Gln Phe Lys Lys Ala Glu Asp
    1190                1195                1200

Glu Lys Leu Asp Lys Val Lys Ile Ala Ile Ser Asn Lys Glu Trp
    1205                1210                1215

Leu Glu Tyr Ala Gln Thr Ser Val Lys His
    1220                1225
```

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: SV40 NLS

<400> SEQUENCE: 42
atggcaccaa agaaaaaaag gaaagtt                                        27

<210> SEQ ID NO 43
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Nucleoplasmin NLS

<400> SEQUENCE: 43
aaacgccccg cggctacaaa gaaggctggc caggcaaaga agaagaag               48

<210> SEQ ID NO 44
<211> LENGTH: 3849
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pGEP296 Ribozyme strategy vector

<400> SEQUENCE: 44
ctgacgcgcc ctgtagcggc ctgcagtgca gcgtgacccg gtcgtgcccc tctctagaga    60
taatgagcat tgcatgtcta agttataaaa aattaccaca tatttttttt gtcacacttg   120
tttgaagtgc agtttatcta tctttataca tatatttaaa ctttactcta cgaataatat   180
aatctatagt actacaataa tatcagtgtt ttagagaatc atataaatga acagttagac   240
atggtctaaa ggacaattga gtattttgac aacaggactc tacagtttta tcttttagt    300

```
gtgcatgtgt tctccttttt ttttgcaaat agcttcacct atataatact tcatccattt    360
tattagtaca tccatttagg gtttagggtt aatggttttt atagactaat ttttttagta    420
catctatttt attctatttt agcctctaaa ttaagaaaac taaaactcta ttttagtttt    480
tttatttaat aatttagata taaaatagaa taaaataaag tgactaaaaa ttaaacaaat    540 acccttttaag aaattaaaaa aactaaggaa acatttttct tgtttcgagt agataatgcc    600
agcctgttaa acgccgtcga tcgacgagtc taacggacac caaccagcga accagcagcg    660
tcgcgtcggg ccaagcgaag cagacggcac ggcatctctg tcgctgcctc tggacccctc    720
tcgagagttc cgctccaccg ttggacttgc tccgctgtcg gcatccagaa attgcgtggc    780
ggagcggcag acgtgagccg gcacggcagg cggcctcctc ctcctctcac ggcaccggca    840
gctacggggg attcctttcc caccgctcct tcgctttccc ttcctcgccc gccgtaataa    900
atagacaccc cctccacacc ctctttcccc aacctcgtgt tgttcggagc gcacacacac    960
acaaccagat ctcccccaaa tccacccgtc ggcacctccg cttcaaggta cgccgctcgt   1020
cctccccccc cccccctctc taccttctct agatcggcgt tccggtccat ggttagggcc   1080
cggtagttct acttctgttc atgtttgtgt tagatccgtg tttgtgttag atccgtgctg   1140
ctagcgttcg tacacggatg cgacctgtac gtcagacacg ttctgattgc taacttgcca   1200
gtgtttctct ttggggaatc ctgggatggc tctagccgtt ccgcagacgg gatcgatcta   1260
ggataggtat acatgttgat gtgggtttta ctgatgcata tacatgatgg catatgcagc   1320
atctattcat atgctctaac cttgagtacc tatctattat aataaacaag tatgttttat   1380
aattattttg atcttgatat acttggatga tggcatatgc agcagctata tgtggatttt   1440
tttagccctg ccttcatacg ctatttattt gcttggtact gtttcttttg tcgatgctca   1500
ccctgttgtt tggtgttact tctgcaggga tccaaattac tgatgagtcc gtgaggacga   1560
aacgagtaag ctcgtctaat ttctactaag tgtagatgag acggagctca gtctgaccgc   1620
ggcgtctctg gccggcatgg tcccagcctc ctcgctggcg ccggctgggc aacatgcttc   1680
ggcatggcga atgggaccga tcgttcaaac atttggcaat aaagtttctt aagattgaat   1740
cctgttgccg gtcttgcgat gattatcata taatttctgt tgaattacgt taagcatgta   1800
ataattaaca tgtaatgcat gacgttattt atgagatggg ttttttatgat tagagtcccg   1860 caattataca tttaatacgc gatagaaaac aaaatatagc gcgcaaacta ggataaatta   1920
tcgcgcgcgg tgtcatctat gttactagat cgatcgtcgt tcggctgcgg cgagcggtat   1980
cagctcactc aaaggcggta atacggttat ccacagaatc agggggataac gcaggaaaga   2040 acatgtgagc aaaaggccag caaaaggcca ggaaccgtaa aaaggccgcg ttgctggcgt   2100
ttttccatag gctccgcccc cctgacgagc atcacaaaaa tcgacgctca agtcagaggt   2160
ggcgaaaccc gacaggacta taaagatacc aggcgtttcc ccctggaagc tccctcgtgc   2220
gctctcctgt tccgaccctg ccgcttaccg gatacctgtc cgcctttctc ccttcgggaa   2280
gcgtggcgct ttctcatagc tcacgctgta ggtatctcag ttcggtgtag tcgttcgct   2340 ccaagctggg ctgtgtgcac gaaccccccg ttcagcccga ccgctgcgcc ttatccggta   2400
actatcgtct tgagtccaac ccggtaagac acgacttatc gccactggca gcagccactg   2460
gtaacaggat tagcagagcg aggtatgtag gcggtgctac agagttcttg aagtggtggc   2520
ctaactacgg ctacactaga agaacagtat ttggtatctg cgctctgctg aagccagtta   2580
ccttcggaaa aagagttggt agctcttgat ccggcaaaca aaccaccgct ggtagcggtg   2640
```

```
gttttttttgt ttgcaagcag cagattacgc gcagaaaaaa aggatctcaa gaagatcctt    2700
tgatcttttc tacggggtct gacgctcagt ggaacgaaaa ctcacgttaa gggattttgg    2760
tcatgagatt atcaaaaagg atcttcacct agatcctttt aaattaaaaa tgaagtttta    2820
aatcaatcta agtatatat gagtaaactt ggtctgacag ttaccaatgc ttaatcagtg     2880
aggcacctat ctcagcgatc tgtctatttc gttcatccat agttgcctga ctccccgtcg    2940
tgtagataac tacgatacgg gagggcttac catctggccc cagtgctgca atgataccgc    3000
gagacccacg ctcaccggct ccagatttat cagcaataaa ccagccagcc ggaagggccg    3060
agcgcagaag tggtcctgca actttatccg cctccatcca gtctattaat tgttgccggg    3120
aagctagagt aagtagttcg ccagttaata gtttgcgcaa cgttgttgcc attgctacag    3180
gcatcgtggt gtcacgctcg tcgtttggta tggcttcatt cagctccggt tcccaacgat    3240
caaggcgagt tacatgatcc cccatgttgt gcaaaaaagc ggttagctcc ttcggtcctc    3300
cgatcgttgt cagaagtaag ttggccgcag tgttatcact catggttatg gcagcactgc    3360
ataattctct tactgtcatg ccatccgtaa gatgcttttc tgtgactggt gagtactcaa    3420
ccaagtcatt ctgagaatag tgtatgcggc gaccgagttg ctcttgcccg gcgtcaatac    3480
gggataatac cgcgccacat agcagaactt taaaagtgct catcattgga aaacgttctt    3540
cggggcgaaa actctcaagg atcttaccgc tgttgagatc cagttcgatg taacccactc    3600
gtgcacccaa ctgatcttca gcatctttta ctttcaccag cgtttctggg tgagcaaaaa    3660
caggaaggca aaatgccgca aaaaagggaa taagggcgac acggaaatgt tgaatactca    3720
tactcttcct ttttcaatat tattgaagca tttatcaggg ttattgtctc atgagcggat    3780
acatatttga atgtatttag aaaaataaac aaataggggt tccgcgcaca tttccccgaa    3840
aagtgccac                                                           3849

<210> SEQ ID NO 45
<211> LENGTH: 3834
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pGEP374 vector with rice HDV-like ribozyme
      sequence

<400> SEQUENCE: 45
ctgacgcgcc ctgtagcggc ctgcagtgca gcgtgacccg gtcgtgcccc tctctagaga      60
taatgagcat tgcatgtcta agttataaaa aattaccaca tattttttt gtcacacttg     120 tttgaagtgc agtttatcta tctttataca tatatttaaa ctttactcta cgaataatat    180
aatctatagt actacaataa tatcagtgtt ttagagaatc atataaatga acagttagac    240
atggtctaaa ggacaattga gtattttgac aacaggactc tacagtttta tcttttagt     300 gtgcatgtgt tctccttttt ttttgcaaat agcttcacct atataatact tcatccattt    360
tattagtaca tccatttagg gtttagggtt aatggttttt atagactaat ttttttagta    420
catctatttt attctatttt agcctctaaa ttaagaaaac taaaactcta ttttagtttt    480
tttatttaat aatttagata taaaatagaa taaaataaag tgactaaaaa ttaaacaaat    540
accctttaag aaattaaaaa actaaggaa acatttttct tgtttcgagt agataatgcc    600
agcctgttaa acgccgtcga tcgacagagtc taacggacac caaccagcga accagcagcg    660
tcgcgtcggg ccaagcgaag cagacggcac ggcatctctg tcgctgcctc tggacccctc    720
```

```
tcgagagttc cgctccaccg ttggacttgc tccgctgtcg gcatccagaa attgcgtggc      780
ggagcggcag acgtgagccg gcacggcagg cggcctcctc ctcctctcac ggcaccggca      840
gctacggggg attcctttcc caccgctcct tcgctttccc ttcctcgccc gccgtaataa      900
atagacaccc cctccacacc ctctttcccc aacctcgtgt tgttcggagc gcacacacac      960
acaaccagat ctcccccaaa tccacccgtc ggcacctccg cttcaaggta cgccgctcgt     1020
cctccccccc cccccctctc taccttctct agatcggcgt tccggtccat ggttagggcc     1080
cggtagttct acttctgttc atgtttgtgt tagatccgtg tttgtgttag atccgtgctg     1140
ctagcgttcg tacacggatg cgacctgtac gtcagacacg ttctgattgc taacttgcca     1200
gtgtttctct ttggggaatc ctgggatggc tctagccgtt ccgcagacgg gatcgatcta     1260
ggataggtat acatgttgat gtgggtttta ctgatgcata tacatgatgg catatgcagc     1320
atctattcat atgctctaac cttgagtacc tatctattat aataaacaag tatgttttat     1380
aattattttg atcttgatat acttggatga tggcatatgc agcagctata tgtggatttt     1440
tttagccctg ccttcatacg ctatttattt gcttggtact gtttctttg tcgatgctca     1500 ccctgttgtt tggtgttact tctgcaggga tccaaattac tgatgagtcc gtgaggacga     1560
aacgagtaag ctcgtctaat ttctactaag tgtagatgag acggagctca gtctgaccgc     1620
ggcgtctctc cgccaacact gccaatgccg gtcccaagcc cggataaaag tggaggggc      1680 ggcgatcgtt caaacatttg gcaataaagt ttcttaagat tgaatcctgt tgccggtctt     1740
gcgatgatta tcatataatt tctgttgaat tacgttaagc atgtaataat taacatgtaa     1800
tgcatgacgt tatttatgag atgggttttt atgattagag tcccgcaatt atacatttaa     1860
tacgcgatag aaaacaaaat atagcgcgca aactaggata aattatcgcg cgcggtgtca     1920
tctatgttac tagatcgatc gtcgttcggc tgcggcgagc ggtatcagct cactcaaagg     1980
cggtaatacg gttatccaca gaatcagggg ataacgcagg aaagaacatg tgagcaaaag     2040
gccagcaaaa ggccaggaac cgtaaaaagg ccgcgttgct ggcgttttc cataggctcc      2100 gcccccctga cgagcatcac aaaaatcgac gctcaagtca gaggtggcga aacccgacag     2160
gactataaag ataccaggcg tttccccctg gaagctccct cgtgcgctct cctgttccga     2220
ccctgccgct taccggatac ctgtccgcct ttctcccttc gggaagcgtg gcgctttctc     2280
atagctcacg ctgtaggtat ctcagttcgg tgtaggtcgt tcgctccaag ctgggctgtg     2340
tgcacgaacc ccccgttcag cccgaccgct gcgccttatc cggtaactat cgtcttgagt     2400
ccaacccggt aagacacgac ttatcgccac tggcagcagc cactggtaac aggattagca     2460
gagcgaggta tgtaggcggt gctacagagt tcttgaagtg gtggcctaac tacggctaca     2520
ctagaagaac agtatttggt atctgcgctc tgctgaagcc agttaccttc ggaaaaagag     2580
ttggtagctc ttgatccggc aaacaaacca ccgctggtag cggtggtttt tttgtttgca     2640
agcagcagat tacgcgcaga aaaaaaggat ctcaagaaga tcctttgatc ttttctacgg     2700
ggtctgacgc tcagtggaac gaaaactcac gttaagggat tttggtcatg agattatcaa     2760
aaaggatctt cacctagatc cttttaaatt aaaaatgaag ttttaaatca atctaaagta     2820
tatatgagta aacttggtct gacagttacc aatgcttaat cagtgaggca cctatctcag     2880
cgatctgtct atttcgttca tccatagttg cctgactccc cgtcgtgtag ataactacga     2940
tacgggaggg cttaccatct ggccccagtg ctgcaatgat accgcgagac ccacgctcac     3000
cggctccaga tttatcagca ataaaccagc cagccggaag ggccgagcgc agaagtggtc     3060
```

-continued

```
ctgcaacttt atccgcctcc atccagtcta ttaattgttg ccgggaagct agagtaagta    3120
gttcgccagt taatagtttg cgcaacgttg ttgccattgc tacaggcatc gtggtgtcac    3180
gctcgtcgtt tggtatggct tcattcagct ccggttccca acgatcaagg cgagttacat    3240
gatcccccat gttgtgcaaa aaagcggtta gctccttcgg tcctccgatc gttgtcagaa    3300
gtaagttggc cgcagtgtta tcactcatgg ttatggcagc actgcataat tctcttactg    3360
tcatgccatc cgtaagatgc ttttctgtga ctggtgagta ctcaaccaag tcattctgag    3420
aatagtgtat gcggcgaccg agttgctctt gcccggcgtc aatacgggat aataccgcgc    3480
cacatagcag aactttaaaa gtgctcatca ttggaaaacg ttcttcgggg cgaaaactct    3540
caaggatctt accgctgttg agatccagtt cgatgtaacc cactcgtgca cccaactgat    3600
cttcagcatc ttttactttc accagcgttt ctgggtgagc aaaaacagga aggcaaaatg    3660
ccgcaaaaaa gggaataagg gcgacacgga aatgttgaat actcatactc ttcctttttc    3720
aatattattg aagcatttat cagggttatt gtctcatgag cggatacata tttgaatgta    3780
tttagaaaaa taaacaaata ggggttccgc gcacatttcc ccgaaaagtg ccac          3834
```

<210> SEQ ID NO 46
<211> LENGTH: 3844
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: pGEP375 vector with sunflower HDV-like sequence

<400> SEQUENCE: 46

```
ctgacgcgcc ctgtagcggc ctgcagtgca gcgtgacccg gtcgtgcccc tctctagaga      60
taatgagcat tgcatgtcta agttataaaa aattaccaca tatttttttt gtcacacttg     120
tttgaagtgc agtttatcta tctttataca tatatttaaa ctttactcta cgaataatat     180
aatctatagt actacaataa tatcagtgtt ttagagaatc atataaatga acagttagac     240
atggtctaaa ggacaattga gtattttgac aacaggactc tacagtttta tcttttttagt    300 gtgcatgtgt tctccttttt ttttgcaaat agcttcacct atataatact tcatccattt     360
tattagtaca tccatttagg gtttaggggt aatggttttt atagactaat ttttttagta    420
catctatttt attctatttt agcctctaaa ttaagaaaac taaaactcta ttttagttttt    480 tttatttaat aatttagata taaaatagaa taaaataaag tgactaaaaa ttaaacaaat    540 acccttttaag aaattaaaaa aactaaggaa acattttttct tgtttcgagt agataatgcc    600
agcctgttaa acgccgtcga tcgacgagtc taacggacac caaccagcga accagcagcg     660
tcgcgtcggg ccaagcgaag cagacggcac ggcatctctg tcgctgcctc tggacccctc     720
tcgagagttc cgctccaccg ttggacttgc tccgctgtcg gcatccagaa attgcgtggc     780
ggagcggcag acgtgagccg gcacggcagg cggcctcctc ctcctctcac ggcaccggca     840
gctacggggg attcctttcc caccgctcct tcgctttccc ttcctcgccc gccgtaataa     900
atagacaccc cctccacacc ctctttcccc aacctcgtgt tgttcggagc gcacacacac     960
acaaccagat ctcccccaaa tccacccgtc ggcacctccg cttcaaggta cgccgctcgt    1020 cctcccccc ccccctctc taccttctct agatcggcgt tccggtccat ggttagggcc    1080
cggtagttct acttctgttc atgtttgtgt tagatccgtg tttgtgttag atccgtgctg    1140
ctagcgttcg tacacggatg cgacctgtac gtcagacacg ttctgattgc taacttgcca    1200
```

```
gtgtttctct ttggggaatc ctgggatggc tctagccgtt ccgcagacgg gatcgatcta    1260
ggataggtat acatgttgat gtgggtttta ctgatgcata tacatgatgg catatgcagc    1320
atctattcat atgctctaac cttgagtacc tatctattat aataaacaag tatgttttat    1380
aattattttg atcttgatat acttggatga tggcatatgc agcagctata tgtggatttt    1440
tttagccctg ccttcatacg ctatttattt gcttggtact gtttcttttg tcgatgctca    1500
ccctgttgtt tggtgttact tctgcaggga tccaaattac tgatgagtcc gtgaggacga    1560
aacgagtaag ctcgtctaat ttctactaag tgtagatgag acggagctca gtctgaccgc    1620
ggcgtctctg cgggggggcgt cagtcctact ctgcacctcc tcgtggtgtc gcctgggaac    1680
cctctttcgc aacgatcgtt caaacatttg gcaataaagt ttcttaagat tgaatcctgt    1740
tgccggtctt gcgatgatta tcatataatt tctgttgaat tacgttaagc atgtaataat    1800
taacatgtaa tgcatgacgt tatttatgag atgggttttt atgattagag tcccgcaatt    1860
atacatttaa tacgcgatag aaaacaaaat atagcgcgca aactaggata aattatcgcg    1920
cgcggtgtca tctatgttac tagatcgatc gtcgttcggc tgcggcgagc ggtatcagct    1980
cactcaaagg cggtaatacg gttatccaca gaatcagggg ataacgcagg aaagaacatg    2040
tgagcaaaag gccagcaaaa ggccaggaac cgtaaaaagg ccgcgttgct ggcgtttttc    2100
cataggctcc gcccccctga cgagcatcac aaaaatcgac gctcaagtca gaggtggcga    2160
aacccgacag gactataaag ataccaggcg tttccccctg gaagctccct cgtgcgctct    2220
cctgttccga ccctgccgct taccggatac ctgtccgcct ttctcccttc gggaagcgtg    2280
gcgctttctc atagctcacg ctgtaggtat ctcagttcgg tgtaggtcgt tcgctccaag    2340
ctgggctgtg tgcacgaacc ccccgttcag cccgaccgct gcgccttatc cggtaactat    2400
cgtcttgagt ccaacccggt aagacacgac ttatcgccac tggcagcagc cactggtaac    2460
aggattagca gagcgaggta tgtaggcggt gctacagagt tcttgaagtg gtggcctaac    2520
tacggctaca ctagaagaac agtatttggt atctgcgctc tgctgaagcc agttaccttc    2580
ggaaaaagag ttggtagctc ttgatccggc aaacaaacca ccgctggtag cggtggtttt    2640
tttgtttgca agcagcagat tacgcgcaga aaaaaaggat ctcaagaaga tcctttgatc    2700
ttttctacgg ggtctgacgc tcagtggaac gaaaactcac gttaagggat tttggtcatg    2760
agattatcaa aaaggatctt cacctagatc cttttaaatt aaaaatgaag ttttaaatca    2820
atctaaagta tatatgagta aacttggtct gacagttacc aatgcttaat cagtgaggca    2880
cctatctcag cgatctgtct atttcgttca tccatagttg cctgactccc cgtcgtgtag    2940
ataactacga tacgggaggg cttaccatct ggccccagtg ctgcaatgat accgcgagac    3000
ccacgctcac cggctccaga tttatcagca ataaaccagc cagccggaag ggccgagcgc    3060
agaagtggtc ctgcaacttt atccgcctcc atccagtcta ttaattgttg ccgggaagct    3120
agagtaagta gttcgccagt taatagtttg cgcaacgttg ttgccattgc tacaggcatc    3180
gtggtgtcac gctcgtcgtt tggtatggct tcattcagct ccggttccca acgatcaagg    3240
cgagttacat gatcccccat gttgtgcaaa aaagcggtta gctccttcgg tcctccgatc    3300
gttgtcagaa gtaagttggc cgcagtgtta tcactcatgg ttatggcagc actgcataat    3360
tctcttactg tcatgccatc cgtaagatgc ttttctgtga ctggtgagta ctcaaccaag    3420
tcattctgag aatagtgtat gcggcgaccg agttgctctt gcccggcgtc aatacgggat    3480
aataccgcgc cacatagcag aactttaaaa gtgctcatca ttggaaaacg ttcttcgggg    3540
cgaaaactct caaggatctt accgctgttg agatccagtt cgatgtaacc cactcgtgca    3600
```

```
cccaactgat cttcagcatc ttttactttc accagcgttt ctgggtgagc aaaaacagga    3660
aggcaaaatg ccgcaaaaaa gggaataagg gcgacacgga aatgttgaat actcatactc    3720
ttcctttttc aatattattg aagcatttat cagggttatt gtctcatgag cggatacata    3780
tttgaatgta tttagaaaaa taaacaaata ggggttccgc gcacatttcc ccgaaaagtg    3840
ccac                                                                 3844
```

<210> SEQ ID NO 47
<211> LENGTH: 3867
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: pGEP375 vector with sunflower HDV-like sequence_long

<400> SEQUENCE: 47

```
ctgacgcgcc ctgtagcggc ctgcagtgca gcgtgacccg gtcgtgcccc tctctagaga      60
taatgagcat tgcatgtcta agttataaaa aattaccaca tatttttttt gtcacacttg     120
tttgaagtgc agtttatcta tctttataca tatatttaaa ctttactcta cgaataatat     180
aatctatagt actacaataa tatcagtgtt ttagagaatc atataaatga acagttagac     240
atggtctaaa ggacaattga gtattttgac aacaggactc tacagtttta tcttttagt     300 gtgcatgtgt tctccttttt ttttgcaaat agcttcacct atataatact tcatccattt     360
tattagtaca tccatttagg gtttagggtt aatggttttt atagactaat ttttttagta     420
catctatttt attctatttt agcctctaaa ttaagaaaac taaaactcta ttttagtttt     480
tttatttaat aatttagata taaatagaa taaaataaag tgactaaaaa ttaaacaaat     540 acccttaag aaattaaaaa aactaaggaa acatttttct tgtttcgagt agataatgcc     600
agcctgttaa acgccgtcga tcgacgagtc taacggacac caaccagcga accagcagcg     660
tcgcgtcggg ccaagcgaag cagacggcac ggcatctctg tcgctgcctc tggacccctc     720
tcgagagttc cgctccaccg ttggacttgc tccgctgtcg gcatccagaa attgcgtggc     780
ggagcggcag acgtgagccg gcacggcagg cggcctcctc ctcctctcac ggcaccggca     840
gctacggggg attcctttcc caccgctcct tcgctttccc ttcctcgccc gccgtaataa     900
atagacaccc cctccacacc ctctttcccc aacctcgtgt tgttcggagc gcacacacac     960
acaaccagat ctcccccaaa tccacccgtc ggcacctccg cttcaaggta cgccgctcgt    1020
cctccccccc ccccccctctc taccttctct agatcggcgt tccggtccat ggttagggcc    1080
cggtagttct acttctgttc atgtttgtgt tagatccgtg tttgtgttag atccgtgctg    1140
ctagcgttcg tacacggatg cgacctgtac gtcagacacg ttctgattgc taacttgcca    1200
gtgtttctct ttggggaatc ctgggatggc tctagccgtt ccgcagacgg gatcgatcta    1260
ggataggtat acatgttgat gtgggtttta ctgatgcata tacatgatgg catatgcagc    1320
atctattcat atgctctaac cttgagtacc tatctattat aataaacaag tatgttttat    1380
aattattttg atcttgatat acttggatga tggcatatgc agcagctata tgtggatttt    1440
tttagccctg ccttcatacg ctatttattt gcttggtact gtttctttg tcgatgctca    1500 ccctgttgtt tggtgttact tctgcaggga tccaaattac tgatgagtcc gtgaggacga    1560
aacgagtaag ctcgtctaat ttctactaag tgtagatgag acggagctca gtctgaccgc    1620
```

```
ggcgtctctg cgggggggcgt cagtcctact ctgcacctcc tcgtggtgtc gcctgggaac    1680
cctctttcgc aagaaagagg agccaagcag agaggcgatc gttcaaacat ttggcaataa    1740
agtttcttaa gattgaatcc tgttgccggt cttgcgatga ttatcatata atttctgttg    1800
aattacgtta agcatgtaat aattaacatg taatgcatga cgttatttat gagatgggtt    1860
tttatgatta gagtcccgca attatacatt taatacgcga tagaaaacaa aatatagcgc    1920
gcaaactagg ataaattatc gcgcgcggtg tcatctatgt tactagatcg atcgtcgttc    1980
ggctgcggcg agcggtatca gctcactcaa aggcggtaat acggttatcc acagaatcag    2040
gggataacgc aggaaagaac atgtgagcaa aaggccagca aaaggccagg aaccgtaaaa    2100
aggccgcgtt gctggcgttt ttccataggc tccgcccccc tgacgagcat cacaaaaatc    2160
gacgctcaag tcagaggtgg cgaaacccga caggactata agataccag gcgtttcccc    2220
ctggaagctc cctcgtgcgc tctcctgttc cgaccctgcc gcttaccgga tacctgtccg    2280
cctttctccc ttcgggaagc gtggcgcttt ctcatagctc acgctgtagg tatctcagtt    2340
cggtgtaggt cgttcgctcc aagctgggct gtgtgcacga accccccgtt cagcccgacc    2400
gctgcgcctt atccggtaac tatcgtcttg agtccaaccc ggtaagacac gacttatcgc    2460
cactggcagc agccactggt aacaggatta gcagagcgag gtatgtaggc ggtgctacag    2520
agttcttgaa gtggtggcct aactacggct acactagaag aacagtattt ggtatctgcg    2580
ctctgctgaa gccagttacc ttcggaaaaa gagttggtag ctcttgatcc ggcaaacaaa    2640
ccaccgctgg tagcggtggt ttttttgttt gcaagcagca gattacgcgc agaaaaaaag    2700
gatctcaaga agatcctttg atcttttcta cggggtctga cgctcagtgg aacgaaaact    2760
cacgttaagg gattttggtc atgagattat caaaaaggat cttcacctag atccttttaa    2820
attaaaaatg aagttttaaa tcaatctaaa gtatatatga gtaaacttgg tctgacagtt    2880
accaatgctt aatcagtgag gcacctatct cagcgatctg tctatttcgt tcatccatag    2940
ttgcctgact ccccgtcgtg tagataacta cgatacggga gggcttacca tctgccccca    3000
gtgctgcaat gataccgcga gacccacgct caccggctcc agatttatca gcaataaacc    3060
agccagccgg aagggccgag cgcagaagtg gtcctgcaac tttatccgcc tccatccagt    3120
ctattaattg ttgccgggaa gctagagtaa gtagttcgcc agttaatagt ttgcgcaacg    3180
ttgttgccat tgctacaggc atcgtggtgt cacgctcgtc gtttggtatg gcttcattca    3240
gctccggttc ccaacgatca aggcgagtta catgatcccc catgttgtgc aaaaaagcgg    3300
ttagctcctt cggtcctccg atcgttgtca gaagtaagtt ggccgcagtg ttatcactca    3360
tggttatggc agcactgcat aattctctta ctgtcatgcc atccgtaaga tgcttttctg    3420
tgactggtga gtactcaacc aagtcattct gagaatagtg tatgcggcga ccgagttgct    3480
cttgcccggc gtcaatacgg gataataccg cgccacatag cagaacttta aaagtgctca    3540
tcattggaaa acgttcttcg gggcgaaaac tctcaaggat cttaccgctg ttgagatcca    3600
gttcgatgta acccactcgt gcacccaact gatcttcagc atcttttact ttcaccagcg    3660
tttctgggtg agcaaaaaca ggaaggcaaa atgccgcaaa aaagggaata agggcgacac    3720
ggaaatgttg aatactcata ctcttccttt ttcaatatta ttgaagcatt tatcagggtt    3780
attgtctcat gagcggatac atatttgaat gtatttagaa aaataaacaa ataggggttc    3840
cgcgcacatt tccccgaaaa gtgccac                                       3867
```

<210> SEQ ID NO 48
<211> LENGTH: 3861

<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: pGEP376 vector with artichoke HDV-like sequence

<400> SEQUENCE: 48

| | | | | | |
|---|---|---|---|---|---|
| ctgacgcgcc | ctgtagcggc | ctgcagtgca | gcgtgacccg | gtcgtgcccc | tctctagaga | 60 |
| taatgagcat | tgcatgtcta | agttataaaa | aattaccaca | tatttttttt | gtcacacttg | 120 |
| tttgaagtgc | agtttatcta | tctttataca | tatatttaaa | ctttactcta | cgaataatat | 180 |
| aatctatagt | actacaataa | tatcagtgtt | ttagagaatc | atataaatga | acagttagac | 240 |
| atggtctaaa | ggacaattga | gtattttgac | aacaggactc | tacagtttta | tcttttagt | 300 |
| gtgcatgtgt | tctccttttt | ttttgcaaat | agcttcacct | atataatact | tcatccattt | 360 |
| tattagtaca | tccatttagg | gtttagggtt | aatggttttt | atagactaat | tttttagta | 420 |
| catctatttt | attctatttt | agcctctaaa | ttaagaaaac | taaaactcta | ttttagtttt | 480 |
| tttatttaat | aatttagata | taaaatagaa | taaaataaag | tgactaaaaa | ttaaacaaat | 540 |
| acccttaag | aaattaaaaa | aactaaggaa | acatttttct | tgtttcgagt | agataatgcc | 600 |
| agcctgttaa | acgccgtcga | tcgacgagtc | taacggacac | caaccagcga | accagcagcg | 660 |
| tcgcgtcggg | ccaagcgaag | cagacggcac | ggcatctctg | tcgctgcctc | tggacccctc | 720 |
| tcgagagttc | cgctccaccg | ttggacttgc | tccgctgtcg | gcatccagaa | attgcgtggc | 780 |
| ggagcggcag | acgtgagccg | gcacggcagg | cggcctcctc | ctcctctcac | ggcaccggca | 840 |
| gctacggggg | attcctttcc | caccgctcct | tcgctttccc | ttcctcgccc | gccgtaataa | 900 |
| atagacaccc | cctccacacc | ctctttcccc | aacctcgtgt | tgttcggagc | gcacacacac | 960 |
| acaaccagat | ctcccccaaa | tccacccgtc | ggcacctccg | cttcaaggta | cgccgctcgt | 1020 |
| cctccccccc | cccccctctc | taccttctct | agatcggcgt | tccggtccat | ggttagggcc | 1080 |
| cggtagttct | acttctgttc | atgtttgtgt | tagatccgtg | tttgtgttag | atccgtgctg | 1140 |
| ctagcgttcg | tacacggatg | cgacctgtac | gtcagacacg | ttctgattgc | taacttgcca | 1200 |
| gtgtttctct | ttggggaatc | ctgggatggc | tctagccgtt | ccgcagacgg | gatcgatcta | 1260 |
| ggataggtat | acatgttgat | gtgggtttta | ctgatgcata | tacatgatgg | catatgcagc | 1320 |
| atctattcat | atgctctaac | cttgagtacc | tatctattat | aataaacaag | tatgttttat | 1380 |
| aattattttg | atcttgatat | acttggatga | tggcatatgc | agcagctata | tgtggatttt | 1440 |
| tttagccctg | ccttcatacg | ctatttattt | gcttggtact | gtttcttttg | tcgatgctca | 1500 |
| ccctgttgtt | tggtgttact | tctgcaggga | tccaaattac | tgatgagtcc | gtgaggacga | 1560 |
| aacgagtaag | ctcgtctaat | ttctactaag | tgtagatgag | acggagctca | gtctgaccgc | 1620 |
| ggcgtctctg | gcgtcagtcc | tactctgcac | ctcctcgtgg | tgtcgcctgg | gaaccctctt | 1680 |
| tcacaagaaa | gaggagccaa | gcagagaggc | gatcgttcaa | acatttggca | ataaagtttc | 1740 |
| ttaagattga | atcctgttgc | cggtcttgcg | atgattatca | tataatttct | gttgaattac | 1800 |
| gttaagcatg | taataattaa | catgtaatgc | atgacgttat | ttatgagatg | ggttttatg | 1860 |
| attagagtcc | cgcaattata | catttaatac | gcgatagaaa | acaaaatata | gcgcgcaaac | 1920 |
| taggataaat | tatcgcgcgc | ggtgtcatct | atgttactag | atcgatcgtc | gttcggctgc | 1980 |
| ggcgagcggt | atcagctcac | tcaaaggcgg | taatacggtt | atccacagaa | tcaggggata | 2040 |
| acgcaggaaa | gaacatgtga | gcaaaaggcc | agcaaaaggc | caggaaccgt | aaaaaggccg | 2100 |

-continued

```
cgttgctggc gttttccat aggctccgcc ccctgacga gcatcacaaa aatcgacgct    2160
caagtcagag gtggcgaaac ccgacaggac tataaagata ccaggcgttt cccctggaa    2220
gctccctcgt gcgctctcct gttccgaccc tgccgcttac cggatacctg tccgcctttc    2280
tcccttcggg aagcgtggcg ctttctcata gctcacgctg taggtatctc agttcggtgt    2340
aggtcgttcg ctccaagctg gctgtgtgc acgaacccc cgttcagccc gaccgctgcg     2400
ccttatccgg taactatcgt cttgagtcca acccggtaag acacgactta tcgccactgg    2460
cagcagccac tggtaacagg attagcagag cgaggtatgt aggcggtgct acagagttct    2520
tgaagtggtg gcctaactac ggctacacta gaagaacagt atttggtatc tgcgctctgc    2580
tgaagccagt taccttcgga aaagagttg gtagctcttg atccggcaaa caaccaccg    2640
ctggtagcgg tggtttttt gtttgcaagc agcagattac gcgcagaaaa aaaggatctc    2700
aagaagatcc tttgatcttt tctacggggt ctgacgctca gtggaacgaa aactcacgtt    2760
aagggatttt ggtcatgaga ttatcaaaaa ggatcttcac ctagatcctt ttaaattaaa    2820
aatgaagttt taaatcaatc taaagtatat atgagtaaac ttggtctgac agttaccaat    2880
gcttaatcag tgaggcacct atctcagcga tctgtctatt tcgttcatcc atagttgcct    2940
gactccccgt cgtgtagata actacgatac gggagggctt accatctggc cccagtgctg    3000
caatgatacc gcgagaccca cgctcaccgg ctccagattt atcagcaata accagccag     3060
ccggaagggc cgagcgcaga agtggtcctg caactttatc cgcctccatc cagtctatta    3120
attgttgccg ggaagctaga gtaagtagtt cgccagttaa tagtttgcgc aacgttgttg    3180
ccattgctac aggcatcgtg gtgtcacgct cgtcgtttgg tatggcttca ttcagctccg    3240
gttcccaacg atcaaggcga gttacatgat cccccatgtt gtgcaaaaaa gcggttagct    3300
ccttcggtcc tccgatcgtt gtcagaagta agttggccgc agtgttatca ctcatggtta    3360
tggcagcact gcataattct cttactgtca tgccatccgt aagatgcttt tctgtgactg    3420
gtgagtactc aaccaagtca ttctgagaat agtgtatgcg gcgaccgagt tgctcttgcc    3480
cggcgtcaat acgggataat accgcgccac atagcagaac tttaaaagtg ctcatcattg    3540
gaaaacgttc ttcggggcga aaactctcaa ggatcttacc gctgttgaga tccagttcga    3600
tgtaacccac tcgtgcaccc aactgatctt cagcatcttt tactttcacc agcgtttctg    3660
ggtgagcaaa aacaggaagg caaaatgccg caaaaaaggg aataagggcg acacggaaat    3720
gttgaatact catactcttc cttttcaat attattgaag catttatcag ggttattgtc     3780
tcatgagcgg atacatattt gaatgtattt agaaaaataa acaaataggg gttccgcgca    3840
catttccccg aaaagtgcca c                                             3861
```

<210> SEQ ID NO 49
<211> LENGTH: 24
<212> TYPE: DNA
<213> ORGANISM: Zea mays

<400> SEQUENCE: 49
ctcgtcacga ttcccctctc ctgg                                             24

<210> SEQ ID NO 50
<211> LENGTH: 24
<212> TYPE: DNA
<213> ORGANISM: Zea mays

<400> SEQUENCE: 50

```
cccacctgaa aagttcgacc agga                                              24

<210> SEQ ID NO 51
<211> LENGTH: 24
<212> TYPE: DNA
<213> ORGANISM: Zea mays

<400> SEQUENCE: 51
tgtgtggtca cacttgccag ccag                                              24

<210> SEQ ID NO 52
<211> LENGTH: 24
<212> TYPE: DNA
<213> ORGANISM: Zea mays

<400> SEQUENCE: 52
gtggtcggat ttctggcatc gctg                                              24

<210> SEQ ID NO 53
<211> LENGTH: 23
<212> TYPE: DNA
<213> ORGANISM: Zea mays

<400> SEQUENCE: 53
gtctatgtcg atgaccagca gat                                               23

<210> SEQ ID NO 54
<211> LENGTH: 24
<212> TYPE: DNA
<213> ORGANISM: Zea mays

<400> SEQUENCE: 54
cctctcctgg tcgaactttt cagg                                              24

<210> SEQ ID NO 55
<211> LENGTH: 24
<212> TYPE: DNA
<213> ORGANISM: Zea mays

<400> SEQUENCE: 55
accaggagag gggaatcgtg acga                                              24

<210> SEQ ID NO 56
<211> LENGTH: 24
<212> TYPE: DNA
<213> ORGANISM: Zea mays

<400> SEQUENCE: 56
ttatagcacg acaaaagtaa aaat                                              24

<210> SEQ ID NO 57
<211> LENGTH: 24
<212> TYPE: DNA
<213> ORGANISM: Zea mays

<400> SEQUENCE: 57
attgtcgtca tcatcggcta acat                                              24

<210> SEQ ID NO 58
<211> LENGTH: 24
<212> TYPE: DNA
<213> ORGANISM: Zea mays

<400> SEQUENCE: 58
```

```
tactttgact tttcccttaa tgac                                              24

<210> SEQ ID NO 59
<211> LENGTH: 24
<212> TYPE: DNA
<213> ORGANISM: Zea mays

<400> SEQUENCE: 59
gggccggtca taaagcagct ctca                                              24

<210> SEQ ID NO 60
<211> LENGTH: 24
<212> TYPE: DNA
<213> ORGANISM: Zea mays

<400> SEQUENCE: 60
acggatagcg ctcctcgttg gcgc                                              24

<210> SEQ ID NO 61
<211> LENGTH: 24
<212> TYPE: DNA
<213> ORGANISM: Zea mays

<400> SEQUENCE: 61
acaatgttag ccgatgatga cgac                                              24

<210> SEQ ID NO 62
<211> LENGTH: 24
<212> TYPE: DNA
<213> ORGANISM: Zea mays

<400> SEQUENCE: 62
ggtaaccgtc ctccgtacgt cgtc                                              24

<210> SEQ ID NO 63
<211> LENGTH: 24
<212> TYPE: DNA
<213> ORGANISM: Zea mays

<400> SEQUENCE: 63
cctctctacg acgacgtacg gagg                                              24

<210> SEQ ID NO 64
<211> LENGTH: 24
<212> TYPE: DNA
<213> ORGANISM: Zea mays

<400> SEQUENCE: 64
gttacgggca gtgcagttga gcaa                                              24

<210> SEQ ID NO 65
<211> LENGTH: 24
<212> TYPE: DNA
<213> ORGANISM: Zea mays

<400> SEQUENCE: 65
ctgactgtcc agtggccacc taga                                              24

<210> SEQ ID NO 66

<400> SEQUENCE: 66

000
```

<210> SEQ ID NO 67
<211> LENGTH: 1226
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: p35S+Adh1 intron promoter sequence

<400> SEQUENCE: 67

```
gttcagaaga ccagagggct attgagactt tcaacaaag ggtaatatcg ggaaacctcc      60
tcggattcca ttgcccagct atctgtcact tcatcgaaag gacagtagaa aaggaagatg     120
gcttctacaa atgccatcat tgcgataaag gaaaggctat cgttcaagat gcctctaccg     180
acagtggtcc caaagatgga cccccaccca cgaggaacat cgtggaaaaa gaagacgttc     240
caaccacgtc ttcaaagcaa gtggattgat gtgatacatg gtggagcacg acactctcgt     300
ctactccaag aatatcaaag atacagtctc agaagaccag agggctattg agacttttca     360
acaaagggta atatcgggaa acctcctcgg attccattgc ccagctatct gtcacttcat     420
cgaaaggaca gtagaaaagg aagatggctt ctacaaatgc catcattgcg ataaaggaaa     480
ggctatcgtt caagatgcct ctaccgacag tggtcccaaa gatggacccc cacccacgag     540
gaacatcgtg gaaaagaag acgttccaac cacgtcttca aagcaagtgg attgatgtga     600
tatctccact gacgtaaggg atgacgcaca atcccactat ccttcgcaag cccttcctc     660 tatataagga agttcatttc atttggagag gtccgccttg tttctcctc tgtctcttga     720 tctgactaat cttggtttat gattcgttga gtaattttgg ggaaagcttc gtccacagtt     780
ttttttcgat gaacagtgcc gcagtggcgc tgatcttgta tgctatcctg caatcgtggt     840
gaacttattt cttttatatc ctttactccc atgaaaaggc tagtaatctt tctcgatgta     900
acatcgtcca gcactgctat taccgtgtgg tccatccgac agtctggctg aacacatcat     960
acgatctatg gagcaaaaat ctatcttccc tgttctttaa tgaaggacgt cattttcatt    1020
agtatgatct aggaatgttg caacttgcaa ggaggcgttt cttctttga atttaactaa    1080 ctcgttgagt ggccctgttt ctcggacgta aggcctttgc tgctccacac atgtccattc    1140
gaattttacc gtgtttagca agggcgaaaa gtttgcatct tgatgattta gcttgactat    1200
gcgattgctt tcctggaccc gtgcag                                         1226
```

<210> SEQ ID NO 68
<211> LENGTH: 5770
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pGEP471 mRNA array vector construct

<400> SEQUENCE: 68

```
ctgacgcgcc ctgtagcggc acgtcacctg catcaggaat tcaggagaag aactcgagag      60
ggaattgcag atcatgaggc agatggctat ttttgtgtca catatgcgca aaagagagg     120 ctatatttgt gtccctaggt tcttcgttgt attgcagttt ccatatcaat ctgacttggt     180
cgcatgagaa attgatggtt aaataatttg aatctctcat gtagtatcaa ctattagata     240
ttattttcac caaatatatt tccatcggag aagaagaggc tacagaggaa gcagaagaga     300
```

```
ggggtgggag aattttttaca cttttgtaca cccacttaaa cagcaaaatc cgtatgaaaa    360
caggcccacc aaaacaatgc cacgataaca atccgtagaa acaaaagctt catttaacag    420
cggcgcaaca aagcacgctt atccatggta gttgtagtcc gtatgcgatc caaagatcac    480
gattcacgcg tgacggacgg acgacgcgtg ccacaccaca actaacgcca tccatggtag    540
ttgtagtccg tatgcgatcc aaagatcacg attcacgcgt gacggacgga cgacgcgcgc    600
cacaccacaa ctaacagcgt gagccagcgt ccaaactccg gatggcaacg gggacgaaac    660
ccgtcgggta gtcactgccc aaacccgtcc ccgcaacctt catcccaaac ccgtccccgt    720
ttccggtcgc gggtttcagt tttctaccag accccgtcccc atcgggtttt tcatccccgt    780
cgggaaatcc gaacccgcca gcatttcagc accaagccaa agttgcagca gcaacatgaa    840
taaaaaacaa cccgtttcaa caccaagata aacaaaaca ttataattta gacaacattt    900
cacacgtata acaataacat atagttctca catataacaa caccatttca cacataaaac    960
aacaccattt gggataaaaa tatgggctat atcaggccat ttttatgggc catattgagt   1020
tttcgtgggt ttcacaggta ccggatttgt agaatgctga accgggtttg aaccgtaaaa   1080
tccgcgggta ttgaatttga cccaatcccg tcgtcccctg gtggggtaaa aacaccatct   1140
tgagtccaaa cggccaccaa ccaaactccg acggcaacaa acaaacggcg ttgctttgct   1200
cctcggtatc tccgtgaccg ctcaatctcc cggctgtttc cccggaattg cgtggactct   1260
ctcatccaca cgcaaaccgc ctctccctcc tctctcgtcc tatccgcccc ggtgccgtag   1320
cctcacggga ctcttcttcc tcccttgcta taaaatcccc gcccctcct gtctcctctc    1380
cacacatcca aactctcaat cgcaccgaga aaaatctcct agcgatcgaa gcgaagcctc   1440
tcccgatcct ctcaaggtac gcccgtttcc cgtcgatcct cctccttccg ttcgtgttct   1500
gtagccgatc gattcgattc ccttacaccc gttcgtgttc tctcgtggat cgatcgattg   1560
tttgttgcta gaaggaactc gtagatctgg cgtttatgaa ctgtgattcg ggttagtcca   1620
gatcgattca ggtcggtcgt cgttgagcct ctcggctatg tctggattat cgtgtagatc   1680
tgctggttca gttgattatg ttcttctagg agtaatttcg ttgggtcagc gcgatttctg   1740
cttaatctat gctgcttatt gcgcctgtac ctatctacta agctatgtgc acctgtaatt   1800
ttgctagatt attcgttcat cctcgtagtt ggtttgtcac agtaatccgt atgggttctg   1860
acgatgttat tgttggtcat acctaggctt ctccagattt tatttttgtta aaattggata   1920
gatctgctac tgatagttga tgatggaatt tggtgctgaa tctatgctat ttattgcgcc   1980
tatacctgat ctatcgggct atgtacggct gtagtttact ggattattcg ttcatcctcg   2040
gtagttggtt catcgtttgg gttctgacga taatattgtt gattatgcgt aggcttctgc   2100
agattgttgt taaaattgga tacatcggtt actgatggtt tgatgatagat ttgtgctgaa   2160
cctatctgtt tattgctcct ataccctgatc tatagggcta tgtatgcctg taatttacca   2220
gattattcgt tcatcctcgt agttggttca tctctataat tcgtatgggt tcttatgatg   2280
ttatcgttga ttatgcctag tcttatacag attattgtgt caagattgaa tatacctgct   2340
actgatcggt gataatttgg ttagtagttt gcaatctgct aggaacacgt taccactgta   2400
atctgtaaac atggtttgcc agagtagttt gttctactac tcttgatatg gttgctgatt   2460
ttagtcgcct ccttttggat catgtattga tgtccttgca gatttccgtg tacttacccc   2520
ggcttttgtg tacttcgtgt taacagctct agaggatcct ctcaacacaa catatacaaa   2580
acaaacgaat ctcaagcaat caagcattct acttctattg cagcaattta aatcatttct   2640
tttaaagcaa aagcaatttt ctgaaaattt tcaccatttta cgaacgatag ggcgcgatcc   2700
```

```
cgccaccatg gtgagcaagg gcgaggaggt catcaaagag ttcatgcgct tcaaggtgcg    2760
catggagggc tccatgaacg gccacgagtt cgagatcgag ggcgagggcg agggccgccc    2820
ctacgagggc acccagaccg ccaagctgaa ggtgaccaag gcggccccc tgcccttcgc    2880 ctgggacatc ctgtcccccc agttcatgta cggctccaag gcgtacgtga agcaccccgc    2940
cgacatcccc gattacaaga agctgtcctt ccccgagggc ttcaagtggg agcgcgtgat    3000
gaacttcgag gacggcggtc tggtgaccgt gacccaggac tcctccctgc aggacggcac    3060
gctgatctac aaggtgaaga tgcgcggcac caacttcccc cccgacggcc ccgtaatgca    3120
gaagaagacc atgggctggg aggcctccac cgagcgcctg taccccgcg acggcgtgct    3180 gaagggcgag atccaccagg ccctgaagct gaaggacggc ggccactacc tggtggagtt    3240
caagaccatc tacatggcca agaagcccgt gcaactgccc ggctactact acgtggacac    3300
caagctggac atcacctccc acaacgagga ctacaccatc gtggaacagt acgagcgctc    3360
cgagggccgc caccacctgt tcctgtacgg catggacgag ctgtacaagt ctagaggtac    3420
ctgataattt ctactaagtg tagatctcgt cacgattccc ctctcctgga atttctactc    3480 ttgtagatt tgtggtcaca cttgccagcc agaatttcta ctcttgtaga tgtctatgtc    3540
gatgaccagc agattaattt ctactaagtg tagatcgaat ttccccgatc gttcaaacat    3600
ttggcaataa agtttcttaa gattgaatcc tgttgccggt cttgcgatga ttatcatata    3660
atttctgttg aattacgtta agcatgtaat aattaacatg taatgcatga cgttatttat    3720
gagatgggtt tttatgatta gagtcccgca attatacatt taatacgcga tagaaaacaa    3780
aatatagcgc gcaaactagg ataaattatc gcgcgcggtg tcatctatgt tactagatcg    3840
ctcgacgcgg ccgccatggc ctctagtgga tcaggtgtcg ttcggctgcg gcgagcggta    3900
tcagctcact caaaggcggt aatacggtta tccacagaat caggggataa cgcaggaaag    3960
aacatgtgag caaaaggcca gcaaaaggcc aggaaccgta aaaaggccgc gttgctggcg    4020 ttttccata ggctccgccc ccctgacgag catcacaaaa atcgacgctc aagtcagagg    4080
tggcgaaacc cgacaggact ataaagatac caggcgtttc cccctggaag ctccctcgtg    4140
cgctctcctg ttccgaccct gccgcttacc ggatacctgt ccgcctttct cccttcggga    4200
agcgtggcgc tttctcatag ctcacgctgt aggtatctca gttcggtgta ggtcgttcgc    4260
tccaagctgg gctgtgtgca cgaaccccc gttcagcccg accgctgcgc cttatccggt    4320
aactatcgtc ttgagtccaa cccggtaaga cacgacttat cgccactggc agcagccact    4380
ggtaacagga ttagcagagc gaggtatgta ggcggtgcta cagagttctt gaagtggtgg    4440
cctaactacg gctacactag aaggacagta tttggtatct gcgctctgct gaagccagtt    4500
accttcggaa aaagagttgg tagctcttga tccggcaaac aaaccaccgc tggtagcggt    4560 ggttttttg tttgcaagca gcagattacg cgcagaaaaa aaggatctca agaagatcct    4620
ttgatctttt ctacggggtc tgacgctcag tggaacgaaa actcacgtta agggattttg    4680
gtcatgagat tatcaaaaag gatcttcacc tagatccttt taaattaaaa atgaagtttt    4740
aaatcaatct aaagtatata tgagtaaact tggtctgaca gttaccaatg cttaatcagt    4800
gaggcaccta tctcagcgat ctgtctattt cgttcatcca tagttgcctg actccccgtc    4860
gtgtagataa ctacgatacg ggagggctta ccatctggcc ccagtgctgc aatgataccg    4920
cgagacccac gctcaccggc tccagattta tcagcaataa accagccagc cggaagggcc    4980
gagcgcagaa gtggtcctgc aactttatcc gcctccatcc agtctattaa ttgttgccgg    5040
```

```
gaagctagag taagtagttc gccagttaat agtttgcgca acgttgttgc cattgctaca      5100
ggcatcgtgg tgtcacgctc gtcgtttggt atggcttcat tcagctccgg ttcccaacga      5160
tcaaggcgag ttacatgatc ccccatgttg tgcaaaaaag cggttagctc cttcggtcct      5220
ccgatcgttg tcagaagtaa gttggccgca gtgttatcac tcatggttat ggcagcactg      5280
cataattctc ttactgtcat gccatccgta agatgctttt ctgtgactgg tgagtactca      5340
accaagtcat tctgagaata gtgtatgcgg cgaccgagtt gctcttgccc ggcgtcaata      5400
cgggataata ccgcgccaca tagcagaact ttaaaagtgc tcatcattgg aaaacgttct      5460
tcggggcgaa aactctcaag gatcttaccg ctgttgagat ccagttcgat gtaacccact      5520
cgtgcaccca actgatcttc agcatctttt actttcacca gcgtttctgg gtgagcaaaa      5580
acaggaaggc aaaatgccgc aaaaaaggga ataaggcga cacggaaatg ttgaatactc       5640
atactcttcc ttttcaata ttattgaagc atttatcagg gttattgtct catgagcgga      5700
tacatatttg aatgtattta gaaaaataaa caaatagggg ttccgcgcac atttccccga      5760
aaagtgccac                                                              5770

<210> SEQ ID NO 69
<211> LENGTH: 5770
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pGEP472 mRNA array vector construct

<400> SEQUENCE: 69
ctgacgcgcc ctgtagcggc acgtcacctg catcaggaat tcaggagaag aactcgagag        60
ggaattgcag atcatgaggc agatggctat ttttgtgtca catatgcgca aaaagagagg       120
ctatatttgt gtccctaggt tcttcgttgt attgcagttt ccatatcaat ctgacttggt       180
cgcatgagaa attgatggtt aaataatttg aatctctcat gtagtatcaa ctattagata       240
ttattttcac caaatatatt tccatcggag aagaagaggc tacagaggaa gcagaagaga       300
ggggtgggag aatttttaca cttttgtaca cccacttaaa cagcaaaatc cgtatgaaaa       360
caggcccacc aaaacaatgc cacgataaca atccgtagaa acaaaagctt catttaacag       420
cggcgcaaca aagcacgctt atccatggta gttgtagtcc gtatgcgatc caaagatcac       480
gattcacgcg tgacggacgg acgacgcgtg ccacaccaca actaacggca tccatggtag       540
ttgtagtccg tatgcgatcc aaagatcacg attcacgcgt gacggacgga cgacgcgcgc       600
cacaccacaa ctaacagcgt gagccagcgt ccaaactccg gatggcaacg gggacgaaac       660
ccgtcgggta gtcactgccc aaacccgtcc ccgcaaccttc atcccaaac ccgtcccccgt     720 ttccggtcgc gggtttcagt tttctaccag accgtccc atcgggtttt tcatccccgt        780
cgggaaatcc gaaccccgcca gcatttcagc accaagccaa agttgcagca gcaacatgaa      840
taaaaaacaa cccgtttcaa caccaagata aaacaaaaca ttataattta gacaacattt      900
cacacgtata acaataacat atagttctca catataacaa caccatttca cataaaaac       960 aacaccattt gggataaaaa tatgggctat atcaggccat ttttatgggc catattgagt      1020
tttcgtgggt ttcacaggta ccggatttgt agaatgctga accgggtttg aaccgtaaaa     1080
tccgcgggta ttgaatttga cccaatcccg tcgtccctg gtggggtaaa acaccatct        1140 tgagtccaaa cggccaccaa ccaaactccg acggcaacaa acaaacggcg ttgctttgct     1200
```

```
cctcggtatc tccgtgaccg ctcaatctcc cggctgtttc cccggaattg cgtggactct    1260
ctcatccaca cgcaaaccgc ctctccctcc tctctcgtcc tatccgcccc ggtgccgtag    1320
cctcacggga ctcttcttcc tcccttgcta taaaatcccc gcccctcct gtctcctctc     1380 cacacatcca aactctcaat cgcaccgaga aaaatctcct agcgatcgaa gcgaagcctc    1440
tcccgatcct ctcaaggtac gcccgtttcc cgtcgatcct cctccttccg ttcgtgttct    1500
gtagccgatc gattcgattc ccttacaccc gttcgtgttc tctcgtggat cgatcgattg    1560
tttgttgcta gaaggaactc gtagatctgg cgtttatgaa ctgtgattcg ggttagtcca    1620
gatcgattca ggtcggtcgt cgttgagcct ctcggctatg tctggattat cgtgtagatc    1680
tgctggttca gttgattatg ttcttctagg agtaatttcg ttgggtcagc gcgatttctg    1740
cttaatctat gctgcttatt gcgcctgtac ctatctacta agctatgtgc acctgtaatt    1800
ttgctagatt attcgttcat cctcgtagtt ggtttgtcac agtaatccgt atgggttctg    1860
acgatgttat tgttggtcat acctaggctt ctccagattt tattttgtta aaattggata    1920
gatctgctac tgatagttga tgatggaatt tggtgctgaa tctatgctat ttattgcgcc    1980
tatacctgat ctatcgggct atgtacggct gtagtttact ggattattcg ttcatcctcg    2040
gtagttggtt catcgtttgg gttctgacga taatattgtt gattatgcgt aggcttctgc    2100
agattgttgt taaaattgga tacatcggtt actgatggtt gatgatagat ttgtgctgaa    2160
cctatctgtt tattgctcct atacctgatc tatagggcta tgtatgcctg taatttacca    2220
gattattcgt tcatcctcgt agttggttca tctctataat tcgtatgggt tcttatgatg    2280
ttatcgttga ttatgcctag tcttatacag attattgtgt caagattgaa ataccctgct    2340
actgatcggt gataatttgg ttagtagttt gcaatctgct aggaacacgt taccactgta    2400
atctgtaaac atggtttgcc agagtagttt gttctactac tcttgatatg gttgctgatt    2460
ttagtcgcct cctttggat catgtattga tgtccttgca gatttccgtg tacttacccc     2520
ggcttttgtg tacttcgtgt taacagctct agaggatcct ctcaacacaa catatacaaa    2580
acaaacgaat ctcaagcaat caagcattct acttctattg cagcaattta aatcatttct    2640
tttaaagcaa aagcaatttt ctgaaaattt tcaccattta cgaacgatag ggcgcgatcc    2700
cgccaccatg gtgagcaagg gcgaggaggt catcaaagag ttcatgcgct tcaaggtgcg    2760
catggagggc tccatgaacg gccacgagtt cgagatcgag ggcgagggcg agggccgccc    2820
ctacgagggc acccagaccg ccaagctgaa ggtgaccaag ggcggccccc tgcccttcgc    2880
ctgggacatc ctgtcccccc agttcatgta cggctccaag gcgtacgtga agcaccccgc    2940
cgacatcccc gattacaaga agctgtcctt ccccgagggc ttcaagtggg agcgcgtgat    3000
gaacttcgag gacggcggtc tggtgaccgt gacccaggac tcctccctgc aggacggcac    3060
gctgatctac aaggtgaaga tgcgcggcac caacttcccc ccgacggcc ccgtaatgca     3120 gaagaagacc atgggctggg aggcctccac cgagcgcctg taccccgcg acggcgtgct     3180 gaagggcgag atccaccagg ccctgaagct gaaggacggc ggccactacc tggtggagtt    3240
caagaccatc tacatggcca agaagcccgt gcaactgccc ggctactact acgtggacac    3300
caagctggac atcacctccc acaacgagga ctacaccatc gtggaacagt acgagcgctc    3360
cgagggccgc caccacctgt tcctgtacgg catggacgag ctgtacaagt ctagaggtac    3420
ctgataattt ctactaagtg tagatgtcta tgtcgatgac cagcagataa tttctactct    3480
tgtagatctc gtcacgattc ccctctcctg gaatttctac tcttgtagat tgtgtggtca    3540
cacttgccag ccagtaattt ctactaagtg tagatcgaat ttccccgatc gttcaaacat    3600
```

-continued

```
ttggcaataa agtttcttaa gattgaatcc tgttgccggt cttgcgatga ttatcatata    3660
atttctgttg aattacgtta agcatgtaat aattaacatg taatgcatga cgttatttat    3720
gagatgggtt tttatgatta gagtcccgca attatacatt taatacgcga tagaaaacaa    3780
aatatagcgc gcaaactagg ataaattatc gcgcgcggtg tcatctatgt tactagatcg    3840
ctcgacgcgg ccgccatggc ctctagtgga tcaggtgtcg ttcggctgcg gcgagcggta    3900
tcagctcact caaaggcggt aatacggtta ccacagaat caggggataa cgcaggaaag     3960
aacatgtgag caaaaggcca gcaaaaggcc aggaaccgta aaaaggccgc gttgctggcg    4020 ttttttccata ggctccgccc ccctgacgag catcacaaaa atcgacgctc aagtcagagg    4080
tggcgaaacc cgacaggact ataaagatac caggcgtttc ccctggaag ctccctcgtg     4140 cgctctcctg ttccgaccct gccgcttacc ggatacctgt ccgcctttct cccttcggga    4200
agcgtggcgc tttctcatag ctcacgctgt aggtatctca gttcggtgta ggtcgttcgc    4260
tccaagctgg gctgtgtgca cgaacccccc gttcagcccg accgctgcgc cttatccggt    4320
aactatcgtc ttgagtccaa cccggtaaga cacgacttat cgccactggc agcagccact    4380
ggtaacagga ttagcagagc gaggtatgta ggcggtgcta cagagttctt gaagtggtgg    4440
cctaactacg gctacactag aaggacagta tttggtatct gcgctctgct gaagccagtt    4500
accttcggaa aaagagttgg tagctcttga tccggcaaac aaaccaccgc tggtagcggt    4560
ggtttttttg tttgcaagca gcagattacg cgcagaaaaa aaggatctca agaagatcct    4620
ttgatctttt ctacggggtc tgacgctcag tggaacgaaa actcacgtta agggattttg    4680
gtcatgagat tatcaaaaag gatcttcacc tagatccttt taaattaaaa atgaagtttt    4740
aaatcaatct aaagtatata tgagtaaact tggtctgaca gttaccaatg cttaatcagt    4800
gaggcaccta tctcagcgat ctgtctattt cgttcatcca tagttgcctg actccccgtc    4860
gtgtagataa ctacgatacg ggagggctta ccatctggcc ccagtgctgc aatgataccg    4920
cgagacccac gctcaccggc tccagattta tcagcaataa accagccagc cggaagggcc    4980
gagcgcagaa gtggtcctgc aactttatcc gcctccatcc agtctattaa ttgttgccgg    5040
gaagctagag taagtagttc gccagttaat agtttgcgca acgttgttgc cattgctaca    5100
ggcatcgtgg tgtcacgctc gtcgtttggt atggcttcat tcagctccgg ttcccaacga    5160
tcaaggcgag ttacatgatc ccccatgttg tgcaaaaaag cggttagctc cttcggtcct    5220
ccgatcgttg tcagaagtaa gttggccgca gtgttatcac tcatggttat ggcagcactg    5280
cataattctc ttactgtcat gccatccgta agatgctttt ctgtgactgg tgagtactca    5340
accaagtcat tctgagaata gtgtatgcgg cgaccgagtt gctcttgccc ggcgtcaata    5400
cgggataata ccgcgccaca tagcagaact ttaaaagtgc tcatcattgg aaaacgttct    5460
tcggggcgaa aactctcaag gatcttaccg ctgttgagat ccagttcgat gtaacccact    5520
cgtgcaccca actgatcttc agcatctttt actttcacca gcgtttctgg gtgagcaaaa    5580
acaggaaggc aaaatgccgc aaaaaaggga ataagggcga cacggaaatg ttgaatactc    5640
atactcttcc ttttcaata ttattgaagc atttatcagg gttattgtct catgagcgga     5700
tacatatttg aatgtattta gaaaaataaa caaatagggg ttccgcgcac atttccccga    5760
aaagtgccac                                                           5770
```

<210> SEQ ID NO 70
<211> LENGTH: 3938
<212> TYPE: DNA

<213> ORGANISM: Artificial Sequence
<220> FEATURE:
<223> OTHER INFORMATION: Description of Artificial Sequence: Synthetic
     polynucleotide
<220> FEATURE:
<223> OTHER INFORMATION: pGEP473 ribozyme array vector construct

<400> SEQUENCE: 70

```
ctgacgcgcc ctgtagcggc ctgcagtgca gcgtgacccg gtcgtgcccc tctctagaga      60
taatgagcat tgcatgtcta agttataaaa aattaccaca tattttttt gtcacacttg      120
tttgaagtgc agtttatcta tctttataca tatatttaaa ctttactcta cgaataatat     180
aatctatagt actacaataa tatcagtgtt ttagagaatc atataaatga acagttagac     240
atggtctaaa ggacaattga gtattttgac aacaggactc tacagtttta tcttttagt     300
gtgcatgtgt tctccttttt ttttgcaaat agcttcacct atataatact tcatccattt     360
tattagtaca tccatttagg gtttagggtt aatggttttt atagactaat tttttagta     420
catctatttt attctatttt agcctctaaa ttaagaaaac taaaactcta ttttagtttt     480
tttatttaat aatttagata taaatagaa taaaataaag tgactaaaaa ttaaacaaat     540
acccttttaag aaattaaaaa aactaaggaa acatttttct tgtttcgagt agataatgcc     600
agcctgttaa acgccgtcga tcgacgagtc taacggacac caaccagcga accagcagcg     660
tcgcgtcggg ccaagcgaag cagacggcac ggcatctctg tcgctgcctc tggacccctc     720
tcgagagttc cgctccaccg ttggacttgc tccgctgtcg gcatccagaa attgcgtggc     780
ggagcggcag acgtgagccg gcacggcagg cggcctcctc ctcctctcac ggcaccggca     840
gctacgggg attcctttcc caccgctcct tcgctttccc ttcctcgccc gccgtaataa     900
atagacaccc cctccacacc ctctttcccc aacctcgtgt tgttcggagc gcacacacac     960
acaaccagat ctcccccaaa tccacccgtc ggcacctccg cttcaaggta cgccgctcgt    1020
cctccccccc cccccctctc taccttctct agatcggcgt tccggtccat ggttagggcc    1080
cggtagttct acttctgttc atgtttgtgt tagatccgtg tttgtgttag atccgtgctg    1140
ctagcgttcg tacacggatg cgacctgtac gtcagacacg ttctgattgc taacttgcca    1200
gtgtttctct ttggggaatc ctgggatggc tctagccgtt ccgcagacgg gatcgatcta    1260
ggataggtat acatgttgat gtgggtttta ctgatgcata tacatgatgg catatgcagc    1320
atctattcat atgctctaac cttgagtacc tatctattat aataaacaag tatgttttat    1380
aattattttg atcttgatat acttggatga tggcatatgc agcagctata tgtggatttt    1440
tttagccctg ccttcatacg ctatttattt gcttggtact gtttcttttg tcgatgctca    1500
ccctgttgtt tggtgttact tctgcaggga tccaaattac tgatgagtcc gtgaggacga    1560
aacgagtaag ctcgtctaat ttctactaag tgtagatctc gtcacgattc ccctctcctg    1620
gaatttctac tcttgtagat tgtgtggtca cacttgccag ccagaatttc tactcttgta    1680
gatgtctatg tcgatgacca gcagatgcg tcagtcctac tctgcacctc ctcgtggtgt    1740
cgcctgggaa ccctctttca aagaaagag gagccaagca gagaggcgat cgttcaaaca    1800
tttggcaata agtttcttaa agattgaatc ctgttgccgg tcttgcgatg attatcatat    1860
aatttctgtt gaattacgtt aagcatgtaa taattaacat gtaatgcatg acgttattta    1920
tgagatgggt ttttatgatt agagtcccgc aattatacat ttaatacgcg atagaaaaca    1980
aaatatagcg cgcaaactag gataaattat cgcgcgcggt gtcatctatg ttactagatc    2040
gatcgtcgtt cggctgcggc gagcggtatc agctcactca aaggcggtaa tacggttatc    2100
```

```
cacagaatca ggggataacg caggaaagaa catgtgagca aaaggccagc aaaaggccag    2160
gaaccgtaaa aaggccgcgt tgctggcgtt tttccatagg ctccgccccc ctgacgagca    2220
tcacaaaaat cgacgctcaa gtcagaggtg gcgaaacccg acaggactat aaagatacca    2280
ggcgtttccc cctggaagct ccctcgtgcg ctctcctgtt ccgaccctgc cgcttaccgg    2340
atacctgtcc gcctttctcc cttcgggaag cgtggcgctt tctcatagct cacgctgtag    2400
gtatctcagt tcggtgtagg tcgttcgctc caagctgggc tgtgtgcacg aaccccccgt    2460
tcagcccgac cgctgcgcct tatccggtaa ctatcgtctt gagtccaacc cggtaagaca    2520
cgacttatcg ccactggcag cagccactgg taacaggatt agcagagcga ggtatgtagg    2580
cggtgctaca gagttcttga agtggtggcc taactacggc tacactagaa gaacagtatt    2640
tggtatctgc gctctgctga agccagttac cttcggaaaa agagttggta gctcttgatc    2700
cggcaaacaa accaccgctg gtagcggtgg tttttttgtt tgcaagcagc agattacgcg    2760
cagaaaaaaa ggatctcaag aagatccttt gatcttttct acggggtctg acgctcagtg    2820
gaacgaaaac tcacgttaag ggattttggt catgagatta tcaaaaagga tcttcaccta    2880
gatcctttta aattaaaaat gaagttttaa atcaatctaa agtatatatg agtaaacttg    2940
gtctgacagt taccaatgct taatcagtga ggcacctatc tcagcgatct gtctatttcg    3000
ttcatccata gttgcctgac tccccgtcgt gtagataact acgatacggg agggcttacc    3060
atctggcccc agtgctgcaa tgataccgcg agacccacgc tcaccggctc cagatttatc    3120
agcaataaac cagccagccg gaagggccga gcgcagaagt ggtcctgcaa ctttatccgc    3180
ctccatccag tctattaatt gttgccggga agctagagta agtagttcgc cagttaatag    3240
tttgcgcaac gttgttgcca ttgctacagg catcgtggtg tcacgctcgt cgtttggtat    3300
ggcttcattc agctccggtt cccaacgatc aaggcgagtt acatgatccc ccatgttgtg    3360
caaaaaagcg gttagctcct tcggtcctcc gatcgttgtc agaagtaagt tggccgcagt    3420
gttatcactc atggttatgg cagcactgca taattctctt actgtcatgc catccgtaag    3480
atgcttttct gtgactggtg agtactcaac caagtcattc tgagaatagt gtatgcggcg    3540
accgagttgc tcttgcccgg cgtcaatacg ggataatacc gcgccacata gcagaacttt    3600
aaaagtgctc atcattggaa aacgttcttc ggggcgaaaa ctctcaagga tcttaccgct    3660
gttgagatcc agttcgatgt aacccactcg tgcacccaac tgatcttcag catcttttac    3720
tttcaccagc gtttctgggt gagcaaaaac aggaaggcaa atgccgcaa aaaagggaat    3780 aagggcgaca cggaaatgtt gaatactcat actcttcctt tttcaatatt attgaagcat    3840
ttatcagggt tattgtctca tgagcggata catatttgaa tgtatttaga aaaataaaca    3900
aataggggtt ccgcgcacat ttccccgaaa agtgccac                           3938
```

<210> SEQ ID NO 71
<211> LENGTH: 3938
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pGEP474 ribozyme array vector construct

<400> SEQUENCE: 71

```
ctgacgcgcc ctgtagcggc gcattaagcg cggcgggtgt ggtggttacg cgcagcgtga    60
taatgagcat tgcatgtcta agttataaaa aattaccaca tattttttt gtcacacttg     120
```

```
tttgaagtgc agtttatcta tctttataca tatatttaaa ctttactcta cgaataatat    180
aatctatagt actacaataa tatcagtgtt ttagagaatc atataaatga acagttagac    240
atggtctaaa ggacaattga gtattttgac aacaggactc tacagtttta tcttttttagt  300 gtgcatgtgt tctccttttt ttttgcaaat agcttcacct atataatact tcatccattt    360
tattagtaca tccatttagg gtttagggtt aatggttttt atagactaat ttttttagta    420
catctatttt attctatttt agcctctaaa ttaagaaaac taaaactcta ttttagtttt    480
tttatttaat aatttagata taaaatagaa taaaataaag tgactaaaaa ttaaacaaat    540 acccttttaag aaattaaaaa aactaaggaa acattttttct tgtttcgagt agataatgcc   600
agcctgttaa acgccgtcga tcgacgagtc taacggacac caaccagcga accagcagcg    660
tcgcgtcggg ccaagcgaag cagacggcac ggcatctctg tcgctgcctc tggacccctc    720
tcgagagttc cgctccaccg ttggacttgc tccgctgtcg gcatccagaa attgcgtggc    780
ggagcggcag acgtgagccg gcacggcagg cggcctcctc ctcctctcac ggcaccggca    840
gctacggggg attcctttcc caccgctcct tcgctttccc ttcctcgccc gccgtaataa    900
atagacaccc cctccacacc ctcttttccc aacctcgtgt tgttcggagc gcacacacac    960
acaaccagat ctcccccaaa tccacccgtc ggcacctccg cttcaaggta cgccgctcgt   1020
cctccccccc cccccctctc taccttctct agatcggcgt tccggtccat ggttagggcc    1080
cggtagttct acttctgttc atgtttgtgt tagatccgtg tttgtgttag atccgtgctg    1140
ctagcgttcg tacacggatg cgacctgtac gtcagacacg ttctgattgc taacttgcca   1200
gtgtttctct ttggggaatc ctgggatggc tctagccgtt ccgcagacgg gatcgatcta   1260
ggataggtat acatgttgat gtgggtttta ctgatgcata tacatgatgg catatgcagc   1320
atctattcat atgctctaac cttgagtacc tatctattat aataaacaag tatgttttat    1380
aattattttg atcttgatat acttggatga tggcatatgc agcagctata tgtggatttt    1440
tttagccctg ccttcatacg ctattttattt gcttggtact gtttcttttg tcgatgctca    1500
ccctgttgtt tggtgttact tctgcaggga tccaaattac tgatgagtcc gtgaggacga    1560
aacgagtaag ctcgtctaat ttctactaag tgtagatgtc tatgtcgatg accagcagat    1620
aatttctact cttgtagatc tcgtcacgat tcccctctcc tggaatttct actcttgtag    1680
attgtgtggt cacacttgcc agccagggcg tcagtcctac tctgcacctc ctcgtggtgt    1740
cgcctgggaa ccctctttca caagaaagag gagccaagca gagaggcgat cgttcaaaca    1800
tttggcaata aagtttctta agattgaatc ctgttgccgg tcttgcgatg attatcatat    1860
aatttctgtt gaattacgtt aagcatgtaa taattaacat gtaatgcatg acgttattta    1920
tgagatgggt tttatgatt agagtcccgc aattatacat ttaatacgcg atagaaaaca     1980
aaatatagcg cgcaaactag gataaattat cgcgcgcggt gtcatctatg ttactagatc   2040
gatcgtcgtt cggctgcggc gagcggtatc agctcactca aaggcggtaa tacggttatc   2100
cacagaatca ggggataacg caggaaagaa catgtgagca aaaggccagc aaaaggccag   2160
gaaccgtaaa aaggccgcgt tgctggcgtt tttccatagg ctccgccccc ctgacgagca   2220
tcacaaaaat cgacgctcaa gtcagaggtg gcgaaacccg acaggactat aaagatacca   2280
ggcgtttccc cctggaagct ccctcgtgcg ctctcctgtt ccgaccctgc cgcttaccgg   2340
atacctgtcc gcctttctcc cttcgggaag cgtggcgctt tctcatagct cacgctgtag   2400
gtatctcagt tcggtgtagg tcgttcgctc caagctgggc tgtgtgcacg aaccccccgt   2460
tcagcccgac cgctgcgcct tatccggtaa ctatcgtctt gagtccaacc cggtaagaca   2520
```

```
cgacttatcg ccactggcag cagccactgg taacaggatt agcagagcga ggtatgtagg    2580
cggtgctaca gagttcttga agtggtggcc taactacggc tacactagaa gaacagtatt    2640
tggtatctgc gctctgctga agccagttac cttcggaaaa agagttggta gctcttgatc    2700
cggcaaacaa accaccgctg gtagcggtgg ttttttttgtt tgcaagcagc agattacgcg    2760
cagaaaaaaa ggatctcaag aagatccttt gatcttttct acggggtctg acgctcagtg    2820
gaacgaaaac tcacgttaag ggattttggt catgagatta tcaaaaagga tcttcaccta    2880
gatcctttta aattaaaaat gaagttttaa atcaatctaa agtatatatg agtaaacttg    2940
gtctgacagt taccaatgct taatcagtga ggcacctatc tcagcgatct gtctatttcg    3000
ttcatccata gttgcctgac tccccgtcgt gtagataact acgatacggg agggcttacc    3060
atctggcccc agtgctgcaa tgataccgcg agacccacgc tcaccggctc cagatttatc    3120
agcaataaac cagccagccg gaagggccga gcgcagaagt ggtcctgcaa ctttatccgc    3180
ctccatccag tctattaatt gttgccggga agctagagta agtagttcgc cagttaatag    3240
tttgcgcaac gttgttgcca ttgctacagg catcgtggtg tcacgctcgt cgtttggtat    3300
ggcttcattc agctccggtt cccaacgatc aaggcgagtt acatgatccc ccatgttgtg    3360
caaaaaagcg gttagctcct tcggtcctcc gatcgttgtc agaagtaagt tggccgcagt    3420
gttatcactc atggttatgg cagcactgca taattctctt actgtcatgc catccgtaag    3480
atgcttttct gtgactggtg agtactcaac caagtcattc tgagaatagt gtatgcggcg    3540
accgagttgc tcttgcccgg cgtcaatacg ggataatacc gcgccacata gcagaacttt    3600
aaaagtgctc atcattggaa aacgttcttc ggggcgaaaa ctctcaagga tcttaccgct    3660
gttgagatcc agttcgatgt aacccactcg tgcacccaac tgatcttcag catcttttac    3720
tttcaccagc gtttctgggt gagcaaaaac aggaaggcaa aatgccgcaa aaaagggaat    3780
aagggcgaca cggaaatgtt gaatactcat actcttcctt tttcaatatt attgaagcat    3840
ttatcagggt tattgtctca tgagcggata catatttgaa tgtatttaga aaaataaaca    3900
aataggggtt ccgcgcacat ttccccgaaa agtgccac                             3938
```

<210> SEQ ID NO 72
<211> LENGTH: 3759
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: codon optimized LbCpf1

<400> SEQUENCE: 72

```
atggcgccga agaagaagcg caaggtgtcc aagctcgaga agttcacgaa ctgctactcc      60
ctctccaaga ccctccgctt caaggccatc cccgtgggca agaccagga gaacatcgac     120 aacaagcgcc tcctggtcga ggacgagaag agggcggagg actacaaggg cgtgaagaag     180
ctcctggacc gctactacct ctccttcatc aacgacgtcc tgcacagcat caagctcaag     240
aacctgaaca actacatctc cctgttccgc aagaagacga ggaccgagaa ggagaacaag     300
gagctcgaga acctggagat caacctccgc aaggagatcg ccaaggcgtt caagggcaac     360
gagggctaca gagcctgtt caagaaggac atcatcgaga cgatcctccc ggagttcctg     420
gacgacaaga acgagatcgc cctcgtgaac tccttcaacg gcttcaccac ggcgttcacc     480
ggcttcttcg acaaccgcga gaacatgttc agcgaggagg ccaagtccac gagcatcgcg     540
```

```
ttccgctgca tcaacgagaa cctgaccagg tacatctcca acatggacat cttcgagaag    600
gtcgacgcca tcttcgacaa gcacgagtg caggagatca aggagaagat cctcaacagc     660
gactacgacg tcgaggactt cttcgagggc gagttcttca acttcgtcct gacgcaggag    720
ggcatcgacg tgtacaacgc catcatcggt ggcttcgtga ccgagtccgg cgagaagatc    780
aagggcctca acgagtacat caacctgtac aaccagaaga ccaagcagaa gctcccgaag    840
ttcaagcccc tctacaagca ggtcctgtcc gaccgcgagt ccctgagctt ctacggcgag    900
ggctacacga gcgacgagga ggtcctcgag gtgttcagga cacccctgaa caagaacagc    960
gagatcttct ccagcatcaa gaagctcgag aagctgttca gaacttcga cgagtactcc    1020
agcgccggca tcttcgtcaa gaacggcccg gcgatctcca cgatcagcaa ggatatcttc    1080
ggcgagtgga acgtgatcag ggacaagtgg aacgccgagt acgacgacat ccacctcaag    1140
aagaaggcgg tggtcaccga gaagtacgag gacgaccgca ggaagtcctt caagaagatc    1200
ggctccttca gcctcgagca gctgcaggag tacgccgacg cggacctctc cgtggtcgag    1260
aagctgaagg agatcatcat ccagaaggtc gacgagatct acaaggtgta cggctccagc    1320
gagaagctgt cgacgccga cttcgtcctc gagaagtccc tgaagaagaa cgacgccgtg    1380
gtcgcgatca tgaaggacct cctggactcc gtgaagagct cgagaactca catcaaggcg    1440
ttcttcggcg agggcaagga gacgaaccgc gacgagtcct ctacggcga cttcgtcctc    1500
gcctacgaca tcctcctgaa ggtggaccac atctacgacg cgatcaggaa ctacgtgacc    1560
cagaagccgt acagcaagga caagttcaag ctgtacttcc agaaccccca gttcatgggc    1620
ggctgggaca aggacaagga gacggactac cgcgccacca tcctccgcta cggcagcaag    1680
tactacctgg ccatcatgga caagaagtac gcgaagtgcc tccagaagat cgacaaggac    1740
gacgtcaacg gcaactacga gaagatcaac tacaagctcc tgccgggccc caacaagatg    1800
ctgccgaagg tgttcttctc caagaagtgg atggcctact acaacccag cgaggacatc    1860
cagaagatct acaagaacgg cacgttcaag aagggcgaca tgttcaacct caacgactgc    1920
cacaagctga tcgacttctt caaggactcc atcagccgct acccgaagtg gtccaacgcc    1980
tacgacttca acttcagcga gacagagaag tacaaggaca tcgcgggctt ctacaggag     2040
gtcgaggagc agggctacaa ggtgtccttc gagtccgcca gcaagaagga ggtcgacaag    2100
ctcgtggagg agggcaagct gtacatgttc cagatctaca acaaggactt ctccgacaag    2160
agccacggca cgcccaacct ccacaccatg tacttcaagc tcctgttcga cgagaacaac    2220
cacggccaga tccgcctctc cggcggcgcc gagctgttca tgaggagggc gagcctcaag    2280
aaggaggagc tggtggtcca ccccgctaac agcccaatcg gaacaagaa cccggacaac    2340
cccaagaaga ccacgaccct ctcctacgac gtgtacaagg acaagcgctt cagcgaggac    2400
cagtacgagc tgcacatccc gatcgccatc aacaagtgcc caagaacat cttcaagatc    2460
aacaccgagg tcagggtgct cctgaagcac gacgacaacc cctacgtgat cggcatcgac    2520
cgcggcgaga ggaacctcct gtacatcgtg gtcgtggacg caagggcaa catcgtggag    2580
cagtactccc tgaacgagat catcaacaac ttcaacggca tccgcatcaa gacggactac    2640
cacagcctcc tggacaagaa ggagaaggag cgcttcgagg ccaggcagaa ctggacctcc    2700
atcgagaaca tcaaggagct caaggcgggc tacatcagcc aggtcgtgca agatctgc     2760
gagctggtcg agaagtacga cgccgtgatc gcgctcgagg acctgaactc cggcttcaag    2820
aacagcaggg tcaaggtgga gaagcaggtc taccagaagt cgagaagat gctcatcgac    2880
```

| | |
|---|---|
| aagctgaact acatggtgga caagaagtcc aacccgtgcg ctacgggcgg cgcgctcaag | 2940 |
| ggctaccaga tcaccaacaa gttcgagagc ttcaagtcca tgagcaccca gaacggcttc | 3000 |
| atcttctaca tcccggcctg gctgacgtcc aagatcgacc ccagcaccgg cttcgtcaac | 3060 |
| ctcctgaaga cgaagtacac ctccatcgcg gacagcaaga agttcatctc cagcttcgac | 3120 |
| cgcatcatgt atgtgccgga ggaggacctc ttcgagttcg ccctggacta caagaacttc | 3180 |
| tccaggacgg acgcggatta catcaagaag tggaagctct acagctacgg caaccgcatc | 3240 |
| aggatcttcc gcaaccccaa gaagaacaac gtcttcgact gggaggaggt gtgcctcacc | 3300 |
| tccgcctaca aggagctgtt caacaagtac ggcatcaact accagcaggg cgacatcagg | 3360 |
| gcgctcctgt gcgagcagag cgacaaggcc ttctactcca gcttcatggc gctcatgtcc | 3420 |
| ctcatgctgc agatgcgcaa cagcatcacg ggcaggaccg acgtcgactt cctgatctcc | 3480 |
| ccggtgaaga cagcgacgg catcttctac gacagccgca actacgaggc ccaggagaac | 3540 |
| gcgatcctgc caaagaacgc ggacgccaac ggcgcctaca acatcgcgag gaaggtgctg | 3600 |
| tgggccatcg ccagttcaa gaaggcggag gacgagaagc tcgacaaggt caagatcgcc | 3660 |
| atctccaaca aggagtggct ggagtacgcg cagacctcgg tgaagcacaa gaggcccgct | 3720 |
| gccaccaaga aggcgggcca ggccaagaag aagaagtga | 3759 |

<210> SEQ ID NO 73
<211> LENGTH: 3759
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: codon optimimized LbCpf1

<400> SEQUENCE: 73

| | |
|---|---|
| atggccccca agaagaagcg caaggtgagc aagctggaga agtttacaaa ctgctactcc | 60 |
| ctgtctaaga ctctgcgctt caaggccatc cctgtgggca gacccagga gaacatcgac | 120 |
| aataagcggc tgctggtgga ggacgagaag agagccgagg attataaggg cgtgaagaag | 180 |
| ctgctggatc gctactatct gtcttttatc aacgacgtgc tgcacagcat caagctgaag | 240 |
| aatctgaaca attacatcag cctgttccgg aagaaaacca gaaccgagaa ggagaataag | 300 |
| gagctggaga acctggagat caatctgcgc aaggagatcg ccaaggcctt caagggcaac | 360 |
| gagggctaca gtccctgtt taagaaggat atcatcgaga caatcctgcc agagttcctg | 420 |
| gacgataaga cgagatcgc cctggtgaac agcttcaatg ctttaccac agccttcacc | 480 |
| ggcttctttg ataacagaga gaatatgttt tccgaggagg ccaagagcac atccatcgcc | 540 |
| ttcaggtgta tcaacgagaa tctgacccgc tacatctcta atatggacat cttcgagaag | 600 |
| gtggacgcca tctttgataa gcacgaggtg caggagatca aggagaagat cctgaacagc | 660 |
| gactatgatg tggaggattt ctttgagggc gagttctta actttgtgct gacacaggag | 720 |
| ggcatcgacg tgtataacgc catcatcggc ggcttcgtga ccgagagcgg cgagaagatc | 780 |
| aagggcctga acgagtacat caacctgtat aatcagaaaa ccaagcagaa gctgcctaag | 840 |
| tttaagccac tgtataagca ggtgctgagc gatcgggagt ctctgagctt ctacggcgag | 900 |
| ggctatacat ccgatgagga ggtgctggag gtgtttagaa acaccctgaa caagaacagc | 960 |
| gagatcttca gctccatcaa gaagctggag aagctgttca gaatttttga cgagtactct | 1020 |
| agcgccggca tctttgtgaa gaacggcccc gccatcagca caatctccaa ggatatcttc | 1080 |

```
ggcgagtgga acgtgatccg ggacaagtgg aatgccgagt atgacgatat ccacctgaag   1140
aagaaggccg tggtgaccga gaagtacgag gacgatcgga gaaagtcctt caagaagatc   1200
ggctcctttt ctctggagca gctgcaggag tacgccgacg ccgatctgtc tgtggtggag   1260
aagctgaagg agatcatcat ccagaaggtg gatgagatct acaaggtgta tggctcctct   1320
gagaagctgt tcgacgccga ttttgtgctg gagaagagcc tgaagaagaa cgacgccgtg   1380
gtggccatca tgaaggacct gctggattct gtgaagagct cgagaatta catcaaggcc   1440 ttctttggcg agggcaagga gacaaacagg gacgagtcct ctatggcga ttttgtgctg   1500 gcctacgaca tcctgctgaa ggtggaccac atctacgatg ccatccgcaa ttatgtgacc   1560
cagaagccct actctaagga taagttcaag ctgtattttc agaaccctca gttcatgggc   1620
ggctgggaca aggataagga gacagactat cgggccacca tcctgagata cggctccaag   1680
tactatctgg ccatcatgga taagaagtac gccaagtgcc tgcagaagat cgacaaggac   1740
gatgtgaacg gcaattacga gaagatcaac tataagctgc tgcccggccc taataagatg   1800
ctgccaaagg tgttcttttc taagaagtgg atggcctact ataaccccag cgaggacatc   1860
cagaagatct acaagaatgg cacattcaag aagggcgata tgtttaacct gaatgactgt   1920
cacaagctga tcgacttctt taaggatagc atctcccggt atccaaagtg gtccaatgcc   1980
tacgatttca cttttctga cagagaag tataaggaca tcgccggctt ttacagagag   2040
gtggaggagc agggctataa ggtgagcttc gagtctgcca gcaagaagga ggtggataag   2100
ctggtggagg agggcaagct gtatatgttc cagatctata caaggacttt tccgataag   2160 tctcacggca cacccaatct gcacaccatg tacttcaagc tgctgtttga cgagaacaat   2220
cacggacaga tcaggctgag cggaggagca gagctgttca tgaggcgcgc ctccctgaag   2280
aaggaggagc tggtggtgca cccagccaac tcccctatcg ccaacaagaa tccagataat   2340
cccaagaaaa ccacaacccc tgtcctacgac gtgtataagg ataagaggtt ttctgaggac   2400
cagtacgagc tgcacatccc aatcgccatc aataagtgcc caagaacat cttcaagatc   2460 aatacagagg tgcgcgtgct gctgaagcac gacgataacc cctatgtgat cggcatcgat   2520
aggggcgagc gcaatctgct gtatatcgtg tggtggacg gcaagggcaa catcgtggag   2580
cagtattccc tgaacgagat catcaacaac ttcaacggca tcaggatcaa gacagattac   2640
cactctctgc tggacaagaa ggagaaggag aggttcgagg cccgccagaa ctggaccttcc   2700 atcgagaata tcaaggagct gaaggccggc tatatctctc aggtggtgca caagatctgc   2760
gagctggtgg agaagtacga tgccgtgatc gccctggagg acctgaactc tggctttaag   2820
aatagccgcg tgaaggtgga gaagcaggtg tatcagaagt cgagaagat gctgatcgat   2880 aagctgaact acatggtgga caagaagtct aatccttgtg caacaggcgg cgccctgaag   2940
ggctatcaga tcaccaataa gttcgagagc tttaagtcca tgtctaccca gaacggcttc   3000
atcttttaca tccctgcctg gctgacatcc aagatcgatc catctaccgg ctttgtgaac   3060
ctgctgaaaa ccaagtatac cagcatcgcc gattccaaga agttcatcag ctcctttgac   3120
aggatcatgt atgtgcccga ggaggatctg ttcgagtttg ccctggacta taagaacttc   3180
tctcgcacag acgccgatta catcaagaag tggaagctgt actcctacgg caaccggatc   3240
agaatcttcc ggaatcctaa gaagaacaac gtgttcgact gggaggaggt gtgcctgacc   3300
agcgcctata aggagctgtt caacaagtac ggcatcaatt atcagcaggg cgatatcaga   3360
gccctgctgt gcgagcagtc cgacaaggcc ttctactcta gctttatggc cctgatgagc   3420
ctgatgctgc agatgcggaa cagcatcaca ggccgcaccg acgtggattt tctgatcagc   3480
```

| | | | |
|---|---|---|---|
| cctgtgaaga | actccgacgg | catcttctac gatagccgga | actatgaggc ccaggagaat | 3540 |
| gccatcctgc | caaagaacgc | cgacgccaat ggcgcctata | acatcgccag aaaggtgctg | 3600 |
| tgggccatcg | ccagttcaa | gaaggccgag gacgagaagc | tggataaggt gaagatcgcc | 3660 |
| atctctaaca | aggagtggct | ggagtacgcc cagaccagcg | tgaagcacaa aaggccggcg | 3720 |
| gccacgaaaa | aggccggcca | ggcaaaaaag aaaaagtga | | 3759 |

<210> SEQ ID NO 74
<211> LENGTH: 3783
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: codon optimized LbCpf1

<400> SEQUENCE: 74

| | | | |
|---|---|---|---|
| atggctccta | agaagaagcg | gaaggttggt attcacgggg | tgcctgcggc ttcaaagctc | 60 |
| gagaaattca | ccaactgtta | ttcgttgagc aaaacactgc | ggtttaaagc gattccagtc | 120 |
| ggcaagactc | aagagaatat | agacaataag cggctgttgg | tggaagatga aaagcgcgcg | 180 |
| gaagactaca | aggggtgaa | gaagttgttg acagatact | acctctcttt tatcaatgat | 240 |
| gtcttgcact | caatcaaatt | gaagaatctg aacaactaca | tctccctctt cagaaagaaa | 300 |
| acaaggacag | aaaaggagaa | taaggaactt gaaaatttgg | agatcaatct gaggaaagag | 360 |
| atcgcgaaag | cctttaaagg | caacgaagga tacaaaagtc | tgttcaagaa ggatataatt | 420 |
| gagacaattt | tgccagagtt | cctcgatgac aaggacgaga | ttgcgctggt caattcgttc | 480 |
| aacggattca | acagcatt | cacaggcttc tttgataatc | gggaaaatat gttctctgag | 540 |
| gaggcaaagt | ccacttctat | tgcgttcagg tgtatcaatg | agaatctcac taggtacatt | 600 |
| tccaacatgg | atatctttga | aaggttgac gcaatttttg | acaagcacga agttcaggag | 660 |
| attaaggaga | agatcctcaa | ttccgattat gacgttgagg | acttcttcga aggtgagttt | 720 |
| tttaatttcg | tgctcactca | agagggtatc gacgtgtata | atgcgatcat cggtgggttc | 780 |
| gtgactgagt | ccggtgaaaa | gattaaggga ttgaacgagt | atatcaacct ttacaaccaa | 840 |
| aagacgaaac | agaagctgcc | aaagttcaag cctctttaca | aacaggttct ttcagaccgc | 900 |
| gagtcactct | cgttctatgg | ggagggctac acttcggatg | aggaagtcct ggaggtgttc | 960 |
| aggaatactc | tcaataagaa | ttcggagatt ttctcttcta | taaaaaaact ggaaaagttg | 1020 |
| tttaagaatt | ttgacgaata | ctctagcgcc ggcatatttg | tgaaaacgg cccggccata | 1080 |
| tcaacgataa | gtaaagatat | cttcggcgaa tggaacgtga | tcagagacaa atggaacgcg | 1140 |
| gagtatgacg | atattcacct | gaagaagaag gctgtcgtaa | cggagaagta cgaggatgat | 1200 |
| cgcaggaaaa | gcttcaaaaa | gatcggaagt ttcagcctgg | aacagttgca ggagtatgct | 1260 |
| gacgccgatc | ttagcgtcgt | cgagaagttg aaggagataa | tcatccaaaa ggtcgacgag | 1320 |
| atatataaag | tctatggatc | aagtgaaaaa ctgttcgacg | ccgacttcgt tttggagaag | 1380 |
| tccctgaaga | gaacgacgc | tgttgttgcc attatgaagg | atctgctcga cagcgtgaag | 1440 |
| agtttcgaga | actatattaa | ggcttttttc gggagggga | aggagactaa cagagatgag | 1500 |
| tccttctacg | agacttcgt | cctcgcgtac gatatactcc | ttaaggtaga ccacatctac | 1560 |
| gacgcaatca | gaaattacgt | gacacaaaag ccgtacagca | aggacaagtt caaactctac | 1620 |
| ttccagaacc | cccagttcat | gggcggctgg gacaaggaca | aggaaacgga ttacagggct | 1680 |

```
acgatcttga ggtatggttc aaaatactac ttggcgatta tggacaagaa gtacgccaag    1740
tgtctccaga agattgacaa agacgatgtc aatggcaatt atgagaagat caactacaag    1800
ctgcttccgg gtccgaacaa gatgctccca aaggttttct tcagcaagaa atggatggcc    1860
tactataacc caagcgagga catccagaag atttataaga acggtacgtt caagaagggc    1920
gacatgttca atcttaacga ctgtcacaag ctgatcgact tcttcaaaga ctcaattagc    1980
cggtacccaa agtggtctaa cgcctatgac ttcaactttt cggaaaccga agtacaag      2040 gatatagccg gattttatag agaggtggaa gagcagggct acaaggtgtc attcgagtcc    2100
gccagcaaga aggaagtgga caagctcgtg aagagggta agctctacat gttccagatt     2160
tataataaag actttagcga taagagccac gggacaccta atctccacac aatgtatttc    2220
aagctgctct tcgacgagaa taaccacggc caaatcaggt tgtcaggagg ggctgaactc    2280
ttcatgcggc gcgctagcct taagaaggag gagcttgtag tccaccctgc gaatagtcca    2340
attgcgaata agaacccgga caatcctaaa aagactacaa cattgagcta cgacgtgtac    2400
aaggataaga ggttttccga ggatcagtac gagctccaca tcccgattgc gatcaacaag    2460
tgcccaaaga atattttcaa gataaacaca gaggtgcgtg tactcctgaa gcatgacgac    2520
aatccttacg tcattgggat tgatcggggc gagaggaacc tcctctatat tgtggtggtg    2580
gacgggaagg ggaacatagt cgaacagtac tcccttaacg aaataattaa caatttcaac    2640
ggcatccgta tcaagaccga ctaccattcg ttgctggaca agaaggagaa ggagagattt    2700
gaggcgcggc aaaattggac aagtatcgag aacatcaagg aactcaaagc aggttatatc    2760
tctcaagttg tgcataagat atgcgagctg gttgagaagt atgacgcagt gatcgctctt    2820
gaggacctca actcgggctt taagaattct agagttaaag tggagaagca ggtctatcaa    2880
aagttcgaga agatgcttat agataagctc aactacatgg tcgataagaa atcgaaccca    2940
tgtgccaccg gcggcgcact caaaggttac caaataacaa acaaattcga gtccttcaaa    3000
tcgatgagta ctcagaatgg gttcatattt tataaaccgg cgtggcttac gtctaagatc    3060
gacccgtcaa ctggttttgt caacctgttg aagacgaaat acacgtccat gccgattcg    3120 aaaaagttca tatctagttt tgatcgtatt atgtacgtcc cagaggaaga tctttccgag    3180
tttgctctcg actacaaaaa cttttcgcgg accgatgcgg attacattaa aaaatggaaa    3240
ctctattcgt acggcaacag aatcaggatt tttcgcaacc ctaagaagaa taacgtcttt    3300
gattgggagg aagtttgctt gactagcgcg tacaaggagc tctttaataa gtatggcatt    3360
aactaccaac agggtgatat cagagcactg ctttgcgaac aatctgacaa ggctttctac    3420
tcatccttca tggctttgat gagcctgatg ctccagatga gaaattcaat tacaggcaga    3480
accgacgtgg atttcttgat ctccccggtt aaaaattctg atggcatctt ttacgatagc    3540
aggaactatg aagcgcaaga gaatgcgatt ctgccaaaaa atgcagacgc caacggtgcc    3600
tataacatcg ccaggaaagt cctgtgggcg atcggccagt tcaaaaaggc cgaagacgaa    3660
aaattggaca aggtcaaaat cgctatcagc aacaaagagt ggctggagta tgctcagaca    3720
tccgtaaagc ataagcgtcc tgctgccacc aaaaaggccg acaggctaa gaaaagaag     3780 tga                                                                 3783
```

<210> SEQ ID NO 75
<211> LENGTH: 3759
<212> TYPE: DNA
<213> ORGANISM: Artificial Sequence
<220> FEATURE:

<223> OTHER INFORMATION: Description of Artificial Sequence: Synthetic
polynucleotide
<220> FEATURE:
<223> OTHER INFORMATION: codon optimized LbCpf1

<400> SEQUENCE: 75

| | | | | | |
|---|---|---|---|---|---|
| atggccccga | agaagaagag | gaaggtcagc | aagctcgaga | agttcaccaa | ctgctacagc | 60 |
| ctgagcaaga | ccctgaggtt | caaggctatc | ccggtgggca | agacccaaga | gaacatcgac | 120 |
| aacaagaggc | tgctggtcga | ggacgagaag | cgcgctgagg | attacaaggg | cgtgaagaag | 180 |
| ctgctggaca | ggtactacct | gagcttcatc | aacgacgtgc | tgcacagcat | caagctgaag | 240 |
| aacctgaaca | actacatcag | cctgttccgc | aagaaaacca | ggaccgagaa | agagaacaaa | 300 |
| gagcttgaga | acctcgagat | caacctgagg | aaagagatcg | ccaaggcctt | caagggcaac | 360 |
| gagggctaca | gagcctgtt | caagaaggac | atcatcgaga | ctatcctgcc | agagttcctg | 420 |
| gacgacaagg | acgagatcgc | cctggtgaac | agcttcaacg | gcttcacgac | cgccttcacc | 480 |
| ggtttcttcg | acaaccgcga | gaatatgttc | agcgaggaag | ccaagagcac | tctctatcgcc | 540 |
| ttccgctgca | tcaacgagaa | cctgacgcgc | tacatctcca | acatggatat | cttcgagaag | 600 |
| gtggacgcca | tcttcgataa | gcacgaggtg | caagagatca | aagaaaagat | cctgaacagc | 660 |
| gactacgacg | tcgaggactt | cttcgagggc | gagttcttca | acttcgtgct | cacccaagag | 720 |
| ggcatcgatg | tgtacaacgc | catcatcggc | ggcttcgtga | ctgagagcgg | cgagaagatc | 780 |
| aagggcctga | acgagtacat | caacctctac | aatcaaaaga | ccaagcagaa | gctgccgaag | 840 |
| ttcaagccgc | tgtacaagca | ggttctgagc | gaccgcgaga | gcctgtctttt | ctacggcgag | 900 |
| ggttacacca | gcgacgaaga | ggtgttggag | gtttttccgca | cacccctgaa | caagaacagc | 960 |
| gagatcttca | gctccatcaa | gaagctggaa | aagctgtttta | agaacttcga | cgagtacagc | 1020 |
| agcgccggca | tcttcgtgaa | gaacggccca | gctatcagca | ccatcagcaa | ggacatcttc | 1080 |
| ggcgagtgga | acgtgatcag | ggacaagtgg | aacgccgagt | acgacgacat | ccacctgaag | 1140 |
| aaaaaggccg | tggtgaccga | gaagtacgag | gacgacaggc | gcaagagctt | caagaagatc | 1200 |
| ggctccttca | gcctcgagca | gctgcaagag | tacgctgacg | ctgacctgag | cgtggtcgag | 1260 |
| aagctcaaag | agatcatcat | ccagaaggtc | gacgagatct | acaaggtgta | cggcagcagc | 1320 |
| gagaagcttt | tcgacgccga | cttcgtcctt | gagaagtccc | tcaagaaaaa | cgacgccgtg | 1380 |
| gtggccatca | tgaaggacct | gctggactcc | gtgaagtcct | tcgagaacta | cattaaggct | 1440 |
| ttcttcggtg | agggcaaaga | gactaacagg | gacgagagct | tctacgggga | tttcgtgctg | 1500 |
| gcctacgaca | tcctgctcaa | ggtggaccac | atctacgacg | ccatccgcaa | ctacgtgacc | 1560 |
| cagaagccgt | actccaagga | caagtttaag | ctgtacttcc | agaatccgca | gttcatgggc | 1620 |
| ggctgggaca | agacaaaga | aaccgactac | agggccacca | tcctgaggta | cggctccaag | 1680 |
| tactacctcg | ccatcatgga | caagaaatac | gccaagtgcc | tgcagaagat | cgataaggac | 1740 |
| gacgtgaacg | gcaactacga | gaagattaac | tacaagctgc | tgccagggcc | gaacaagatg | 1800 |
| ctcccgaagg | tgttctttag | caagaaatgg | atggcctact | acaacccgag | cgaggatatc | 1860 |
| cagaaaatct | acaagaacgg | caccttcaag | aaaggcgaca | tgttcaacct | gaacgactgc | 1920 |
| cacaagctga | tcgatttctt | caaggacagc | atctctcgct | acccgaagtg | gtccaacgcc | 1980 |
| tacgatttca | acttcagcga | gactgaaaag | tacaaggata | tcgccggctt | ctaccgcgag | 2040 |
| gtcgaggaac | agggttacaa | ggtgagcttc | gagagcgcca | gcaagaaaga | ggtggacaag | 2100 |
| ctggtcgaag | agggcaagct | gtacatgttc | cagatctata | acaaggactt | ctccgacaag | 2160 |

| | | |
|---|---|---|
| agccacggca ccccaaacct gcacaccatg tacttcaagt tgctgttcga cgagaacaac | 2220 |
| cacggccaga tcaggctttc tggcggcgct gagcttttca tgagaagggc cagcctgaaa | 2280 |
| aaagaggaac tggtcgttca cccggcgaac agcccaatcg ccaacaagaa cccggacaac | 2340 |
| ccgaaaaaga ccaccacgct gagctacgac gtgtacaagg acaaaaggtt ctccgaggac | 2400 |
| cagtacgagc tgcacatccc gatcgccatc aacaagtgcc gaagaacat cttcaagatc | 2460 |
| aacaccgagg tgagggtgct gctgaagcac gacgacaacc catacgtgat cggcatcgat | 2520 |
| aggggcgagc gcaacctgct ctacatcgtg gtggttgacg gcaagggcaa tatcgtcgag | 2580 |
| cagtacagcc ttaacgagat cattaacaac ttcaatggca tcaggatcaa gaccgactac | 2640 |
| cacagcctgc tcgacaagaa agaaaaagag cgcttcgagg ccaggcagaa ctggaccagc | 2700 |
| atcgagaata tcaaagagct gaaggccggc tacattagcc aggtggtgca agatctgc | 2760 |
| gagctggtgg aaaagtacga cgcggtgatc gctctcgagg acctgaactc cgggttcaag | 2820 |
| aactcccgcg tgaaggttga gaagcaggtc taccaaaagt tcgagaagat gctgatcgac | 2880 |
| aagctcaact acatggtgga caaaaagagc aaccctgcg ccacaggcgg cgctcttaag | 2940 |
| ggctaccaga tcacgaacaa gttcgagtcc ttcaagagca tgagcaccca gaatggcttc | 3000 |
| atcttctaca tcccggcctg gctgaccagc aagatcgatc catctaccgg cttcgtcaac | 3060 |
| ctcctcaaga ccaagtacac cagcattgcc gacagcaaga gttcatctc cagcttcgac | 3120 |
| aggatcatgt acgtgccgga gaggacctg ttcgagttcg cgctcgatta caagaacttc | 3180 |
| agcaggaccg acgcggacta tattaagaag tggaagctct acagctacgg caacaggatc | 3240 |
| cgcatcttca gaaacccgaa gaaaacaac gtgttcgact gggaagaagt gtgcctgacc | 3300 |
| agcgcctaca agaactgtt caacaagtac ggcatcaact accagcaggg cgacatcagg | 3360 |
| gctctgctgt gcgagcagtc tgacaaggcg ttctacagct ccttcatggc cctgatgagc | 3420 |
| ctgatgctgc agatgaggaa cagcatcacc ggcaggacgg acgtcgactt cctgatcagc | 3480 |
| ccagtgaaga attccgacgg catttttctac gactctagga actacgaggc tcaagagaac | 3540 |
| gccatcctgc gaagaacgc cgatgctaac ggcgcgtaca acattgcccg caaggtgctg | 3600 |
| tgggctatcg ccagtttaa gaaggccgag gacgaaaac tggacaaggt gaagatcgcc | 3660 |
| attagcaaca agagtggct cgagtacgcc cagaccagcg tgaagcacaa aaggccagcc | 3720 |
| gccactaaga aggctggcca ggccaaaaag aagaagtga | 3759 |

<210> SEQ ID NO 76
<211> LENGTH: 3759
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: codon optimized LbCpf1

<400> SEQUENCE: 76

| | | |
|---|---|---|
| atggcaccca agaagaagcg caaagtgtca agctcgaga agttcacaaa ctgttactcc | 60 |
| ttatctaaaa ccctgcgctt taaagcaatt cctgtcggta aacccaagaa gaacatcgac | 120 |
| aacaagagac tgctcgttga agatgaaaag agagccgagg attacaaggg cgtgaagaag | 180 |
| ctcctcgatc gctattacct gtccttcatt aacgatgtgc tccatagcat caagctcaag | 240 |
| aaccttaaca actatatctc attattccgc aagaaaacta gaacgagaa ggaaaacaaa | 300 |
| gagctagaga accttgaaat caacctcaga aaggaaatag ccaaggcgtt taaggggaat | 360 |

```
gaaggctaca agagtttgtt taagaaagac atcattgaga caatattacc tgaattcctt    420
gatgacaagg acgagatcgc tctagtgaac agctttaatg gtttcaccac tgcgttcacg    480
ggcttcttcg ataacaggga gaatatgttt tctgaggaag ccaagtcaac ttccatcgcg    540
tttcgctgca tcaacgagaa tctgacccgt tacataagta acatggacat attcgagaaa    600
gttgacgcta tcttcgacaa gcatgaggtg caagaaatca aggaaaagat ccttaactct    660
gactacgacg tcgaggactt cttcgaggga gaattcttca atttcgttct gacccaggag    720
ggcatcgacg tgtacaatgc tattatcggt ggattcgtga cagagtccgg agaaaagatt    780
aagggcctta acgagtatat caacctttat aaccaaaaga cgaagcaaaa actccccaag    840
tttaaacctc tttacaaaca agttctatcg gatagagaaa gcctttcgtt ttacggggaa    900
ggatacacct ctgatgaaga ggttctcgag gtgttccgta caccctgaac aagaactcc     960 gagatattct cgtcgattaa gaaactcgaa aagttgttca aaacttcga cgaatactca    1020 tctgccggaa ttttgtgaa gaacggcccg gctatttcga ccatttccaa ggatatcttc    1080
ggagagtgga acgttatacg agataagtgg aacgcagagt atgatgatat ccaccttaag    1140
aagaaggcgg tcgtgacgga aaaatacgag gacgatcgta ggaagtcttt caagaagatt    1200
ggtagcttca gcctcgagca actgcaggaa tacgcggatg ctgatctgag cgtggtcgag    1260
aagcttaagg agataatcat ccaaaaggtt gacgagatat acaaggttta tggttcgtca    1320
gagaagttgt tcgacgccga cttcgtcctt gagaagtccc tgaagaagaa tgacgcggtc    1380
gtggcaatca tgaaagacct cctcgactcc gtcaaatcct ttgagaatta tattaaggcg    1440
ttcttcggcg aagggaagga gacaaatagg gatgagagtt tttacggcga ttttgtgcta    1500
gcttacgaca ttctgctgaa agttgaccac atatacgacg ctatccgaaa ctatgtcacc    1560
caaaagcctt actcaaaaga caagttcaag ctgtactttc aaaacccgca gttcatggga    1620
ggatgggata aggacaagga aactgactac agagccacga ttctccgcta cgggtccaaa    1680
tactacctcg ccattatgga taagaagtac gcgaagtgcc tgcagaagat cgacaaagac    1740
gacgtgaacg gaaactacga gaagatcaac tataagctgc tgccagggcc caacaagatg    1800
ctgccgaagg ttttcttag caagaagtgg atggcctact acaacccgtc cgaggacata    1860
cagaaaatct acaaaaatgg aactttcaaa aagggcgaca tgttcaactt gaacgattgc    1920
cacaagttaa ttgacttctt caaggacagc atttcgcgat atccgaagtg gtctaatgcc    1980
tatgacttca attttctga aaccgagaag tataaggata tcgcgggttt ttatagggaa    2040
gttgaggagc aaggttacaa agtatcattt gaatctgcct ccaaaaagga ggtcgacaaa    2100
ctggttgaag agggcaaact atacatgttt cagatctaca caaagatttt ctcggataag    2160
tcgcacggga cgccgaactt acacaccatg tacttcaaac tgctgtttga tgagaacaat    2220
cacggccaga tccgtctaag cggcggtgcc gagcttttca tgcgccgcgc gagcttgaaa    2280
aaggaggagt tggtggtcca ccctgctaat tcaccgattg ctaacaagaa ccccgataac    2340
cccaaaaaga ccaccactct tagctacgat gtctataagg ataagcgctt cagcgaagat    2400
cagtatgagt tgcatattcc gattgccatc aacaaatgcc ccaaaaatat tttcaagatc    2460
aacactgagg tccgcgtgct gctcaaacat gacgataacc cgtacgtaat cggcatcgat    2520
agaggcgaac ggaacttact atacatcgtg gtagtagacg ggaagggaaa tatcgtcgaa    2580
cagtacagtc tgaatgaaat tattaacaat ttcaacggga tccggatcaa gacagactac    2640
cactccttgc tcgacaagaa ggaaaaggag cggttcgagg cccgacaaaa ctggactcg     2700 attgagaaca ttaaggagct caaagcgggg tacatctccc aagtggtgca taaaatctgt    2760
```

```
gaactggttg agaaatatga tgcagtgata gctctcgagg acctcaattc tggcttcaag    2820
aactccaggg ttaaggtaga aaaacaggtc taccaaaaat ttgaaagat gcttattgat    2880 aagttaaatt acatggtcga caaaaagtcg aatccgtgtg ccacaggagg cgccctcaag    2940
ggataccaga ttacgaataa gtttgaatcc ttcaagtcta tgagcacaca gaacggcttc    3000
attttctata tccccgcgtg gctcacttct aaaatcgacc catccaccgg cttcgtgaat    3060
ttgcttaaga caaagtacac tagcatcgcg gactcgaaga aattcattc gtcgtttgac    3120 cggattatgt atgtgccaga agaagatcta ttcgagtttg ctctcgacta taaaaacttc    3180
tcccgcaccg acgccgacta cataaagaag tggaagttgt atagctacgg gaaccgcatc    3240
aggatattcc ggaatccgaa gaagaacaat gtgtttgatt gggaggaggt ctgcctcacg    3300
tcagcttaca aggagctgtt caacaaatac ggtataaact atcagcaggg cgacatccgg    3360
gcccttctgt gtgaacagag cgacaaagca ttttactctt cttttatggc tctgatgtcc    3420
ttgatgctgc aaatgcgcaa ttcaatcacg gggagaaccg atgtagactt tctgattagt    3480
ccggtcaaga atagcgacgg catattctac gattcaagga attacgaagc ccaggagaac    3540
gcgatcctgc caaaaaatgc agatgcgaat ggtgcataca atattgcaag gaaagtgtta    3600
tgggccatcg ccagttcaa gaaagctgag gacgagaagc ttgacaaggt caagatcgca    3660
atctcaaaca aggaatggct tgaatatgcg cagactagtg tgaaacataa gcgcccagct    3720
gccaccaaga aggccggcca ggccaagaaa aagaagtga                          3759
```

```
<210> SEQ ID NO 77
<211> LENGTH: 24
<212> TYPE: DNA
<213> ORGANISM: Triticum aestivum

<400> SEQUENCE: 77
cagcatggca tggagggtga cgat                                          24

<210> SEQ ID NO 78
<211> LENGTH: 24
<212> TYPE: DNA
<213> ORGANISM: Triticum aestivum

<400> SEQUENCE: 78
agcatggcat ggagggtgac gatg                                          24

<210> SEQ ID NO 79
<211> LENGTH: 24
<212> TYPE: DNA
<213> ORGANISM: Triticum aestivum

<400> SEQUENCE: 79
cgcaggagga ggaggagctc atcg                                          24

<210> SEQ ID NO 80
<211> LENGTH: 24
<212> TYPE: DNA
<213> ORGANISM: Triticum aestivum

<400> SEQUENCE: 80
cgcaccgctt cagccctgca gcac                                          24

<210> SEQ ID NO 81
<211> LENGTH: 24
<212> TYPE: DNA
```

<213> ORGANISM: Triticum aestivum

<400> SEQUENCE: 81
gcaccgcttc agccctgcag cacg                                              24

<210> SEQ ID NO 82
<211> LENGTH: 21
<212> TYPE: DNA
<213> ORGANISM: Beta vulgaris

<400> SEQUENCE: 82
gctgctaaac aatcaacatt t                                                 21

<210> SEQ ID NO 83
<211> LENGTH: 21
<212> TYPE: DNA
<213> ORGANISM: Beta vulgaris

<400> SEQUENCE: 83
taaacaatca acatttaggt a                                                 21

<210> SEQ ID NO 84
<211> LENGTH: 20
<212> TYPE: DNA
<213> ORGANISM: Beta vulgaris

<400> SEQUENCE: 84
atttaggtat ggttgtccaa                                                   20

<210> SEQ ID NO 85
<211> LENGTH: 20
<212> TYPE: DNA
<213> ORGANISM: Beta vulgaris

<400> SEQUENCE: 85
tttagcagca ttatcttaac                                                   20

<210> SEQ ID NO 86
<211> LENGTH: 20
<212> TYPE: DNA
<213> ORGANISM: Beta vulgaris

<400> SEQUENCE: 86
tatagaacct atcttcccat                                                   20

<210> SEQ ID NO 87
<211> LENGTH: 86
<212> TYPE: RNA
<213> ORGANISM: Helianthus annuus

<400> SEQUENCE: 87 gcgggggggcg ucaguccuac ucugcaccuc cucguggugu cgccugggaa cccucuuucg      60
caagaaagag gagccaagca gagagg                                            86

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: crALS1 protospacer

```
<400> SEQUENCE: 88
caccctaatt gtagccaact cttg                                           24

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: crALS2 protospacer

<400> SEQUENCE: 89
gcagcattat cttaactggg agat                                           24

<210> SEQ ID NO 90
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: crALS3 protospacer

<400> SEQUENCE: 90
ggtatggttg tccaatggga agat                                           24

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: crALS4 protospacer

<400> SEQUENCE: 91
caaggtatgt atgtgcccgg ttag                                           24

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: crALS5 protospacer

<400> SEQUENCE: 92
gaagggtttc caaggtatgt atgt                                           24

<210> SEQ ID NO 93
<211> LENGTH: 8828
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: expression plasmid

<400> SEQUENCE: 93
gattgaaaga aatatagttt aaatatttat tgataaaata acaagtcagg tattatagtc    60
```

| | |
|---|---|
| caagcaaaaa cataaattta ttgatgcaag tttaaattca gaaatatttc aataactgat | 120 |
| tatatcagct ggtacattgc cgtagatgaa agactgagtg cgatattatg tgtaatacat | 180 |
| aaattgatga tatagctagc ttagctcatc gggtcagaag aactcgtcaa gaaggcgata | 240 |
| gaaggcgatg cgctgcgaat cgggagcggc gataccgtaa agcacgagga agcggtcagc | 300 |
| ccattcgccg ccaagctctt cagcaatatc acgggtagcc aacgctatgt cctgatagcg | 360 |
| gtccgccaca cccagccggc cacagtcgat gaatccagaa aagcggccat tttccaccat | 420 |
| gatattcggc aagcaggcat cgccatgagt cacgacgaga tcctcgccgt cgggcatgcg | 480 |
| cgccttgagc ctggcgaaca gttcggctgg cgcgagcccc tgatgctctt cgtccagatc | 540 |
| atcctgatcg acaagaccgg cttccatccg agtacgtgct cgctcgatgc gatgtttcgc | 600 |
| ttggtggtcg aatgggcagg tagccggatc aagcgtatgc agccgccgca ttgcatcagc | 660 |
| catgatggat actttctcgg caggagcaag gtgagatgac aggagatcct gccccggcac | 720 |
| ttcgcccaat agcagccagt cccttcccgc ttcagtgaca acgtcgagca cagctgcgca | 780 |
| aggaacgccc gtcgtggcca gccacgatag ccgcgctgcc tcgtcctgaa gttcattcag | 840 |
| ggcaccggac aggtcggtct tgacaaaaag aaccgggcgc cctgcgctg acagccggaa | 900 |
| cacggcggca tcagagcagc cgattgtctg ttgtgcccag tcatagccga atagcctctc | 960 |
| cacccaagcg gccggagaac ctgcgtgcaa tccatcttgt tcaatccaag ctcccatttt | 1020 |
| ctgtgatttt ggatgtgttt ttgtatggat tgagagtgaa tatgagactc taattggata | 1080 |
| ccgaggggaa tttatggaac gtcagtggag cattttgac aagaaatatt tgctagctga | 1140 |
| tagtgacctt aggcgacttt tgaacgcgca ataatggttt ctgacgtatg tgcttagctc | 1200 |
| attaaactcc agaaacccgc ggctgagtgg ctccttcaac gttgcggttc tgtcagttcc | 1260 |
| aaacgtaaaa cggcttgtcc cgcgtcatcg gcggggtca ttccggactg ggggccata | 1320 |
| tcccagaact ggttgagtcg gtccaacacc tgggtgccaa tcatgtcgat ggtggggtat | 1380 |
| ggccaatttt ttttcaattc aaaaatgtag atgtccgcag cgttattata aaatgaaagt | 1440 |
| acatttgat aaaacgacaa attacgatcc gtcgtattta taggcgaaag caataaacaa | 1500 |
| attattctaa ttcggaaatc tttatttcga cgtgtctaca ttcacgtcca aatgggggct | 1560 |
| tagatgagaa acttcacgat cggctctaga ggccatggcg gccgctcgag cgatctagta | 1620 |
| acatagatga caccgcgcgc gataatttat cctagtttgc gcgctatatt ttgttttcta | 1680 |
| tcgcgtatta aatgtataat tgcgggactc taatcataaa aacccatctc ataaataacg | 1740 |
| tcatgcatta catgttaatt attacatgct aacgtaatt caacagaaat tatatgataa | 1800 |
| tcatcgcaag accggcaaca ggattcaatc ttaagaaact ttattgccaa atgtttgaac | 1860 |
| gatcggggaa attcgatcta cacttagtag aaaattacaag agttggctac aattagggtg | 1920 |
| atctacactt agtagaaatt atcaggtacc tctagacttg tacagctcgt ccatgccgta | 1980 |
| caggaacagg tggtggcggc cctcggagcg ctcgtactgt tccacgatgg tgtagtcctc | 2040 |
| gttgtgggag gtgatgtcca gcttggtgtc cacgtagtag tagccgggca gttgcacggg | 2100 |
| cttcttggcc atgtagatgg tcttgaactc caccaggtag tggccgccgt ccttcagctt | 2160 |
| cagggcctgg tggatctcgc ccttcagcac ggcgtcgcgg gggtacaggc gctcggtgga | 2220 |
| ggcctcccag cccatggtct tcttctgcat tacggggccg tcgggggga gttggtgcc | 2280 |
| gcgcatcttc accttgtaga tcagcgtgcc gtcctgcagg gaggagtcct gggtcacggt | 2340 |
| caccagaccg ccgtcctcga agttcatcac gcgctcccac ttgaagccct cggggaagga | 2400 |
| cagcttcttg taatcgggga tgtcggcggg gtgcttcacg tacgccttgg agccgtacat | 2460 |

```
gaactgggggg gacaggatgt cccaggcgaa gggcaggggg ccgcccttgg tcaccttcag    2520
cttggcggtc tgggtgccct cgtagggcg gccctcgccc tcgccctcga tctcgaactc     2580
gtggccgttc atggagccct ccatgcgcac cttgaagcgc atgaactctt tgatgacctc    2640
ctcgcccttg ctcaccatgg atccctctc caaatgaaat gaacttcctt atatagagga    2700
agggtcttgc gaaggatagt gggattgtgc gtcatcccttt acgtcagtgg agatatcaca   2760
tcaatccact tgctttgaag acgtggttgg aacgtcttct ttttccacga tgttcctcgt    2820
gggtgggggt ccatctttgg gaccactgtc ggtagaggca tcttgaacga tagcctttcc   2880
tttatcgcaa tgatggcatt tgtagaagcc atcttccttt tctactgtcc tttcgatgaa   2940
gtgacagata gctgggcaat ggaatccgag gaggtttccc gatattaccc tttgttgaaa   3000
agtctcaata gccctctggt cttctgagac tgtatctttg atattcttgg agtagacgag   3060
agtgtcgtgc tccaccatgt atcacatcaa tccacttgct ttgaagacgt ggttggaacg   3120
tcttcttttt ccacgatgtt cctcgtgggt ggggtccat ctttgggacc actgtcggta    3180
gaggcatctt gaacgatagc cttcctttta tcgcaatgat ggcatttgta gaagccatct   3240 tcctttcta ctgtcctttc gatgaagtga cagatagctg ggcaatggaa tccgaggagg    3300
tttcccgata ttacccttg ttgaaaagtc tcaatagccc tctggtcttc tgaacactag     3360
taaggcctta agggccagat cccccgggct gcaggaattc gatctggcac gacaggtttc    3420
ccgactggaa agcgggcagt gagcgcaacg caattaatgt gagttagctc actcattagg    3480
cacccccagg ctttacactt tatgcttccgg ctcgtatgtt gtgtggaatt gtgagcggat    3540
aacaatttca cacaggaaac agctatgaca tgattacgaa ttcaaaaatt acggatatga    3600
atataggcat atccgtatcc gaattatccg tttgacagct agcaacgatt gtacaattgc    3660
ttctttaaaa aaggaagaaa gaaagaaaga aagaatcaa catcagcgtt aacaaacggc    3720
cccgttacgg cccaaaccggt catatagagt aacggcgtta agcgttgaaa gactcctatc   3780
gaaatacgta accgcaaacg tgtcatagtc agatcccctc ttccttcacc gcctcaaaca    3840
caaaaataat cttctacagc ctatatatac aaccccccct tctatctctc ctttctcaca    3900
attcatcatc tttcttttctc tacccccaat tttaagaaat cctctcttct cctcttcatt    3960
ttcaaggtaa atctctctct ctctctctct ctctgttatt ccttgtttta attaggtatg    4020
tattattgct agtttgttaa tctgcttatc ttatgtatgc cttatgtgaa tatctttatc    4080
ttgttcatct catccgttta gaagctataa atttgttgat ttgactgtgt atctacacgt    4140
ggttatgttt atatctaatc agatatgaat ttcttcatat tgttgcgttt gtgtgtacca    4200
atccgaaatc gttgattttt ttcatttaat cgtgtagcta attgtacgta tacatatgga    4260
tctacgtatc aattgttcat ctgtttgtgt ttgtatgtat acagatctga aaacatcact    4320
tctctcatct gattgtgttg ttacatacat agatatagat ctgttatatc attttttta    4380 ttaattgtgt atatatatat gtgcatagat ctggattaca tgattgtgat tatttacatg    4440
attttgttat ttacgtatgt atatatgtag atctggactt tttggagttg ttgacttgat    4500
tgtatttgtg tgtgtatatg tgtgttctga tcttgatatg ttatgtatgt gcagcgaatt    4560
cggcgcgcca acaatggct tcctccatgg ctcctaagaa gaagaggaag gttagcaagc    4620
tcgagaagtt taccaactgc tacagcctct ctaagaccct caggttcaag gctatccctg   4680
tgggaaagac ccaagagaat atcgacaaca agaggctcct cgtcgaggat gagaagagag    4740
ctgaagatta caagggcgtg aagaagctcc tcgacaggta ctacctcagc ttcatcaacg    4800
```

```
atgtgctcca cagcatcaag ctcaagaacc tcaacaacta catcagcctc ttccgtaaga    4860
aaaccaggac cgagaaagag aacaaagagc ttgagaacct cgagatcaac ctccgtaaag    4920
agatcgccaa ggcttttcaag ggaaacgagg atacaagag cctcttcaag aaggatatta    4980
tcgagacaat cctgcctgag ttcctggacg ataaggatga gatcgctctc gtgaacagct    5040
tcaacggatt cactactgcc ttcaccggat tcttcgacaa cagggaaaac atgttcagcg    5100
aagaggccaa gagcacctct atcgctttca gatgcatcaa cgagaacctc acgcgttaca    5160
tcagcaacat ggacatcttc gagaaggtgg acgccatctt cgataagcac gaggtgcaag    5220
aaatcaaaga gaagatcctc aacagcgact cgacgtcga ggactttttt gaagggagt     5280 tcttcaactt cgttctcacc caagagggca tcgacgtgta caacgctatt atcggaggat    5340
tcgtgaccga gtctggggag aagattaagg gactcaacga gtacatcaac ctgtacaacc    5400
agaaaacgaa gcagaagctc ccgaagttca agccgctcta aagcaggtt ctctctgatc     5460 gtgagagcct ctcatttac ggtgagggtt acacctctga cgaggaagtg cttgaggttt     5520
tccgtaacac cctcaacaag aacagcgaga tcttctcgtc catcaagaag ttggagaaac    5580
ttttcaagaa cttcgacgag tacagcagcg ctgggatctt cgttaagaac ggacctgcta    5640
tcagcaccat cagcaaggat attttcggcg agtggaacgt gatcagggac aagtggaatg    5700
ctgagtacga tgacatccac ctcaagaaga aggctgtcgt cactgagaag tacgaggatg    5760
acaggcgtaa gtcgttcaag aagatcggct ctttcagcct cgagcagctt caagaatacg    5820
ctgatgctga tctcagcgtg gtcgagaagc tcaaagagat catcatccag aaggtcgacg    5880
agatctacaa ggtgtacggg tcctctgaga gttgttcga tgctgatttc gtcctcgaga    5940
agagtctgaa gaagaacgac gctgtcgtcg cgatcatgaa ggatttgctc gacagcgtga    6000
agtccttcga gaactatatc aaggccttct tcggagaggg caaagagact aatagggacg    6060 agtcttttcta cggggatttc gtgctcgctt acgatatcct cctcaaggtg gaccatatct    6120
acgacgccat cagaaactac gtgacccaga agccttacag caaggacaag ttcaagttgt    6180
actttcagaa cccgcagttc atgggcggat gggacaaaga caaagagaca gattacaggg    6240
ccaccatcct caggtacggg tctaagtact acctggccat catggacaag aaatacgcca    6300
agtgcctcca aaagatcgac aaggatgacg tgaacgggaa ctatgagaag atcaactaca    6360
agctccttcc gggaccgaac aagatgcttc ctaaggtgtt cttcagcaag aaatggatgg    6420
cctactacaa cccgtctgag gacatccaga aaatctacaa gaacgggacc ttcaagaaag    6480
gcgacatgtt caacctcaac gactgccaca agctcatcga tttcttcaag gacagcatct    6540
cgcgttaccc gaagtggtct aacgcttacg actttaactt cagcgagaca gaaaagtaca    6600
aggatatcgc cgggttctac cgtgaggttg aggaacaggg ttacaaggtt agcttcgaga    6660
gcgcctccaa gaaagaggtt gacaagttgg tcgaagaggg caagctctac atgttccaga    6720
tctataacaa ggacttctcc gacaagagcc acggaactcc taacctccat acgatgtact    6780
tcaagctgct tttcgacgag aacaaccacg gcagatcag actttctggt ggtgctgaac    6840
tcttcatgcg taggcctca ctcaagaaag aagagttggt tgttcacccg ccaactctc     6900 caatcgctaa caagaatcct gacaacccga aaaagaccac cacgctgtct tacgacgtct    6960
acaaggacaa aaggttcagc gaggaccagt acgagcttca tatcccgatc gctatcaaca    7020
agtgcccgaa gaacatcttc aagatcaata ccgaggtgag ggtgctgctc aagcacgatg    7080 ataacccctta cgtgatcgga atcgatcgtg gtgagagaaa cctcctctac atcgttgtgg    7140
tggacggaaa gggaaacatc gtcgagcagt acagcctgaa cgagattatc aacaatttca    7200
```

```
acggcatcag gatcaagacc gactaccact cactcctcga taagaaagaa aaagagcgtt    7260
tcgaggccag gcagaactgg acttctatcg aaaacatcaa agagttgaag gccggctaca    7320
tctctcaggt ggtgcataag atctgcgagc tggtggaaaa gtacgatgct gtgatcgctc    7380
ttgaggacct caactctggg ttcaagaaca gtagagtgaa ggttgagaag caggtctacc    7440
aaaagttcga gaagatgctc atcgacaagc tcaactacat ggtggacaaa agagcaacc     7500 cttgcgctac cggtggtgct cttaagggat accagatcac gaacaagttc gagtccttca    7560
agagcatgag cacccagaac ggcttcatct tctatatccc tgcttggctc accagcaaga    7620
tcgatccttc tactggtttc gtgaacctgc tcaagaccaa gtacacctcg atcgccgaca    7680
gcaagaagtt catctcgtct ttcgacagga tcatgtacgt gccggaagag gatctttcg     7740 agttcgctct cgactataag aacttcagca ggaccgacgc cgactacatt aagaagtgga    7800
agctctactc ctacgggaac cgtatcagga tcttccgaaa tccgaagaaa aacaacgtgt    7860
tcgactggga agaagtgtgc ctcacctctg cctacaaaga actgttcaac aagtacggca    7920
tcaactacca gcagggtgat atcagggctc ttttgtgcga gcagagcgac aaggcattct    7980
acagctcatt catggccctc atgtctctca tgctccagat gaggaactct atcaccggaa    8040
ggaccgatgt ggacttcctt atctctccgg tcaagaactc tgacgggatc ttctacgaca    8100
gccgtaacta tgaggctcaa gagaacgcta tcctgccgaa gaatgctgat gcaaacgggg    8160
cttacaacat tgcgagaaag gttctctggg ctatcgggca gtttaagaaa gcggaagatg    8220
agaagctcga caaggtgaag atcgccatct ccaacaaaga gtggcttgag tacgctcaga    8280
cctccgttaa gcacaagagg cctgctgcta ctaagaaagc tggccaggcc aaaaagaaga    8340
agtgaggcgc gccgagctcc aggcctccca gctttcgtcc gtatcatcgg tttcgacaac    8400
gttcgtcaag ttcaatgcat cagtttcatt gcccacacac cagaatccta ctaagtttga    8460
gtattatggc attggaaaag ctgttttctt ctatcatttg ttctgcttgt aatttactgt    8520
gttctttcag ttttttgtttt cggacatcaa aatgcaaatg gatggataag agttaataaa    8580
tgatatggtc cttttgttca ttctcaaatt attattatct gttgttttta ctttaatggg    8640
ttgaatttaa gtaagaaagg aactaacagt gtgatattaa ggtgcaatgt tagacatata    8700
aaacagtctt tcacctctct ttggttatgt cttgaattgg tttgtttctt cacttatctg    8760
tgtaatcaag tttactatga gtctatgatc aagtaattat gcaatcaagt taagtacagt    8820
ataggctt                                                            8828
```

<210> SEQ ID NO 94
<211> LENGTH: 8201
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: expression plasmid

<400> SEQUENCE: 94

```
ttgaaagaaa tatagtttaa atatttattg ataaaataac aagtcaggta ttatagtcca      60
agcaaaaaca taaatttatt gatgcaagtt taaattcaga aatatttcaa taactgatta     120
tatcagctgg tacattgccg tagatgaaag actgagtgcg atattatgtg taatacataa     180
attgatgata tagctagctt agctcatcgg gtcagaagaa ctcgtcaaga aggcgataga     240
aggcgatgcg ctgcgaatcg ggagcggcga taccgtaaag cacgaggaag cggtcagccc     300
```

```
attcgccgcc aagctcttca gcaatatcac gggtagccaa cgctatgtcc tgatagcggt      360
ccgccacacc cagccggcca cagtcgatga atccagaaaa gcggccattt tccaccatga      420
tattcggcaa gcaggcatcg ccatgagtca cgacgagatc ctcgccgtcg gcatgcgcg       480 ccttgagcct ggcgaacagt tcggctggcg cgagcccctg atgctcttcg tccagatcat      540
cctgatcgac aagaccggct tccatccgag tacgtgctcg ctcgatgcga tgtttcgctt      600
ggtggtcgaa tgggcaggta gccggatcaa gcgtatgcag ccgccgcatt gcatcagcca      660
tgatggatac tttctcggca ggagcaaggt gagatgacag gagatcctgc cccggcactt      720
cgcccaatag cagccagtcc cttcccgctt cagtgacaac gtcgagcaca gctgcgcaag      780
gaacgcccgt cgtggccagc cacgatagcc gcgctgcctc gtcctgaagt tcattcaggg      840
caccggacag gtcggtcttg acaaaaagaa ccgggcgccc ctgcgctgac agccggaaca      900
cggcggcatc agagcagccg attgtctgtt gtgcccagtc atagccgaat agcctctcca      960
cccaagcggc cggagaacct gcgtgcaatc catcttgttc aatccaagct cccattttct     1020
gtgattttgg atgtgttttt gtatggattg agagtgaata tgagactcta attggatacc     1080
gaggggaatt tatggaacgt cagtggagca ttttttgacaa gaaatatttg ctagctgata    1140
gtgaccttag gcgacttttg aacgcgcaat aatggtttct gacgtatgtg cttagctcat     1200
taaactccag aaacccgcgg ctgagtggct ccttcaacgt tgcggttctg tcagttccaa     1260
acgtaaaacg gcttgtcccg cgtcatcggc gggggtcatt ccggactgtg gggccatatc     1320
ccagaactgg ttgagtcggt ccaacacctg ggtgccaatc atgtcgatgg tggggtatgg     1380 ccaattttt ttcaattcaa aaatgtagat gtccgcagcg ttattataaa atgaaagtac      1440
attttgataa aacgacaaat tacgatccgt cgtatttata ggcgaaagca ataaacaaat     1500
tattctaatt cggaaatctt tatttcgacg tgtctacatt cacgtccaaa tggggcctta    1560
gatgagaaac ttcacgatcg gctctagagg ccatggcggc cgctcgagcg atctagtaac    1620
atagatgaca ccgcgcgcga taatttatcc tagtttgcgc gctatatttt gttttctatc    1680
gcgtattaaa tgtataattg cgggactcta atcataaaaa cccatctcat aaataacgtc    1740
atgcattaca tgttaattat tacatgctta acgtaattca acagaaatta tatgataatc    1800
atcgcaagac cggcaacagg attcaatctt aagaaacttt attgccaaat gtttgaacga    1860
tcgcctctct gcttggctcc tctttcttgt gaaagagggt tcccaggcga caccacgagg    1920
aggtgcagag taggactgac gcccaagagt tggctacaat tagggtgatc tacacttagt    1980
agaaattaga cgagcttact cgtttcgtcc tcacggactc atcagtaatt tggatccct     2040 ctccaaatga aatgaacttc cttatataga ggaagggtct tgcgaaggat agtgggattg    2100
tgcgtcatcc cttacgtcag tggagatatc acatcaatcc acttgctttg aagacgtggt    2160
tggaacgtct tcttttttcca cgatgttcct cgtgggtggg ggtccatctt tgggaccact   2220
gtcggtagag gcatcttgaa cgatagcctt tcctttatcg caatgatggc atttgtagaa    2280
gccatcttcc ttttctactg tcctttcgat gaagtgacag atagctgggc aatggaatcc    2340
gaggaggttt cccgatatta ccctttgttg aaaagtctca atagccctct ggtcttctga    2400
gactgtatct ttgatattct tggagtagac gagagtgtcg tgctccacca tgtatcacat    2460
caatccactt gctttgaaga cgtggttgga acgtcttctt tttccacgat gttcctcgtg    2520
ggtgggggtc catctttggg accactgtcg gtagaggcat cttgaacgat agcctttcct    2580
ttatcgcaat gatggcattt gtagaagcca tcttcctttt ctactgtcct ttcgatgaag    2640
```

```
tgacagatag ctgggcaatg gaatccgagg aggtttcccg atattaccct ttgttgaaaa    2700
gtctcaatag ccctctggtc ttctgaacac tagtaaggcc ttaagggcca gatccccgg     2760 gctgcaggaa ttcgatctgg cacgacaggt ttcccgactg gaaagcgggc agtgagcgca    2820
acgcaattaa tgtgagttag ctcactcatt aggcacccca ggctttacac tttatgcttc    2880
cggctcgtat gttgtgtgga attgtgagcg ataacaatt tcacacagga aacagctatg     2940
acatgattac gaattcaaaa attacggata tgaatatagg catatccgta tccgaattat    3000
ccgtttgaca gctagcaacg attgtacaat tgcttcttta aaaaggaag aaagaaagaa     3060 agaaaagaat caacatcagc gttaacaaac ggccccgtta cggcccaaac ggtcatatag    3120
agtaacggcg ttaagcgttg aaagactcct atcgaaatac gtaaccgcaa acgtgtcata    3180
gtcagatccc ctcttccttc accgcctcaa acacaaaaat aatcttctac agcctatata    3240
tacaaccccc ccttctatct ctcctttctc acaattcatc atctttcttt ctctaccccc    3300
aattttaaga atcctctct tctcctcttc attttcaagg taaatctctc tctctctctc     3360
tctctctgtt attccttgtt ttaattaggt atgtattatt gctagtttgt taatctgctt    3420
atcttatgta tgccttatgt gaatatcttt atcttgttca tctcatccgt ttagaagcta    3480
taaatttgtt gatttgactg tgtatctaca cgtggttatg tttatatcta atcagatatg    3540
aatttcttca tattgttgcg tttgtgtgta ccaatccgaa atcgttgatt tttttcattt    3600
aatcgtgtag ctaattgtac gtatacatat ggatctacgt atcaattgtt catctgtttg    3660
tgtttgtatg tatacagatc tgaaaacatc acttctctca tctgattgtg ttgttacata    3720
catagatata gatctgttat atcattttt ttattaattg tgtatatata tatgtgcata     3780
gatctggatt acatgattgt gattatttac atgattttgt tatttacgta tgtatatatg    3840
tagatctgga cttttttggag ttgttgactt gattgtattt gtgtgtgtat atgtgtgttc   3900
tgatcttgat atgttatgta tgtgcagcga attcggcgcg ccaaacaatg cttcctcca    3960 tggctcctaa gaagaagagg aaggttagca agctcgagaa gtttaccaac tgctacagcc    4020
tctctaagac cctcaggttc aaggctatcc ctgtgggaaa gacccaagag aatatcgaca    4080
acaagaggct cctcgtcgag gatgagaaga gagctgaaga ttacaagggc gtgaagaagc    4140
tcctcgacag gtactacctc agcttcatca acgatgtgct ccacagcatc aagctcaaga    4200
acctcaacaa ctacatcagc ctcttccgta gaaaaccag gaccgagaaa gagaacaaag    4260
agcttgagaa cctcgagatc aacctccgta aagagatcgc caaggctttc aagggaaacg    4320
agggatacaa gagcctcttc aagaaggata ttatcgagac aatcctgcct gagttcctgg    4380
acgataagga tgagatcgct ctcgtgaaca gcttcaacgg attcactact gccttcaccg    4440
gattcttcga caacagggaa acatgttca gcgaagaggc caagagcacc tctatcgctt     4500
tcagatgcat caacgagaac ctcacgcgtt acatcagcaa catggacatc ttcgagaagg    4560
tggacgccat cttcgataag cacgaggtgc aagaaatcaa agagaagatc ctcaacagcg    4620
actacgacgt cgaggacttt tttgaagggg agttcttcaa cttcgttctc acccaagagg    4680
gcatcgacgt gtacaacgct attatcggag gattcgtgac cgagtctggg gagaagatta    4740
agggactcaa cgagtacatc aacctgtaca accagaaaac gaagcagaag ctcccgaagt    4800
tcaagccgct ctacaagcag gttctctctg atcgtgagag cctctcattt tacggtgagg    4860
gttacacctc tgacgaggaa gtgcttgagg ttttccgtaa caccctcaac aagaacagcg    4920
agatcttctc gtccatcaag aagttggaga aacttttcaa gaacttcgac gagtacagca    4980
gcgctgggat cttcgttaag aacggacctg ctatcagcac catcagcaag gatatttcg     5040
```

```
gcgagtggaa cgtgatcagg gacaagtgga atgctgagta cgatgacatc cacctcaaga    5100
agaaggctgt cgtcactgag aagtacgagg atgacaggcg taagtcgttc aagaagatcg    5160
gctctttcag cctcgagcag cttcaagaat acgctgatgc tgatctcagc gtggtcgaga    5220
agctcaaaga gatcatcatc cagaaggtcg acgagatcta caaggtgtac gggtcctctg    5280
agaagttgtt cgatgctgat ttcgtcctcg agaagagtct gaagaagaac gacgctgtcg    5340
tcgcgatcat gaaggatttg ctcgacagcg tgaagtcctt cgagaactat atcaaggcct    5400
tcttcggaga gggcaaagag actaataggg acgagtcttt ctacggggat ttcgtgctcg    5460
cttacgatat cctcctcaag gtggaccata tctacgacgc catcagaaac tacgtgaccc    5520
agaagcctta cagcaaggac aagttcaagt tgtactttca gaacccgcag ttcatgggcg    5580
gatgggacaa agacaaagag acagattaca gggccaccat cctcaggtac gggtctaagt    5640
actacctggc catcatggac aagaaatacg ccaagtgcct ccaaaagatc gacaaggatg    5700
acgtgaacgg gaactatgag aagatcaact acaagctcct tccgggaccg aacaagatgc    5760
ttcctaaggt gttcttcagc aagaaatgga tggcctacta caacccgtct gaggacatcc    5820
agaaaatcta caagaacggg accttcaaga aaggcgacat gttcaacctc aacgactgcc    5880
acaagctcat cgatttcttc aaggacagca tctcgcgtta cccgaagtgg tctaacgctt    5940
acgactttaa cttcagcgag acagaaaagt caaggatat cgccgggttc taccgtgagg    6000
ttgaggaaca gggttacaag gttagcttcg agagcgcctc caagaaagag gttgacaagt    6060
tggtcgaaga gggcaagctc tacatgttcc agatctataa caaggacttc tccgacaaga    6120
gccacggaac tcctaacctc catacgatgt acttcaagct gcttttcgac gagaacaacc    6180
acgggcagat cagactttct ggtggtgctg aactcttcat gcgtagggcc tcactcaaga    6240
aagaagagtt ggttgttcac ccggccaact ctccaatcgc taacaagaat cctgacaacc    6300
cgaaaaagac caccacgctg tcttacgacg tctacaagga caaaaggttc agcgaggacc    6360
agtacgagct tcatatcccg atcgctatca acaagtgccc gaagaacatc ttcaagatca    6420
ataccgaggt gagggtgctg ctcaagcacg atgataaccc ttacgtgatc ggaatcgatc    6480
gtggtgagag aaacctcctc tacatcgttg tggtggacgg aaagggaaac atcgtcgagc    6540
agtacagcct gaacgagatt atcaacaatt tcaacggcat caggatcaag accgactacc    6600
actcactcct cgataagaaa gaaaagagc gtttcgaggc caggcagaac tggacttcta    6660
tcgaaaacat caaagagttg aaggccggct acatctctca ggtggtgcat aagatctgcg    6720
agctggtgga aaagtacgat gctgtgatcg ctcttgagga cctcaactct gggttcaaga    6780
acagtagagt gaaggttgag aagcaggtct accaaaagtt cgagaagatg ctcatcgaca    6840
agctcaacta catggtggac aaaaagagca acccttgcgc taccggtggt gctcttaagg    6900
gataccagat cacgaacaag ttcgagtcct tcaagagcat gagcacccag aacggcttca    6960
tcttctatat ccctgcttgg ctcaccagca agatcgatcc ttctactggt ttcgtgaacc    7020
tgctcaagac caagtacacc tcgatcgccg acagcaagaa gttcatctcg tctttcgaca    7080
ggatcatgta cgtgccggaa gaggatcttt tcgagttcgc tctcgactat aagaacttca    7140
gcaggaccga cgccgactac attaagaagt ggaagctcta ctcctacggg aaccgtatca    7200
ggatcttccg aaatccgaag aaaaacaacg tgttcgactg ggaagaagtg tgcctcacct    7260
ctgcctacaa agaactgttc aacaagtacg gcatcaacta ccagcagggt gatatcaggg    7320
ctcttttgtg cgagcagagc gacaaggcat tctacagctc attcatggcc ctcatgtctc    7380
```

```
tcatgctcca gatgaggaac tctatcaccg gaaggaccga tgtggacttc cttatctctc    7440
cggtcaagaa ctctgacggg atcttctacg acagccgtaa ctatgaggct caagagaacg    7500
ctatcctgcc gaagaatgct gatgcaaacg gggcttacaa cattgcgaga aaggttctct    7560
gggctatcgg gcagtttaag aaagcggaag atgagaagct cgacaaggtg aagatcgcca    7620
tctccaacaa agagtggctt gagtacgctc agacctccgt taagcacaag aggcctgctg    7680
ctactaagaa agctggccag gccaaaaaga agaagtgagg cgcgccgagc tccaggcctc    7740
ccagctttcg tccgtatcat cggtttcgac aacgttcgtc aagttcaatg catcagtttc    7800
attgcccaca caccagaatc ctactaagtt tgagtattat ggcattggaa aagctgtttt    7860
cttctatcat ttgttctgct tgtaatttac tgtgttcttt cagttttgt tttcggacat     7920 caaaatgcaa atggatggat aagagttaat aaatgatatg gtccttttgt tcattctcaa    7980
attattatta tctgttgttt ttactttaat gggttgaatt taagtaagaa aggaactaac    8040
agtgtgatat taaggtgcaa tgttagacat ataaaacagt ctttcacctc tctttggtta    8100
tgtcttgaat tggtttgttt cttcacttat ctgtgtaatc aagtttacta tgagtctatg    8160
atcaagtaat tatgcaatca agttaagtac agtataggct t                       8201

<210> SEQ ID NO 95
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: expression casssette

<400> SEQUENCE: 95
cggggaaatt cgatctacac ttagtagaaa ttacaagagt tggctacaat tagggtgatc     60
tacacttagt agaaattatc aggtacc                                        87

<210> SEQ ID NO 96
<211> LENGTH: 141
<212> TYPE: DNA
<213> ORGANISM: Beta vulgaris

<400> SEQUENCE: 96
ggacaaccat acctaaatgt tgattgttta gcagcattat cttaactggg agattttcca     60
ccctaattgt agccaactct tgaacattca taataaaact gccatcccca tcaatatcga    120
caaccactgc atctggtcga g                                             141

<210> SEQ ID NO 97
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: InDel1

<400> SEQUENCE: 97
ggacaaccat acctaaatgt tgattgttta gcagcattat cttaactttt tccaccctaa     60
ttgtagccaa ctcttgaaca ttcataataa aactgccatc cccatcaata tcgacaacca    120
ctgcatctgg tcgag                                                    135
```

```
<210> SEQ ID NO 98
<211> LENGTH: 134
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: InDel2

<400> SEQUENCE: 98
ggacaaccat acctaaatgt tgattgttta gcagcattat cttagatttt ccaccctaat    60
tgtagccaac tcttgaacat tcataataaa actgccatcc ccatcaatat cgacaaccac   120
tgcatctggt cgag                                                     134

<210> SEQ ID NO 99
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: InDel3

<400> SEQUENCE: 99
ggacaaccat acctaaatgt tgattgttta gcagcattat ttccacccta attgtagcca    60
actcttgaac attcataata aaactgccat ccccatcaat atcgacaacc actgcatctg   120
gtcgag                                                              126

<210> SEQ ID NO 100
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: InDel4

<400> SEQUENCE: 100
ggacaaccat acctaaatgt tgattgttta gcagcattat cttgaacatt cataataaaa    60
ctgccatccc catcaatatc gacaaccact gcatctggtc gag                     103

<210> SEQ ID NO 101
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel5

<400> SEQUENCE: 101
ggacaaccat acctaaatgt tgattgttta gcagcattat ctgccatccc catcaatatc    60
gacaaccact gcatctggtc gag                                            83

<210> SEQ ID NO 102
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
```

<220> FEATURE:
<223> OTHER INFORMATION: InDel6

<400> SEQUENCE: 102
ggacaaccat acctaaatgt tgattgttta gcagcattat ccccatcaat atcgacaacc  60
actgcatctg gtcgag  76

<210> SEQ ID NO 103
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel7

<400> SEQUENCE: 103
ggacaaccat acctaaatgt tgattgttta gcagcattat cgacaaccac tgcatctggt  60
cgag  64

<210> SEQ ID NO 104
<211> LENGTH: 59
<212> TYPE: DNA
<213> ORGANISM: Zea mays

<400> SEQUENCE: 104
tttaatttac tgtcacgatt cccctctcct ggtcgaactt ttcaggtggg gaaagctgc  59

<210> SEQ ID NO 105
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel at crGEP5 target locus

<400> SEQUENCE: 105
tttgatttac tgtcacgatt ccctggtcga acttttcagg tggggaaagc tgc  53

<210> SEQ ID NO 106
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel at crGEP5 target locus

<400> SEQUENCE: 106
tttgatttac tgtcacgatt cccctctcct gtcgaacttt tcaggtgggg aaagctgc  58

<210> SEQ ID NO 107

<400> SEQUENCE: 107

000

<210> SEQ ID NO 108

<400> SEQUENCE: 108

000

<210> SEQ ID NO 109
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel at crGEP5 target locus

<400> SEQUENCE: 109
tttgatttac tgtctaactt ttcaggtggg gaaagctgc                    39

<210> SEQ ID NO 110
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel at crGEP5 target locus

<400> SEQUENCE: 110
tttgatttac tgtcatgatt cccctccctg gtcgaactttt tcaggtgggg aaagctgc    58

<210> SEQ ID NO 111
<211> LENGTH: 60
<212> TYPE: DNA
<213> ORGANISM: Zea mays

<400> SEQUENCE: 111
ctgtggcact accaagctcc tgctcaccat tccaagaatc cttgagcttg ctgaagagct   60

<210> SEQ ID NO 112
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel at crGEP75 target locus

<400> SEQUENCE: 112
ctgtggcact accaagctcc tgctcaccag aatccttgag cttgctgaag agct         54

<210> SEQ ID NO 113
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel at crGEP75 target locus

<400> SEQUENCE: 113
ctgtggcact accaagctcc tgctcacctt ggaatccttg agcttgctga agagct       56

<210> SEQ ID NO 114
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: InDel at crGEP75 target locus

<400> SEQUENCE: 114
ctgtggcact accaagctcc tgctcagaat ccttgagctt gctgaagagc t            51

<210> SEQ ID NO 115
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel at crGEP75 target locus

<400> SEQUENCE: 115
ctgtggcact accaagctcc tgcttgctga agagct                              36

<210> SEQ ID NO 116
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel at crGEP75 target locus

<400> SEQUENCE: 116
ctgtggcact accaagctcc tgctcaatga atccttgagc ttgctgaaga gct           53

<210> SEQ ID NO 117
<211> LENGTH: 57
<212> TYPE: DNA
<213> ORGANISM: Zea mays

<400> SEQUENCE: 117
gcaggagctg cctggaggcg ggctcctcgt gtaccagagc ttctgtgctg aagacgc       57

<210> SEQ ID NO 118
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel at crGEP77 target locus

<400> SEQUENCE: 118
gcaggagctg cctggaggcg ggctcctcga gcttctgtgc tgaagacgc                49

<210> SEQ ID NO 119
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel at crGEP77 target locus

<400> SEQUENCE: 119
gcaggagctg cctggaggcg ggctctgtgc tgaagacgc                           39

<210> SEQ ID NO 120
```

```
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gcaggagctg cctggaggcg ggctcctcgt gagcttctgt gctgaagacg c            51

<210> SEQ ID NO 121
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel at crGEP77 target locus

<400> SEQUENCE: 121
gcaggagctg cctggaggcg ggctcctgag cttctgtgct gaagacgc               48

<210> SEQ ID NO 122
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel at crGEP77 target locus

<400> SEQUENCE: 122
gcaggagctg cctggaggcg ggctcctcgg gagcttctgt gctgaagacg c            51

<210> SEQ ID NO 123
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel at crGEP77 target locus

<400> SEQUENCE: 123
gcaggagctg cctggaggcg ggctcctcag cttctgtgct gaagacgc               48

<210> SEQ ID NO 124
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel at crGEP77 target locus

<400> SEQUENCE: 124
gcaggagctg cctggaggcg ggctcctcgt agcttctgtg ctgaagacgc             50

<210> SEQ ID NO 125
<211> LENGTH: 60
<212> TYPE: DNA
<213> ORGANISM: Triticum aestivum

<400> SEQUENCE: 125
```
gctcttcccg caccgcttca gccctgcagc acgcacccat ccatgacgca acacacatca        60

<210> SEQ ID NO 126
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel in A genome

<400> SEQUENCE: 126
gctcttcccg caccgcttca gccctgcacg cacccatcca tgacgcaaca cacatca        57

<210> SEQ ID NO 127
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel in A genome

<400> SEQUENCE: 127
gctcttcccg caccgcttca gccccgcacc catccatgac gcaacacaca tca        53

<210> SEQ ID NO 128
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel in A genome

<400> SEQUENCE: 128
gctcttcccg caccgcttca gccctacgca cccatccatg acgcaacaca catca        55

<210> SEQ ID NO 129
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel in A genome

<400> SEQUENCE: 129
gctcttcccg caccgcttca gcctgcacgc acccatccat gacgcaacac acatca        56

<210> SEQ ID NO 130
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel in A genome

<400> SEQUENCE: 130
gctcttcccg caccgcttca gccctggcac ccatccatga cgcaacacac atca        54

<210> SEQ ID NO 131

```
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel in A genome

<400> SEQUENCE: 131
gctcttcccg caccgcttca gcccatccat gacgcaacac acatca              46

<210> SEQ ID NO 132
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel in A genome

<400> SEQUENCE: 132
gctcttcccg caccgcttca gcccccatcc atgacgcaac acacatca            48

<210> SEQ ID NO 133
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel in A genome

<400> SEQUENCE: 133
gctcttcccg caccgcttca gcacccatcc atgacgcaac acacatca            48

<210> SEQ ID NO 134
<211> LENGTH: 60
<212> TYPE: DNA
<213> ORGANISM: Triticum aestivum

<400> SEQUENCE: 134
gctcttcccg caccgcttca gccctgcagc acgcacccat ccatgacgca acacacatca    60

<210> SEQ ID NO 135
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel in B genome

<400> SEQUENCE: 135
gctcttcccg caccgcttca gcccacccat ccatgacgca acacacatca          50

<210> SEQ ID NO 136
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel in B genome
```

<400> SEQUENCE: 136
gctcttcccg caccgcttca gcccacgcac ccatccatga cgcaacacac atca          54

<210> SEQ ID NO 137
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel in B genome

<400> SEQUENCE: 137
gctcttcccg caccgcttca gccacgcacc catccatgac gcaacacaca tca           53

<210> SEQ ID NO 138
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel in B genome

<400> SEQUENCE: 138
gctcttcccg caccgcttca gccgcaccca tccatgacgc aacacacatc a             51

<210> SEQ ID NO 139
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel in B genome

<400> SEQUENCE: 139
gctcttcccg caccgcttca gcgcacccat ccatgacgca acacacatca               50

<210> SEQ ID NO 140
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel in B genome

<400> SEQUENCE: 140
catccatgac gcaccacaca tcagcccagc acgcacccat ccatgacgca acacacatca    60

<210> SEQ ID NO 141
<211> LENGTH: 60
<212> TYPE: DNA
<213> ORGANISM: Triticum aestivum

<400> SEQUENCE: 141
gctcttcccg caccgcttca gccctgcagc acgcacccat ccatgacgca acacacatca    60

<210> SEQ ID NO 142
<211> LENGTH: 53
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: InDel in D genome

<400> SEQUENCE: 142
gctcttcccg caccgcttca gccccgcacc catccatgac gcaacacaca tca            53

<210> SEQ ID NO 143
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel in D genome

<400> SEQUENCE: 143
gctcttcccg caccgcttca gcccatcca tgacgcaaca cacatca                    47

<210> SEQ ID NO 144
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: InDel in D genome

<400> SEQUENCE: 144
gctcttcccg caccgcttca gccctaccca tccatgacgc aacacacatc a              51

<210> SEQ ID NO 145
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: expression cassette

<400> SEQUENCE: 145
aattcgatct acacttagta gaaattaatc tcccagtaga aattaatctc ccagttaaga     60
taatgctgca tctacactta gtagaaatta tcaggt                               96

<210> SEQ ID NO 146
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: protospacer

<400> SEQUENCE: 146
caccctaatt gtagccaact cttg                                            24

<210> SEQ ID NO 147
<211> LENGTH: 24
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<223> OTHER INFORMATION: protospacer

<400> SEQUENCE: 147
gcagcattat cttaactggg agat                                          24

<210> SEQ ID NO 148
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: protospacer

<400> SEQUENCE: 148
ggtatggttg tccaatggga agat                                          24

<210> SEQ ID NO 149
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: protospacer

<400> SEQUENCE: 149
caaggtatgt atgtgcccgg ttag                                          24

<210> SEQ ID NO 150
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: protospacer

<400> SEQUENCE: 150
gaagggtttc caaggtatgt atgt                                          24

<210> SEQ ID NO 151
<211> LENGTH: 187
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: expression cassettte

<400> SEQUENCE: 151
cgatcgcctc tctgcttggc tcctctttct tgtgaaagag ggttcccagg cgacaccacg    60
aggaggtgca gagtaggact gacgcccaag agttggctac aattagggtg atctacactt   120
agtagaaatt agacgagctt actcgtttcg tcctcacgga ctcatcagta atttggatcc   180
cctctcc                                                            187

<210> SEQ ID NO 152
<211> LENGTH: 1252
<212> TYPE: PRT
<213> ORGANISM: Unknown
```

<220> FEATURE:
<223> OTHER INFORMATION: Description of Unknown:
      Lachnospiraceae bacterium sequence

<400> SEQUENCE: 152

Met Ala Pro Lys Lys Arg Lys Val Ser Lys Leu Glu Lys Phe Thr
1               5                   10                  15

Asn Cys Tyr Ser Leu Ser Lys Thr Leu Arg Phe Lys Ala Ile Pro Val
            20                  25                  30

Gly Lys Thr Gln Glu Asn Ile Asp Asn Lys Arg Leu Leu Val Glu Asp
        35                  40                  45

Glu Lys Arg Ala Glu Asp Tyr Lys Gly Val Lys Lys Leu Leu Asp Arg
    50                  55                  60

Tyr Tyr Leu Ser Phe Ile Asn Asp Val Leu His Ser Ile Lys Leu Lys
65                  70                  75                  80

Asn Leu Asn Asn Tyr Ile Ser Leu Phe Arg Lys Lys Thr Arg Thr Glu
                85                  90                  95

Lys Glu Asn Lys Glu Leu Glu Asn Leu Glu Ile Asn Leu Arg Lys Glu
            100                 105                 110

Ile Ala Lys Ala Phe Lys Gly Asn Glu Gly Tyr Lys Ser Leu Phe Lys
        115                 120                 125

Lys Asp Ile Ile Glu Thr Ile Leu Pro Glu Phe Leu Asp Asp Lys Asp
    130                 135                 140

Glu Ile Ala Leu Val Asn Ser Phe Asn Gly Phe Thr Thr Ala Phe Thr
145                 150                 155                 160

Gly Phe Phe Asp Asn Arg Glu Asn Met Phe Ser Glu Glu Ala Lys Ser
                165                 170                 175

Thr Ser Ile Ala Phe Arg Cys Ile Asn Glu Asn Leu Thr Arg Tyr Ile
            180                 185                 190

Ser Asn Met Asp Ile Phe Glu Lys Val Asp Ala Ile Phe Asp Lys His
        195                 200                 205

Glu Val Gln Glu Ile Lys Glu Lys Ile Leu Asn Ser Asp Tyr Asp Val
    210                 215                 220

Glu Asp Phe Phe Glu Gly Glu Phe Phe Asn Phe Val Leu Thr Gln Glu
225                 230                 235                 240

Gly Ile Asp Val Tyr Asn Ala Ile Ile Gly Gly Phe Val Thr Glu Ser
                245                 250                 255

Gly Glu Lys Ile Lys Gly Leu Asn Glu Tyr Ile Asn Leu Tyr Asn Gln
            260                 265                 270

Lys Thr Lys Gln Lys Leu Pro Lys Phe Lys Pro Leu Tyr Lys Gln Val
        275                 280                 285

Leu Ser Asp Arg Glu Ser Leu Ser Phe Tyr Gly Glu Gly Tyr Thr Ser
    290                 295                 300

Asp Glu Glu Val Leu Glu Val Phe Arg Asn Thr Leu Asn Lys Asn Ser
305                 310                 315                 320

Glu Ile Phe Ser Ser Ile Lys Lys Leu Glu Lys Leu Phe Lys Asn Phe
                325                 330                 335

Asp Glu Tyr Ser Ser Ala Gly Ile Phe Val Lys Asn Gly Pro Ala Ile
            340                 345                 350

Ser Thr Ile Ser Lys Asp Ile Phe Gly Glu Trp Asn Val Ile Arg Asp
        355                 360                 365

Lys Trp Asn Ala Glu Tyr Asp Asp Ile His Leu Lys Lys Lys Ala Val
    370                 375                 380

Val Thr Glu Lys Tyr Glu Asp Asp Arg Arg Lys Ser Phe Lys Lys Ile

```
                385                 390                 395                 400
        Gly Ser Phe Ser Leu Glu Gln Leu Gln Glu Tyr Ala Asp Ala Asp Leu
                        405                 410                 415

Ser Val Val Glu Lys Leu Lys Glu Ile Ile Gln Lys Val Asp Glu
                        420                 425                 430

Ile Tyr Lys Val Tyr Gly Ser Glu Lys Leu Phe Asp Ala Asp Phe
                        435                 440                 445

Val Leu Glu Lys Ser Leu Lys Lys Asn Asp Ala Val Ala Ile Met
                450                 455                 460

Lys Asp Leu Leu Asp Ser Val Lys Ser Phe Glu Asn Tyr Ile Lys Ala
        465                 470                 475                 480

Phe Phe Gly Glu Gly Lys Glu Thr Asn Arg Asp Glu Ser Phe Tyr Gly
                        485                 490                 495

Asp Phe Val Leu Ala Tyr Asp Ile Leu Leu Lys Val Asp His Ile Tyr
                        500                 505                 510

Asp Ala Ile Arg Asn Tyr Val Thr Gln Lys Pro Tyr Ser Lys Asp Lys
                        515                 520                 525

Phe Lys Leu Tyr Phe Gln Asn Pro Gln Phe Met Gly Gly Trp Asp Lys
                530                 535                 540

Asp Lys Glu Thr Asp Tyr Arg Ala Thr Ile Leu Arg Tyr Gly Ser Lys
        545                 550                 555                 560

Tyr Tyr Leu Ala Ile Met Asp Lys Lys Tyr Ala Lys Cys Leu Gln Lys
                        565                 570                 575

Ile Asp Lys Asp Asp Val Asn Gly Asn Tyr Glu Lys Ile Asn Tyr Lys
                        580                 585                 590

Leu Leu Pro Gly Pro Asn Lys Met Leu Pro Lys Val Phe Phe Ser Lys
                        595                 600                 605

Lys Trp Met Ala Tyr Tyr Asn Pro Ser Glu Asp Ile Gln Lys Ile Tyr
                        610                 615                 620

Lys Asn Gly Thr Phe Lys Lys Gly Asp Met Phe Asn Leu Asn Asp Cys
        625                 630                 635                 640

His Lys Leu Ile Asp Phe Phe Lys Asp Ser Ile Ser Arg Tyr Pro Lys
                        645                 650                 655

Trp Ser Asn Ala Tyr Asp Phe Asn Phe Ser Glu Thr Glu Lys Tyr Lys
                        660                 665                 670

Asp Ile Ala Gly Phe Tyr Arg Glu Val Glu Glu Gln Gly Tyr Lys Val
                        675                 680                 685

Ser Phe Glu Ser Ala Ser Lys Lys Glu Val Asp Lys Leu Val Glu Glu
                        690                 695                 700

Gly Lys Leu Tyr Met Phe Gln Ile Tyr Asn Lys Asp Phe Ser Asp Lys
        705                 710                 715                 720

Ser His Gly Thr Pro Asn Leu His Thr Met Tyr Phe Lys Leu Leu Phe
                        725                 730                 735

Asp Glu Asn Asn His Gly Gln Ile Arg Leu Ser Gly Gly Ala Glu Leu
                        740                 745                 750

Phe Met Arg Arg Ala Ser Leu Lys Lys Glu Glu Leu Val Val His Pro
                        755                 760                 765

Ala Asn Ser Pro Ile Ala Asn Lys Asn Pro Asp Asn Pro Lys Lys Thr
                        770                 775                 780

Thr Thr Leu Ser Tyr Asp Val Tyr Lys Asp Lys Arg Phe Ser Glu Asp
        785                 790                 795                 800

Gln Tyr Glu Leu His Ile Pro Ile Ala Ile Asn Lys Cys Pro Lys Asn
                        805                 810                 815
```

-continued

```
Ile Phe Lys Ile Asn Thr Glu Val Arg Val Leu Leu Lys His Asp Asp
            820                 825                 830

Asn Pro Tyr Val Ile Gly Ile Asp Arg Gly Glu Arg Asn Leu Leu Tyr
            835                 840                 845

Ile Val Val Val Asp Gly Lys Gly Asn Ile Val Glu Gln Tyr Ser Leu
            850                 855                 860

Asn Glu Ile Ile Asn Asn Phe Asn Gly Ile Arg Ile Lys Thr Asp Tyr
865                 870                 875                 880

His Ser Leu Leu Asp Lys Lys Glu Lys Glu Arg Phe Glu Ala Arg Gln
                    885                 890                 895

Asn Trp Thr Ser Ile Glu Asn Ile Lys Glu Leu Lys Ala Gly Tyr Ile
            900                 905                 910

Ser Gln Val Val His Lys Ile Cys Glu Leu Val Glu Lys Tyr Asp Ala
            915                 920                 925

Val Ile Ala Leu Glu Asp Leu Asn Ser Gly Phe Lys Asn Ser Arg Val
            930                 935                 940

Lys Val Glu Lys Gln Val Tyr Gln Lys Phe Glu Lys Met Leu Ile Asp
945                 950                 955                 960

Lys Leu Asn Tyr Met Val Asp Lys Lys Ser Asn Pro Cys Ala Thr Gly
                    965                 970                 975

Gly Ala Leu Lys Gly Tyr Gln Ile Thr Asn Lys Phe Glu Ser Phe Lys
            980                 985                 990

Ser Met Ser Thr Gln Asn Gly Phe Ile Phe Tyr Ile Pro Ala Trp Leu
            995                 1000                1005

Thr Ser Lys Ile Asp Pro Ser Thr Gly Phe Val Asn Leu Leu Lys
         1010                1015                 1020

Thr Lys Tyr Thr Ser Ile Ala Asp Ser Lys Lys Phe Ile Ser Ser
         1025                1030                 1035

Phe Asp Arg Ile Met Tyr Val Pro Glu Glu Asp Leu Phe Glu Phe
         1040                1045                 1050

Ala Leu Asp Tyr Lys Asn Phe Ser Arg Thr Asp Ala Asp Tyr Ile
         1055                1060                 1065

Lys Lys Trp Lys Leu Tyr Ser Tyr Gly Asn Arg Ile Arg Ile Phe
         1070                1075                 1080

Arg Asn Pro Lys Lys Asn Asn Val Phe Asp Trp Glu Glu Val Cys
         1085                1090                 1095

Leu Thr Ser Ala Tyr Lys Glu Leu Phe Asn Lys Tyr Gly Ile Asn
         1100                1105                 1110

Tyr Gln Gln Gly Asp Ile Arg Ala Leu Leu Cys Glu Gln Ser Asp
         1115                1120                 1125

Lys Ala Phe Tyr Ser Ser Phe Met Ala Leu Met Ser Leu Met Leu
         1130                1135                 1140

Gln Met Arg Asn Ser Ile Thr Gly Arg Thr Asp Val Asp Phe Leu
         1145                1150                 1155

Ile Ser Pro Val Lys Asn Ser Asp Gly Ile Phe Tyr Asp Ser Arg
         1160                1165                 1170

Asn Tyr Glu Ala Gln Glu Asn Ala Ile Leu Pro Lys Asn Ala Asp
         1175                1180                 1185

Ala Asn Gly Ala Tyr Asn Ile Ala Arg Lys Val Leu Trp Ala Ile
         1190                1195                 1200

Gly Gln Phe Lys Lys Ala Glu Asp Glu Lys Leu Asp Lys Val Lys
         1205                1210                 1215
```

```
Ile Ala Ile Ser Asn Lys Glu Trp Leu Glu Tyr Ala Gln Thr Ser
    1220            1225               1230

Val Lys His Lys Arg Pro Ala Ala Thr Lys Lys Ala Gly Gln Ala
    1235            1240               1245

Lys Lys Lys Lys
    1250

<210> SEQ ID NO 153
<211> LENGTH: 1252
<212> TYPE: PRT
<213> ORGANISM: Unknown
<220> FEATURE:
<223> OTHER INFORMATION: Description of Unknown:
      Lachnospiraceae bacterium sequence

<400> SEQUENCE: 153

Met Ala Pro Lys Lys Arg Lys Val Ser Lys Leu Glu Lys Phe Thr
1               5                   10                  15

Asn Cys Tyr Ser Leu Ser Lys Thr Leu Arg Phe Lys Ala Ile Pro Val
            20                  25                  30

Gly Lys Thr Gln Glu Asn Ile Asp Asn Lys Arg Leu Leu Val Glu Asp
        35                  40                  45

Glu Lys Arg Ala Glu Asp Tyr Lys Gly Val Lys Lys Leu Leu Asp Arg
    50                  55                  60

Tyr Tyr Leu Ser Phe Ile Asn Asp Val Leu His Ser Ile Lys Leu Lys
65                  70                  75                  80

Asn Leu Asn Asn Tyr Ile Ser Leu Phe Arg Lys Lys Thr Arg Thr Glu
                85                  90                  95

Lys Glu Asn Lys Glu Leu Glu Asn Leu Glu Ile Asn Leu Arg Lys Glu
            100                 105                 110

Ile Ala Lys Ala Phe Lys Gly Asn Glu Gly Tyr Lys Ser Leu Phe Lys
        115                 120                 125

Lys Asp Ile Ile Glu Thr Ile Leu Pro Glu Phe Leu Asp Asp Lys Asp
    130                 135                 140

Glu Ile Ala Leu Val Asn Ser Phe Asn Gly Phe Thr Thr Ala Phe Thr
145                 150                 155                 160

Gly Phe Phe Asp Asn Arg Glu Asn Met Phe Ser Glu Glu Ala Lys Ser
                165                 170                 175

Thr Ser Ile Ala Phe Arg Cys Ile Asn Glu Asn Leu Thr Arg Tyr Ile
            180                 185                 190

Ser Asn Met Asp Ile Phe Glu Lys Val Asp Ala Ile Phe Asp Lys His
        195                 200                 205

Glu Val Gln Glu Ile Lys Glu Lys Ile Leu Asn Ser Asp Tyr Asp Val
    210                 215                 220

Glu Asp Phe Phe Glu Gly Glu Phe Phe Asn Phe Val Leu Thr Gln Glu
225                 230                 235                 240

Gly Ile Asp Val Tyr Asn Ala Ile Ile Gly Gly Phe Val Thr Glu Ser
                245                 250                 255

Gly Glu Lys Ile Lys Gly Leu Asn Glu Tyr Ile Asn Leu Tyr Asn Gln
            260                 265                 270

Lys Thr Lys Gln Lys Leu Pro Lys Phe Lys Pro Leu Tyr Lys Gln Val
        275                 280                 285

Leu Ser Asp Arg Glu Ser Leu Ser Phe Tyr Gly Glu Gly Tyr Thr Ser
    290                 295                 300

Asp Glu Glu Val Leu Glu Val Phe Arg Asn Thr Leu Asn Lys Asn Ser
305                 310                 315                 320
```

```
Glu Ile Phe Ser Ser Ile Lys Lys Leu Glu Lys Leu Phe Lys Asn Phe
                325                 330                 335

Asp Glu Tyr Ser Ser Ala Gly Ile Phe Val Lys Asn Gly Pro Ala Ile
            340                 345                 350

Ser Thr Ile Ser Lys Asp Ile Phe Gly Glu Trp Asn Val Ile Arg Asp
        355                 360                 365

Lys Trp Asn Ala Glu Tyr Asp Asp Ile His Leu Lys Lys Lys Ala Val
    370                 375                 380

Val Thr Glu Lys Tyr Glu Asp Asp Arg Arg Lys Ser Phe Lys Lys Ile
385                 390                 395                 400

Gly Ser Phe Ser Leu Glu Gln Leu Gln Glu Tyr Ala Asp Ala Asp Leu
                405                 410                 415

Ser Val Val Glu Lys Leu Lys Glu Ile Ile Gln Lys Val Asp Glu
            420                 425                 430

Ile Tyr Lys Val Tyr Gly Ser Ser Glu Lys Leu Phe Asp Ala Asp Phe
        435                 440                 445

Val Leu Glu Lys Ser Leu Lys Lys Asn Asp Ala Val Val Ala Ile Met
    450                 455                 460

Lys Asp Leu Leu Asp Ser Val Lys Ser Phe Glu Asn Tyr Ile Lys Ala
465                 470                 475                 480

Phe Phe Gly Glu Gly Lys Glu Thr Asn Arg Asp Glu Ser Phe Tyr Gly
                485                 490                 495

Asp Phe Val Leu Ala Tyr Asp Ile Leu Leu Lys Val Asp His Ile Tyr
            500                 505                 510

Asp Ala Ile Arg Asn Tyr Val Thr Gln Lys Pro Tyr Ser Lys Asp Lys
        515                 520                 525

Phe Lys Leu Tyr Phe Gln Asn Pro Gln Phe Met Gly Gly Trp Asp Lys
    530                 535                 540

Asp Lys Glu Thr Asp Tyr Arg Ala Thr Ile Leu Arg Tyr Gly Ser Lys
545                 550                 555                 560

Tyr Tyr Leu Ala Ile Met Asp Lys Lys Tyr Ala Lys Cys Leu Gln Lys
                565                 570                 575

Ile Asp Lys Asp Asp Val Asn Gly Asn Tyr Glu Lys Ile Asn Tyr Lys
            580                 585                 590

Leu Leu Pro Gly Pro Asn Lys Met Leu Pro Lys Val Phe Phe Ser Lys
        595                 600                 605

Lys Trp Met Ala Tyr Tyr Asn Pro Ser Glu Asp Ile Gln Lys Ile Tyr
    610                 615                 620

Lys Asn Gly Thr Phe Lys Lys Gly Asp Met Phe Asn Leu Asn Asp Cys
625                 630                 635                 640

His Lys Leu Ile Asp Phe Phe Lys Asp Ser Ile Ser Arg Tyr Pro Lys
                645                 650                 655

Trp Ser Asn Ala Tyr Asp Phe Asn Phe Ser Glu Thr Glu Lys Tyr Lys
            660                 665                 670

Asp Ile Ala Gly Phe Tyr Arg Glu Val Glu Glu Gln Gly Tyr Lys Val
        675                 680                 685

Ser Phe Glu Ser Ala Ser Lys Lys Glu Val Asp Lys Leu Val Glu Glu
    690                 695                 700

Gly Lys Leu Tyr Met Phe Gln Ile Tyr Asn Lys Asp Phe Ser Asp Lys
705                 710                 715                 720

Ser His Gly Thr Pro Asn Leu His Thr Met Tyr Phe Lys Leu Leu Phe
                725                 730                 735
```

```
Asp Glu Asn Asn His Gly Gln Ile Arg Leu Ser Gly Gly Ala Glu Leu
                740                 745                 750

Phe Met Arg Arg Ala Ser Leu Lys Lys Glu Glu Leu Val Val His Pro
        755                 760                 765

Ala Asn Ser Pro Ile Ala Asn Lys Asn Pro Asp Asn Pro Lys Lys Thr
770                 775                 780

Thr Thr Leu Ser Tyr Asp Val Tyr Leu Asp Lys Arg Phe Ser Glu Asp
785                 790                 795                 800

Gln Tyr Glu Leu His Ile Pro Ile Ala Ile Asn Lys Cys Pro Lys Asn
                805                 810                 815

Ile Phe Lys Ile Asn Thr Glu Val Arg Val Leu Leu Lys His Asp Asp
        820                 825                 830

Asn Pro Tyr Val Ile Gly Ile Asp Arg Gly Glu Arg Asn Leu Leu Tyr
        835                 840                 845

Ile Val Val Val Asp Gly Lys Gly Asn Ile Val Glu Gln Tyr Ser Leu
850                 855                 860

Asn Glu Ile Ile Asn Asn Phe Asn Gly Ile Arg Ile Lys Thr Asp Tyr
865                 870                 875                 880

His Ser Leu Leu Asp Lys Lys Glu Lys Glu Arg Phe Glu Ala Arg Gln
                885                 890                 895

Asn Trp Thr Ser Ile Glu Asn Ile Lys Glu Leu Lys Ala Gly Tyr Ile
                900                 905                 910

Ser Gln Val Val His Lys Ile Cys Glu Leu Val Glu Lys Tyr Asp Ala
                915                 920                 925

Val Ile Ala Leu Glu Asp Leu Asn Ser Gly Phe Lys Asn Ser Arg Val
930                 935                 940

Lys Val Glu Lys Gln Val Tyr Gln Lys Phe Glu Lys Met Leu Ile Asp
945                 950                 955                 960

Lys Leu Asn Tyr Met Val Asp Lys Lys Ser Asn Pro Cys Ala Thr Gly
                965                 970                 975

Gly Ala Leu Lys Gly Tyr Gln Ile Thr Asn Lys Phe Glu Ser Phe Lys
                980                 985                 990

Ser Met Ser Thr Gln Asn Gly Phe Ile Phe Tyr Ile Pro Ala Trp Leu
        995                 1000                1005

Thr Ser Lys Ile Asp Pro Ser Thr Gly Phe Val Asn Leu Leu Lys
    1010                1015                1020

Thr Lys Tyr Thr Ser Ile Ala Asp Ser Lys Lys Phe Ile Ser Ser
    1025                1030                1035

Phe Asp Arg Ile Met Tyr Val Pro Glu Glu Asp Leu Phe Glu Phe
    1040                1045                1050

Ala Leu Asp Tyr Lys Asn Phe Ser Arg Thr Asp Ala Asp Tyr Ile
    1055                1060                1065

Lys Lys Trp Lys Leu Tyr Ser Tyr Gly Asn Arg Ile Arg Ile Phe
    1070                1075                1080

Arg Asn Pro Lys Lys Asn Asn Val Phe Asp Trp Glu Glu Val Cys
    1085                1090                1095

Leu Thr Ser Ala Tyr Lys Glu Leu Phe Asn Lys Tyr Gly Ile Asn
    1100                1105                1110

Tyr Gln Gln Gly Asp Ile Arg Ala Leu Leu Cys Glu Gln Ser Asp
    1115                1120                1125

Lys Ala Phe Tyr Ser Ser Phe Met Ala Leu Met Ser Leu Met Leu
    1130                1135                1140

Gln Met Arg Asn Ser Ile Thr Gly Arg Thr Asp Val Asp Phe Leu
```

```
                1145                1150                1155

Ile Ser  Pro Val Lys Asn  Ser Asp Gly Ile  Phe Tyr Asp Ser  Arg
        1160                1165                1170

Asn Tyr  Glu Ala Gln Glu  Asn Ala Ile Leu  Pro Lys Asn Ala  Asp
        1175                1180                1185

Ala Asn  Gly Ala Tyr Asn  Ile Ala Arg Lys  Val Leu Trp Ala  Ile
        1190                1195                1200

Gly Gln  Phe Lys Lys Ala  Glu Asp Glu Lys  Leu Asp Lys Val  Lys
        1205                1210                1215

Ile Ala  Ile Ser Asn Lys  Glu Trp Leu Glu  Tyr Ala Gln Thr  Ser
        1220                1225                1230

Val Lys  His Lys Arg Pro  Ala Ala Thr Lys  Lys Ala Gly Gln  Ala
        1235                1240                1245

Lys Lys  Lys Lys
        1250

<210> SEQ ID NO 154
<211> LENGTH: 1260
<212> TYPE: PRT
<213> ORGANISM: Unknown
<220> FEATURE:
<223> OTHER INFORMATION: Description of Unknown:
      Lachnospiraceae bacterium sequence

<400> SEQUENCE: 154

Met Ala Pro Lys Lys Arg Lys Val Gly Ile His Gly Val Pro Ala
1                5                  10                 15

Ala Ser Lys Leu Glu Lys Phe Thr Asn Cys Tyr Ser Leu Ser Lys Thr
                20                  25                  30

Leu Arg Phe Lys Ala Ile Pro Val Gly Lys Thr Gln Glu Asn Ile Asp
            35                  40                  45

Asn Lys Arg Leu Leu Val Glu Asp Glu Lys Arg Ala Glu Asp Tyr Lys
50                  55                  60

Gly Val Lys Lys Leu Leu Asp Arg Tyr Tyr Leu Ser Phe Ile Asn Asp
65                  70                  75                  80

Val Leu His Ser Ile Lys Leu Lys Asn Leu Asn Asn Tyr Ile Ser Leu
                85                  90                  95

Phe Arg Lys Lys Thr Arg Thr Glu Lys Glu Asn Lys Glu Leu Glu Asn
                100                 105                 110

Leu Glu Ile Asn Leu Arg Lys Glu Ile Ala Lys Ala Phe Lys Gly Asn
            115                 120                 125

Glu Gly Tyr Lys Ser Leu Phe Lys Lys Asp Ile Ile Glu Thr Ile Leu
130                 135                 140

Pro Glu Phe Leu Asp Asp Lys Asp Glu Ile Ala Leu Val Asn Ser Phe
145                 150                 155                 160

Asn Gly Phe Thr Thr Ala Phe Thr Gly Phe Phe Asp Asn Arg Glu Asn
                165                 170                 175

Met Phe Ser Glu Glu Ala Lys Ser Thr Ser Ile Ala Phe Arg Cys Ile
                180                 185                 190

Asn Glu Asn Leu Thr Arg Tyr Ile Ser Asn Met Asp Ile Phe Glu Lys
            195                 200                 205

Val Asp Ala Ile Phe Asp Lys His Glu Val Gln Glu Ile Lys Glu Lys
210                 215                 220

Ile Leu Asn Ser Asp Tyr Asp Val Glu Asp Phe Phe Glu Gly Glu Phe
225                 230                 235                 240
```

```
Phe Asn Phe Val Leu Thr Gln Glu Gly Ile Asp Val Tyr Asn Ala Ile
                245                 250                 255
Ile Gly Gly Phe Val Thr Glu Ser Gly Glu Lys Ile Lys Gly Leu Asn
            260                 265                 270
Glu Tyr Ile Asn Leu Tyr Asn Gln Lys Thr Lys Gln Lys Leu Pro Lys
            275                 280                 285
Phe Lys Pro Leu Tyr Lys Gln Val Leu Ser Asp Arg Glu Ser Leu Ser
290                 295                 300
Phe Tyr Gly Glu Gly Tyr Thr Ser Asp Glu Val Leu Glu Val Phe
305                 310                 315                 320
Arg Asn Thr Leu Asn Lys Asn Ser Glu Ile Phe Ser Ser Ile Lys Lys
                325                 330                 335
Leu Glu Lys Leu Phe Lys Asn Phe Asp Glu Tyr Ser Ser Ala Gly Ile
                340                 345                 350
Phe Val Lys Asn Gly Pro Ala Ile Ser Thr Ile Ser Lys Asp Ile Phe
            355                 360                 365
Gly Glu Trp Asn Val Ile Arg Asp Lys Trp Asn Ala Glu Tyr Asp Asp
            370                 375                 380
Ile His Leu Lys Lys Lys Ala Val Val Thr Glu Lys Tyr Glu Asp Asp
385                 390                 395                 400
Arg Arg Lys Ser Phe Lys Lys Ile Gly Ser Phe Ser Leu Glu Gln Leu
                405                 410                 415
Gln Glu Tyr Ala Asp Ala Asp Leu Ser Val Val Glu Lys Leu Lys Glu
            420                 425                 430
Ile Ile Ile Gln Lys Val Asp Glu Ile Tyr Lys Val Tyr Gly Ser Ser
            435                 440                 445
Glu Lys Leu Phe Asp Ala Asp Phe Val Leu Glu Lys Ser Leu Lys Lys
        450                 455                 460
Asn Asp Ala Val Val Ala Ile Met Lys Asp Leu Leu Asp Ser Val Lys
465                 470                 475                 480
Ser Phe Glu Asn Tyr Ile Lys Ala Phe Phe Gly Glu Gly Lys Glu Thr
                485                 490                 495
Asn Arg Asp Glu Ser Phe Tyr Gly Asp Phe Val Leu Ala Tyr Asp Ile
            500                 505                 510
Leu Leu Lys Val Asp His Ile Tyr Asp Ala Ile Arg Asn Tyr Val Thr
            515                 520                 525
Gln Lys Pro Tyr Ser Lys Asp Lys Phe Lys Leu Tyr Phe Gln Asn Pro
        530                 535                 540
Gln Phe Met Gly Gly Trp Asp Lys Asp Lys Glu Thr Asp Tyr Arg Ala
545                 550                 555                 560
Thr Ile Leu Arg Tyr Gly Ser Lys Tyr Tyr Leu Ala Ile Met Asp Lys
                565                 570                 575
Lys Tyr Ala Lys Cys Leu Gln Lys Ile Asp Lys Asp Asp Val Asn Gly
            580                 585                 590
Asn Tyr Glu Lys Ile Asn Tyr Lys Leu Leu Pro Gly Pro Asn Lys Met
            595                 600                 605
Leu Pro Lys Val Phe Phe Ser Lys Lys Trp Met Ala Tyr Tyr Asn Pro
        610                 615                 620
Ser Glu Asp Ile Gln Lys Ile Tyr Lys Asn Gly Thr Phe Lys Lys Gly
625                 630                 635                 640
Asp Met Phe Asn Leu Asn Asp Cys His Lys Leu Ile Asp Phe Phe Lys
                645                 650                 655
Asp Ser Ile Ser Arg Tyr Pro Lys Trp Ser Asn Ala Tyr Asp Phe Asn
```

-continued

```
                660                 665                 670
Phe Ser Glu Thr Glu Lys Tyr Lys Asp Ile Ala Gly Phe Tyr Arg Glu
            675                 680                 685
Val Glu Glu Gln Gly Tyr Lys Val Ser Phe Glu Ser Ala Ser Lys Lys
            690                 695                 700
Glu Val Asp Lys Leu Val Glu Glu Gly Lys Leu Tyr Met Phe Gln Ile
705                 710                 715                 720
Tyr Asn Lys Asp Phe Ser Asp Lys Ser His Gly Thr Pro Asn Leu His
                725                 730                 735
Thr Met Tyr Phe Lys Leu Leu Phe Asp Glu Asn Asn His Gly Gln Ile
                740                 745                 750
Arg Leu Ser Gly Gly Ala Glu Leu Phe Met Arg Arg Ala Ser Leu Lys
            755                 760                 765
Lys Glu Glu Leu Val Val His Pro Ala Asn Ser Pro Ile Ala Asn Lys
            770                 775                 780
Asn Pro Asp Asn Pro Lys Lys Thr Thr Thr Leu Ser Tyr Asp Val Tyr
785                 790                 795                 800
Lys Asp Lys Arg Phe Ser Glu Asp Gln Tyr Glu Leu His Ile Pro Ile
                805                 810                 815
Ala Ile Asn Lys Cys Pro Lys Asn Ile Phe Lys Ile Asn Thr Glu Val
                820                 825                 830
Arg Val Leu Leu Lys His Asp Asp Asn Pro Tyr Val Ile Gly Ile Asp
            835                 840                 845
Arg Gly Glu Arg Asn Leu Leu Tyr Ile Val Val Val Asp Gly Lys Gly
            850                 855                 860
Asn Ile Val Glu Gln Tyr Ser Leu Asn Glu Ile Ile Asn Asn Phe Asn
865                 870                 875                 880
Gly Ile Arg Ile Lys Thr Asp Tyr His Ser Leu Leu Asp Lys Lys Glu
                885                 890                 895
Lys Glu Arg Phe Glu Ala Arg Gln Asn Trp Thr Ser Ile Glu Asn Ile
            900                 905                 910
Lys Glu Leu Lys Ala Gly Tyr Ile Ser Gln Val Val His Lys Ile Cys
            915                 920                 925
Glu Leu Val Glu Lys Tyr Asp Ala Val Ile Ala Leu Glu Asp Leu Asn
930                 935                 940
Ser Gly Phe Lys Asn Ser Arg Val Lys Val Glu Lys Gln Val Tyr Gln
945                 950                 955                 960
Lys Phe Glu Lys Met Leu Ile Asp Lys Leu Asn Tyr Met Val Asp Lys
                965                 970                 975
Lys Ser Asn Pro Cys Ala Thr Gly Gly Ala Leu Lys Gly Tyr Gln Ile
                980                 985                 990
Thr Asn Lys Phe Glu Ser Phe Lys  Ser Met Ser Thr Gln Asn Gly Phe
            995                1000                1005
Ile Phe Tyr Ile Pro Ala Trp  Leu Thr Ser Lys Ile  Asp Pro Ser
            1010                1015                1020
Thr Gly Phe Val Asn Leu Leu  Lys Thr Lys Tyr Thr  Ser Ile Ala
            1025                1030                1035
Asp Ser Lys Lys Phe Ile Ser  Ser Phe Asp Arg Ile  Met Tyr Val
            1040                1045                1050
Pro Glu Glu Asp Leu Phe Glu  Phe Ala Leu Asp Tyr  Lys Asn Phe
            1055                1060                1065
Ser Arg Thr Asp Ala Asp Tyr  Ile Lys Lys Trp Lys  Leu Tyr Ser
            1070                1075                1080
```

```
Tyr Gly Asn Arg Ile Arg Ile Phe Arg Asn Pro Lys Lys Asn Asn
1085                1090                1095

Val Phe Asp Trp Glu Glu Val Cys Leu Thr Ser Ala Tyr Lys Glu
1100                1105                1110

Leu Phe Asn Lys Tyr Gly Ile Asn Tyr Gln Gln Gly Asp Ile Arg
1115                1120                1125

Ala Leu Leu Cys Glu Gln Ser Asp Lys Ala Phe Tyr Ser Ser Phe
1130                1135                1140

Met Ala Leu Met Ser Leu Met Leu Gln Met Arg Asn Ser Ile Thr
1145                1150                1155

Gly Arg Thr Asp Val Asp Phe Leu Ile Ser Pro Val Lys Asn Ser
1160                1165                1170

Asp Gly Ile Phe Tyr Asp Ser Arg Asn Tyr Glu Ala Gln Glu Asn
1175                1180                1185

Ala Ile Leu Pro Lys Asn Ala Asp Ala Asn Gly Ala Tyr Asn Ile
1190                1195                1200

Ala Arg Lys Val Leu Trp Ala Ile Gly Gln Phe Lys Lys Ala Glu
1205                1210                1215

Asp Glu Lys Leu Asp Lys Val Lys Ile Ala Ile Ser Asn Lys Glu
1220                1225                1230

Trp Leu Glu Tyr Ala Gln Thr Ser Val Lys His Lys Arg Pro Ala
1235                1240                1245

Ala Thr Lys Lys Ala Gly Gln Ala Lys Lys Lys
1250                1255

<210> SEQ ID NO 155
<211> LENGTH: 1252
<212> TYPE: PRT
<213> ORGANISM: Unknown
<220> FEATURE:
<223> OTHER INFORMATION: Description of Unknown:
      Lachnospiraceae bacterium sequence

<400> SEQUENCE: 155

Met Ala Pro Lys Lys Lys Arg Lys Val Ser Lys Leu Glu Lys Phe Thr
1               5                   10                  15

Asn Cys Tyr Ser Leu Ser Lys Thr Leu Arg Phe Lys Ala Ile Pro Val
                20                  25                  30

Gly Lys Thr Gln Glu Asn Ile Asp Asn Lys Arg Leu Leu Val Glu Asp
            35                  40                  45

Glu Lys Arg Ala Glu Asp Tyr Lys Gly Val Lys Lys Leu Leu Asp Arg
        50                  55                  60

Tyr Tyr Leu Ser Phe Ile Asn Asp Val Leu His Ser Ile Lys Leu Lys
65                  70                  75                  80

Asn Leu Asn Asn Tyr Ile Ser Leu Phe Arg Lys Lys Thr Arg Thr Glu
                85                  90                  95

Lys Glu Asn Lys Glu Leu Glu Asn Leu Glu Ile Asn Leu Arg Lys Glu
            100                 105                 110

Ile Ala Lys Ala Phe Lys Gly Asn Glu Gly Tyr Lys Ser Leu Phe Lys
        115                 120                 125

Lys Asp Ile Ile Glu Thr Ile Leu Pro Glu Phe Leu Asp Asp Lys Asp
    130                 135                 140

Glu Ile Ala Leu Val Asn Ser Phe Asn Gly Phe Thr Thr Ala Phe Thr
145                 150                 155                 160

Gly Phe Phe Asp Asn Arg Glu Asn Met Phe Ser Glu Glu Ala Lys Ser
```

```
            165                 170                 175
Thr Ser Ile Ala Phe Arg Cys Ile Asn Glu Asn Leu Thr Arg Tyr Ile
            180                 185                 190
Ser Asn Met Asp Ile Phe Glu Lys Val Asp Ala Ile Phe Asp Lys His
            195                 200                 205
Glu Val Gln Glu Ile Lys Glu Lys Ile Leu Asn Ser Asp Tyr Asp Val
            210                 215                 220
Glu Asp Phe Phe Glu Gly Glu Phe Phe Asn Phe Val Leu Thr Gln Glu
225                 230                 235                 240
Gly Ile Asp Val Tyr Asn Ala Ile Ile Gly Phe Val Thr Glu Ser
                245                 250                 255
Gly Glu Lys Ile Lys Gly Leu Asn Glu Tyr Ile Asn Leu Tyr Asn Gln
            260                 265                 270
Lys Thr Lys Gln Lys Leu Pro Lys Phe Lys Pro Leu Tyr Lys Gln Val
            275                 280                 285
Leu Ser Asp Arg Glu Ser Leu Ser Phe Tyr Gly Glu Gly Tyr Thr Ser
            290                 295                 300
Asp Glu Glu Val Leu Glu Val Phe Arg Asn Thr Leu Asn Lys Asn Ser
305                 310                 315                 320
Glu Ile Phe Ser Ser Ile Lys Lys Leu Glu Lys Leu Phe Lys Asn Phe
                325                 330                 335
Asp Glu Tyr Ser Ser Ala Gly Ile Phe Val Lys Asn Gly Pro Ala Ile
            340                 345                 350
Ser Thr Ile Ser Lys Asp Ile Phe Gly Glu Trp Asn Val Ile Arg Asp
            355                 360                 365
Lys Trp Asn Ala Glu Tyr Asp Asp Ile His Leu Lys Lys Lys Ala Val
370                 375                 380
Val Thr Glu Lys Tyr Glu Asp Asp Arg Arg Lys Ser Phe Lys Lys Ile
385                 390                 395                 400
Gly Ser Phe Ser Leu Glu Gln Leu Gln Glu Tyr Ala Asp Ala Asp Leu
                405                 410                 415
Ser Val Val Glu Lys Leu Lys Glu Ile Ile Ile Gln Lys Val Asp Glu
            420                 425                 430
Ile Tyr Lys Val Tyr Gly Ser Ser Glu Lys Leu Phe Asp Ala Asp Phe
            435                 440                 445
Val Leu Glu Lys Ser Leu Lys Lys Asn Asp Ala Val Val Ala Ile Met
450                 455                 460
Lys Asp Leu Leu Asp Ser Val Lys Ser Phe Glu Asn Tyr Ile Lys Ala
465                 470                 475                 480
Phe Phe Gly Glu Gly Lys Glu Thr Asn Arg Asp Glu Ser Phe Tyr Gly
                485                 490                 495
Asp Phe Val Leu Ala Tyr Asp Ile Leu Leu Lys Val Asp His Ile Tyr
            500                 505                 510
Asp Ala Ile Arg Asn Tyr Val Thr Gln Lys Pro Tyr Ser Lys Asp Lys
            515                 520                 525
Phe Lys Leu Tyr Phe Gln Asn Pro Gln Phe Met Gly Gly Trp Asp Lys
            530                 535                 540
Asp Lys Glu Thr Asp Tyr Arg Ala Thr Ile Leu Arg Tyr Gly Ser Lys
545                 550                 555                 560
Tyr Tyr Leu Ala Ile Met Asp Lys Lys Tyr Ala Lys Cys Leu Gln Lys
                565                 570                 575
Ile Asp Lys Asp Asp Val Asn Gly Asn Tyr Glu Lys Ile Asn Tyr Lys
            580                 585                 590
```

```
Leu Leu Pro Gly Pro Asn Lys Met Leu Pro Lys Val Phe Ser Lys
            595                 600                 605

Lys Trp Met Ala Tyr Tyr Asn Pro Ser Glu Asp Ile Gln Lys Ile Tyr
            610                 615                 620

Lys Asn Gly Thr Phe Lys Lys Gly Asp Met Phe Asn Leu Asn Asp Cys
625                 630                 635                 640

His Lys Leu Ile Asp Phe Phe Lys Asp Ser Ile Ser Arg Tyr Pro Lys
                645                 650                 655

Trp Ser Asn Ala Tyr Asp Phe Asn Phe Ser Glu Thr Glu Lys Tyr Lys
            660                 665                 670

Asp Ile Ala Gly Phe Tyr Arg Glu Val Glu Gln Gly Tyr Lys Val
            675                 680                 685

Ser Phe Glu Ser Ala Ser Lys Lys Glu Val Asp Lys Leu Val Glu Glu
            690                 695                 700

Gly Lys Leu Tyr Met Phe Gln Ile Tyr Asn Lys Asp Phe Ser Asp Lys
705                 710                 715                 720

Ser His Gly Thr Pro Asn Leu His Thr Met Tyr Phe Lys Leu Leu Phe
                725                 730                 735

Asp Glu Asn Asn His Gly Gln Ile Arg Leu Ser Gly Gly Ala Glu Leu
            740                 745                 750

Phe Met Arg Arg Ala Ser Leu Lys Lys Glu Glu Leu Val Val His Pro
            755                 760                 765

Ala Asn Ser Pro Ile Ala Asn Lys Asn Pro Asp Asn Pro Lys Lys Thr
            770                 775                 780

Thr Thr Leu Ser Tyr Asp Val Tyr Lys Asp Lys Arg Phe Ser Glu Asp
785                 790                 795                 800

Gln Tyr Glu Leu His Ile Pro Ile Ala Ile Asn Lys Cys Pro Lys Asn
                805                 810                 815

Ile Phe Lys Ile Asn Thr Glu Val Arg Val Leu Leu Lys His Asp Asp
                820                 825                 830

Asn Pro Tyr Val Ile Gly Ile Asp Arg Gly Glu Arg Asn Leu Leu Tyr
            835                 840                 845

Ile Val Val Val Asp Gly Lys Gly Asn Ile Val Glu Gln Tyr Ser Leu
            850                 855                 860

Asn Glu Ile Ile Asn Asn Phe Asn Gly Ile Arg Ile Lys Thr Asp Tyr
865                 870                 875                 880

His Ser Leu Leu Asp Lys Lys Glu Lys Glu Arg Phe Glu Ala Arg Gln
                885                 890                 895

Asn Trp Thr Ser Ile Glu Asn Ile Lys Glu Leu Lys Ala Gly Tyr Ile
            900                 905                 910

Ser Gln Val Val His Lys Ile Cys Glu Leu Val Glu Lys Tyr Asp Ala
            915                 920                 925

Val Ile Ala Leu Glu Asp Leu Asn Ser Gly Phe Lys Asn Ser Arg Val
            930                 935                 940

Lys Val Glu Lys Gln Val Tyr Gln Lys Phe Glu Lys Met Leu Ile Asp
945                 950                 955                 960

Lys Leu Asn Tyr Met Val Asp Lys Lys Ser Asn Pro Cys Ala Thr Gly
                965                 970                 975

Gly Ala Leu Lys Gly Tyr Gln Ile Thr Asn Lys Phe Glu Ser Phe Lys
            980                 985                 990

Ser Met Ser Thr Gln Asn Gly Phe Ile Phe Tyr Ile Pro Ala Trp Leu
            995                 1000                1005
```

Thr Ser Lys Ile Asp Pro Ser Thr Gly Phe Val Asn Leu Leu Lys
    1010                1015                1020

Thr Lys Tyr Thr Ser Ile Ala Asp Ser Lys Lys Phe Ile Ser Ser
    1025                1030                1035

Phe Asp Arg Ile Met Tyr Val Pro Glu Glu Asp Leu Phe Glu Phe
    1040                1045                1050

Ala Leu Asp Tyr Lys Asn Phe Ser Arg Thr Asp Ala Asp Tyr Ile
    1055                1060                1065

Lys Lys Trp Lys Leu Tyr Ser Tyr Gly Asn Arg Ile Arg Ile Phe
    1070                1075                1080

Arg Asn Pro Lys Lys Asn Asn Val Phe Asp Trp Glu Glu Val Cys
    1085                1090                1095

Leu Thr Ser Ala Tyr Lys Glu Leu Phe Asn Lys Tyr Gly Ile Asn
    1100                1105                1110

Tyr Gln Gln Gly Asp Ile Arg Ala Leu Leu Cys Glu Gln Ser Asp
    1115                1120                1125

Lys Ala Phe Tyr Ser Ser Phe Met Ala Leu Met Ser Leu Met Leu
    1130                1135                1140

Gln Met Arg Asn Ser Ile Thr Gly Arg Thr Asp Val Asp Phe Leu
    1145                1150                1155

Ile Ser Pro Val Lys Asn Ser Asp Gly Ile Phe Tyr Asp Ser Arg
    1160                1165                1170

Asn Tyr Glu Ala Gln Glu Asn Ala Ile Leu Pro Lys Asn Ala Asp
    1175                1180                1185

Ala Asn Gly Ala Tyr Asn Ile Ala Arg Lys Val Leu Trp Ala Ile
    1190                1195                1200

Gly Gln Phe Lys Lys Ala Glu Asp Glu Lys Leu Asp Lys Val Lys
    1205                1210                1215

Ile Ala Ile Ser Asn Lys Glu Trp Leu Glu Tyr Ala Gln Thr Ser
    1220                1225                1230

Val Lys His Lys Arg Pro Ala Ala Thr Lys Lys Ala Gly Gln Ala
    1235                1240                1245

Lys Lys Lys Lys
    1250

<210> SEQ ID NO 156
<211> LENGTH: 1252
<212> TYPE: PRT
<213> ORGANISM: Unknown
<220> FEATURE:
<223> OTHER INFORMATION: Description of Unknown:
      Lachnospiraceae bacterium sequence

<400> SEQUENCE: 156

Met Ala Pro Lys Lys Lys Arg Lys Val Ser Lys Leu Glu Lys Phe Thr
1               5                   10                  15

Asn Cys Tyr Ser Leu Ser Lys Thr Leu Arg Phe Lys Ala Ile Pro Val
                20                  25                  30

Gly Lys Thr Gln Glu Asn Ile Asp Asn Lys Arg Leu Leu Val Glu Asp
            35                  40                  45

Glu Lys Arg Ala Glu Asp Tyr Lys Gly Val Lys Lys Leu Leu Asp Arg
        50                  55                  60

Tyr Tyr Leu Ser Phe Ile Asn Asp Val Leu His Ser Ile Lys Leu Lys
65                  70                  75                  80

Asn Leu Asn Asn Tyr Ile Ser Leu Phe Arg Lys Lys Thr Arg Thr Glu
                85                  90                  95

```
Lys Glu Asn Lys Glu Leu Glu Asn Leu Glu Ile Asn Leu Arg Lys Glu
                100                 105                 110

Ile Ala Lys Ala Phe Lys Gly Asn Glu Gly Tyr Lys Ser Leu Phe Lys
            115                 120                 125

Lys Asp Ile Ile Glu Thr Ile Leu Pro Glu Phe Leu Asp Asp Lys Asp
        130                 135                 140

Glu Ile Ala Leu Val Asn Ser Phe Asn Gly Phe Thr Thr Ala Phe Thr
145                 150                 155                 160

Gly Phe Phe Asp Asn Arg Glu Asn Met Phe Ser Glu Ala Lys Ser
                165                 170                 175

Thr Ser Ile Ala Phe Arg Cys Ile Asn Glu Asn Leu Thr Arg Tyr Ile
            180                 185                 190

Ser Asn Met Asp Ile Phe Glu Lys Val Asp Ala Ile Phe Asp Lys His
        195                 200                 205

Glu Val Gln Glu Ile Lys Glu Lys Ile Leu Asn Ser Asp Tyr Asp Val
        210                 215                 220

Glu Asp Phe Phe Glu Gly Glu Phe Phe Asn Phe Val Leu Thr Gln Glu
225                 230                 235                 240

Gly Ile Asp Val Tyr Asn Ala Ile Ile Gly Gly Phe Val Thr Glu Ser
                245                 250                 255

Gly Glu Lys Ile Lys Gly Leu Asn Glu Tyr Ile Asn Leu Tyr Asn Gln
            260                 265                 270

Lys Thr Lys Gln Lys Leu Pro Lys Phe Lys Pro Leu Tyr Lys Gln Val
        275                 280                 285

Leu Ser Asp Arg Glu Ser Leu Ser Phe Tyr Gly Glu Gly Tyr Thr Ser
        290                 295                 300

Asp Glu Glu Val Leu Glu Val Phe Arg Asn Thr Leu Asn Lys Asn Ser
305                 310                 315                 320

Glu Ile Phe Ser Ser Ile Lys Lys Leu Glu Lys Leu Phe Lys Asn Phe
                325                 330                 335

Asp Glu Tyr Ser Ser Ala Gly Ile Phe Val Lys Asn Gly Pro Ala Ile
            340                 345                 350

Ser Thr Ile Ser Lys Asp Ile Phe Gly Glu Trp Asn Val Ile Arg Asp
        355                 360                 365

Lys Trp Asn Ala Glu Tyr Asp Asp Ile His Leu Lys Lys Lys Ala Val
        370                 375                 380

Val Thr Glu Lys Tyr Glu Asp Asp Arg Arg Lys Ser Phe Lys Lys Ile
385                 390                 395                 400

Gly Ser Phe Ser Leu Glu Gln Leu Gln Glu Tyr Ala Asp Ala Asp Leu
                405                 410                 415

Ser Val Val Glu Lys Leu Lys Glu Ile Ile Gln Lys Val Asp Glu
            420                 425                 430

Ile Tyr Lys Val Tyr Gly Ser Ser Glu Lys Leu Phe Asp Ala Asp Phe
        435                 440                 445

Val Leu Glu Lys Ser Leu Lys Lys Asn Asp Ala Val Val Ala Ile Met
        450                 455                 460

Lys Asp Leu Leu Asp Ser Val Lys Ser Phe Glu Asn Tyr Ile Lys Ala
465                 470                 475                 480

Phe Phe Gly Glu Gly Lys Glu Thr Asn Arg Asp Glu Ser Phe Tyr Gly
                485                 490                 495

Asp Phe Val Leu Ala Tyr Asp Ile Leu Leu Lys Val Asp His Ile Tyr
            500                 505                 510
```

```
Asp Ala Ile Arg Asn Tyr Val Thr Gln Lys Pro Tyr Ser Lys Asp Lys
            515                 520                 525

Phe Lys Leu Tyr Phe Gln Asn Pro Gln Phe Met Gly Gly Trp Asp Lys
            530                 535                 540

Asp Lys Glu Thr Asp Tyr Arg Ala Thr Ile Leu Arg Tyr Gly Ser Lys
545                 550                 555                 560

Tyr Tyr Leu Ala Ile Met Asp Lys Lys Tyr Ala Lys Cys Leu Gln Lys
            565                 570                 575

Ile Asp Lys Asp Asp Val Asn Gly Asn Tyr Glu Lys Ile Asn Tyr Lys
            580                 585                 590

Leu Leu Pro Gly Pro Asn Lys Met Leu Pro Lys Val Phe Phe Ser Lys
            595                 600                 605

Lys Trp Met Ala Tyr Tyr Asn Pro Ser Glu Asp Ile Gln Lys Ile Tyr
            610                 615                 620

Lys Asn Gly Thr Phe Lys Lys Gly Asp Met Phe Asn Leu Asn Asp Cys
625                 630                 635                 640

His Lys Leu Ile Asp Phe Phe Lys Asp Ser Ile Ser Arg Tyr Pro Lys
            645                 650                 655

Trp Ser Asn Ala Tyr Asp Phe Asn Phe Ser Glu Thr Glu Lys Tyr Lys
            660                 665                 670

Asp Ile Ala Gly Phe Tyr Arg Glu Val Glu Glu Gln Gly Tyr Lys Val
            675                 680                 685

Ser Phe Glu Ser Ala Ser Lys Lys Glu Val Asp Lys Leu Val Glu Glu
            690                 695                 700

Gly Lys Leu Tyr Met Phe Gln Ile Tyr Asn Lys Asp Phe Ser Asp Lys
705                 710                 715                 720

Ser His Gly Thr Pro Asn Leu His Thr Met Tyr Phe Lys Leu Leu Phe
            725                 730                 735

Asp Glu Asn Asn His Gly Gln Ile Arg Leu Ser Gly Gly Ala Glu Leu
            740                 745                 750

Phe Met Arg Arg Ala Ser Leu Lys Lys Glu Glu Leu Val Val His Pro
            755                 760                 765

Ala Asn Ser Pro Ile Ala Asn Lys Asn Pro Asp Asn Pro Lys Lys Thr
            770                 775                 780

Thr Thr Leu Ser Tyr Asp Val Tyr Lys Asp Lys Arg Phe Ser Glu Asp
785                 790                 795                 800

Gln Tyr Glu Leu His Ile Pro Ile Ala Ile Asn Lys Cys Pro Lys Asn
            805                 810                 815

Ile Phe Lys Ile Asn Thr Glu Val Arg Val Leu Leu Lys His Asp Asp
            820                 825                 830

Asn Pro Tyr Val Ile Gly Ile Asp Arg Gly Glu Arg Asn Leu Leu Tyr
            835                 840                 845

Ile Val Val Val Asp Gly Lys Gly Asn Ile Val Glu Gln Tyr Ser Leu
850                 855                 860

Asn Glu Ile Ile Asn Asn Phe Asn Gly Ile Arg Ile Lys Thr Asp Tyr
865                 870                 875                 880

His Ser Leu Leu Asp Lys Lys Glu Lys Glu Arg Phe Glu Ala Arg Gln
            885                 890                 895

Asn Trp Thr Ser Ile Glu Asn Ile Lys Glu Leu Lys Ala Gly Tyr Ile
            900                 905                 910

Ser Gln Val Val His Lys Ile Cys Glu Leu Val Glu Lys Tyr Asp Ala
            915                 920                 925

Val Ile Ala Leu Glu Asp Leu Asn Ser Gly Phe Lys Asn Ser Arg Val
```

930             935             940
Lys Val Glu Lys Gln Val Tyr Gln Lys Phe Glu Lys Met Leu Ile Asp
945                 950             955                 960

Lys Leu Asn Tyr Met Val Asp Lys Lys Ser Asn Pro Cys Ala Thr Gly
                965             970                 975

Gly Ala Leu Lys Gly Tyr Gln Ile Thr Asn Lys Phe Glu Ser Phe Lys
                980              985                990

Ser Met Ser Thr Gln Asn Gly Phe Ile Phe Tyr Ile Pro Ala Trp Leu
        995             1000            1005

Thr Ser Lys Ile Asp Pro Ser Thr Gly Phe Val Asn Leu Leu Lys
    1010            1015            1020

Thr Lys Tyr Thr Ser Ile Ala Asp Ser Lys Lys Phe Ile Ser Ser
    1025            1030            1035

Phe Asp Arg Ile Met Tyr Val Pro Glu Glu Asp Leu Phe Glu Phe
    1040            1045            1050

Ala Leu Asp Tyr Lys Asn Phe Ser Arg Thr Asp Ala Asp Tyr Ile
    1055            1060            1065

Lys Lys Trp Lys Leu Tyr Ser Tyr Gly Asn Arg Ile Arg Ile Phe
    1070            1075            1080

Arg Asn Pro Lys Lys Asn Asn Val Phe Asp Trp Glu Glu Val Cys
    1085            1090            1095

Leu Thr Ser Ala Tyr Lys Glu Leu Phe Asn Lys Tyr Gly Ile Asn
    1100            1105            1110

Tyr Gln Gln Gly Asp Ile Arg Ala Leu Leu Cys Glu Gln Ser Asp
    1115            1120            1125

Lys Ala Phe Tyr Ser Ser Phe Met Ala Leu Met Ser Leu Met Leu
    1130            1135            1140

Gln Met Arg Asn Ser Ile Thr Gly Arg Thr Asp Val Asp Phe Leu
    1145            1150            1155

Ile Ser Pro Val Lys Asn Ser Asp Gly Ile Phe Tyr Asp Ser Arg
    1160            1165            1170

Asn Tyr Glu Ala Gln Glu Asn Ala Ile Leu Pro Lys Asn Ala Asp
    1175            1180            1185

Ala Asn Gly Ala Tyr Asn Ile Ala Arg Lys Val Leu Trp Ala Ile
    1190            1195            1200

Gly Gln Phe Lys Lys Ala Glu Asp Glu Lys Leu Asp Lys Val Lys
    1205            1210            1215

Ile Ala Ile Ser Asn Lys Glu Trp Leu Glu Tyr Ala Gln Thr Ser
    1220            1225            1230

Val Lys His Lys Arg Pro Ala Ala Thr Lys Lys Ala Gly Gln Ala
    1235            1240            1245

Lys Lys Lys Lys
    1250

<210> SEQ ID NO 157
<211> LENGTH: 3948
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: variant I of Cpf1 (SEQ ID NO: 72) including an
      intronic sequence
<220> FEATURE:
<221> NAME/KEY: Intron
<222> LOCATION: (862)..(1050)

<400> SEQUENCE: 157

```
atggcgccga agaagaagcg caaggtgtcc aagctcgaga agttcacgaa ctgctactcc      60
ctctccaaga ccctccgctt caaggccatc cccgtgggca agacccagga gaacatcgac     120
aacaagcgcc tcctggtcga ggacgagaag agggcggagg actacaaggg cgtgaagaag     180
ctcctggacc gctactacct ctccttcatc aacgacgtcc tgcacagcat caagctcaag     240
aacctgaaca actacatctc cctgttccgc aagaagacga ggaccgagaa ggagaacaag     300
gagctcgaga acctggagat caacctccgc aaggagatcg ccaaggcgtt caagggcaac     360
gagggctaca gagcctgtt caagaaggac atcatcgaga cgatcctccc ggagttcctg     420
gacgacaagg acgagatcgc cctcgtgaac tccttcaacg gcttcaccac ggcgttcacc     480
ggcttcttcg acaaccgcga gaacatgttc agcgaggagg ccaagtccac gagcatcgcg     540
ttccgctgca tcaacgagaa cctgaccagg tacatctcca acatggacat cttcgagaag     600
gtcgacgcca tcttcgacaa gcacgagtg caggagatca aggagaagat cctcaacagc     660
gactacgacg tcgaggactt cttcgagggc gagttcttca acttcgtcct gacgcaggag     720
ggcatcgacg tgtacaacgc catcatcggt ggcttcgtga ccgagtccgg cgagaagatc     780
aagggcctca acgagtacat caacctgtac aaccagaaga ccaagcagaa gctcccgaag     840
ttcaagcccc tctacaagca ggtaagtttc tgcttctacc tttgatatat atataataat     900
tatcattaat tagtagtaat ataatatttc aaatattttt ttcaaaataa aagaatgtag     960
tatatagcaa ttgcttttct gtagtttata agtgtgtata ttttaattta taacttttct    1020
aatatatgac caaaacatgg tgatgtgcag gtcctgtccg accgcgagtc cctgagcttc    1080
tacggcgagg gctacacgag cgacgaggag gtcctcgagg tgttcaggaa caccctgaac    1140
aagaacagcg agatcttctc cagcatcaag aagctcgaga gctgttcaa gaacttcgac    1200
gagtactcca cgccggcat cttcgtcaag aacggcccgg cgatctccac gatcagcaag    1260
gatatcttcg gcgagtggaa cgtgatcagg gacaagtgga cgccgagta cgacgacatc    1320
cacctcaaga agaaggcggt ggtcaccgag aagtacgagg acgaccgcag gaagtccttc    1380
aagaagatcg gctccttcag cctcgagcag ctgcaggagt acgccgacgc ggacctctcc    1440
gtggtcgaga gctgaagga gatcatcatc cagaaggtcg acgagatcta caaggtgtac    1500
ggctccagcg agaagctgtt cgacgccgac ttcgtcctcg agaagtccct gaagaagaac    1560
gacgccgtgg tcgcgatcat gaaggacctc ctggactccg tgaagagctt cgagaactac    1620
atcaaggcgt tcttcggcga gggcaaggag acgaaccgcg acgagtcctt ctacggcgac    1680
ttcgtcctcg cctacgacat cctcctgaag gtggaccaca tctacgacgc gatcaggaac    1740
tacgtgaccc agaagccgta cagcaaggac aagttcaagc tgtacttcca gaaccccag    1800
ttcatgggcg gctgggacaa ggacaaggag acggactacc gcgccaccat cctccgctac    1860
ggcagcaagt actacctggc catcatggac aagaagtacg cgaagtgcct ccagaagatc    1920
gacaaggacg acgtcaacgg caactacgag aagatcaact acaagctcct gccgggcccc    1980
aacaagatgc tgccgaaggt gttcttctcc aagaagtgga tggcctacta caaccccagc    2040
gaggacatcc agaagatcta caagaacggc acgttcaaga agggcgacat gttcaacctc    2100
aacgactgcc acaagctgat cgacttcttc aaggactcca tcagccgcta cccgaagtgg    2160
tccaacgcct acgacttcaa cttcagcgag acagagaagt acaaggacat cgcgggcttc    2220
tacagggagg tcgaggagca gggctacaag gtgtccttcg agtccgccag caagaaggag    2280
```

```
gtcgacaagc tcgtggagga gggcaagctg tacatgttcc agatctacaa caaggacttc    2340
tccgacaaga gccacggcac gcccaacctc cacaccatgt acttcaagct cctgttcgac    2400
gagaacaacc acggccagat ccgcctctcc ggcggcgccg agctgttcat gagggagggcg   2460 agcctcaaga aggaggagct ggtggtccac cccgctaaca gcccaatcgc gaacaagaac    2520
ccggacaacc ccaagaagac cacgaccctc tcctacgacg tgtacaagga caagcgcttc    2580
agcgaggacc agtacgagct gcacatcccg atcgccatca acaagtgccc caagaacatc    2640
ttcaagatca acaccgaggt cagggtgctc ctgaagcacg acgacacccc ctacgtgatc    2700
ggcatcgacc gcggcgagag gaacctcctg tacatcgtgg tcgtggacgg caagggcaac    2760
atcgtggagc agtactccct gaacgagatc atcaacaact tcaacggcat ccgcatcaag    2820
acggactacc acagcctcct ggacaagaag gagaaggagc gcttcgaggc caggcagaac    2880
tggacctcca tcgagaacat caaggagctc aaggcgggct acatcagcca ggtcgtgcac    2940
aagatctgcg agctggtcga agtacgacgc gccgtgatcg cgctcgagga cctgaactcc    3000
ggcttcaaga acagcagggt caaggtggag aagcaggtct accagaagtt cgagaagatg    3060
ctcatcgaca agctgaacta catggtggac aagaagtcca acccgtgcgc tacgggcggc    3120
gcgctcaagg gctaccagat caccaacaag ttcgagagct tcaagtccat gagcacccag    3180
aacggcttca tcttctacat cccggcctgg ctgacgtcca agatcgaccc cagcaccggc    3240
ttcgtcaacc tcctgaagac gaagtacacc tccatcgcgg acagcaagaa gttcatctcc    3300
agcttcgacc gcatcatgta tgtgccggag gaggacctct tcgagttcgc cctggactac    3360
aagaacttct ccaggacgga cgcggattac atcaagaagt ggaagctcta cagctacggc    3420
aaccgcatca ggatcttccg caaccccaag aagaacaacg tcttcgactg ggaggaggtg    3480
tgcctcacct ccgcctacaa ggagctgttc aacaagtacg gcatcaacta ccagcagggc    3540
gacatcaggg cgctcctgtg cgagcagagc gacaaggcct tctactccag cttcatggcg    3600
ctcatgtccc tcatgctgca gatgcgcaac agcatcacgg gcaggaccga cgtcgacttc    3660
ctgatctccc cggtgaagaa cagcgacggc atcttctacg acagccgcaa ctacgaggcc    3720
caggagaacg cgatcctgcc aaagaacgcg gacgccaacg gcgcctacaa catcgcgagg    3780
aaggtgctgt gggccatcgg ccagttcaag aaggcggagg acgagaagct cgacaaggtc    3840
aagatcgcca tctccaacaa ggagtggctg gagtacgcgc agacctcggt gaagcacaag    3900
aggcccgctg ccaccaagaa ggcgggccag gccaagaaga agaagtga                 3948

<210> SEQ ID NO 158
<211> LENGTH: 3948
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: variant III of Cpf1 (SEQ ID NO: 75) including
      an intronic
<220> FEATURE:
<221> NAME/KEY: Intron
<222> LOCATION: (628)..(816)

<400> SEQUENCE: 158
atggccccga agaagaagag gaaggtcagc aagctcgaga agttcaccaa ctgctacagc     60
ctgagcaaga ccctgaggtt caaggctatc ccggtgggca agacccaaga gaacatcgac    120
aacaagaggc tgctggtcga ggacgagaag cgcgctgagg attacaaggg cgtgaagaag    180
```

-continued

```
ctgctggaca ggtactacct gagcttcatc aacgacgtgc tgcacagcat caagctgaag    240
aacctgaaca actacatcag cctgttccgc aagaaaacca ggaccgagaa agagaacaaa    300
gagcttgaga acctcgagat caacctgagg aaagagatcg ccaaggcctt caagggcaac    360
gagggctaca gagcctgtt  caagaaggac atcatcgaga ctatcctgcc agagttcctg    420
gacgacaagg acgagatcgc cctggtgaac agcttcaacg gcttcacgac cgccttcacc    480
ggtttcttcg acaaccgcga gaatatgttc agcgaggaag ccaagagcac ctctatcgcc    540
ttccgctgca tcaacgagaa cctgacgcgc tacatctcca acatggatat cttcgagaag    600
gtggacgcca tcttcgataa gcacgaggta agtttctgct tctacctttg atatatatat    660
aataattatc attaattagt agtaatataa tatttcaaat attttttca  aaataaaaga    720
atgtagtata tagcaattgc ttttctgtag tttataagtg tgtatatttt aatttataac    780
ttttctaata tatgaccaaa acatggtgat gtgcaggtgc aagagatcaa agaaaagatc    840
ctgaacagcg actacgacgt cgaggacttc ttcgagggcg agttcttcaa cttcgtgctc    900
acccaagagg gcatcgatgt gtacaacgcc atcatcggcg gcttcgtgac tgagagcggc    960
gagaagatca agggcctgaa cgagtacatc aacctctaca atcaaaagac caagcagaag   1020
ctgccgaagt tcaagccgct gtacaagcag gttctgagcg accgcgagag cctgtctttc   1080
tacggcgagg gttacaccag cgacgaagag gtgttggagg ttttccgcaa caccctgaac   1140
aagaacagcg agatcttcag ctccatcaag aagctgaaaa agctgtttaa gaacttcgac   1200
gagtacagca gcgccggcat cttcgtgaag aacggcccag ctatcagcac catcagcaag   1260
gacatcttcg gcgagtggaa cgtgatcagg gacaagtgga acgccgagta cgacgacatc   1320
cacctgaaga aaaaggccgt ggtgaccgag aagtacgagg acgacaggcg caagagcttc   1380
aagaagatcg gctccttcag cctcgagcag ctgcaagagt acgctgacgc tgacctgagc   1440
gtggtcgaga agctcaaaga gatcatcatc cagaaggtcg acgagatcta caaggtgtac   1500
ggcagcagcg agaagctttt cgacgccgac ttcgtccttg agaagtccct caagaaaaac   1560
gacgccgtgg tggccatcat gaaggacctg ctggactccg tgaagtcctt cgagaactac   1620
attaaggctt tcttcggtga gggcaaagag actaacaggg acgagagctt ctacggggat   1680
ttcgtgctgg cctacgacat cctgctcaag gtggaccaca tctacgacgc catccgcaac   1740
tacgtgaccc agaagccgta ctccaaggac aagtttaagc tgtacttcca gaatccgcag   1800
ttcatgggcg gctgggacaa agacaaagaa accgactaca gggccaccat cctgaggtac   1860
ggctccaagt actacctcgc catcatggac aagaaatacg ccaagtgcct gcagaagatc   1920
gataaggacg acgtgaacgg caactacgag aagattaact acaagctgct gccagggccg   1980
aacaagatgc tcccgaaggt gttctttagc aagaaatgga tggcctacta caacccgagc   2040
gaggatatcc agaaaatcta caagaacggc accttcaaga aggcgacat  gttcaacctg   2100
aacgactgcc acaagctgat cgatttcttc aaggacagca tctctcgcta cccgaagtgg   2160
tccaacgcct acgatttcaa cttcagcgag actgaaaagt acaaggatat cgccggcttc   2220
taccgcgagg tcgaggaaca gggttacaag gtgagcttcg agagcgccag caagaaagag   2280
gtggacaagc tggtcgaaga gggcaagctg tacatgttcc agatctataa caaggacttc   2340
tccgacaaga gccacggcac cccaaacctg cacaccatgt acttcaagtt gctgttcgac   2400
gagaacaacc acggccagat caggctttct ggcggcgctg agcttttcat gagaagggcc   2460
agcctgaaaa agaggaact  ggtcgttcac ccggcgaaca gcccaatcgc caacaagaac   2520
ccggacaacc cgaaaaagac caccacgctg agctacgacg tgtacaagga caaaaggttc   2580
```

```
tccgaggacc agtacgagct gcacatcccg atcgccatca acaagtgccc gaagaacatc    2640
ttcaagatca acaccgaggt gagggtgctg ctgaagcacg acgacaaccc atacgtgatc    2700
ggcatcgata ggggcgagcg caacctgctc tacatcgtgg tggttgacgg caagggcaat    2760
atcgtcgagc agtacagcct taacgagatc attaacaact tcaatggcat caggatcaag    2820
accgactacc acagcctgct cgacaagaaa gaaaaagagc gcttcgaggc caggcagaac    2880
tggaccagca tcgagaatat caagagctg aaggccggct acattagcca ggtggtgcac     2940
aagatctgcg agctggtgga aaagtacgac gcggtgatcg ctctcgagga cctgaactcc    3000
gggttcaaga actcccgcgt gaaggttgag aagcaggtct accaaaagtt cgagaagatg    3060
ctgatcgaca agctcaacta catggtggac aaaaagagca cccctgcgc cacaggcggc     3120 gctcttaagg gctaccagat cacgaacaag ttcgagtcct tcaagagcat gagcacccag    3180
aatggcttca tcttctacat cccggcctgg ctgaccagca agatcgatcc atctaccggc    3240
ttcgtcaacc tcctcaagac caagtacacc agcattgccg acagcaagaa gttcatctcc    3300
agcttcgaca ggatcatgta cgtgccggaa gaggacctgt tcgagttcgc gctcgattac    3360
aagaacttca gcaggaccga cgcggactat attaagaagt ggaagctcta cagctacggc    3420
aacaggatcc gcatcttcag aaacccgaag aaaaacaacg tgttcgactg ggaagaagtg    3480
tgcctgacca gcgcctacaa agaactgttc aacaagtacg gcatcaacta ccagcagggc    3540
gacatcaggg ctctgctgtg cgagcagtct gacaaggcgt tctacagctc cttcatggcc    3600
ctgatgagcc tgatgctgca gatgaggaac agcatcaccg gcaggacgga cgtcgacttc    3660
ctgatcagcc cagtgaagaa ttccgacggc attttctacg actctaggaa ctacgaggct    3720
caagagaacg ccatcctgcc gaagaacgcc gatgctaacg gcgcgtacaa cattgcccgc    3780
aaggtgctgt gggctatcgg ccagtttaag aaggccgagg acgaaaaact ggacaaggtg    3840
aagatcgcca ttagcaacaa agagtggctc gagtacgccc agaccagcgt gaagcacaaa    3900
aggccagccg ccactaagaa ggctggccag gccaaaaaga agaagtga                 3948
```

<210> SEQ ID NO 159
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(20)
<223> OTHER INFORMATION: a, c, t, g, unknown or other

<400> SEQUENCE: 159

```
ggnnnnnnnn nnnnnnnnnn gg                                                22
```

<210> SEQ ID NO 160
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160

```
tttgatttac tcgtcacgat tccctggtcg aactttt                                37
```

<210> SEQ ID NO 161

```
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
tttaatttac tcgtcacgat tccctggtcg aactttt                                37

<210> SEQ ID NO 162
<211> LENGTH: 43
<212> TYPE: DNA
<213> ORGANISM: Zea mays

<400> SEQUENCE: 162
tttgatttac tcgtcacgat tcccctctcc tggtcgaact ttt                         43

<210> SEQ ID NO 163
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
aattcgatct acacttagta gaaattaatc tcccagttaa gataatgctg catctacact       60
tagtagaaat tatcaggt                                                     78
```